United States Patent
Oberboersch et al.

(10) Patent No.: US 8,058,475 B2
(45) Date of Patent: Nov. 15, 2011

(54) SUBSTITUTED CYCLOHEXYLMETHYL COMPOUNDS

(75) Inventors: Stefan Oberboersch, Aachen (DE); Beatrix Merla, Aachen (DE); Bernd Sundermann, Aachen (DE); Werner Englberger, Stolberg (DE); Hagen-Heinrich Hennies, Simmerath (DE); Achim Kless, Aachen (DE); Petra Bloms-Funke, Wuerselen (DE); Babette-Yvonne Koegel, Langer-wehe-Hamich (DE); Heinze Graubaum, Erkner (DE)

(73) Assignee: Gruenenthal GmbH, Aachen (DE)

( * ) Notice: Subject to any disclaimer, the term of this patent is extended or adjusted under 35 U.S.C. 154(b) by 752 days.

(21) Appl. No.: 12/143,433

(22) Filed: Jun. 20, 2008

(65) Prior Publication Data

US 2009/0286833 A1   Nov. 19, 2009

Related U.S. Application Data

(63) Continuation of application No. PCT/EP2006/012224, filed on Dec. 19, 2006.

(30) Foreign Application Priority Data

Dec. 22, 2005 (DE) .................. 10 2005 061 428

(51) Int. Cl.
*C07C 251/34* (2006.01)
*A61K 31/15* (2006.01)

(52) U.S. Cl. .......... 564/267; 564/57; 564/453; 564/461; 564/462; 560/128; 549/29; 548/567; 546/268.1; 514/331; 514/343; 514/428; 514/438; 514/528; 514/588; 514/613; 514/640; 514/659

(58) Field of Classification Search .......... 564/57, 564/267, 453, 461, 462; 560/128; 549/29; 548/567; 546/268.1; 514/331, 343, 428, 514/438, 528, 588, 613, 640, 659
See application file for complete search history.

(56) References Cited

U.S. PATENT DOCUMENTS

| 3,665,037 A * | 5/1972 | Murakami et al. ............ 564/300 |
| 6,410,790 B1 | 6/2002 | Sundermann et al. |
| 7,589,113 B2 * | 9/2009 | Merla et al. .................. 514/364 |

FOREIGN PATENT DOCUMENTS

| EP | 1 043 307 A2 | 10/2000 |
| WO | WO 02/066432 A1 | 8/2002 |
| WO | WO 02/090317 | 11/2002 |
| WO | WO 2004/043899 A1 | 5/2004 |

OTHER PUBLICATIONS

English translation of the International Preliminary Report on Patentability dated Dec. 19, 2006 (Eight (8) pages).
International Search Report dated May 2, 2007 with English translation (Six (6) pages).

* cited by examiner

*Primary Examiner* — Shailendra Kumar
(74) *Attorney, Agent, or Firm* — Crowell & Moring LLP

(57) ABSTRACT

Novel cyclohexylmethyl compounds corresponding to formula I

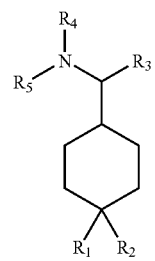

wherein $R_1$, $R_2$, $R_3$, $R_4$ and $R_5$, have the meanings given in the description. Pharmaceutical formulations containing these compounds, as well as a processes for preparing these compounds and related methods of treatment are also provided.

45 Claims, No Drawings

SUBSTITUTED CYCLOHEXYLMETHYL COMPOUNDS

This application is a continuation of International Patent Application No. PCT/EP2006/012224, filed Dec. 19, 2006, designating the United States of America, and published in German as WO 2007/079930, the entire disclosure of which is incorporated herein by reference. Priority is claimed based on the following Federal Republic of Germany patent application: Application No. DE 10 2005 061 428.0, filed Dec. 22, 2005.

FIELD OF THE INVENTION

The present invention relates to substituted cyclohexylmethyl derivatives, to processes for the preparation thereof, to pharmaceutical formulations containing these compounds; to the use of substituted cyclohexylmethyl derivatives in the preparation of pharmaceutical formulations and to methods of treating patients with these compounds.

BACKGROUND OF THE INVENTION

The treatment of chronic and non-chronic pain is of great importance in medicine. There is a worldwide need for highly effective therapies for pain. The urgent need for action in respect of a specific treatment for chronic and non-chronic pain that is fair to the patient, which is to be understood as meaning the successful and satisfactory treatment of pain for the patient, is documented in the large number of scientific works that have appeared recently in the field of applied analgesia or fundamental research into nociception.

Conventional opioids such as morphine are highly effective in the therapy of severe to very severe pain. However, their use is limited by the known side-effects, for example respiratory depression, vomiting, sedation, constipation and the development of tolerance. In addition, they are less effective in cases of neuropathic or incidental pain, from which tumour patients in particular suffer.

WO 0290317 discloses compounds in which two substituted amines are linked directly to the cyclohexane ring, an aminomethyl group not being described. These compounds are suitable for the treatment of pain.

SUMMARY OF THE INVENTION

One object of the present invention was to provide novel substances having analgesic activity which are suitable for the therapy of pain—in particular also of chronic and neuropathic pain.

Accordingly, the invention provides substituted cyclohexylmethyl derivatives of the general formula I

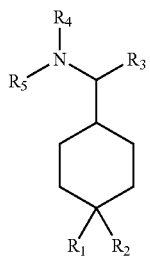

wherein
$R^1$ denotes $C_{1-8}$-alkyl, in each case branched or unbranched, saturated or unsaturated, unsubstituted or mono- or poly-substituted; aryl or heteroaryl, unsubstituted or mono- or poly-substituted; $C_{3-10}$-cycloalkyl, saturated or unsaturated, unsubstituted or mono- or poly-substituted; an aryl or heteroaryl radical linked via a $C_{1-4}$-alkyl chain and in each case unsubstituted or mono- or poly-substituted; $(CH_2)_m$CHN—OH, $(CH_2)_n NR^6 R^7$ or $(CH_2)_n OR^8$, wherein n represents 0, 1, 2 or 3 and m represents 0, 1 or 2; or $C(O)OR^9$ linked via a $C_{1-3}$-alkyl group, which can be saturated or unsaturated; $CONR^{10}R^{11}$;

$R^2$ denotes H or OH;

or $R^1$ and $R^2$ together represent

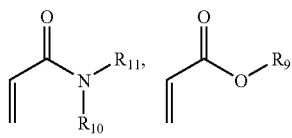

or =N—OH;

$R^3$ denotes aryl or heteroaryl, unsubstituted or mono- or poly-substituted; or an aryl radical which is linked via a $C_{1-3}$-alkyl group and can be unsubstituted or mono- or poly-substituted;

$R^4$ and $R^5$ independently of one another denote H; $C_{1-3}$-alkyl, unsubstituted, wherein $R^4$ and $R^5$ do not simultaneously denote H;

or the radicals $R^4$ and $R^5$ together denote $CH_2CH_2OCH_2CH_2$ or $(CH_2)_{3-6}$;

$R^6$ denotes H; $C_{1-8}$-alkyl, saturated or unsaturated, branched or unbranched, unsubstituted or mono- or poly-substituted; aryl, heteroaryl or $C_{3-10}$-cycloalkyl, in each case unsubstituted or mono- or poly-substituted; or an aryl or heteroaryl radical linked via a $C_{1-4}$-alkyl chain and in each case unsubstituted or mono- or poly-substituted;

$R^7$ denotes H; $C_{1-8}$-alkyl, saturated or unsaturated, branched or unbranched, unsubstituted or mono- or poly-substituted; aryl, heteroaryl or $C_{3-10}$-cycloalkyl, in each case unsubstituted or mono- or poly-substituted; or an aryl or heteroaryl radical linked via a $C_{1-4}$-alkyl chain and in each case unsubstituted or mono- or poly-substituted; $C(O)NR^{10}R^{11}$, $C(S)NR^{10}R^{11}$, $SO_2R^{12}$ or $C(O)R^{13}$;

$R^8$ denotes H; $C_{1-8}$-alkyl, in each case branched or unbranched, saturated or unsaturated, unsubstituted or mono- or poly-substituted; $C_{3-10}$-cycloalkyl, saturated or unsaturated, unsubstituted or mono- or poly-substituted; an aryl or heteroaryl radical linked via a $C_{1-4}$-alkyl group and unsubstituted or mono- or poly-substituted;

$R^9$ denotes H; $C_{1-8}$-alkyl, saturated or unsaturated, branched or unbranched, unsubstituted or mono- or poly-substituted;

$R^{10}$ and $R^{11}$ independently of one another denote H; $C_{3-10}$-cycloalkyl, saturated or unsaturated, unsubstituted or mono- or poly-substituted; aryl or heteroaryl, in each case unsubstituted or mono- or poly-substituted; or an aryl or heteroaryl radical linked via a $C_{1-4}$-alkyl chain and in each case unsubstituted or mono- or poly-substituted;

$R^{12}$ denotes aryl or heteroaryl, in each case unsubstituted or mono- or poly-substituted; $C_{1-8}$-alkyl, in each case saturated or unsaturated, branched or unbranched, unsubstituted or mono- or poly-substituted; $C_{3-10}$-cycloalkyl, saturated or unsaturated, unsubstituted or mono- or poly-substituted; or an aryl or heteroaryl radical linked via a $C_{1-3}$-alkyl chain and in each case unsubstituted or mono- or poly-substituted;

$R^{13}$ denotes $C_{1-8}$-alkyl, saturated or unsaturated, branched or unbranched, unsubstituted or mono- or poly-substituted; $C_{3-10}$-cycloalkyl, aryl or heteroaryl, in each case unsubstituted or mono- or poly-substituted; or an aryl or heteroaryl radical linked via a $C_{1-4}$-alkyl chain and in each case unsubstituted or mono- or poly-substituted, wherein the alkyl chain can be branched or unbranched, unsubstituted or mono- or poly-substituted;

in the form of the racemate; of the enantiomers, diastereoisomers, mixtures of the enantiomers or diastereoisomers or of an individual enantiomer or diastereoisomer; of the bases and/or salts of physiologically acceptable acids.

The compounds have affinity for the μ-opioid receptor.

Within the scope of this invention, the expressions "$C_{1-3}$-alkyl", $C_{1-4}$-alkyl" and "$C_{1-8}$-alkyl" include acyclic saturated or unsaturated hydrocarbon radicals which can be branched- or straight-chained as well as unsubstituted or mono- or poly-substituted, having from 1 to 3 carbon atoms or from 1 to 4 carbon atoms or from 1 to 8 carbon atoms, respectively, that is to say $C_{1-3}$-alkanyls, $C_{2-3}$-alkenyls and $C_{2-3}$-alkynyls or $C_{1-4}$-alkanyls, $C_{2-4}$-alkenyls and $C_{2-4}$-alkynyls or $C_{1-8}$-alkanyls, $C_{2-8}$-alkenyls and $C_{2-8}$-alkynyls. Alkenyls have at least one C—C double bond and alkynyls have at least one C—C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, n-hexyl, 2-hexyl, n-heptyl, n-octyl, ethylenyl (vinyl), ethynyl, propenyl (—CH$_2$CH=CH$_2$, —CH=CH—CH$_3$, —C(=CH$_2$)—CH$_3$), propynyl (—CH—C≡CH, —C≡C—CH$_3$), butenyl, butynyl, pentenyl, pentynyl, hexenyl, hexynyl, heptenyl, heptynyl, octenyl and octynyl. Methyl, ethyl, n-propyl, isopropyl, 2,2-dimethylpropyl, n-butyl, sec-butyl, isobutyl, 3-pentyl, n-pentyl, n-hexyl are particularly advantageous.

For the purposes of this invention, the term "cycloalkyl" or "$C_{3-10}$-cycloalkyl" means cyclic hydrocarbons having 3, 4, 5, 6, 7, 8, 9 or 10 carbon atoms, wherein the hydrocarbons can be saturated or unsaturated (but not aromatic), unsubstituted or mono- or poly-substituted. The rings can be bridged, as, for example, in adamantane or in bicyclo[2.2.1]heptane, or unbridged. In relation to cycloalkyl, the term also includes saturated or unsaturated (but not aromatic) cycloalkyls in which one or two carbon atoms have been replaced by a heteroatom S, N or O. $C_{3-10}$-Cycloalkyl is advantageously selected from the group comprising cyclopropyl, adamantyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl. Adamantyl, cyclopentyl and cyclohexyl are particularly preferred.

Within the scope of this invention, the term "aryl" denotes aromatic hydrocarbons, including phenyls and naphthyls. The aryl radicals can also be fused with further saturated, (partially) unsaturated or aromatic ring systems, such as, for example, in 2,3-dihydrobenzofuran. Each aryl radical can be unsubstituted or mono- or poly-substituted, wherein the aryl substituents can be identical or different and can be located at any desired and possible position of the aryl. Aryl is advantageously selected from the group comprising phenyl, 1-naphthyl, 2-naphthyl, each of which can be unsubstituted or mono- or poly-substituted.

The term "heteroaryl" denotes a 5-, 6- or 7-membered cyclic aromatic radical containing at least 1, optionally also 2, 3, 4 or 5, heteroatom(s), the heteroatoms being identical or different and the heterocycle being unsubstituted or mono- or poly-substituted; in the case of substitution on the heterocycle, the substituents can be identical or different and can be located at any desired and possible position of the heteroaryl. The heterocycle can also be part of a bi- or poly-cyclic system, a single heteroatom in the ring system defining the system as heteroaryl. Preferred heteroatoms are nitrogen, oxygen and sulfur. It is preferred for the heteroaryl radical to be selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl and oxadiazolyl, it being possible for bonding to the compounds of the general structure I to take place via any desired and possible ring member of the heteroaryl radical. Pyridyl, benzothiadiazolyl, isoxazolyl, benzothienyl, thiazolyl, pyrazolyl, furyl, thienyl and indolyl are particularly preferred.

The expression "aryl or heteroaryl bonded via $C_{1-3}$-alkyl" or "aryl or heteroaryl bonded via $C_{1-4}$-alkyl" means, for the purposes of the present invention, that $C_{1-3}$-alkyl, $C_{1-4}$-alkyl and aryl or heteroaryl have the meanings defined above and the aryl or heteroaryl radical is bonded to the compound of the general structure I via a $C_{1-3}$-alkyl group or a $C_{1-4}$-alkyl group. Benzyl, 1-phenylpropyl, diphenyl-methyl, phenethyl, methylthienyl, 2-indolylethyl, 1-methyl-2-indolyl-ethyl and 4-phenylbutyl are particularly advantageous within the scope of this invention.

In connection with "alkyl" and "cycloalkyl", the term "substituted" within the scope of this invention is understood as meaning the substitution of a hydrogen radical by F, Cl, Br, I, —CN, NH$_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, NO$_2$, SH, S—$C_{1-6}$-alkyl, S-benzyl, O—$C_{1-6}$-alkyl, OH, O—$C_{1-6}$-alkyl-OH, =O, O-benzyl, O-phenyl, C(=O)$C_{1-6}$-alkyl, CO$_2$H, CO$_2$—$C_{1-6}$-alkyl, phenyl or benzyl, wherein polysubstituted radicals are to be understood as being those radicals that are polysubstituted, for example di- or tri-substituted, either on different atoms or on the same atom, for example trisubstituted on the same carbon atom, as in the case of CF$_3$ or —CH$_2$CF$_3$, or at different positions, as in the case of —CH(OH)—CH=CH—CHCl$_2$. Polysubstitution can be carried out with the same or with different substituents. Methyl, phenyl, 4-chlorophenyl and CO$_2$CH$_3$ are particularly preferred.

In relation to "aryl" and "heteroaryl", "mono- or poly-substituted" within the scope of this invention is understood as meaning the substitution of one or more hydrogen atoms of the ring system one or more times, for example two, three or four times, by F, Cl, Br, I, CN, NH$_2$, NH—$C_{1-6}$-alkyl, NH—$C_{1-6}$-alkyl-OH, N($C_{1-6}$-alkyl)$_2$, N($C_{1-6}$-alkyl-OH)$_2$, NO$_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O) $C_{1-6}$-alkyl, CO$_2$H, CO$_2$—$C_{1-6}$-alkyl, CF$_3$, $C_{1-6}$-alkyl, optionally also by SO$_2$phenyl or SO$_2$$C_{1-6}$-alkyl; on one atom or optionally on different atoms (wherein a substituent can itself optionally be substituted). Polysubstitution is carried out with the same or with different substituents. Preferred substituents for "aryl" and "heteroaryl" are OCH$_3$, CN, Cl, Br, CH$_3$, 2,3-dihydrobenzofuran, S—CH$_3$, F, NO$_2$, n-propyl, S—C$_2$H$_5$, ethyl, CF$_3$, pyridyl and tert-butyl; S-phenyl, phenyl and O-phenyl, wherein the phenyl radicals can themselves in turn be substituted by Cl, F, OCH$_3$, CN or CH$_3$. OCH$_3$, CN, Cl, Br, S-(4-chlorophenyl), CH$_3$, 2,6-dichlorophenyl, 2,3-dihydro-benzofuran, phenyl, S—CH$_3$, F, NO$_2$, n-propyl, O-(4-methylphenyl), S—C$_2$H$_5$, O-(4-chlorophenyl), ethyl, $CF_3$, 4-chlorophenyl, pyridyl, $SO_2$-isopropyl, $SO_2$—$CH_3$, $SO_2$-(4-chlorophenyl) and tert-butyl are particularly preferred.

When $R^2$ denotes OH, it is preferred for $R^1$ to denote $C_{1-8}$-alkyl, in each case branched or unbranched, saturated or unsaturated, unsubstituted or mono- or poly-substituted; aryl or heteroaryl, unsubstituted or mono- or poly-substituted; $C_{3-10}$-cycloalkyl, saturated or unsaturated, unsubstituted or mono- or poly-substituted; an aryl or heteroaryl radical linked via a $C_{1-4}$-alkyl chain and in each case unsubstituted or mono- or poly-substituted.

When $R^2$ denotes H, it is additionally preferred for $R^1$ to denote $(CH_2)_m CHN$—OH, $(CH_2)_n NR^6 R^7$ or $(CH_2)_n OR^8$, wherein n represents 0, 1, 2 or 3 and m represents 0, 1 or 2; or $C(O)OR^9$ linked via a $C_{1-3}$-alkyl group, which can be saturated or unsaturated; $CONR^{10}R^{11}$.

It is further preferred for $R^1$ and $R^2$ together to represent

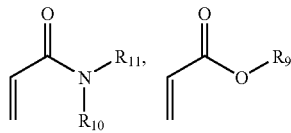

or =N—OH.

Preference is given within the scope of this invention to substituted cyclohexyl-methyl derivatives wherein
$R^1$ denotes $C_{1-8}$-alkyl, in each case branched or unbranched, saturated or unsaturated, unsubstituted or mono- or poly-substituted by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O) $C_{1-6}$-alkyl, $CO_2H$, $CO_2$—$C_{1-6}$-alkyl, phenyl or benzyl; aryl or heteroaryl, unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O) $C_{1-6}$-alkyl, $CO_2H$, $CO_2$—$C_{1-6}$-alkyl, $CF_3$, $C_{1-6}$-alkyl; cycloalkyl, saturated or unsaturated, unsubstituted or mono- or poly-substituted by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl or benzyl; an aryl or heteroaryl radical linked via a $C_{1-4}$-alkyl chain and in each case unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl;

in particular
$R^1$ denotes $C_{1-8}$-alkyl, in each case branched or unbranched, saturated or unsaturated, unsubstituted or mono- or poly-substituted by methyl, =O, phenyl or $CO_2CH_3$; phenyl, naphthyl, benzyl, phenethyl, 2-pyridyl or 2-thienyl, unsubstituted or mono- or poly-substituted by F, $CH_3$, Cl, tert-butyl, methoxy or $CF_3$; cyclohexyl or cyclopentyl.

Particular preference is given to substituted cyclohexylmethyl derivatives in which $R^1$ represents 2,4-difluorophenyl, 4-fluoro-3-methylphenyl, phenyl, 3-methoxybenzyl, 4-chlorophenyl, benzyl, 2-methylphenyl, 4-tert-butylphenyl, cyclopentyl, 4-fluorophenyl, phenethyl, 2-thienyl, 2,4-dichlorophenyl, 3-methoxy-phenyl, 4-methylphenyl, 4-methoxyphenyl, 3,5-difluorophenyl, isopropyl, butyl, ethyl, hexyl, sec-butyl, 2,4,6-trimethylphenyl, pentyl, propyl, 3-fluorophenyl, 3,5-dichlorophenyl, 4-fluorobenzyl, 4-chloro-3-trifluoromethylphenyl, cyclohexyl, isobutyl or 2,5-dimethoxyphenyl.

Within the scope of this invention, preference is also given to substituted cyclohexylmethyl derivatives wherein
$R^3$ denotes phenyl, thienyl or pyridyl, in each case unsubstituted or mono- or poly-substituted by F, Cl, CN, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$- alkyl, $CF_3$, $C_{1-6}$-alkyl; an aryl radical bonded via a $C_{1-3}$-alkyl chain and in each case unsubstituted or mono- or poly-substituted by F, Cl, CN, NH—$C_{1-6}$-alkyl, NH—$C_{1-6}$- alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl;

preferably
$R^3$ denotes phenyl or thienyl, in each case unsubstituted or mono- or poly-substituted by F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl; a phenyl radical bonded via a $C_{1-3}$-alkyl chain and in each case unsubstituted or mono- or poly-substituted by F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl;

in particular
$R^3$ denotes phenyl, unsubstituted or mono- or poly-substituted by F, Cl, OH, $OCH_3$, $CF_3$ or $CH_3$; thienyl; or a phenyl radical bonded via a $C_{1-3}$-alkyl chain and unsubstituted or mono- or poly-substituted by F, Cl, CN, OH, $OCH_3$, $CF_3$ or $CH_3$.

Most particular preference is given to cyclohexylmethyl derivatives wherein $R^3$ denotes phenyl, unsubstituted or monosubstituted by Cl or F; phenethyl or thienyl.

Preference is further given to cyclohexylmethyl derivatives wherein $R^4$ and $R^5$ represent H or $CH_3$, wherein $R^4$ and $R^5$ do not simultaneously denote H.

Preference is also given to substituted cyclohexylmethyl derivatives wherein $R^4$ and $R^5$ together denote $(CH_2)_{3-6}$.

Preference is additionally given to substituted cyclohexylmethyl derivatives wherein
$R^5$ denotes H; $C_{1-8}$-alkyl, saturated or unsaturated, branched or unbranched, unsubstituted or mono- or poly-substituted by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl or benzyl; aryl or heteroaryl, in each case unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl; or an aryl or heteroaryl radical linked via a $C_{1-4}$-alkyl chain and in each case unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl, wherein the alkyl chain can be branched or unbranched, unsubstituted or mono- or poly-substituted by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl or benzyl;

preferably $R^5$ denotes H; $C_{1-8}$-alkyl, saturated or unsaturated, branched or unbranched, unsubstituted or mono- or poly-substituted by F, Cl, —CN, SH, $SCH_3$, $OCH_3$, OH, =O, $CO_2C_2H_5$ or $CO_2CH_3$; aryl, unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl; or an aryl or heteroaryl radical linked via a $C_{1-4}$-alkyl chain and in each case unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl, wherein the alkyl chain can be branched or unbranched, unsubstituted or mono- or poly-substituted by $CO_2C_2H_5$ or $CO_2CH_3$;

in particular $R^6$ denotes H; phenyl, unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl; or a phenyl or indolyl radical linked via a $C_{1-4}$-alkyl chain and in each case unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl, wherein the alkyl chain can be branched or unbranched, unsubstituted or mono- or poly-substituted by $CO_2C_2H_5$ or $CO_2CH_3$.

Most particular preference is given to substituted cyclohexylmethyl derivatives wherein $R^6$ denotes 2-indolylethyl, phenethyl, 3-phenylpropyl, benzyl, phenyl, 4-phenylbutyl, 1-(1H-indol-3-yl)propan-2-yl, 4 2-(3-indolyl)propionic acid methyl ester, in each case unsubstituted or mono- or poly-substituted by F or $OCH_3$.

Most particular preference is likewise given to substituted cyclohexylmethyl derivatives in which $R^6$ denotes H.

Preference is additionally given to substituted cyclohexylmethyl derivatives wherein $R^7$ denotes C(O)$R^{13}$.

Preference is further given to substituted cyclohexylmethyl derivatives wherein $R^8$ denotes H; an aryl or heteroaryl radical linked via a $C_{1-4}$-alkyl group and unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl;

in particular $R^8$ denotes H; a phenyl radical linked via a $C_{1-4}$-alkyl group and unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl.

Particular preference is given to cyclohexylmethyl derivatives wherein $R^8$ denotes benzyl, unsubstituted or mono- or poly-substituted by F.

Preference is likewise given to substituted cyclohexylmethyl derivatives wherein $R^9$ denotes $C_{1-8}$-alkyl, saturated or unsaturated, branched or unbranched, unsubstituted or mono- or poly-substituted by F, Cl, —CN, SH, $SCH_3$, $OCH_3$, OH, =O, $CO_2C_2H_5$ or $CO_2CH_3$;

in particular $R^9$ denotes $C_{1-8}$-alkyl, branched or unbranched.

Particular preference is given to substituted cyclohexylmethyl derivatives wherein $R^9$ denotes ethyl.

Preference is additionally given to substituted cyclohexylmethyl derivatives wherein $R^{10}$ and $R^{11}$ independently of one another denote H; $C_{3-10}$-cycloalkyl, saturated or unsaturated, unsubstituted or mono- or poly-substituted by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl or benzyl; aryl or heteroaryl, in each case unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl; or an aryl or heteroaryl radical linked via a $C_{1-4}$-alkyl chain and in each case unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl;

in particular $R^{10}$ and $R^{11}$ independently of one another denote H; phenyl, naphthyl, or a phenyl or indolyl radical linked via a $C_{1-4}$-alkyl chain, in each case unsubstituted or substituted by F, Cl, Br, CN, $NH_2$, $NO_2$, SH, $SCH_3$, OH, $OCH_3$, $CF_3$, methyl, ethyl, propyl, butyl or tert-butyl.

Particular preference is given to substituted cyclohexylmethyl derivatives wherein $R^{10}$ and $R^{11}$ independently of one another denote H; naphthyl, phenyl or benzyl, in each case unsubstituted or mono- or poly-substituted by $CF_3$, F, $NO_2$ or Br; or cyclohexyl, wherein $R^{10}$ and $R^{11}$ do not simultaneously denote H.

Preference is also given to substituted cyclohexylmethyl derivatives wherein $R^{12}$ denotes aryl or heteroaryl, in each case unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl; $C_{1-8}$-alkyl, in each case saturated or unsaturated, branched or unbranched, unsubstituted or mono- or poly-substituted by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl or benzyl; or an aryl or heteroaryl radical linked via a $C_{1-3}$-alkyl chain and in each case unsubstituted or mono- or poly-substituted by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl; $C_{1-8}$-alkyl;

in particular $R^{12}$ denotes naphthyl, phenyl or benzyl, in each case unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl.

Particular preference is given to substituted cyclohexylmethyl derivatives wherein $R^{12}$ denotes phenyl, unsubstituted or mono- or poly-substituted by Cl, $OCH_3$, tert-butyl or $NO_2$.

Preference is also given to substituted cyclohexylmethyl derivatives wherein $R^{13}$ denotes $C_{1-8}$-alkyl, saturated or unsaturated, branched or unbranched, unsubstituted or monoor poly-substituted by F, Cl, Br, I, —CN, NH$_2$, NH—C$_{1-6}$-alkyl, NH—C$_{1-6}$-alkyl-OH, C$_{1-6}$-alkyl, N(C$_{1-6}$-alkyl)$_2$, N(C$_{1-6}$-alkyl-OH)$_2$, NO$_2$, SH, S—C$_{1-6}$-alkyl, S-benzyl, O—C$_{1-6}$-alkyl, OH, O—C$_{1-6}$-alkyl-OH, =O, O-benzyl, O-phenyl, C(=O)C$_{1-6}$-alkyl, CO$_2$H, CO$_2$—C$_{1-6}$-alkyl, phenyl or benzyl; C$_{3-10}$-cycloalkyl, unsubstituted or mono- or poly-substituted by F, Cl, Br, I, —CN, NH$_2$, C$_{1-6}$-alkyl, NH—C$_{1-6}$-alkyl, NH—C$_{1-6}$-alkyl-OH, C$_{1-6}$-alkyl, N(C$_{1-6}$-alkyl)$_2$, N(C$_{1-6}$-alkyl-OH)$_2$, NO$_2$, SH, S—C$_{1-6}$-alkyl, S-benzyl, O—C$_{1-6}$-alkyl, OH, O—C$_{1-6}$-alkyl-OH, =O, O-benzyl, C(=O)C$_{1-6}$-alkyl, CO$_2$H, CO$_2$—C$_{1-6}$-alkyl, phenyl or benzyl; aryl or heteroaryl, in each case unsubstituted or mono- or poly-substituted by F, Cl, Br, I, CN, NH$_2$, NH—C$_{1-6}$-alkyl, NH—C$_{1-6}$-alkyl-OH, N(C$_{1-6}$-alkyl)$_2$, N(C$_{1-6}$-alkyl-OH)$_2$, NO$_2$, SH, pyridyl, S—C$_{1-6}$-alkyl, S-phenyl, OH, O—C$_{1-6}$-alkyl, O—C$_{1-6}$-alkyl-OH, O-phenyl, phenyl, benzyl, C(=O)C$_{1-6}$-alkyl, CO$_2$H, CO$_2$—C$_{1-6}$-alkyl, CF$_3$, C$_{1-6}$-alkyl, dihydro-benzofuran, SO$_2$-phenyl or SO$_2$C$_{1-6}$-alkyl; or an aryl or heteroaryl radical linked via a C$_{1-4}$-alkyl chain and in each case unsubstituted or mono- or poly-substituted by F, Cl, Br, I, CN, NH$_2$, NH—C$_{1-6}$-alkyl, NH—C$_{1-6}$-alkyl-OH, N(C$_{1-6}$-alkyl)$_2$, N(C$_{1-6}$-alkyl-OH)$_2$, NO$_2$, SH, pyridyl, S—C$_{1-6}$-alkyl, S-phenyl, OH, O—C$_{1-6}$-alkyl, O—C$_{1-6}$-alkyl-OH, O-phenyl, phenyl, benzyl, C(=O)C$_{1-6}$-alkyl, CO$_2$H, CO$_2$—C$_{1-6}$-alkyl, CF$_3$, C$_{1-6}$-alkyl, SO$_2$-phenyl or SO$_2$C$_{1-6}$-alkyl, wherein the alkyl chain can be branched or unbranched, unsubstituted or mono- or poly-substituted by F, Cl, Br, I, —CN, NH$_2$, NH—C$_{1-6}$-alkyl, NH—C$_{1-6}$-alkyl-OH, C$_{1-6}$-alkyl, N(C$_{1-6}$-alkyl)$_2$, N(C$_{1-6}$-alkyl-OH)$_2$, NO$_2$, SH, S—C$_{1-6}$-alkyl, S-benzyl, O—C$_{1-6}$-alkyl, OH, O—C$_{1-6}$-alkyl-OH, =O, O-benzyl, C(=O)C$_{1-6}$-alkyl, CO$_2$H, CO$_2$—C$_{1-6}$-alkyl, phenyl or benzyl;

preferably

R$^{13}$ denotes C$_{1-8}$-alkyl, saturated or unsaturated, branched or unbranched, unsubstituted or mono- or poly-substituted by F, Cl, —CN, NH—C$_{1-6}$-alkyl, C$_{1-6}$-alkyl, N(C$_{1-6}$-alkyl)$_2$, SH, S—C$_{1-6}$-alkyl, S-benzyl, O—C$_{1-6}$-alkyl, OH, =O, O-benzyl, O-phenyl, C(=O)C$_{1-6}$-alkyl, CO$_2$H, CO$_2$—C$_{1-6}$-alkyl, phenyl or benzyl; C$_{3-10}$-cyclo-alkyl, unsubstituted or mono- or poly-substituted by F, Cl, —CN, NH—C$_{1-6}$-alkyl, C$_{1-6}$-alkyl, N(C$_{1-6}$-alkyl)$_2$, SH, S—C$_{1-6}$-alkyl, C$_{1-6}$-alkyl, S-benzyl, O—C$_{1-6}$-alkyl, OH, =O, O-benzyl, C(=O)C$_{1-6}$-alkyl, CO$_2$H, CO$_2$—C$_{1-6}$-alkyl, phenyl or benzyl; aryl or heteroaryl, in each case unsubstituted or mono- or poly-substituted by F, Cl, Br, CN, NH$_2$, NH—C$_{1-6}$-alkyl, N(C$_{1-6}$-alkyl)$_2$, NO$_2$, SH, pyridyl, S—C$_{1-6}$-alkyl, S-phenyl, OH, (CH$_2$)$_{0-3}$O—C$_{1-6}$-alkyl, C$_{1-3}$-alkyl-C$_{3-6}$-cycloalkyl, O—C$_{1-6}$-alkyl-OH, O-phenyl, phenyl, benzyl, C(=O)C$_{1-6}$-alkyl, CO$_2$H, CO$_2$—C$_{1-6}$-alkyl, CF$_3$, C$_{1-6}$-alkyl, dihydro-benzofuran, SO$_2$-phenyl or SO$_2$C$_{1-6}$-alkyl; or an aryl or heteroaryl radical linked via a C$_{1-4}$-alkyl chain and in each case unsubstituted or mono- or poly-substituted by F, Cl, Br, CN, NH$_2$, NH—C$_{1-6}$-alkyl, N(C$_{1-6}$-alkyl)$_2$, NO$_2$, SH, pyridyl, S—C$_{1-6}$-alkyl, S-phenyl, OH, O—C$_{1-6}$-alkyl, O—C$_{1-6}$-alkyl-OH, O-phenyl, phenyl, benzyl, C(=O)C$_{1-6}$-alkyl, CO$_2$H, CO$_2$—C$_{1-6}$-alkyl, CF$_3$, C$_{1-6}$-alkyl, SO$_2$-phenyl or SO$_2$C$_{1-6}$-alkyl, wherein the alkyl chain can be branched or unbranched, unsubstituted or mono- or poly-substituted by F, Cl, —CN, SH, S—C$_{1-6}$-alkyl, S-benzyl, O—C$_{1-6}$-alkyl, OH, O—C$_{1-6}$-alkyl-OH, O-benzyl, CO$_2$—C$_{1-6}$-alkyl, phenyl or benzyl;

in particular

R$^{13}$ denotes C$_{1-8}$-alkyl, saturated or unsaturated, branched or unbranched, unsubstituted or mono- or poly-substituted by F, Cl, —CN, C$_{1-6}$-alkyl, O-phenyl, O-benzyl, SH, S—C$_{1-6}$-alkyl, O—C$_{1-6}$-alkyl or OH; cyclopentyl, cyclohexyl or adamantyl, unsubstituted or mono- or poly-substituted by F, Cl, —CN, O—C$_{1-6}$-alkyl, OH, =O, C$_{1-6}$-alkyl, CO$_2$—C$_{1-6}$-alkyl; phenyl, naphthyl, thienyl, furyl, oxadiazolyl, benzothiophenyl, pyrazolyl, pyridyl, thiazolyl, benzofuranyl, isoxazolyl or benzothiadiazolyl, in each case unsubstituted or mono- or poly-substituted by F, Cl, Br, CN, NH$_2$, NH—C$_{1-6}$-alkyl, N(C$_{1-6}$-alkyl)$_2$, NO$_2$, SH, pyridyl, S—C$_{1-6}$-alkyl, S-phenyl, OH, (CH$_2$)$_{0-3}$O—C$_{1-6}$-alkyl, C$_{1-3}$-alkyl-C$_{3-6}$-cycloalkyl, O—C$_{1-6}$-alkyl-OH, O-phenyl, phenyl, benzyl, C(=O)C$_{1-6}$-alkyl, CO$_2$H, CO$_2$—C$_{1-6}$-alkyl, CF$_3$, C$_{1-6}$-alkyl, dihydrobenzofuran, SO$_2$-phenyl, wherein phenyl can be substituted by Cl, or SO$_2$C$_{1-6}$-alkyl; or a phenyl or thienyl radical linked via a C$_{1-4}$-alkyl chain and in each case unsubstituted or mono- or poly-substituted by F, Cl, Br, CN, NO$_2$, SH, S—C$_{1-6}$-alkyl, OH, O—C$_{1-6}$-alkyl, CF$_3$ or C$_{1-6}$-alkyl, wherein the alkyl chain can be branched or unbranched, unsubstituted or mono- or poly-substituted by phenyl.

Particular preference is given to substituted cyclohexylmethyl derivatives wherein R$^{13}$ denotes methyl, ethyl, phenyl, benzyl, 3-pentyl, n-propyl, benzothienyl, 1-(4-chlorophenyl)-cyclopentyl, 4-propylphenyl, 3-cyanophenyl, 3-chlorophenyl, 5-chloro-4-methoxy-thiophen-3-yl, 3-fluoro-5-trifluoromethylphenyl, 4-fluoro-5-trifluoromethylphenyl, 2-thienyl, 3,5-dichlorophenyl, 2,4,5-trifluorophenyl, 3-bromophenyl, 4-methylphenyl, 3-methoxyphenyl, 2,2-dimethylpropyl, 2-tert-butyl-5-methyl-pyrazol-3-yl, 2,4-dimethoxyphenyl, 3-trifluoromethylphenyl, 3,5-difluorophenyl, 2-fluoro-5-trifluoromethylphenyl, 4-chlorobenzyl, 2-methoxyphenyl, 2-methylsulfanyl-3-pyridyl, 3,4,5-trimethoxyphenyl, 2-ethylsulfanyl-3-pyridyl, 2-methyl-5-phenyl-furan-3-yl, 1-phenoxyethyl, tert-butylphenyl, 2-(4-chlorophenylsulfanyl)-3-pyridyl, 2-p-tolyloxy-3-pyridyl, 3-chloro-4-(sulfonyl-2-propyl)-thiophen-2-yl, 5-methylisoxazol-3-yl, 5-bromo-3-pyridyl, naphthyl, 2-methyl-5-(4-chloro-phenyl)-furan-3-yl, 4-(4-chloro-phenylsulfonyl)-3-methyl-thiophen-2-yl, 1-phenylpropyl, adamantyl, 2-phenyl-thiazol-4-yl, 4-methyl-2-phenyl-thiazol-5-yl, 2-(2,3-dihydro-benzofuran-5-yl)-thiazol-4-yl, 3-methylphenyl, 3-chloro-4-methylsulfonyl-thiophen-2-yl, benzyloxymethyl, methylthienyl, 4-bromo-2-ethyl-5-methyl-pyrazol-3-yl, 2,5-dimethylfuryl, 5-pyridin-2-yl-thiophene, 3-chloro-4-fluorophenyl, cyclohexyl, 3-nitrophenyl, 2,5-difluorophenyl, 2,6-difluorophenyl, 2-trifluoromethyl-5-fluoro-phenyl, 4-chlorophenoxy-methyl, 2-bromophenyl, cyclopentyl, benzothiadiazolyl, diphenylmethyl, 2-methylphenyl, 3-methoxybenzyl, 2,4,6-trichlorophenyl, 2-butyl, 2-chlorophenyl, 3,5-dinitrophenyl, 4-cyanophenyl, 2,4-dichloro-5-fluorophenyl, 2-chloro-3-pyridyl, 4-nitrophenyl, 2,3,4,5,6-pentafluorophenyl or 3-(2,6-dichloro-phenyl)-5-methyl-isoxazol-4-yl, 5-chloro-4-methylthiophen-3-yl, 4-fluorophenyl, 4-chlorophenyl, 2-fluorophenyl, 3-methylphenyl, 3-bromophenyl, 2,6-dichlorophenyl, 3,4-dichlorophenyl, 4-cyanophenyl, 2,4-difluorophenyl, 2,4-dichlorophenyl, 2,4-dichloro-5-fluorophenyl, 2-chloropyridin-3-yl, 3,5-dimethoxyphenyl, 2,6-dimethoxyphenyl, 2,3,6-trifluorophenyl, 2-(4-chlorophenoxy)-3-pyridyl, 3,4-difluorophenyl, 2-(2,3-dihydro-benzofuran-5-yl)-4-methyl-thiazol-5-yl, 3-methyl-oxadiazolyl, 3-phenyl-oxadiazolyl, 3-cyclopropylmethyl-oxadiazolyl, 3-methoxymethyl-oxadiazolyl or 2,4-dimethoxy-phenyl.

It is further preferred for the radicals $R^8$ and $R^9$ not to denote H.

It is additionally preferred for the radicals $R^{10}$ and $R^{11}$ or $R^6$ and $R^7$ in each case not to denote H simultaneously.

It is additionally preferred for $R^4$ and $R^5$ not to denote H.

Most particular preference is given to substituted cyclohexylmethyl derivatives (subgroup oximes, primary amines, alcohols and esters) from the group

(16) 4-(dimethylamino-phenyl-methyl)-cyclohexanone oxime
(17) 4-(dimethylamino-phenyl-methyl)-cyclohexylamine
(18) 4-[dimethylamino-(4-fluorophenyl)-methyl]-cyclohexanone oxime
(19) 4-[dimethylamino-(4-fluorophenyl)-methyl]-cyclohexylamine
(20) 4-[dimethylamino-(3-fluorophenyl)-methyl]-cyclohexanone oxime
(21) 4-[dimethylamino-(3-fluorophenyl)-methyl]-cyclohexylamine
(22) 4-[(4-chlorophenyl)-dimethylamino-methyl]-cyclohexanone oxime
(23) 4-[(4-chlorophenyl)-dimethylamino-methyl]-cyclohexylamine
(24) 4-(dimethylamino-thiophen-2-yl-methyl)-cyclohexanone oxime
(25) 4-(dimethylamino-thiophen-2-yl-methyl)-cyclohexylamine
(26) 4-(1-dimethylamino-3-phenyl-propyl)-cyclohexanone oxime
(27) 4-(1-dimethylamino-3-phenyl-propyl)-cyclohexylamine
(29) 4-(dimethylamino-phenyl-methyl)-cyclohexane-carbaldehyde oxime
(30) [(4-aminomethyl-cyclohexyl)-phenyl-methyl]-dimethylamine
(32) 4-[dimethylamino-(4-fluorophenyl)-methyl]-cyclohexanecarbaldehyde oxime
(33) [(4-aminomethyl-cyclohexyl)-(4-fluorophenyl)-methyl]-dimethylamine
(35) 4-[dimethylamino-(3-fluorophenyl)-methyl]-cyclohexanecarbaldehyde oxime
(36) [(4-aminomethyl-cyclohexyl)-(3-fluorophenyl)-methyl]-dimethylamine
(38) 4-[(4-chlorophenyl)-dimethylamino-methyl]-cyclohexanecarbaldehyde oxime
(39) [(4-aminomethyl-cyclohexyl)-(4-chlorophenyl)-methyl]-dimethylamine
(41) 4-(dimethylamino-thiophen-2-yl-methyl)-cyclohexanecarbaldehyde oxime
(42) [(4-aminomethyl-cyclohexyl)-thiophen-2-yl-methyl]-dimethylamine
(44) 4-(1-dimethylamino-3-phenyl-propyl)-cyclohexanecarbaldehyde oxime
(45) [1-(4-aminomethyl-cyclohexyl)-3-phenyl-propyl]-dimethylamine
(47) [4-(dimethylamino-phenyl-methyl)-cyclohexyl]-acetaldehyde oxime
(48) 2-[4-dimethylamino-phenyl-methyl)-cyclohexyl]-ethylamine
(50) {4-[dimethylamino-(4-fluorophenyl)-methyl]-cyclohexyl}-acetaldehyde oxime
(51) 2-{4-[dimethylamino-(4-fluorophenyl)-methyl]-cyclohexyl}-ethylamine
(53) {4-[dimethylamino-(3-fluorophenyl)-methyl]-cyclohexyl}-acetaldehyde oxime
(54) 2-{4-[dimethylamino-(3-fluorophenyl)-methyl]-cyclohexyl}-ethylamine
(56) {4-[dimethylamino-(4-chlorophenyl)-methyl]-cyclohexyl}-acetaldehyde oxime
(66) 2-{4-[dimethylamino-(4-chlorophenyl)-methyl]-cyclohexyl}-ethylamine
(68) 2-(4-((dimethylamino)(thiophen-2-yl)methyl)cyclohexyl)acetaldehyde oxime
(69) 2-[4-(dimethylamino-thiophen-2-yl-methyl)-cyclohexyl]-ethylamine
(71) [4-(1-dimethylamino-3-phenyl-propyl)-cyclohexyl]-acetaldehyde oxime
(72) {1-[4-(2-amino-ethyl)-cyclohexyl]-3-phenyl-propyl}-dimethylamine
(111) 4-[dimethylamino-phenyl-methyl]-cyclohexanol
(112) 4-[dimethylamino-(4-fluorophenyl)-methyl]-cyclohexanol
(113) 4-[dimethylamino-(3-fluorophenyl)-methyl]-cyclohexanol
(114) 4-[(4-chlorophenyl)-dimethylamino-methyl]-cyclohexanol
(115) 4-(dimethylamino-thiophen-2-yl-methyl)-cyclohexanol
(116) 4-(1-dimethylamino-3-phenyl-propyl)-cyclohexanol
(117) [4-(dimethylamino-phenyl-methyl)-cyclohexyl]-methanol
(118) {4-[dimethylamino-(4-fluorophenyl)-methyl]-cyclohexyl}-methanol
(119) {4-[dimethylamino-(3-fluorophenyl)-methyl]-cyclohexyl}-methanol
(120) {4-[(4-chlorophenyl)-dimethylamino-methyl]-cyclohexyl}-methanol
(121) [4-(dimethylamino-thiophen-2-yl-methyl)-cyclohexyl]-methanol
(122) [4-(1-dimethylamino-3-phenyl-propyl)-cyclohexyl]-methanol
(123) [4-(dimethylamino-phenyl-methyl)-cyclohexylidene]-acetic acid ethyl ester
(124) [4-(dimethylamino-phenyl-methyl)-cyclohexyl]-acetic acid ethyl ester
(125) 2-[4-(dimethylamino-phenyl-methyl)-cyclohexyl]-ethanol
(126) {4-[dimethylamino-(4-fluorophenyl)-methyl]-cyclohexylidene}-acetic acid ethyl ester
(127) {4-[dimethylamino-(4-fluorophenyl)-methyl]-cyclohexyl}-acetic acid ethyl ester
(128) 2-{4-[dimethylamino-(4-fluorophenyl)-methyl]-cyclohexyl}-ethanol
(129) {4-[dimethylamino-(3-fluorophenyl)-methyl]-cyclohexylidene}-acetic acid ethyl ester
(130) {4-[dimethylamino-(3-fluorophenyl)-methyl]-cyclohexyl}-acetic acid ethyl ester
(131) 2-{4-[dimethylamino-(3-fluorophenyl)-methyl]-cyclohexyl}-ethanol
(132) 3-[4-(dimethylamino-phenyl-methyl)-cyclohexyl]-acrylic acid ethyl ester
(133) 3-[4-(dimethylamino-phenyl-methyl)-cyclohexyl]-propionic acid ethyl ester
(134) 3-[4-(dimethylamino-phenyl-methyl)-cyclohexyl]-propan-1-ol
(135) 3-{4-[dimethylamino-(4-fluorophenyl)-methyl]-cyclohexyl}-acrylic acid ethyl ester
(136) 3-{4-[dimethylamino-(4-fluorophenyl)-methyl]-cyclohexyl}-propionic acid ethyl ester
(137) 3-{4-[dimethylamino-(4-fluorophenyl)-methyl]-cyclohexyl}-propan-1-ol
(138) 3-{4-[dimethylamino-(3-fluorophenyl)-methyl]-cyclohexyl}-acrylic acid ethyl ester (139) 3-{4-[dimethylamino-(3-fluorophenyl)-methyl]-cyclohexyl}-propionic acid ethyl ester
(140) 3-{4-[dimethylamino-(3-fluorophenyl)-methyl]-cyclohexyl}-propan-1-ol
(141) 3-[4-(1-dimethylamino-3-phenyl-propyl)-cyclohexyl]-acrylic acid ethyl ester
(142) 3-[4-(1-dimethylamino-3-phenyl-propyl)-cyclohexyl]-propionic acid ethyl ester
(143) 3-[4-(1-dimethylamino-3-phenyl-propyl)-cyclohexyl]-propan-1-ol Most particular preference is further given to substituted cyclohexylmethyl derivatives (subgroup amides, secondary and tertiary amines, ureas, Grignard products and ethers) from the group

(73) 1-(4-((dimethylamino)(phenyl)methyl)cyclohexyl)-3-(naphthalen-1-yl)urea
(74) 1-(2,4-difluorophenyl)-3-(4-((dimethylamino)(phenyl)methyl)cyclohexyl)urea hydrochloride
(75) 1-(4-((dimethylamino)(phenyl)methyl)cyclohexyl)-3-(3-(trifluoromethyl)-phenyl)urea hydrochloride
(76) 1-(4-((dimethylamino)(phenyl)methyl)cyclohexyl)-3-(2-nitrophenyl)urea hydrochloride
(77) 1-(3-bromophenyl)-3-(4-((dimethylamino)(phenyl)methyl)cyclohexyl)urea hydrochloride
(78) 1-(4-((dimethylamino)(phenyl)methyl)cyclohexyl)-3-phenylurea hydrochloride
(79) 1-benzyl-3-(4-((dimethylamino)(phenyl)methyl)cyclohexyl)urea
(80) 1-cyclohexyl-3-(4-((dimethylamino)(phenyl)methyl)cyclohexyl)urea
(81) 1-(4-bromophenyl)-3-(4-((dimethylamino)(phenyl)methyl)cyclohexyl)urea
(82) 1-(4-((dimethylamino)(phenyl)methyl)cyclohexyl)-3-(4-methoxyphenyl)urea
(83) N-(2-(1H-indol-3-yl)ethyl)-4-((dimethylamino)(phenyl)methyl)-cyclohexanamine hydrochloride
(84) 4-((dimethylamino)(phenyl)methyl)-N-phenethylcyclohexanamine hydrochloride
(85) 4-((dimethylamino)(phenyl)methyl)-N-(3-phenylpropyl)cyclohexanamine dihydrochloride
(86) N-benzyl-4-((dimethylamino)(phenyl)methyl)cyclohexanamine hydrochloride
(87) 4-((dimethylamino)(phenyl)methyl)-N-(4-phenylbutyl)cyclohexanamine hydrochloride
(88) N-(1-(1H-indol-3-yl)propan-2-yl)-4-((dimethylamino)(phenyl)methyl)-cyclohexanamine hydrochloride
(89) N-(4-((dimethylamino)(phenyl)methyl)cyclohexyl)-4-methoxybenzenamine hydrochloride
(90) 4-((dimethylamino)(phenyl)methyl)-N-(4-methoxybenzyl)cyclohexanamine dihydrochloride
(91) 4-((dimethylamino)(phenyl)methyl)-N-(4-fluorobenzyl)cyclohexanamine hydrochloride
(92) N-(4-((dimethylamino)(phenyl)methyl)cyclohexyl)benzenamine hydrochloride
(93) N-(4-((dimethylamino)(phenyl)methyl)cyclohexyl)-2-ethylbutanamide hydrochloride
(94) N-(4-((dimethylamino)(phenyl)methyl)cyclohexyl)benzamide hydrochloride
(95) N-(4-((dimethylamino)(phenyl)methyl)cyclohexyl)-N-(3-phenylpropyl)acetamide hydrochloride
(96) N-(4-((dimethylamino)(phenyl)methyl)cyclohexyl)-N-phenylacetamide hydrochloride
(97) N-(4-((dimethylamino)(phenyl)methyl)cyclohexyl)-N-(4-phenylbutyl)propionamide hydrochloride
(98) N-(4-((dimethylamino)(phenyl)methyl)cyclohexyl)-N-(4-phenylbutyl)-acetamide hydrochloride
(99) N-(4-((dimethylamino)(phenyl)methyl)cyclohexyl)-N-(4-methoxyphenyl)-acetamide hydrochloride
(100) N-benzyl-N-(4-((dimethylamino)(phenyl)methyl)cyclohexyl)acetamide hydrochloride
(101) N-benzyl-N-(4-((dimethylamino)(phenyl)methyl)cyclohexyl)-2-ethylbutanamide hydrochloride
(102) N-benzyl-N-(4-((dimethylamino)(phenyl)methyl)cyclohexyl)butyramide hydrochloride
(103) N-benzyl-N-(4-((dimethylamino)(phenyl)methyl)cyclohexyl)-4-fluoro-benzamide hydrochloride
(104) N-benzyl-N-(4-((dimethylamino)(phenyl)methyl)cyclohexyl)benzamide hydrochloride
(105) N-(4-((dimethylamino)(phenyl)methyl)cyclohexyl)-2-ethyl-N-phenylbutanamide hydrochloride
(106) 4-chloro-N-(4-((dimethylamino)(phenyl)methyl)cyclohexyl)benzene-sulfonamide hydrochloride
(107) N-(4-((dimethylamino)(phenyl)methyl)cyclohexyl)-4-methoxybenzene-sulfonamide hydrochloride
(108) 4-tert-butyl-N-(4-((dimethylamino)(phenyl)methyl)cyclohexyl)benzene-sulfonamide hydrochloride
(109) N-(4-((dimethylamino)(phenyl)methyl)cyclohexyl)-2-nitrobenzene-sulfonamide hydrochloride
(110) N-(4-((dimethylamino)(phenyl)methyl)cyclohexyl)benzenesulfonamide hydrochloride
(144) 4-(benzyloxy)cyclohexyl)-N,N-dimethyl(phenyl)methanamine hydrochloride
(145) 4-(4-fluorobenzyloxy)cyclohexyl)-N,N-dimethyl(phenyl)methanamine hydrochloride
(146) trans-N,N-dimethyl(4-phenethylcyclohexyl)(phenyl)methanamine hydrochloride
(147) 1-benzyl-4-((dimethylamino)(phenyl)methyl)cyclohexanol hydrochloride
(148) 4-((dimethylamino)(phenyl)methyl)-1-(4-fluorobenzyl)cyclohexanol hydrochloride
(149) 1-(2,5-dimethoxyphenyl)-4-((dimethylamino)(phenyl)methyl)cyclohexanol
(150) 4-((dimethylamino)(phenyl)methyl)-1-(4-fluoro-3-methylphenyl)cyclohexanol
(151) 4-(dimethylamino-phenyl-methyl)-1-(4-fluoro-3-methyl-phenyl)-cyclohexanol
(152) 1-benzyl-4-[dimethylamino-(3-fluoro-phenyl)-methyl]-cyclohexanol
(153) 4-[dimethylamino-(3-fluoro-phenyl)-methyl]-1-phenethyl-cyclohexanol
(154) 4-[dimethylamino-(3-fluoro-phenyl)-methyl]-1-pentyl-cyclohexanol
(155) 1-(3,5-dichloro-phenyl)-4-[dimethylamino-(3-fluoro-phenyl)-methyl]-cyclohexanol
(156) 4-[dimethylamino-(3-fluoro-phenyl)-methyl]-1-(3-methoxy-benzyl)-cyclohexanol
(157) 1-(4-chloro-3-trifluoromethyl-phenyl)-4-[dimethylamino-(3-fluoro-phenyl)-methyl]-cyclohexanol
(158) 4-[(4-chloro-phenyl)-dimethylamino-methyl]-1-phenyl-cyclohexanol
(159) 1-benzyl-4-[(4-chloro-phenyl)-dimethylamino-methyl]-cyclohexanol
(160) 4-[(4-chloro-phenyl)-dimethylamino-methyl]-1-(4-fluoro-3-methyl-phenyl)-cyclohexanol
(161) 4-[(4-chloro-phenyl)-dimethylamino-methyl]-1-o-tolyl-cyclohexanol
(162) 4-[(4-chloro-phenyl)-dimethylamino-methyl]-1-(4-fluoro-phenyl)-cyclohexanol
(163) 4-[(4-chloro-phenyl)-dimethylamino-methyl]-1-phenethyl-cyclohexanol
(164) 4-[(4-chloro-phenyl)-dimethylamino-methyl]-1-(3-methoxy-phenyl)-cyclohexanol (165) 4-[(4-chloro-phenyl)-dimethylamino-methyl]-1-p-tolyl-cyclohexanol
(166) 4-[(4-chloro-phenyl)-dimethylamino-methyl]-1-(3,5-difluoro-phenyl)-cyclohexanol
(167) 1-butyl-4-[(4-chloro-phenyl)-dimethylamino-methyl]-cyclohexanol
(168) 4-[(4-chloro-phenyl)-dimethylamino-methyl]-1-hexyl-cyclohexanol
(169) 4-[(4-chloro-phenyl)-dimethylamino-methyl]-1-pentyl-cyclohexanol (more polar diastereoisomer)
(170) 4-[(4-chloro-phenyl)-dimethylamino-methyl]-1-pentyl-cyclohexanol (less polar diastereoisomer)
(171) 4-[(4-chloro-phenyl)-dimethylamino-methyl]-1-(3-fluoro-phenyl)-cyclohexanol
(172) 4-[(4-chloro-phenyl)-dimethylamino-methyl]-1-(4-fluoro-benzyl)-cyclohexanol
(173) 4-[(4-chloro-phenyl)-dimethylamino-methyl]-1-(3-methoxy-benzyl)-cyclohexanol
(174) methyl 2-(4-((dimethylamino)(phenyl)methyl)cyclohexylamino)-3-(1H-indol-3-yl)propanoate (more polar diastereoisomer)
(175) methyl 2-(4-((dimethylamino)(phenyl)methyl)cyclohexylamino)-3-(1H-indol-3-yl)propanoate (less polar diastereoisomer)
(176) N-(4-((dimethylamino)(phenyl)methyl)cyclohexyl)-N-(4-methoxybenzyl)-acetamide
(177) N-(1-(1H-indol-3-yl)propan-2-yl)-N-(4-(dimethylamino)(phenyl)methyl)-cyclohexyl)acetamide (more polar diastereoisomer)
(178) N-(1-(1H-indol-3-yl)propan-2-yl)-N-(4-((dimethylamino)(phenyl)methyl)-cyclohexyl)acetamide (less polar diastereoisomer)
(179) N-(4-((dimethylamino)(phenyl)methyl)cyclohexyl)-N-(4-fluorobenzyl)acetamide
(180) N-(4-((dimethylamino)(phenyl)methyl)cyclohexyl)-N-phenylbutyramide
(181) N-(2-(1H-indol-3-yl)ethyl)-N-(4-((dimethylamino)(phenyl)methyl)-cyclohexyl)butyramide
(182) N-(2-(1H-indol-3-yl)ethyl)-N-(4-((dimethylamino)(phenyl)methyl)cyclohexyl)-acetamide
(183) benzo[b]thiophene-3-carboxylic acid [4-(dimethylamino-phenyl-methyl)-cyclohexyl]-amide
(184) 1-(4-chloro-phenyl)-cyclopentanecarboxylic acid [4-(dimethylamino-phenyl-methyl)-cyclohexyl]-amide
(185) N-[4-(dimethylamino-thiophen-2-yl-methyl)-cyclohexyl]-4-propyl-benzamide
(186) 3-cyano-N-[4-(dimethylamino-thiophen-2-yl-methyl)-cyclohexyl]-benzamide
(187) 3-chloro-N-[4-(dimethylamino-phenyl-methyl)-cyclohexyl]-benzamide
(188) 5-chloro-4-methoxy-thiophene-3-carboxylic acid [4-(dimethylamino-phenyl-methyl)-cyclohexyl]-amide
(189) 3,4-dichloro-N-[4-(dimethylamino-phenyl-methyl)-cyclohexyl]-benzamide
(190) N-[4-(dimethylamino-phenyl-methyl)-cyclohexyl]-3-fluoro-5-trifluoromethyl-benzamide
(191) 5-chloro-4-methoxy-thiophene-3-carboxylic acid {4-[dimethylamino-(3-fluoro-phenyl)-methyl]-cyclohexyl}-amide
(192) N-[4-(dimethylamino-thiophen-2-yl-methyl)-cyclohexyl]-4-fluoro-3-trifluoromethyl-benzamide
(193) thiophene-2-carboxylic acid [4-(dimethylamino-thiophen-2-yl-methyl)-cyclohexyl]-amide
(194) 3,5-dichlorro-N-[4-(dimethylamino-thiophen-2-yl-methyl)-cyclohexyl]-benzamide
(195) 5-chloro-4-methoxy-thiophene-3-carboxylic acid [4-(dimethylamino-thiophen-2-yl-methyl)-cyclohexyl]-amide
(196) N-[4-(dimethylamino-phenyl-methyl)-cyclohexyl]-2,4,5-trifluoro-benzamide
(197) 3-bromo-N-[4-(dimethylamino-phenyl-methyl)-cyclohexyl]-benzamide
(198) N-[4-(dimethylamino-thiophen-2-yl-methyl)-cyclohexyl]-4-methyl-benzamide
(199) N-[4-(dimethylamino-thiophen-2-yl-methyl)-cyclohexyl]-3-methoxy-benzamide
(200) N-[4-(dimethylamino-thiophen-2-yl-methyl)-cyclohexyl]-3,3-dimethyl-butyramide
(201) 2-tert-butyl-5-methyl-2H-pyrazole-3-carboxylic acid [4-(dimethylamino-thiophen-2-yl-methyl)-cyclohexyl]-amide
(202) N-[4-(dimethylamino-thiophen-2-yl-methyl)-cyclohexyl]-2,4-dimethoxy-benzamide
(203) N-[4-(dimethylamino-phenyl-methyl)-cyclohexyl]-3-trifluoromethyl-benzamide
(204) N-{4-[dimethylamino-(3-fluoro-phenyl)-methyl]-cyclohexyl}-3,5-difluoro-benzamide
(205) N-[4-(dimethylamino-phenyl-methyl)-cyclohexyl]-2-fluoro-5-trifluoromethyl-benzamide
(206) 2-(4-chloro-phenyl)-N-[4-(dimethylamino-phenyl-methyl)-cyclohexyl]-acetamide
(207) N-[4-(dimethylamino-thiophen-2-yl-methyl)-cyclohexyl]-2-methoxy-benzamide
(208) N-[4-(dimethylamino-thiophen-2-yl-methyl)-cyclohexyl]-2-methylsulfanyl-nicotinamide
(209) 3,4-dichloro-N-{4-[dimethylamino-(3-fluoro-phenyl)-methyl]-cyclohexyl}-benzamide
(210) N-[4-(1-dimethylamino-3-phenyl-propyl)-cyclohexyl]-4-fluoro-3-trifluoromethyl-benzamide (more polar diastereoisomer)
(211) 5-chloro-4-methoxy-thiophene-3-carboxylic acid {4-[dimethylamino-(4-fluoro-phenyl)-methyl]-cyclohexyl}-amide
(212) N-[4-(dimethylamino-thiophen-2-yl-methyl)-cyclohexyl]-3,4,5-trimethoxy-benzamide
(213) N-[4-(dimethylamino-thiophen-2-yl-methyl)-cyclohexyl]-2-ethylsulfanyl-nicotinamide
(214) 2-methyl-5-phenyl-furan-3-carboxylic acid [4-(dimethylamino-phenyl-methyl)-cyclohexyl]-amide
(215) N-{4-[dimethylamino-(3-fluoro-phenyl)-methyl]-cyclohexyl}-2-phenoxy-propionamide (less polar diastereoisomer)
(216) N-[4-(dimethylamino-phenyl-methyl)-cyclohexyl]-2,4-dimethoxy-benzamide
(217) 4-tert-butyl-N-[4-(dimethylamino-phenyl-methyl)-cyclohexyl]-benzamide
(218) 2-(4-chloro-phenylsulfanyl)-N-[4-(dimethylamino-thiophen-2-yl-methyl)-cyclohexyl]-nicotinamide
(219) 2-(4-chloro-phenyl)-N-[4-(dimethylamino-thiophen-2-yl-methyl)-cyclohexyl]-acetamide
(220) N-[4-(dimethylamino-thiophen-2-yl-methyl)-cyclohexyl]-2-p-tolyloxy-nicotinamide
(221) 3-chloro-4-(propan-2-sulfonyl)-thiophene-2-carboxylic acid [4-(dimethylamino-thiophen-2-yl-methyl)-cyclohexyl]-amide
(222) N-{4-[dimethylamino-(3-fluoro-phenyl)-methyl]-cyclohexyl}-2-phenoxy-propionamide (more polar diastereoisomer)
(223) 2-tert-butyl-5-methyl-2H-pyrazole-3-carboxylic acid [4-(dimethylamino-phenyl-methyl)-cyclohexyl]-amide
(224) 5-Methyl-isoxazole-3-carboxylic acid [4-(dimethylamino-thiophen-2-yl-methyl)-cyclohexyl]-amide (225) 5-bromo-N-[4-(dimethylamino-thiophen-2-yl-methyl)-cyclohexyl]-nicotinamide
(226) naphthyl-1-carboxylic acid [4-(dimethylamino-phenyl-methyl)-cyclohexyl]-amide
(227) N-[4-(1-dimethylamino-3-phenyl-propyl)-cyclohexyl]-4-fluoro-3-trifluoromethyl-benzamide (less polar diastereoisomer)
(228) N-[4-(dimethylamino-phenyl-methyl)-cyclohexyl]-3,3-dimethyl-butyramide (more polar diastereoisomer)
(229) 5-(4-chloro-phenyl)-2-methyl-furan-3-carboxylic acid [4-(dimethylamino-thiophen-2-yl-methyl)-cyclohexyl]-amide
(230) N-[4-(dimethylamino-phenyl-methyl)-cyclohexyl]-2-phenoxy-propionamide
(231) benzo[b]thiophene-2-carboxylic acid {4-[dimethylamino-(3-fluoro-phenyl)-methyl]-cyclohexyl}-amide
(232) 5-(4-chloro-phenyl)-2-methyl-furan-3-carboxylic acid [4-(dimethylamino-phenyl-methyl)-cyclohexyl]-amide
(233) 4-(4-chloro-benzenesulfonyl)-3-methyl-thiophene-2-carboxylic acid [4-(dimethylamino-phenyl-methyl)-cyclohexyl]-amide
(234) N-[4-(dimethylamino-phenyl-methyl)-cyclohexyl]-2-phenyl-butyramide (less polar diastereoisomer)
(235) 5-bromo-N-[4-(dimethylamino-phenyl-methyl)-cyclohexyl]-nicotinamide
(236) adamantane-1-carboxylic acid [4-(dimethylamino-phenyl-methyl)-cyclohexyl]-amide
(237) 2-phenyl-thiazole-4-carboxylic acid [4-(dimethylamino-phenyl-methyl)-cyclohexyl]-amide
(238) 4-methyl-2-phenyl-thiazole-5-carboxylic acid [4-(dimethylamino-phenyl-methyl)-cyclohexyl]-amide
(239) 2-(2,3-dihydro-benzofuran-5-yl)-thiazole-4-carboxylic acid [4-(dimethylamino-thiophen-2-yl-methyl)-cyclohexyl]-amide
(240) N-{4-[dimethylamino-(3-fluoro-phenyl)-methyl]-cyclohexyl}-2-phenyl-acetamide
(241) 3-chloro-N-[4-(1-dimethylamino-3-phenyl-propyl)-cyclohexyl]-benzamide
(242) N-[4-(dimethylamino-phenyl-methyl)-cyclohexyl]-4-methyl-benzamide
(243) 3,5-dichloro-N-{4-[dimethylamino-(3-fluoro-phenyl)-methyl]-cyclohexyl}-benzamide
(244) N-[4-(dimethylamino-phenyl-methyl)-cyclohexyl]-2,3,6-trifluoro-benzamide
(245) thiophene-2-carboxylic acid [4-(dimethylamino-phenyl-methyl)-cyclohexyl]-amide (less polar diastereoisomer)
(246) N-[4-(dimethylamino-phenyl-methyl)-cyclohexyl]-3,3-dimethyl-butyramide (less polar diastereoisomer)
(247) 2-tert-butyl-5-methyl-2H-pyrazole-3-carboxylic acid [4-(dimethylamino-phenyl-methyl)-cyclohexyl]-amide
(248) N-[4-(1-dimethylamino-3-phenyl-propyl)-cyclohexyl]-3-methyl-benzamide
(249) thiophene-2-carboxylic acid [4-(dimethylamino-phenyl-methyl)-cyclohexyl]-amide (more polar diastereoisomer)
(250) N-[4-(dimethylamino-phenyl-methyl)-cyclohexyl]-2-phenyl-butyramide (more polar diastereoisomer)
(251) N-{4-[dimethylamino-(3-fluoro-phenyl)-methyl]-cyclohexyl}-3,3-dimethyl-butyramide
(252) 3-chloro-4-methanesulfonyl-thiophene-2-carboxylic acid [4-(dimethylamino-phenyl-methyl)-cyclohexyl]-amide
(253) 4-(4-chloro-benzenesulfonyl)-3-methyl-thiophene-2-carboxylic acid [4-(dimethylamino-phenyl-methyl)-cyclohexyl]-amide
(254) 2-benzyloxy-N-[4-(dimethylamino-phenyl-methyl)-cyclohexyl]-acetamide
(255) N-[4-(dimethylamino-phenyl-methyl)-cyclohexyl]-2-thiophen-2-yl-acetamide
(256) 4-methyl-2-phenyl-thiazole-5-carboxylic acid {4-[dimethylamino-(3-fluoro-phenyl)-methyl]-cyclohexyl}-amide
(257) 2-(4-chloro-phenoxy)-N-[4-(dimethylamino-thiophen-2-yl-methyl)-cyclohexyl]-nicotinamide
(258) N-[4-(1-dimethylamino-3-phenyl-propyl)-cyclohexyl]-4-fluoro-benzamide
(259) 5-bromo-N-[4-(dimethylamino-phenyl-methyl)-cyclohexyl]-nicotinamide
(260) 4-bromo-2-ethyl-5-methyl-2H-pyrazole-3-carboxylic acid [4-(dimethylamino-thiophen-2-yl-methyl)-cyclohexyl]-amide
(261) 3-cyano-N-[4-(dimethylamino-phenyl-methyl)-cyclohexyl]-benzamide
(262) N-{4-[dimethylamino-(4-fluoro-phenyl)-methyl]-cyclohexyl}-4-fluoro-benzamide
(263) 3-bromo-N-{4-[dimethylamino-(4-fluoro-phenyl)-methyl]-cyclohexyl}-benzamide
(264) 2-phenyl-thiazole-4-carboxylic acid {4-[dimethylamino-(3-fluoro-phenyl)-methyl]-cyclohexyl}-amide
(265) 2,5-dimethyl-furan-3-carboxylic acid {4-[dimethylamino-(3-fluoro-phenyl)-methyl]-cyclohexyl}-amide
(266) 2-methyl-5-phenyl-furan-3-carboxylic acid {4-[dimethylamino-(3-fluoro-phenyl)-methyl]-cyclohexyl}-amide
(267) 5-pyridin-2-yl-thiophene-2-carboxylic acid {4-[dimethylamino-(3-fluoro-phenyl)-methyl]-cyclohexyl}-amide
(268) 4-bromo-2-ethyl-5-methyl-2H-pyrazole-3-carboxylic acid [4-(dimethylamino-phenyl-methyl)-cyclohexyl]-amide
(269) 3-chloro-N-{4-[dimethylamino-(3-fluoro-phenyl)-methyl]-cyclohexyl}-4-fluoro-benzamide
(270) 3,4-dichloro-N-{4-[dimethylamino-(4-fluoro-phenyl)-methyl]-cyclohexyl}-benzamide
(271) N-{4-[dimethylamino-(4-fluoro-phenyl)-methyl]-cyclohexyl}-2,4,5-trifluoro-benzamide
(272) cyclohexanecarboxylic acid [4-(dimethylamino-phenyl-methyl)-cyclohexyl]-amide
(273) N-{4-[dimethylamino-(3-fluoro-phenyl)-methyl]-cyclohexyl}-2-phenyl-butyramide
(274) 2-(4-chloro-phenyl)-N-{4-[dimethylamino-(3-fluoro-phenyl)-methyl]-cyclohexyl}-acetamide
(275) N-[4-(dimethylamino-phenyl-methyl)-cyclohexyl]-3-nitro-benzamide
(276) N-[4-(1-dimethylamino-3-phenyl-propyl)-cyclohexyl]-2,5-difluoro-benzamide
(277) 3-bromo-N-[4-(1-dimethylamino-3-phenyl-propyl)-cyclohexyl]-benzamide
(278) N-{4-[dimethylamino-(3-fluoro-phenyl)-methyl]-cyclohexyl}-2,6-difluoro-benzamide
(279) 2,5-dimethyl-furan-3-carboxylic acid [4-(dimethylamino-phenyl-methyl)-cyclohexyl]-amide
(280) 3-chloro-N-{4-[dimethylamino-(4-fluoro-phenyl)-methyl]-cyclohexyl}-4-fluoro-benzamide
(281) N-[4-(dimethylamino-phenyl-methyl)-cyclohexyl]-5-fluoro-2-trifluoromethyl-benzamide
(282) 5-methyl-isoxazole-3-carboxylic acid [4-(dimethylamino-phenyl-methyl)-cyclohexyl]-amide
(283) 2-(2,3-dihydro-benzofuran-5-yl)-4-methyl-thiazole-5-carboxylic acid [4-(dimethylamino-thiophen-2-yl-methyl)-cyclohexyl]-amide (284) 2-(4-chloro-phenoxy)-N-[4-(dimethylamino-phenyl-methyl)-cyclohexyl]-acetamide
(285) 5-(4-chloro-phenyl)-2-methyl-furan-3-carboxylic acid {4-[dimethylamino-(3-fluoro-phenyl)-methyl]-cyclohexyl}-amide
(286) 2-bromo-N-[4-(dimethylamino-phenyl-methyl)-cyclohexyl]-benzamide
(287) N-[4-(dimethylamino-phenyl-methyl)-cyclohexyl]-2,6-dimethoxy-benzamide
(288) cyclopentanecarboxylic acid [4-(dimethylamino-phenyl-methyl)-cyclohexyl]-amide
(289) 2-(2,3-dihydro-benzofuran-5-yl)-thiazole-4-carboxylic acid [4-(dimethylamino-phenyl-methyl)-cyclohexyl]-amide
(290) benzo[1,2,5]thiadiazole-5-carboxylic acid {4-[dimethylamino-(3-fluoro-phenyl)-methyl]-cyclohexyl}-amide
(291) N-[4-(dimethylamino-thiophen-2-yl-methyl)-cyclohexylmethyl]-2-thiophen-2-yl-acetamide
(292) benzo[b]thiophene-3-carboxylic acid [4-(dimethylamino-phenyl-methyl)-cyclohexylmethyl]-amide
(293) 5-chloro-4-methoxy-thiophene-3-carboxylic acid [4-(dimethylamino-phenyl-methyl)-cyclohexylmethyl]-amide
(294) N-[4-(dimethylamino-phenyl-methyl)-cyclohexylmethyl]-3,4-difluoro-benzamide (less polar diastereoisomer)
(295) N-{4-[dimethylamino-(3-fluoro-phenyl)-methyl]-cyclohexylmethyl}-3,3-dimethyl-butyramide
(296) 2-bromo-N-[4-(dimethylamino-thiophen-2-yl-methyl)-cyclohexylmethyl]-benzamide
(297) N-[4-(dimethylamino-thiophen-2-yl-methyl)-cyclohexylmethyl]-2,2-diphenyl-acetamide
(298) N-[4-(dimethylamino-phenyl-methyl)-cyclohexylmethyl]-3,3-dimethyl-butyramide
(299) N-[4-(dimethylamino-phenyl-methyl)-cyclohexylmethyl]-2-methylsulfanyl-nicotinamide
(300) N-[4-(dimethylamino-thiophen-2-yl-methyl)-cyclohexylmethyl]-2,6-dimethoxy-benzamide
(301) N-[4-(dimethylamino-thiophen-2-yl-methyl)-cyclohexylmethyl]-3,3-dimethyl-butyramide
(302) benzo[b]thiophene-3-carboxylic acid [4-(dimethylamino-thiophen-2-yl-methyl)-cyclohexylmethyl]-amide
(303) 5-chloro-4-methoxy-thiophene-3-carboxylic acid {4-[dimethylamino-(3-fluoro-phenyl)-methyl]-cyclohexylmethyl}-amide
(304) N-[4-(dimethylamino-thiophen-2-yl-methyl)-cyclohexylmethyl]-2-phenoxy-propionamide
(305) N-[4-(dimethylamino-thiophen-2-yl-methyl)-cyclohexylmethyl]-2-methoxy-benzamide
(306) N-[4-(dimethylamino-phenyl-methyl)-cyclohexylmethyl]-2-phenyl-acetamide
(307) 3-bromo-N-[4-(dimethylamino-thiophen-2-yl-methyl)-cyclohexylmethyl]-benzamide
(308) N-[4-(dimethylamino-thiophen-2-yl-methyl)-cyclohexylmethyl]-3-fluoro-5-trifluoromethyl-benzamide
(309) N-{4-[(4-chloro-phenyl)-dimethylamino-methyl]-cyclohexylmethyl}-3,3-dimethyl-butyramide
(310) N-[4-(dimethylamino-phenyl-methyl)-cyclohexylmethyl]-2-ethylsulfanyl-nicotinamide
(311) 2-(4-chloro-phenyl)-N-[4-(dimethylamino-thiophen-2-yl-methyl)-cyclohexyl-methyl]-acetamide
(312) N-{4-[(4-chloro-phenyl)-dimethylamino-methyl]-cyclohexylmethyl}-2,2-diphenyl-acetamide
(313) N-[4-(dimethylamino-thiophen-2-yl-methyl)-cyclohexylmethyl]-2,6-difluoro-benzamide
(314) benzo[b]thiophene-3-carboxylic acid {4-[dimethylamino-(3-fluoro-phenyl)-methyl]-cyclohexylmethyl}-amide
(315) N-{4-[(4-chloro-phenyl)-dimethylamino-methyl]-cyclohexylmethyl}-2-methyl-sulfanyl-nicotinamide
(316) N-{4-[(4-chloro-phenyl)-dimethylamino-methyl]-cyclohexylmethyl}-2-thiophen-2-yl-acetamide
(317) N-[4-(dimethylamino-phenyl-methyl)-cyclohexylmethyl]-2-methyl-benzamide (less polar diastereoisomer)
(318) 1-(4-chloro-phenyl)-cyclopentane-carboxylic acid [4-(dimethylamino-phenyl-methyl)-cyclohexylmethyl]-amide
(319) N-{4-[dimethylamino-(3-fluoro-phenyl)-methyl]-cyclohexylmethyl}-2-phenyl-acetamide (more polar diastereoisomer)
(320) N-{4-[(4-chloro-phenyl)-dimethylamino-methyl]-cyclohexylmethyl}-2-(3-methoxy-phenyl)-acetamide
(321) N-[4-(dimethylamino-phenyl-methyl)-cyclohexylmethyl]-2-phenyl-butyramide
(322) N-{4-[dimethylamino-(4-fluoro-phenyl)-methyl]-cyclohexylmethyl}-3,3-dimethyl-butyramide
(323) N-[4-(dimethylamino-phenyl-methyl)-cyclohexylmethyl]-2-phenoxy-propionamide
(324) 2-(4-chloro-phenyl)-N-[4-(dimethylamino-phenyl-methyl)-cyclohexylmethyl]-acetamide
(325) N-[4-(dimethylamino-phenyl-methyl)-cyclohexylmethyl]-2-methyl-benzamide (more polar diastereoisomer)
(326) N-[4-(dimethylamino-phenyl-methyl)-cyclohexylmethyl]-3-trifluoromethyl-benzamide (less polar diastereoisomer)
(327) 1-(4-chloro-phenyl)-cyclopentane-carboxylic acid {4-[dimethylamino-(3-fluoro-phenyl)-methyl]-cyclohexylmethyl}-amide
(328) thiophene-2-carboxylic acid [4-(dimethylamino-phenyl-methyl)-cyclohexyl-methyl]-amide
(329) 3,5-dichloro-N-[4-(dimethylamino-phenyl-methyl)-cyclohexylmethyl]-benzamide
(330) 2-methyl-5-phenyl-furan-3-carboxylic acid {4-[(4-chloro-phenyl)-dimethylamino-methyl]-cyclohexylmethyl}-amide
(331) 3-chloro-N-[4-(dimethylamino-phenyl-methyl)-cyclohexylmethyl]-benzamide
(332) N-{4-[dimethylamino-(3-fluoro-phenyl)-methyl]-cyclohexylmethyl}-2-phenoxy-propionamide (more polar diastereoisomer)
(333) N-[4-(dimethylamino-phenyl-methyl)-cyclohexylmethyl]-3-trifluoromethyl-benzamide (more polar diastereoisomer)
(334) thiophene-2-carboxylic acid {4-[dimethylamino-(3-fluoro-phenyl)-methyl]-cyclohexylmethyl}-amide (more polar diastereoisomer)
(335) 2-phenyl-thiazole-4-carboxylic acid [4-(dimethylamino-phenyl-methyl)-cyclohexylmethyl]-amide
(336) benzo[b]thiophene-3-carboxylic acid {4-[(4-chloro-phenyl)-dimethylamino-methyl]-cyclohexylmethyl}-amide (less polar diastereoisomer)
(337) N-{4-[dimethylamino-(3-fluoro-phenyl)-methyl]-cyclohexylmethyl}-2-p-tolyloxy-nicotinamide
(338) 2,4,6-trichloro-N-[4-(dimethylamino-phenyl-methyl)-cyclohexylmethyl]-benzamide
(339) 1-(4-chloro-phenyl)-cyclopentane-carboxylic acid [4-(dimethylamino-phenyl-methyl)-cyclohexylmethyl]-amide
(340) thiophene-2-carboxylic acid {4-[dimethylamino-(3-fluoro-phenyl)-methyl]-cyclohexylmethyl}-amide (less polar diastereoisomer)

(341) N-{4-[dimethylamino-(3-fluoro-phenyl)-methyl]-cyclohexylmethyl}-2-phenoxy-propionamide (less polar diastereoisomer)
(342) N-{4-[dimethylamino-(3-fluoro-phenyl)-methyl]-cyclohexylmethyl}-2-methyl-butyramide (more polar diastereoisomer)
(343) N-{4-[dimethylamino-(3-fluoro-phenyl)-methyl]-cyclohexylmethyl}-2-thiophen-2-yl-acetamide
(344) benzo[b]thiophene-3-carboxylic acid {4-[dimethylamino-(4-fluoro-phenyl)-methyl]-cyclohexylmethyl}-amide
(345) 2-methyl-5-phenyl-furan-3-carboxylic acid [4-(dimethylamino-phenyl-methyl)-cyclohexylmethyl]-amide
(346) N-{4-[dimethylamino-(3-fluoro-phenyl)-methyl]-cyclohexylmethyl}-2-phenoxy-propionamide
(347) 3-cyano-N-[4-(dimethylamino-thiophen-2-yl-methyl)-cyclohexylmethyl]-benzamide
(348) N-{4-[dimethylamino-(3-fluoro-phenyl)-methyl]-cyclohexylmethyl}-2-phenyl-acetamide (less polar diastereoisomer)
(349) N-[4-(dimethylamino-phenyl-methyl)-cyclohexylmethyl]-2-(3-methoxy-phenyl)-acetamide
(350) N-{4-[dimethylamino-(3-fluoro-phenyl)-methyl]-cyclohexylmethyl}-4-fluoro-3-trifluoromethyl-benzamide
(351) N-{4-[(4-chloro-phenyl)-dimethylamino-methyl]-cyclohexylmethyl}-2-ethyl-sulfanyl-nicotinamide
(352) N-[4-(dimethylamino-thiophen-2-yl-methyl)-cyclohexyl methyl]-2-p-tolyloxy-nicotinamide (more polar diastereoisomer)
(353) 2-methyl-5-phenyl-furan-3-carboxylic acid {4-[dimethylamino-(3-fluoro-phenyl)-methyl]-cyclohexylmethyl}-amide
(354) 2-chloro-N-{4-[(4-chloro-phenyl)-dimethylamino-methyl]-cyclohexylmethyl}-benzamide
(355) 2-chloro-N-[4-(dimethylamino-phenyl-methyl)-cyclohexylmethyl]-nicotinamide
(356) N-[4-(dimethylamino-thiophen-2-yl-methyl)-cyclohexylmethyl]-4-propyl-benzamide
(357) N-[4-(dimethylamino-phenyl-methyl)-cyclohexylmethyl]-3,4-difluoro-benzamide (more polar diastereoisomer)
(358) 3-bromo-N-[4-(dimethylamino-phenyl-methyl)-cyclohexylmethyl]-benzamide
(359) N-{4-[dimethylamino-(4-fluoro-phenyl)-methyl]-cyclohexylmethyl}-2-thiophen-2-yl-acetamide
(360) 2-(4-chloro-phenoxy)-N-[4-(dimethylamino-phenyl-methyl)-cyclohexylmethyl]-nicotinamide (less polar diastereoisomer)
(361) 2,4-dichloro-N-[4-(dimethylamino-phenyl-methyl)-cyclohexylmethyl]-benzamide
(362) N-[4-(dimethylamino-phenyl-methyl)-cyclohexylmethyl]-3-methyl-benzamide
(363) 2-bromo-N-{4-[dimethylamino-(3-fluoro-phenyl)-methyl]-cyclohexylmethyl}-benzamide
(364) N-{4-[dimethylamino-(3-fluoro-phenyl)-methyl]-cyclohexylmethyl}-3-trifluoro-methyl-benzamide
(365) 2-phenyl-thiazole-4-carboxylic acid {4-[dimethylamino-(3-fluoro-phenyl)-methyl]-cyclohexylmethyl}-amide
(366) 2-tert-butyl-5-methyl-2H-pyrazole-3-carboxylic acid [4-(dimethylamino-thiophen-2-yl-methyl)-cyclohexylmethyl]-amide
(367) 3-chloro-4-(propane-2-sulfonyl)-thiophene-2-carboxylic acid [4-(dimethylamino-thiophen-2-yl-methyl)-cyclohexylmethyl]-amide
(368) N-{4-[dimethylamino-(3-fluoro-phenyl)-methyl]-cyclohexylmethyl}-2-methoxy-benzamide
(369) N-{4-[(4-chloro-phenyl)-dimethylamino-methyl]-cyclohexylmethyl}-3-trifluoromethyl-benzamide
(370) 1-(4-chloro-phenyl)-cyclopentane-carboxylic acid {4-[dimethylamino-(4-fluoro-phenyl)-methyl]-cyclohexylmethyl}-amide
(371) 3,5-dichloro-N-{4-[dimethylamino-(3-fluoro-phenyl)-methyl]-cyclohexylmethyl}-benzamide
(372) benzo[b]thiophene-3-carboxylic acid {4-[(4-chloro-phenyl)-dimethylamino-methyl]-cyclohexylmethyl}-amide (more polar diastereoisomer)
(373) 2-methyl-5-phenyl-furan-3-carboxylic acid {4-[dimethylamino-(3-fluoro-phenyl)-methyl]-cyclohexylmethyl}-amide
(374) 2-(4-chloro-phenylsulfanyl)-N-[4-(dimethylamino-phenyl-methyl)-cyclohexyl-methyl]-nicotinamide
(375) 4-bromo-2-ethyl-5-methyl-2H-pyrazole-3-carboxylic acid [4-(dimethylamino-thiophen-2-yl-methyl)-cyclohexylmethyl]-amide
(376) 5-chloro-4-methoxy-thiophene-3-carboxylic acid {4-[dimethylamino-(4-fluoro-phenyl)-methyl]-cyclohexylmethyl}-amide
(378) N-{4-[dimethylamino-(3-fluoro-phenyl)-methyl]-cyclohexylmethyl}-2-methyl-butyramide (less polar diastereoisomer)
(379) 5-methyl-isoxazole-3-carboxylic acid [4-(dimethylamino-phenyl-methyl)-cyclohexylmethyl]-amide
(380) benzo[b]thiophene-3-carboxylic acid [4-(1-dimethylamino-3-phenyl-propyl)-cyclohexylmethyl]-amide
(381) N-{4-[dimethylamino-(4-fluoro-phenyl)-methyl]-cyclohexylmethyl}-2-methyl-sulfanyl-nicotinamide
(382) N-{4-[(4-chloro-phenyl)-dimethylamino-methyl]-cyclohexylmethyl}-2-p-tolyloxy-nicotinamide
(383) 2-(4-chloro-phenoxy)-N-[4-(dimethylamino-phenyl-methyl)-cyclohexylmethyl]-nicotinamide (more polar diastereoisomer)
(384) N-{4-[dimethylamino-(3-fluoro-phenyl)-methyl]-cyclohexylmethyl}-2-methyl-benzamide
(385) 5-methyl-isoxazole-3-carboxylic acid {4-[(4-chloro-phenyl)-dimethylamino-methyl]-cyclohexylmethyl}-amide
(386) 5-bromo-N-[4-(dimethylamino-phenyl-methyl)-cyclohexylmethyl]-nicotinamide
(387) N-[4-(dimethylamino-phenyl-methyl)-cyclohexylmethyl]-2-methyl-butyramide
(388) N-{4-[dimethylamino-(3-fluoro-phenyl)-methyl]-cyclohexylmethyl}-2-ethylsulfanyl-nicotinamide
(389) N-[4-(dimethylamino-thiophen-2-yl-methyl)-cyclohexyl methyl]-2-p-tolyloxy-nicotinamide (less polar diastereoisomer)
(390) 4-bromo-2-ethyl-5-methyl-2H-pyrazole-3-carboxylic acid [4-(dimethylamino-phenyl-methyl)-cyclohexylmethyl]-amide
(391) N-{4-[(4-chloro-phenyl)-dimethylamino-methyl]-cyclohexylmethyl}-2-phenoxy-propionamide
(392) N-[4-(dimethylamino-phenyl-methyl)-cyclohexylmethyl]-3,5-dinitro-benzamide
(393) N-{4-[(4-chloro-phenyl)-dimethylamino-methyl]-cyclohexylmethyl}-3-methoxy-benzamide
(394) 2-bromo-N-{4-[(4-chloro-phenyl)-dimethylamino-methyl]-cyclohexylmethyl}-benzamide
(395) 2-bromo-N-(2-{4-[(4-chloro-phenyl)-dimethylamino-methyl]-cyclohexyl}-ethyl)-benzamide
(396) 2-bromo-N-(2-{4-[dimethylamino-(3-fluoro-phenyl)-methyl]-cyclohexyl}-ethyl)-benzamide
(397) 3-chloro-N-{2-[4-(dimethylamino-phenyl-methyl)-cyclohexyl]-ethyl}-benzamide (more polar diastereoisomer)

(398) 3-chloro-N-{2-[4-(dimethylamino-phenyl-methyl)-cyclohexyl]-ethyl}-benzamide (less polar diastereoisomer)
(399) 3-chloro-N-(2-{4-[(4-chloro-phenyl)-dimethylamino-methyl]-cyclohexyl}-ethyl)-benzamide
(400) 3-chloro-N-(2-{4-[dimethylamino-(3-fluoro-phenyl)-methyl]-cyclohexyl}-ethyl)-benzamide (less polar diastereoisomer)
(401) 3-chloro-N-(2-{4-[dimethylamino-(3-fluoro-phenyl)-methyl]-cyclohexyl}-ethyl)-benzamide (more polar diastereoisomer)
(402) 2-chloro-N-{2-[4-(dimethylamino-phenyl-methyl)-cyclohexyl]-ethyl}-benzamide
(403) 2-chloro-N-(2-{4-[(4-chloro-phenyl)-dimethylamino-methyl]-cyclohexyl}-ethyl)-benzamide
(404) 2-chloro-N-(2-{4-[dimethylamino-(3-fluoro-phenyl)-methyl]-cyclohexyl}-ethyl)-benzamide
(405) 4-chloro-N-{2-[4-(dimethylamino-phenyl-methyl)-cyclohexyl]-ethyl}-benzamide
(406) 4-chloro-N-(2-{4-[dimethylamino-(3-fluoro-phenyl)-methyl]-cyclohexyl}-ethyl)-benzamide
(407) N-{2-[4-(dimethylamino-phenyl-methyl)-cyclohexyl]-ethyl}-4-fluoro-benzamide
(408) N-(2-{4-[(4-chloro-phenyl)-dimethylamino-methyl]-cyclohexyl}-ethyl)-4-fluoro-benzamide
(409) N-(2-{4-[dimethylamino-(3-fluoro-phenyl)-methyl]-cyclohexyl}-ethyl)-4-fluoro-benzamide
(410) N-{2-[4-(dimethylamino-phenyl-methyl)-cyclohexyl]-ethyl}-2-fluoro-benzamide
(411) N-(2-{4-[dimethylamino-(3-fluoro-phenyl)-methyl]-cyclohexyl}-ethyl)-2-fluoro-benzamide
(412) N-(2-{4-[dimethylamino-(3-fluoro-phenyl)-methyl]-cyclohexyl}-ethyl)-3-methyl-benzamide
(413) 2,6-dichloro-N-{2-[4-(dimethylamino-phenyl-methyl)-cyclohexyl]-ethyl}-benzamide
(414) N-{2-[4-(dimethylamino-phenyl-methyl)-cyclohexyl]-ethyl}-2-methoxy-benzamide
(415) N-(2-{4-[dimethylamino-(3-fluoro-phenyl)-methyl]-cyclohexyl}-ethyl)-2-methoxy-benzamide
(416) 3,4-dichloro-N-{2-[4-(dimethylamino-phenyl-methyl)-cyclohexyl]-ethyl}-benzamide
(417) N-{2-[4-(dimethylamino-phenyl-methyl)-cyclohexyl]-ethyl}-2-methyl-benzamide (more polar diastereoisomer)
(418) N-{2-[4-(dimethylamino-phenyl-methyl)-cyclohexyl]-ethyl}-2-methyl-benzamide (less polar diastereoisomer)
(419) N-(2-{4-[(4-chloro-phenyl)-dimethylamino-methyl]-cyclohexyl}-ethyl)-2-methyl-benzamide
(420) N-(2-{4-[dimethylamino-(3-fluoro-phenyl)-methyl]-cyclohexyl}-ethyl)-2-methyl-benzamide
(421) 4-cyano-N-{2-[4-(dimethylamino-phenyl-methyl)-cyclohexyl]-ethyl}-benzamide
(422) 3-chloro-N-(2-{4-[dimethylamino-(4-fluoro-phenyl)-methyl]-cyclohexyl}-ethyl)-benzamide (more polar diastereoisomer)
(423) 3-chloro-N-(2-{4-[dimethylamino-(4-fluoro-phenyl)-methyl]-cyclohexyl}-ethyl)-benzamide (less polar diastereoisomer)
(424) 3-chloro-N-{2-[4-(dimethylamino-thiophen-2-yl-methyl)-cyclohexyl]-ethyl}-benzamide
(425) 2-chloro-N-{2-[4-(dimethylamino-thiophen-2-yl-methyl)-cyclohexyl]-ethyl}-benzamide
(426) N-{2-[4-(dimethylamino-thiophen-2-yl-methyl)-cyclohexyl]-ethyl}-4-fluoro-benzamide
(427) N-(2-{4-[dimethylamino-(4-fluoro-phenyl)-methyl]-cyclohexyl}-ethyl)-2-fluoro-benzamide
(428) N-{2-[4-(dimethylamino-thiophen-2-yl-methyl)-cyclohexyl]-ethyl}-2-fluoro-benzamide
(429) N-(2-{4-[dimethylamino-(4-fluoro-phenyl)-methyl]-cyclohexyl}-ethyl)-3-methyl-benzamide
(430) N-{2-[4-(dimethylamino-thiophen-2-yl-methyl)-cyclohexyl]-ethyl}-3-methyl-benzamide
(431) 2,6-dichloro-N-{2-[4-(dimethylamino-thiophen-2-yl-methyl)-cyclohexyl]-ethyl}-benzamide
(432) N-(2-{4-[dimethylamino-(4-fluoro-phenyl)-methyl]-cyclohexyl}-ethyl)-2-methoxy-benzamide
(433) N-{2-[4-(dimethylamino-phenyl-methyl)-cyclohexyl]-ethyl}-3,5-difluoro-benzamide
(434) N-(2-{4-[(4-chloro-phenyl)-dimethylamino-methyl]-cyclohexyl}-ethyl)-3,5-difluoro-benzamide
(435) N-(2-{4-[dimethylamino-(3-fluoro-phenyl)-methyl]-cyclohexyl}-ethyl)-3,5-difluoro-benzamide
(436) N-(2-{4-[(4-chloro-phenyl)-dimethylamino-methyl]-cyclohexyl}-ethyl)-2,4-difluoro-benzamide
(437) 2,4-dichloro-N-(2-{4-[(4-chloro-phenyl)-dimethylamino-methyl]-cyclohexyl}-ethyl)-5-fluoro-benzamide
(438) 2,4-dichloro-N-(2-{4-[dimethylamino-(3-fluoro-phenyl)-methyl]-cyclohexyl}-ethyl)-5-fluoro-benzamide (more polar diastereoisomer)
(439) 2,4-dichloro-N-(2-{4-[dimethylamino-(3-fluoro-phenyl)-methyl]-cyclohexyl}-ethyl)-5-fluoro-benzamide (less polar diastereoisomer)
(440) 2,4-dichloro-N-{2-[4-(dimethylamino-thiophen-2-yl-methyl)-cyclohexyl]-ethyl}-5-fluoro-benzamide
(441) 2-chloro-N-(2-{4-[(4-chloro-phenyl)-dimethylamino-methyl]-cyclohexyl}-ethyl)-nicotinamide
(442) naphthalene-2-carboxylic acid (2-{4-[dimethylamino-(4-fluoro-phenyl)-methyl]-cyclohexyl}-ethyl)-amide
(443) N-{2-[4-(dimethylamino-thiophen-2-yl-methyl)-cyclohexyl]-ethyl}-4-propyl-benzamide
(444) N-{2-[4-(dimethylamino-phenyl-methyl)-cyclohexyl]-ethyl}-3,4-difluoro-benzamide
(445) N-(2-{4-[(4-chloro-phenyl)-dimethylamino-methyl]-cyclohexyl}-ethyl)-3,4-difluoro-benzamide
(446) N-{2-[4-(dimethylamino-thiophen-2-yl-methyl)-cyclohexyl]-ethyl}-3,4-difluoro-benzamide
(447) N-(2-{4-[dimethylamino-(4-fluoro-phenyl)-methyl]-cyclohexyl}-ethyl)-3-methoxy-benzamide
(448) N-{2-[4-(dimethylamino-phenyl-methyl)-cyclohexyl]-ethyl}-2,2-diphenyl-acetamide
(449) 1-(4-chloro-phenyl)-cyclopentane-carboxylic acid {2-[4-(dimethylamino-phenyl-methyl)-cyclohexyl]-ethyl}-amide
(450) 2-benzyloxy-N-{2-[4-(dimethylamino-phenyl-methyl)-cyclohexyl]-ethyl}-acetamide
(451) N-{2-[4-(dimethylamino-phenyl-methyl)-cyclohexyl]-ethyl}-2-phenyl-acetamide
(452) thiophene-2-carboxylic acid {2-[4-(dimethylamino-phenyl-methyl)-cyclohexyl]-ethyl}-amide
(453) N-(2-{4-[dimethylamino-(3-fluoro-phenyl)-methyl]-cyclohexyl}-ethyl)-2-(3-methoxy-phenyl)-acetamide
(454) N-{2-[4-(dimethylamino-thiophen-2-yl-methyl)-cyclohexyl]-ethyl}-2-(3-methoxy-phenyl)-acetamide
(455) N-(2-{4-[(4-chloro-phenyl)-dimethylamino-methyl]-cyclohexyl}-ethyl)-2-phenyl-butyramide
(456) N-{2-[4-(dimethylamino-thiophen-2-yl-methyl)-cyclohexyl]-ethyl}-2-phenyl-butyramide
(457) benzo[b]thiophene-2-carboxylic acid {2-[4-(dimethylamino-phenyl-methyl)-cyclohexyl]-ethyl}-amide
(458) N-{2-[4-(dimethylamino-phenyl-methyl)-cyclohexyl]-ethyl}-4-nitro-benzamide
(459) 3-bromo-N-(2-{4-[dimethylamino-(4-fluoro-phenyl)-methyl]-cyclohexyl}-ethyl)-benzamide (460) N-{2-[4-(dimethylamino-phenyl-methyl)-cyclohexyl]-ethyl}-2,3,4,5,6-pentafluoro-benzamide
(461) N-{2-[4-(dimethylamino-phenyl-methyl)-cyclohexyl]-ethyl}-2,6-difluoro-benzamide
(462) N-(2-{4-[dimethylamino-(3-fluoro-phenyl)-methyl]-cyclohexyl}-ethyl)-2,6-difluoro-benzamide
(463) 2-phenyl-thiazole-4-carboxylic acid {2-[4-(dimethylamino-phenyl-methyl)-cyclohexyl]-ethyl}-amide
(464) 2-phenyl-thiazole-4-carboxylic acid (2-{4-[dimethylamino-(4-fluoro-phenyl)-methyl]-cyclohexyl}-ethyl)-amide
(465) benzo[b]thiophene-3-carboxylic acid {2-[4-(dimethylamino-thiophen-2-yl-methyl)-cyclohexyl]-ethyl}-amide
(466) N-{2-[4-(dimethylamino-phenyl-methyl)-cyclohexyl]-ethyl}-2-methylsulfanyl-nicotinamide
(467) 2-methyl-5-phenyl-furan-3-carboxylic acid {2-[4-(dimethylamino-phenyl-methyl)-cyclohexyl]-ethyl}-amide
(468) 2-(2,3-dihydro-benzofuran-5-yl)-thiazole-4-carboxylic acid {2-[4-(dimethylamino-phenyl-methyl)-cyclohexyl]-ethyl}-amide
(469) 3-(2,6-dichloro-phenyl)-5-methyl-isoxazole-4-carboxylic acid {2-[4-(dimethylamino-thiophen-2-yl-methyl)-cyclohexyl]-ethyl}-amide
(470) 2-(4-chloro-phenylsulfanyl)-N-{2-[4-(dimethylamino-phenyl-methyl)-cyclohexyl]-ethyl}-nicotinamide (more polar diastereoisomer)
(471) 2-(4-chloro-phenylsulfanyl)-N-{2-[4-(dimethylamino-phenyl-methyl)-cyclohexyl]-ethyl}-nicotinamide (less polar diastereoisomer)
(472) benzo[1,2,3]thiadiazole-5-carboxylic acid {2-[4-(dimethylamino-phenyl-methyl)-cyclohexyl]-ethyl}-amide
(473) 5-bromo-N-{2-[4-(dimethylamino-phenyl-methyl)-cyclohexyl]-ethyl}-nicotinamide
(474) 5-chloro-4-methoxy-thiophene-3-carboxylic acid {2-[4-(dimethylamino-phenyl-methyl)-cyclohexyl]-ethyl}-amide
(475) 5-chloro-4-methoxy-thiophene-3-carboxylic acid (2-{4-[dimethylamino-(4-fluoro-phenyl)-methyl]-cyclohexyl}-ethyl)-amide
(476) 5-chloro-4-methoxy-thiophene-3-carboxylic acid {2-[4-(1-dimethylamino-3-phenyl-propyl)-cyclohexyl]-ethyl}-amide
(477) 3-cyano-N-{2-[4-(dimethylamino-phenyl-methyl)-cyclohexyl]-ethyl}-benzamide
(478) N-{2-[4-(dimethylamino-phenyl-methyl)-cyclohexyl]-ethyl}-2,4-dimethoxy-benzamide
(479) 2-chloro-N-((4-((dimethylamino)(phenyl)methyl)cyclohexyl)methyl)-benzamide
(480) N-((4-((dimethylamino)(phenyl)methyl)cyclohexyl)methyl)-4-fluoro-benzamide
(481) N-(2-(4-((dimethylamino)(phenyl)methyl)cyclohexyl)ethyl)-4-fluoro-benzamide
(482) N-((4-((dimethylamino)(phenyl)methyl)cyclohexyl)methyl)-2-fluoro-benzamide
(483) N-((4-((dimethylamino)(phenyl)methyl)cyclohexyl)methyl)-3-methyl-benzamide
(484) N-((4-((dimethylamino)(phenyl)methyl)cyclohexyl)methyl)-2-methoxy-benzamide
(485) N-(2-(4-((dimethylamino)(phenyl)methyl)cyclohexyl)ethyl)-3,5-dimethoxy-benzamide
(486) N-((4-((dimethylamino)(3-fluorophenyl)methyl)cyclohexyl)methyl)-2,6-dimethoxybenzamide
(487) N-((4-((dimethylamino)(phenyl)methyl)cyclohexyl)methyl)-2,4-difluoro-benzamide
(488) N-((4-((dimethylamino)(thiophen-2-yl)methyl)cyclohexyl)methyl)-3-methoxy-benzamide
(489) N-((4-((dimethylamino)(thiophen-2-yl)methyl)cyclohexyl)methyl)-3,4,5-trimethoxybenzamide
(490) 4-((dimethylamino)(phenyl)methyl)-1-(4-fluoro-3-methylphenyl)cyclohexanol in the form of the racemate; of the enantiomers, diastereoisomers, mixtures of the enantiomers or diastereoisomers or of an individual enantiomer or diastereoisomer; of the bases and/or salts of physiologically acceptable acids.

The invention further provides a process for the preparation of a cyclohexyl-methyl derivative according to the invention. In this process, the keto function of 4-oxo-cyclohexanecarboxylic acid ester

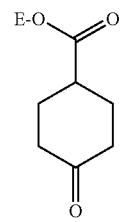

wherein E represents a $C_{1-6}$-alkyl radical, preferably ethyl, is protected by methods known to the person skilled in the art

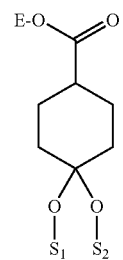

C wherein $S^1$ and $S^2$ each represent a protecting group, preferably form a ring and together represent —$CH_2$—$CH_2$—. The ester C is reduced by means of a reducing agent, for example diisobutylaluminium hydride, to the aldehyde D

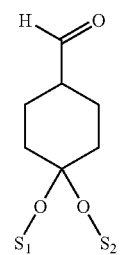

D

By addition of an amine of the general formula $R^5R^6NH$ and of a cyanide, for example KCN or NaCN, the aldehyde D is converted into the nitrile E with addition of an acid, for example hydrochloric acid, in an organic solvent, for example methanol or ethanol.

E

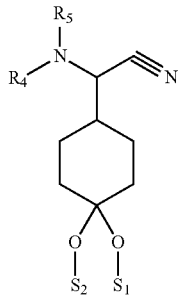

The nitrile E is converted into a compound of the general formula F with a Grignard reagent of the general formula $R^2MgHal$, wherein Hal represents Br, Cl or I, or with an organometallic compound of the general formula $R^2Li$ in an organic solvent, for example diethyl ether, dioxan or tetrahydrofuran.

F

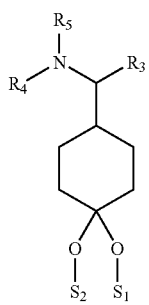

The protecting groups are removed by conventional methods to yield the ketone G.

G

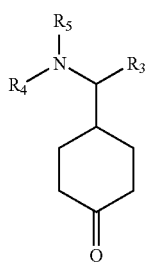

The aldehyde H according to the invention

H

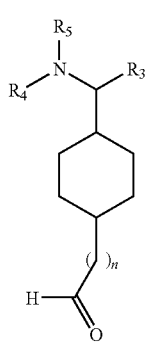

can be obtained by reacting the ketone G with (methoxymethyl)triphenyl-phosphonium chloride and a strong base, for example potassium tert-butylate, at a temperature of from −20° C. to +30° C., it being possible for the reaction step to be repeated, where appropriate, for compounds wherein n>0.

The ketone G or the aldehydes H can be converted into oximes of the general formula K by reaction with hydroxylamine hydrochloride in an organic solvent, for example ethanol or methanol, with the addition of a base, for example a basic ion exchanger Amberlyst. The amines of the general formula L can be obtained by reaction with a reducing agent, for example $LiAlH_4$.

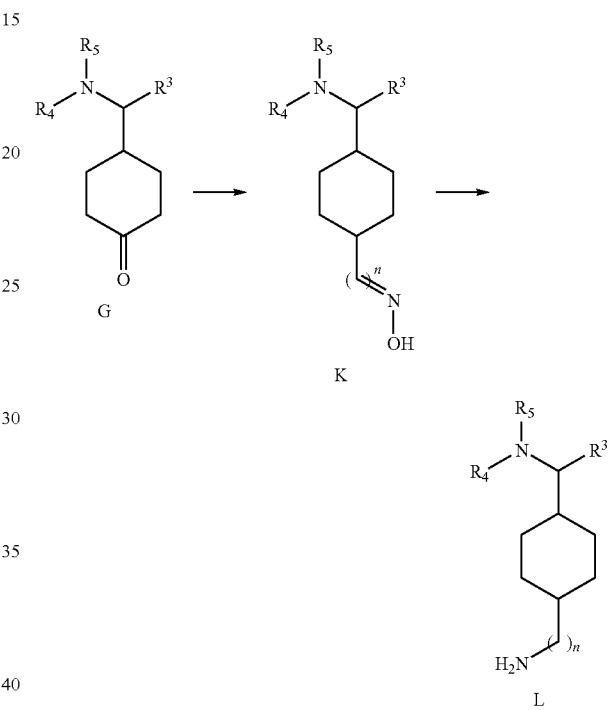

Substances according to the invention of the general formula L can be converted into further substances according to the invention in which $R^1$ denotes $(CH_2)_nNHC(O)R^{13}$ by the following methods:

In principle, the many different methods known to the person skilled in the art for the preparation of amides are suitable for the preparation of the substances. The process according to the invention is preferably based on linking substituted cyclohexylmethyl derivatives of the general formula L with suitable carboxylic acids and/or carboxylic acid derivatives, in particular carboxylic acid chlorides or bromides, and thus converting them into compounds according to the invention in which $R^1$ denotes $(CH_2)_nNHC(O)R^{13}$. In the case of reactions with acid chlorides and bromides there are used polar or non-polar aprotic solvents to which an organic or inorganic auxiliary base, preferably tertiary amines such as triethylamine, diisopropylethylamine or DMAP, has been added. In addition to such amines, pyridine, for example, is also suitable as base and as solvent. Preferably, acid chlorides are reacted with amines at from −30 to +40° C. in dichloromethane or chloroform in the presence of triethylamine or pyridine and optionally catalytic amounts of DMAP.

For the reaction of carboxylic acids with a substituted cyclohexylmethyl derivative of the general formula L, the entire range of methods known to the person skilled in the art for the preparation of amides is also available. It is advantageous to use organic or inorganic water-removing agents, such as, for example, molecular sieve, magnesium sulfate, sulfuric acid or carbodiimides such as DCC or DIC, the latter optionally in the presence of HOBt. These reactions too are preferably carried out in polar or non-polar aprotic solvents at temperatures of from −30 to +110° C., preferably from −10 to +40° C.

The protecting groups are subsequently optionally removed.

Substances according to the invention of the general formula L can be converted into further substances according to the invention in which $R^1$ denotes $(CH_2)_nNHC(O)NR^{10}R^{11}$ or $(CH_2)_nNHC(S)NR^{10}R^{11}$ by the following methods:

In principle, the many different methods known to the person skilled in the art for the preparation of ureas and thioureas are suitable for the preparation of the substances.

The process according to the invention is preferably based on reacting substituted cyclohexylmethyl derivatives of the general formula L in a reaction medium with suitable isocyanates of the general formula $R^{10}$—N=C=O or isothiocyanates of the general formula $R^{10}$—N=C=S, optionally in the presence of at least one base, preferably in the presence of at least one base selected from the group consisting of triethylamine, 4,4-dimethylaminopyridine and diisopropyl-ethylamine, to give at least one compound of the general formula I wherein $R^1$ denotes $(CH_2)_nNHC(O)NR^{10}R^{11}$ or $(CH_2)_n NHC(S)NR^{10}R^{11}$, and this compound is optionally purified and/or isolated. These compounds in which $R^{11}$ denotes H can optionally be reacted in a reaction medium, in the presence of at least one base, preferably in the presence of at least one metal hydride salt or metal alcoholate salt, particularly preferably in the presence of a metal hydride salt or of a metal alcoholate salt, for example sodium hydride, potassium hydride, potassium tert-butanolate, sodium tert-butanolate, potassium methanolate, sodium methanolate, sodium ethanolate and potassium ethanolate, with at least one compound of the general formula LG-$R^{11}$, wherein LG represents a leaving group, preferably a halogen atom, particularly preferably a chlorine atom, and $R^{11}$ has the meaning given above with the exception of hydrogen, to give at least one compound of the general formula I wherein $R^1$ denotes $(CH_2)_nNHC(O)NR^{10}R^{11}$ or $(CH_2)_nNHC(S)NR^{10}R^{11}$, wherein $R^{11}$ does not denote H, and this compound is optionally purified and/or isolated.

In principle, the entire range of methods known to the person skilled in the art for the preparation of sulfonic acid amides is available for the preparation of sulfonic acid amides according to the invention of the general formula I wherein $R^1$ denotes $(CH_2)_nNHSO_2R^{12}$. The compounds according to the invention are preferably prepared by the following process:

The process according to the invention is preferably based on linking substituted cyclohexylmethyl derivatives of the general formula L with suitable sulfonic acid derivatives, in particular sulfonic acid chlorides, and thus converting them into compounds according to the invention in which $R^1$ denotes $(CH_2)NHSO_2R^{12}$. In the reaction of amines of the general formula L there are used polar or non-polar aprotic solvents to which an organic or inorganic auxiliary base, preferably tertiary amines such as triethylamine, diisopropylethylamine or DMAP, has been added. In addition to such amines, pyridine, for example, is also suitable as base and as solvent. Preferably, sulfonic acid chlorides are reacted with amines at from −30 to +40° C. in dichloromethane or chloroform in the presence of triethylamine or pyridine and optionally catalytic amounts of DMAP.

The ketone G or the aldehydes H can be converted into compounds according to the invention in which $R^1$ denotes $(CH_2)_nOH$ by reaction with a reducing agent, for example sodium borohydride.

A phosphonoacetic acid ester, preferably phosphonoacetic acid trimethyl ester or phosphonoacetic acid triethyl ester, is first reacted with a strong base, preferably potassium tert-butylate, sodium hydride or butyllithium, and then with a ketone of the general formula G or an aldehyde H or. The α,β-unsaturated esters according to the invention are thereby formed.

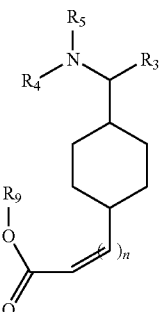

The esters can be hydrolysed with a suitable aqueous, basic solution, preferably with potassium hydroxide or lithium hydroxide solution, at RT or slightly elevated temperature to give the corresponding carboxylic acids.

The double bond can optionally also be reduced. After the first step, the reaction with the phosphonoacetic acid ester, the double bond is reduced by methods known in the literature, preferably by heterogeneous, catalytic hydrogenation on palladium or platinum catalysts or by homogeneously catalysed hydrogenation with rhodium catalysts, in each case at temperatures of from RT to 60° C. and under hydrogen pressures of from 1 bar to 6 bar, particularly preferably at RT under a hydrogen pressure of from 2 to 3 bar and on palladium-on-carbon. The ester hydrolysis is then continued as described above. The esters can be reduced to the corresponding alcohols with a reducing agent, for example $LiAlH_4$.

The compounds according to the invention in which $R^1$ represents $(CH_2)_nOR^8$ can be obtained from the alcohols in a reaction medium, with the addition of a base, for example NaH, by reaction with a compound of the general formula $R^8$Hal, wherein Hal preferably represents Cl.

In principle, the entire range of methods known to the person skilled in the art for the preparation of acid amides is available for the preparation of compounds according to the invention in which $R^1$ represents $(CH_2)_nC(O)NR^{10}R^{11}$. The compounds according to the invention are preferably prepared by the following process:

Carboxylic acids of the general formula J

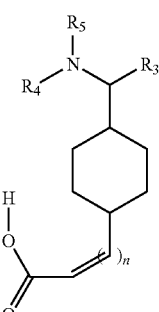

J are reacted in the presence of water-removing agents with a primary or secondary amines amide. It can be advantageous to activate the carboxylic acid function of the cyclohexylmethyl derivative before the amide is prepared by converting it into a carboxylic acid equivalent (e.g. acid chloride or active ester).

In reactions with acid chlorides there are used polar or non-polar aprotic solvents to which an organic or inorganic auxiliary base, preferably tertiary amines such as triethylamine, diisopropylethylamine or DMAP, has been added. In addition to such amines, pyridine, for example, is also suitable as base and also as solvent. Preferably, acid chlorides are reacted with amines at from −10 to +40° C. in dichloromethane or chloroform in the presence of triethylamine or pyridine and optionally catalytic amounts of DMAP. For the reaction of the carboxylic acid function with a further amine, the entire range of methods known to the person skilled in the art for the preparation of amides is available. It is advantageous to use organic or inorganic water-removing agents, such as, for example, molecular sieve, magnesium sulfate, sulfuric acid or carbodiimides such as DCC or DIC, the latter optionally in the presence of HOBt (1-hydroxy-benzotriazole). These reactions too are preferably carried out in polar or non-polar aprotic solvents at temperatures of from −20 to +110° C., preferably from −10 to +40° C.

In principle, the entire range of methods known to the person skilled in the art for reductive amination is available for the preparation of compounds of the general formula I wherein $R^1$ denotes $(CH_2)_n NHR^6$.

The compounds according to the invention are preferably prepared by the following process:

The ketone G or the aldehydes H are dissolved in polar, aprotic solvents, for example THF, and the corresponding amine of the general formula $NH_2R^6$ is first added. After addition of glacial acetic acid, reaction with suitable reducing agents, for example sodium borohydride, yields the compounds according to the invention.

For the preparation of the compounds according to the invention in which $R^2$ denotes OH and $R^1$ denotes $C_{1-8}$-alkyl, in each case branched or unbranched, saturated or unsaturated, unsubstituted or mono- or poly-substituted; aryl or heteroaryl, unsubstituted or mono- or poly-substituted; $C_{3-10}$-cycloalkyl, saturated or unsaturated, unsubstituted or mono- or poly-substituted; an aryl or heteroaryl radical linked via a $C_{1-4}$-alkyl chain and in each case unsubstituted or mono- or poly-substituted (=$R^{1a}$), ketones of the general formula G are reacted with organometallic compounds of the general formula $R^{1a}MgHal$, wherein Hal=Cl or Br, or $R^{1a}Li$, while cooling to −30 to +10° C., in an organic solvent, for example diethyl ether or THF.

Alternatively, an aryl iodide can be introduced into an organic solvent, for example THF; isopropylmagnesium chloride solution can be added at a temperature of from −30° C. to 0° C. and, after a stirring time of at least 10 minutes, can be reacted with the ketone of the general formula G to give compounds of the general formula I wherein $R^1$ denotes aryl.

The diastereoisomers that are optionally formed in the syntheses can be separated by methods known to the person skilled in the art for the separation of diastereoisomers, for example by chromatography, in particular on silica gel, normal phase or reverse phase. RP-HPLC (mobile phase acetonitrile/water or methanol/water) is particularly suitable for the separation of the diastereoisomers.

It has been shown that the substances according to the invention not only bind to the μ-opioid receptor but also inhibit serotonin and noradrenaline reuptake. Noradrenaline and serotonin reuptake inhibitors have antidepressive and anxiolytic activity but are also suitable for the treatment of pain (Analgesics—from Chemistry and Pharmacology to Clinical Application, Wiley 2002, p. 265-284).

The substances according to the invention are suitable as pharmaceutical active ingredients in medicaments. The invention accordingly further provides medicaments comprising at least one substituted cyclohexylmethyl derivative according to the invention as well as, optionally, suitable additives and/or auxiliary substances and/or optionally further active ingredients.

Surprisingly, the intermediates in the synthesis of the amides, secondary and tertiary amides, of the Grignard products, ethers, ureas and thioureas, namely the oximes, esters, primary amines and alcohols, already exhibit activity and are therefore suitable as pharmaceutical active ingredients in medicaments.

The medicaments according to the invention optionally comprise, in addition to at least one substituted cyclohexylmethyl derivative according to the invention, suitable additives and/or auxiliary substances, that is to say also carriers, fillers, solvents, diluents, colourings and/or binders, and can be administered as liquid medicament forms in the form of injection solutions, drops or juices, or as semi-solid medicament forms in the form of granules, tablets, pellets, patches, capsules, plasters or aerosols. The choice of the auxiliary substances etc., and the amounts thereof to be employed, depend on whether the medicament is to be administered orally, perorally, parenterally, intravenously, intraperitoneally, intradermally, intramuscularly, intranasally, buccally, rectally or locally, for example to the skin, the mucous membranes or into the eyes. Preparations in the form of tablets, dragées, capsules, granules, drops, juices and syrups are suitable for oral administration, and solutions, suspensions, readily reconstitutable dry formulations and sprays are suitable for parenteral, topical and inhalatory administration. Cyclohexylmethyl derivatives according to the invention in a depot, in dissolved form or in a plaster, optionally with the addition of agents which promote penetration through the skin, are suitable preparations for percutaneous administration. Forms of preparation which can be used orally or percutaneously can release the cyclohexylmethyl derivatives according to the invention in a delayed manner. In principle, other further active ingredients known to the person skilled in the art can be added to the medicaments according to the invention.

The amount of active ingredient to be administered to the patient varies in dependence on the weight of the patient, the mode of administration, the indication and the severity of the disease. From 0.005 to 20 mg/kg, preferably from 0.05 to 5 mg/kg, of at least one cyclohexylmethyl derivative according to the invention are conventionally administered.

In a preferred form of the medicament, a cyclohexylmethyl derivative according to the invention that is present is in the form of a pure diastereoisomer and/or enantiomer, in the form of the racemate or in the form of a non-equimolar or equimolar mixture of the diastereoisomers and/or enantiomers.

The invention further provides the use of a cyclohexylmethyl derivative according to the invention in the preparation of a medicament for the treatment of pain, in particular of acute, neuropathic or chronic pain.

The invention further provides the use of a cyclohexylmethyl derivative according to the invention in the preparation of a medicament for the treatment of depression and/or for anxiolysis.

The substituted cyclohexylmethyl derivatives of the general formula I are also suitable for the treatment of urinary incontinence, diarrhoea, pruritus, alcohol and drug abuse, medicament dependency and lack of drive.

The invention therefore also provides the use of a substituted cyclohexylmethyl derivative of the general formula I in the preparation of a medicament for the treatment of urinary incontinence, diarrhoea, pruritus, alcohol and drug abuse, medicament dependency and lack of drive.

Particularly preferably, the substituted cyclohexylmethyl derivatives according to the invention which are used in the preparation of a medicament for the treatment of pain, in particular of acute, neuropathic or chronic pain, of depression and/or for anxiolysis, in the treatment of urinary incontinence, diarrhoea, pruritus, alcohol and drug abuse, medicament dependency and lack of drive, are selected from the following group:

(16) 4-(dimethylamino-phenyl-methyl)-cyclohexanone oxime
(17) 4-(dimethylamino-phenyl-methyl)-cyclohexylamine
(18) 4-[dimethylamino-(4-fluorophenyl)-methyl]-cyclohexanone oxime
(19) 4-[dimethylamino-(4-fluorophenyl)-methyl]-cyclohexylamine
(20) 4-[dimethylamino-(3-fluorophenyl)-methyl]-cyclohexanone oxime
(21) 4-[dimethylamino-(3-fluorophenyl)-methyl]-cyclohexylamine
(22) 4-[(4-chlorophenyl)-dimethylamino-methyl]-cyclohexanone oxime
(23) 4-[(4-chlorophenyl)-dimethylamino-methyl]-cyclohexylamine
(24) 4-(dimethylamino-thiophen-2-yl-methyl)-cyclohexanone oxime
(25) 4-(dimethylamino-thiophen-2-yl-methyl)-cyclohexylamine
(26) 4-(1-dimethylamino-3-phenyl-propyl)-cyclohexanone oxime
(27) 4-(1-dimethylamino-3-phenyl-propyl)-cyclohexylamine
(29) 4-(dimethylamino-phenyl-methyl)-cyclohexane-carbaldehyde oxime
(30) [(4-aminomethyl-cyclohexyl)-phenyl-methyl]-dimethylamine
(32) 4-[dimethylamino-(4-fluorophenyl)-methyl]-cyclohexanecarbaldehyde oxime
(33) [(4-aminomethyl-cyclohexyl)-(4-fluorophenyl)-methyl]-dimethylamine
(35) 4-[dimethylamino-(3-fluorophenyl)-methyl]-cyclohexanecarbaldehyde oxime
(36) [(4-aminomethyl-cyclohexyl)-(3-fluorophenyl)-methyl]-dimethylamine
(38) 4-[(4-chlorophenyl)-dimethylamino-methyl]-cyclohexanecarbaldehyde oxime
(39) [(4-aminomethyl-cyclohexyl)-(4-chlorophenyl)-methyl]-dimethylamine
(41) 4-(dimethylamino-thiophen-2-yl-methyl)-cyclohexanecarbaldehyde oxime
(42) [(4-aminomethyl-cyclohexyl)-thiophen-2-yl-methyl]-dimethylamine
(44) 4-(1-dimethylamino-3-phenyl-propyl)-cyclohexanecarbaldehyde oxime
(45) [1-(4-aminomethyl-cyclohexyl)-3-phenyl-propyl]-dimethylamine
(47) [4-(dimethylamino-phenyl-methyl)-cyclohexyl]-acetaldehyde oxime
(48) 2-[4-dimethylamino-phenyl-methyl)-cyclohexyl]-ethylamine
(50) {4-[dimethylamino-(4-fluorophenyl)-methyl]-cyclohexyl}-acetaldehyde oxime
(51) 2-{4-[dimethylamino-(4-fluorophenyl)-methyl]-cyclohexyl}-ethylamine
(53) {4-[dimethylamino-(3-fluorophenyl)-methyl]-cyclohexyl}-acetaldehyde oxime
(54) 2-{4-[dimethylamino-(3-fluorophenyl)-methyl]-cyclohexyl}-ethylamine
(56) {4-[dimethylamino-(4-chlorophenyl)-methyl]-cyclohexyl}-acetaldehyde oxime
(66) 2-{4-[dimethylamino-(4-chlorophenyl)-methyl]-cyclohexyl}-ethylamine
(68) 2-(4-((dimethylamino)(thiophen-2-yl)methyl)cyclohexyl)acetaldehyde oxime
(69) 2-[4-(dimethylamino-thiophen-2-yl-methyl)-cyclohexyl]-ethylamine
(71) [4-(1-dimethylamino-3-phenyl-propyl)-cyclohexyl]-acetaldehyde oxime
(72) {1-[4-(2-amino-ethyl)-cyclohexyl]-3-phenyl-propyl}-dimethylamine
(111) 4-[dimethylamino-phenyl-methyl)-cyclohexanol
(112) 4-[dimethylamino-(4-fluorophenyl)-methyl]-cyclohexanol
(113) 4-[dimethylamino-(3-fluorophenyl)-methyl]-cyclohexanol
(114) 4-[(4-chlorophenyl)-dimethylamino-methyl]-cyclohexanol
(115) 4-(dimethylamino-thiophen-2-yl-methyl)-cyclohexanol
(116) 4-(1-dimethylamino-3-phenyl-propyl)-cyclohexanol
(117) [4-(dimethylamino-phenyl-methyl)-cyclohexyl]-methanol
(118) {4-[dimethylamino-(4-fluorophenyl)-methyl]-cyclohexyl}-methanol
(119) {4-[dimethylamino-(3-fluorophenyl)-methyl]-cyclohexyl}-methanol
(120) {4-[(4-chlorophenyl)-dimethylamino-methyl]-cyclohexyl}-methanol
(121) [4-(dimethylamino-thiophen-2-yl-methyl)-cyclohexyl]-methanol
(122) [4-(1-dimethylamino-3-phenyl-propyl)-cyclohexyl]-methanol
(123) [4-(dimethylamino-phenyl-methyl)-cyclohexylidene]-acetic acid ethyl ester
(124) [4-(dimethylamino-phenyl-methyl)-cyclohexyl]-acetic acid ethyl ester
(125) 2-[4-(dimethylamino-phenyl-methyl)-cyclohexyl]-ethanol
(126) {4-[dimethylamino-(4-fluorophenyl)-methyl]-cyclohexylidene}-acetic acid ethyl ester
(127) {4-[dimethylamino-(4-fluorophenyl)-methyl]-cyclohexyl}-acetic acid ethyl ester
(128) 2-{4-[dimethylamino-(4-fluorophenyl)-methyl]-cyclohexyl}-ethanol
(129) {4-[dimethylamino-(3-fluorophenyl)-methyl]-cyclohexylidene}-acetic acid ethyl ester
(130) {4-[dimethylamino-(3-fluorophenyl)-methyl]-cyclohexyl}-acetic acid ethyl ester
(131) 2-{4-[dimethylamino-(3-fluorophenyl)-methyl]-cyclohexyl}-ethanol
(132) 3-[4-(dimethylamino-phenyl-methyl)-cyclohexyl]-acrylic acid ethyl ester
(133) 3-[4-(dimethylamino-phenyl-methyl)-cyclohexyl]-propionic acid ethyl ester
(134) 3-[4-(dimethylamino-phenyl-methyl)-cyclohexyl]-propan-1-ol (135) 3-{4-[dimethylamino-(4-fluorophenyl)-methyl]-cyclohexyl}-acrylic acid ethyl ester
(136) 3-{4-[dimethylamino-(4-fluorophenyl)-methyl]-cyclohexyl}-propionic acid ethyl ester
(137) 3-{4-[dimethylamino-(4-fluorophenyl)-methyl]-cyclohexyl}-propan-1-ol
(138) 3-{4-[dimethylamino-(3-fluorophenyl)-methyl]-cyclohexyl}-acrylic acid ethyl ester
(139) 3-{4-[dimethylamino-(3-fluorophenyl)-methyl]-cyclohexyl}-propionic acid ethyl ester
(140) 3-{4-[dimethylamino-(3-fluorophenyl)-methyl]-cyclohexyl}-propan-1-ol
(141) 3-[4-(1-dimethylamino-3-phenyl-propyl)-cyclohexyl]-acrylic acid ethyl ester
(142) 3-[4-(1-dimethylamino-3-phenyl-propyl)-cyclohexyl]-propionic acid ethyl ester
(143) 3-[4-(1-dimethylamino-3-phenyl-propyl)-cyclohexyl]-propan-1-ol
(73) 1-(4-((dimethylamino)(phenyl)methyl)cyclohexyl)-3-(naphthalen-1-yl)urea
(74) 1-(2,4-difluorophenyl)-3-(4-((dimethylamino)(phenyl)methyl)cyclohexyl)urea hydrochloride
(75) 1-(4-((dimethylamino)(phenyl)methyl)cyclohexyl)-3-(3-(trifluoromethyl)-phenyl)urea hydrochloride
(76) 1-(4-((dimethylamino)(phenyl)methyl)cyclohexyl)-3-(2-nitrophenyl)urea hydrochloride
(77) 1-(3-bromophenyl)-3-(4-((dimethylamino)(phenyl)methyl)cyclohexyl)urea hydrochloride
(78) 1-(4-((dimethylamino)(phenyl)methyl)cyclohexyl)-3-phenylurea hydrochloride
(79) 1-benzyl-3-(4-((dimethylamino)(phenyl)methyl)cyclohexyl)urea
(80) 1-cyclohexyl-3-(4-((dimethylamino)(phenyl)methyl)cyclohexyl)urea
(81) 1-(4-bromophenyl)-3-(4-((dimethylamino)(phenyl)methyl)cyclohexyl)urea
(82) 1-(4-((dimethylamino)(phenyl)methyl)cyclohexyl)-3-(4-methoxyphenyl)urea
(83) N-(2-(1H-indol-3-yl)ethyl)-4-((dimethylamino)(phenyl)methyl)-cyclohexanamine hydrochloride
(84) 4-((dimethylamino)(phenyl)methyl)-N-phenethylcyclohexanamine hydrochloride
(85) 4-((dimethylamino)(phenyl)methyl)-N-(3-phenylpropyl)cyclohexanamine dihydrochloride
(86) N-benzyl-4-((dimethylamino)(phenyl)methyl)cyclohexanamine hydrochloride
(87) 4-((dimethylamino)(phenyl)methyl)-N-(4-phenylbutyl)cyclohexanamine hydrochloride
(88) N-(1-(1H-indol-3-yl)propan-2-yl)-4-((dimethylamino)(phenyl)methyl)-cyclohexanamine hydrochloride
(89) N-(4-((dimethylamino)(phenyl)methyl)cyclohexyl)-4-methoxybenzenamine hydrochloride
(90) 4-((dimethylamino)(phenyl)methyl)-N-(4-methoxybenzyl)cyclohexanamine dihydrochloride
(91) 4-((dimethylamino)(phenyl)methyl)-N-(4-fluorobenzyl)cyclohexanamine hydrochloride
(92) N-(4-((dimethylamino)(phenyl)methyl)cyclohexyl)benzenamine hydrochloride
(93) N-(4-((dimethylamino)(phenyl)methyl)cyclohexyl)-2-ethylbutanamide hydrochloride
(94) N-(4-((dimethylamino)(phenyl)methyl)cyclohexyl)benzamide hydrochloride
(95) N-(4-((dimethylamino)(phenyl)methyl)cyclohexyl)-N-(3-phenylpropyl)acetamide hydrochloride
(96) N-(4-((dimethylamino)(phenyl)methyl)cyclohexyl)-N-phenylacetamide hydrochloride
(97) N-(4-((dimethylamino)(phenyl)methyl)cyclohexyl)-N-(4-phenylbutyl)propionamide hydrochloride
(98) N-(4-((dimethylamino)(phenyl)methyl)cyclohexyl)-N-(4-phenylbutyl)-acetamide hydrochloride
(99) N-(4-((dimethylamino)(phenyl)methyl)cyclohexyl)-N-(4-methoxyphenyl)-acetamide hydrochloride
(100) N-benzyl-N-(4-((dimethylamino)(phenyl)methyl)cyclohexyl)acetamide hydrochloride
(101) N-benzyl-N-(4-((dimethylamino)(phenyl)methyl)cyclohexyl)-2-ethylbutanamide hydrochloride
(102) N-benzyl-N-(4-((dimethylamino)(phenyl)methyl)cyclohexyl)butyramide hydrochloride
(103) N-benzyl-N-(4-((dimethylamino)(phenyl)methyl)cyclohexyl)-4-fluoro-benzamide hydrochloride
(104) N-benzyl-N-(4-((dimethylamino)(phenyl)methyl)cyclohexyl)benzamide hydrochloride
(105) N-(4-((dimethylamino)(phenyl)methyl)cyclohexyl)-2-ethyl-N-phenylbutanamide hydrochloride
(106) 4-chloro-N-(4-((dimethylamino)(phenyl)methyl)cyclohexyl)benzene-sulfonamide hydrochloride
(107) N-(4-((dimethylamino)(phenyl)methyl)cyclohexyl)-4-methoxybenzene-sulfonamide hydrochloride
(108) 4-tert-butyl-N-(4-((dimethylamino)(phenyl)methyl)cyclohexyl)benzene-sulfonamide hydrochloride
(109) N-(4-((dimethylamino)(phenyl)methyl)cyclohexyl)-2-nitrobenzene-sulfonamide hydrochloride
(110) N-(4-((dimethylamino)(phenyl)methyl)cyclohexyl)benzenesulfonamide hydrochloride
(144) 4-(benzyloxy)cyclohexyl-N,N-dimethyl(phenyl)methanamine hydrochloride
(145) 4-(4-fluorobenzyloxy)cyclohexyl-N,N-dimethyl(phenyl)methanamine hydrochloride
(146) trans-N,N-dimethyl(4-phenethylcyclohexyl)(phenyl)methanamine hydrochloride
(147) 1-benzyl-4-((dimethylamino)(phenyl)methyl)cyclohexanol hydrochloride
(148) 4-((dimethylamino)(phenyl)methyl)-1-(4-fluorobenzyl)cyclohexanol hydrochloride
(149) 1-(2,5-dimethoxyphenyl)-4-((dimethylamino)(phenyl)methyl)cyclohexanol
(150) 4-((dimethylamino)(phenyl)methyl)-1-(4-fluoro-3-methylphenyl)cyclohexanol
(151) 4-(dimethylamino-phenyl-methyl)-1-(4-fluoro-3-methyl-phenyl)-cyclohexanol
(152) 1-benzyl-4-[dimethylamino-(3-fluoro-phenyl)-methyl]-cyclohexanol
(153) 4-[dimethylamino-(3-fluoro-phenyl)-methyl]-1-phenethyl-cyclohexanol
(154) 4-[dimethylamino-(3-fluoro-phenyl)-methyl]-1-pentyl-cyclohexanol
(155) 1-(3,5-dichloro-phenyl)-4-[dimethylamino-(3-fluoro-phenyl)-methyl]-cyclohexanol
(156) 4-[dimethylamino-(3-fluoro-phenyl)-methyl]-1-(3-methoxy-benzyl)-cyclohexanol
(157) 1-(4-chloro-3-trifluoromethyl-phenyl)-4-[dimethylamino-(3-fluoro-phenyl)-methyl]-cyclohexanol
(158) 4-[(4-chloro-phenyl)-dimethylamino-methyl]-1-phenyl-cyclohexanol
(159) 1-benzyl-4-[(4-chloro-phenyl)-dimethylamino-methyl]-cyclohexanol
(160) 4-[(4-chloro-phenyl)-dimethylamino-methyl]-1-(4-fluoro-3-methyl-phenyl)-cyclohexanol
(161) 4-[(4-chloro-phenyl)-dimethylamino-methyl]-1-o-tolyl-cyclohexanol
(162) 4-[(4-chloro-phenyl)-dimethylamino-methyl]-1-(4-fluoro-phenyl)-cyclohexanol (163) 4-[(4-chloro-phenyl)-dimethylamino-methyl]-1-phenethyl-cyclohexanol
(164) 4-[(4-chloro-phenyl)-dimethylamino-methyl]-1-(3-methoxy-phenyl)-cyclohexanol
(165) 4-[(4-chloro-phenyl)-dimethylamino-methyl]-1-p-tolyl-cyclohexanol
(166) 4-[(4-chloro-phenyl)-dimethylamino-methyl]-1-(3,5-difluoro-phenyl)-cyclohexanol
(167) 1-butyl-4-[(4-chloro-phenyl)-dimethylamino-methyl]-cyclohexanol
(168) 4-[(4-chloro-phenyl)-dimethylamino-methyl]-1-hexyl-cyclohexanol
(169) 4-[(4-chloro-phenyl)-dimethylamino-methyl]-1-pentyl-cyclohexanol (more polar diastereoisomer)
(170) 4-[(4-chloro-phenyl)-dimethylamino-methyl]-1-pentyl-cyclohexanol (less polar diastereoisomer)
(171) 4-[(4-chloro-phenyl)-dimethylamino-methyl]-1-(3-fluoro-phenyl)-cyclohexanol
(172) 4-[(4-chloro-phenyl)-dimethylamino-methyl]-1-(4-fluoro-benzyl)-cyclohexanol
(173) 4-[(4-chloro-phenyl)-dimethylamino-methyl]-1-(3-methoxy-benzyl)-cyclohexanol
(174) methyl 2-(4-((dimethylamino)(phenyl)methyl)cyclohexylamino)-3-(1H-indol-3-yl)propanoate (more polar diastereoisomer)
(175) methyl 2-(4-((dimethylamino)(phenyl)methyl)cyclohexylamino)-3-(1H-indol-3-yl)propanoate (less polar diastereoisomer)
(176) N-(4-((dimethylamino)(phenyl)methyl)cyclohexyl)-N-(4-methoxybenzyl)-acetamide
(177) N-(1-(1H-indol-3-yl)propan-2-yl)-N-(4-(dimethylamino)(phenyl)methyl)-cyclohexyl)acetamide (more polar diastereoisomer)
178) N-(1-(1H-indol-3-yl)propan-2-yl)-N-(4-((dimethylamino)(phenyl)methyl)-cyclohexyl)acetamide (less polar diastereoisomer)
(179) N-(4-((dimethylamino)(phenyl)methyl)cyclohexyl)-N-(4-fluorobenzyl)acetamide
(180) N-(4-((dimethylamino)(phenyl)methyl)cyclohexyl)-N-phenylbutyramide
(181) N-(2-(1H-indol-3-yl)ethyl)-N-(4-((dimethylamino)(phenyl)methyl)-cyclohexyl)butyramide
(182) N-(2-(1H-indol-3-yl)ethyl)-N-(4-((dimethylamino)(phenyl)methyl)cyclohexyl)-acetamide
(183) benzo[b]thiophene-3-carboxylic acid [4-(dimethylamino-phenyl-methyl)-cyclohexyl]-amide
(184) 1-(4-chloro-phenyl)-cyclopentanecarboxylic acid [4-(dimethylamino-phenyl-methyl)-cyclohexyl]-amide
(185) N-[4-(dimethylamino-thiophen-2-yl-methyl)-cyclohexyl]-4-propyl-benzamide
(186) 3-cyano-N-[4-(dimethylamino-thiophen-2-yl-methyl)-cyclohexyl]-benzamide
(187) 3-chloro-N-[4-(dimethylamino-phenyl-methyl)-cyclohexyl]-benzamide
(188) 5-chloro-4-methoxy-thiophene-3-carboxylic acid [4-(dimethylamino-phenyl-methyl)-cyclohexyl]-amide
(189) 3,4-dichloro-N-[4-(dimethylamino-phenyl-methyl)-cyclohexyl]-benzamide
(190) N-[4-(dimethylamino-phenyl-methyl)-cyclohexyl]-3-fluoro-5-trifluoromethyl-benzamide
(191) 5-chloro-4-methoxy-thiophene-3-carboxylic acid {4-[dimethylamino-(3-fluoro-phenyl)-methyl]-cyclohexyl}-amide
(192) N-[4-(dimethylamino-thiophen-2-yl-methyl)-cyclohexyl]-4-fluoro-3-trifluoromethyl-benzamide
(193) thiophene-2-carboxylic acid [4-(dimethylamino-thiophen-2-yl-methyl)-cyclohexyl]-amide
(194) 3,5-dichloro-N-[4-(dimethylamino-thiophen-2-yl-methyl)-cyclohexyl]-benzamide
(195) 5-chloro-4-methoxy-thiophene-3-carboxylic acid [4-(dimethylamino-thiophen-2-yl-methyl)-cyclohexyl]-amide
(196) N-[4-(dimethylamino-phenyl-methyl)-cyclohexyl]-2,4,5-trifluoro-benzamide
(197) 3-bromo-N-[4-(dimethylamino-phenyl-methyl)-cyclohexyl]-benzamide
(198) N-[4-(dimethylamino-thiophen-2-yl-methyl)-cyclohexyl]-4-methyl-benzamide
(199) N-[4-(dimethylamino-thiophen-2-yl-methyl)-cyclohexyl]-3-methoxy-benzamide
(200) N-[4-(dimethylamino-thiophen-2-yl-methyl)-cyclohexyl]-3,3-dimethyl-butyramide
(201) 2-tert-butyl-5-methyl-2H-pyrazole-3-carboxylic acid [4-(dimethylamino-thiophen-2-yl-methyl)-cyclohexyl]-amide
(202) N-[4-(dimethylamino-thiophen-2-yl-methyl)-cyclohexyl]-2,4-dimethoxy-benzamide
(203) N-[4-(dimethylamino-phenyl-methyl)-cyclohexyl]-3-trifluoromethyl-benzamide
(204) N-{4-[dimethylamino-(3-fluoro-phenyl)-methyl]-cyclohexyl}-3,5-difluoro-benzamide
(205) N-[4-(dimethylamino-phenyl-methyl)-cyclohexyl]-2-fluoro-5-trifluoromethyl-benzamide
(206) 2-(4-chloro-phenyl)-N-[4-(dimethylamino-phenyl-methyl)-cyclohexyl]-acetamide
(207) N-[4-(dimethylamino-thiophen-2-yl-methyl)-cyclohexyl]-2-methoxy-benzamide
(208) N-[4-(dimethylamino-thiophen-2-yl-methyl)-cyclohexyl]-2-methylsulfanyl-nicotinamide
(209) 3,4-dichloro-N-{4-[dimethylamino-(3-fluoro-phenyl)-methyl]-cyclohexyl}-benzamide
(210) N-[4-(1-dimethylamino-3-phenyl-propyl)-cyclohexyl]-4-fluoro-3-trifluoromethyl-benzamide (more polar diastereoisomer)
(211) 5-chloro-4-methoxy-thiophene-3-carboxylic acid {4-[dimethylamino-(4-fluoro-phenyl)-methyl]-cyclohexyl}-amide
(212) N-[4-(dimethylamino-thiophen-2-yl-methyl)-cyclohexyl]-3,4,5-trimethoxy-benzamide
(213) N-[4-(dimethylamino-thiophen-2-yl-methyl)-cyclohexyl]-2-ethylsulfanyl-nicotinamide
(214) 2-methyl-5-phenyl-furan-3-carboxylic acid [4-(dimethylamino-phenyl-methyl)-cyclohexyl]-amide
(215) N-{4-[dimethylamino-(3-fluoro-phenyl)-methyl]-cyclohexyl}-2-phenoxy-propionamide (less polar diastereoisomer)
(216) N-[4-(dimethylamino-phenyl-methyl)-cyclohexyl]-2,4-dimethoxy-benzamide
(217) 4-tert-butyl-N-[4-(dimethylamino-phenyl-methyl)-cyclohexyl]-benzamide
(218) 2-(4-chloro-phenylsulfanyl)-N-[4-(dimethylamino-thiophen-2-yl-methyl)-cyclohexyl]-nicotinamide
(219) 2-(4-chloro-phenyl)-N-[4-(dimethylamino-thiophen-2-yl-methyl)-cyclohexyl]-acetamide
(220) N-[4-(dimethylamino-thiophen-2-yl-methyl)-cyclohexyl]-2-p-tolyloxy-nicotinamide
(221) 3-chloro-4-(propan-2-sulfonyl)-thiophene-2-carboxylic acid [4-(dimethylamino-thiophen-2-yl-methyl)-cyclohexyl]-amide
(222) N-{4-[dimethylamino-(3-fluoro-phenyl)-methyl]-cyclohexyl}-2-phenoxy-propionamide (more polar diastereoisomer)
(223) 2-tert-butyl-5-methyl-2H-pyrazole-3-carboxylic acid [4-(dimethylamino-phenyl-methyl)-cyclohexyl]-amide (224) 5-Methyl-isoxazole-3-carboxylic acid [4-(dimethylamino-thiophen-2-yl-methyl)-cyclohexyl]-amide
(225) 5-bromo-N-[4-(dimethylamino-thiophen-2-yl-methyl)-cyclohexyl]-nicotinamide
(226) naphthyl-1-carboxylic acid [4-(dimethylamino-phenyl-methyl)-cyclohexyl]-amide
(227) N-[4-(1-dimethylamino-3-phenyl-propyl)-cyclohexyl]-4-fluoro-3-trifluoromethyl-benzamide (less polar diastereoisomer)
(228) N-[4-(dimethylamino-phenyl-methyl)-cyclohexyl]-3,3-dimethyl-butyramide (more polar diastereoisomer)
(229) 5-(4-chloro-phenyl)-2-methyl-furan-3-carboxylic acid [4-(dimethylamino-thiophen-2-yl-methyl)-cyclohexyl]-amide
(230) N-[4-(dimethylamino-phenyl-methyl)-cyclohexyl]-2-phenoxy-propionamide
(231) benzo[b]thiophene-2-carboxylic acid {4-[dimethylamino-(3-fluoro-phenyl)-methyl]-cyclohexyl}-amide
(232) 5-(4-chloro-phenyl)-2-methyl-furan-3-carboxylic acid [4-(dimethylamino-phenyl-methyl)-cyclohexyl]-amide
(233) 4-(4-chloro-benzenesulfonyl)-3-methyl-thiophene-2-carboxylic acid [4-(dimethylamino-phenyl-methyl)-cyclohexyl]-amide
(234) N-[4-(dimethylamino-phenyl-methyl)-cyclohexyl]-2-phenyl-butyramide (less polar diastereoisomer)
(235) 5-bromo-N-[4-(dimethylamino-phenyl-methyl)-cyclohexyl]-nicotinamide
(236) adamantane-1-carboxylic acid [4-(dimethylamino-phenyl-methyl)-cyclohexyl]-amide
(237) 2-phenyl-thiazole-4-carboxylic acid [4-(dimethylamino-phenyl-methyl)-cyclohexyl]-amide
(238) 4-methyl-2-phenyl-thiazole-5-carboxylic acid [4-(dimethylamino-phenyl-methyl)-cyclohexyl]-amide
(239) 2-(2,3-dihydro-benzofuran-5-yl)-thiazole-4-carboxylic acid [4-(dimethylamino-thiophen-2-yl-methyl)-cyclohexyl]-amide
(240) N-{4-[dimethylamino-(3-fluoro-phenyl)-methyl]-cyclohexyl}-2-phenyl-acetamide
(241) 3-chloro-N-[4-(1-dimethylamino-3-phenyl-propyl)-cyclohexyl]-benzamide
(242) N-[4-(dimethylamino-phenyl-methyl)-cyclohexyl]-4-methyl-benzamide
(243) 3,5-dichloro-N-{4-[dimethylamino-(3-fluoro-phenyl)-methyl]-cyclohexyl}-benzamide
(244) N-[4-(dimethylamino-phenyl-methyl)-cyclohexyl]-2,3,6-trifluoro-benzamide
(245) thiophene-2-carboxylic acid [4-(dimethylamino-phenyl-methyl)-cyclohexyl]-amide (less polar diastereoisomer)
(246) N-[4-(dimethylamino-phenyl-methyl)-cyclohexyl]-3,3-dimethyl-butyramide (less polar diastereoisomer)
(247) 2-tert-butyl-5-methyl-2H-pyrazole-3-carboxylic acid [4-(dimethylamino-phenyl-methyl)-cyclohexyl]-amide
(248) N-[4-(1-dimethylamino-3-phenyl-propyl)-cyclohexyl]-3-methyl-benzamide
(249) thiophene-2-carboxylic acid [4-(dimethylamino-phenyl-methyl)-cyclohexyl]-amide (more polar diastereoisomer)
(250) N-[4-(dimethylamino-phenyl-methyl)-cyclohexyl]-2-phenyl-butyramide (more polar diastereoisomer)
(251) N-{4-[dimethylamino-(3-fluoro-phenyl)-methyl]-cyclohexyl}-3,3-dimethyl-butyramide
(252) 3-chloro-4-methanesulfonyl-thiophene-2-carboxylic acid [4-(dimethylamino-phenyl-methyl)-cyclohexyl]-amide
(253) 4-(4-chloro-benzenesulfonyl)-3-methyl-thiophene-2-carboxylic acid [4-(dimethylamino-phenyl-methyl)-cyclohexyl]-amide
(254) 2-benzyloxy-N-[4-(dimethylamino-phenyl-methyl)-cyclohexyl]-acetamide
(255) N-[4-(dimethylamino-phenyl-methyl)-cyclohexyl]-2-thiophen-2-yl-acetamide
(256) 4-methyl-2-phenyl-thiazole-5-carboxylic acid {4-[dimethylamino-(3-fluoro-phenyl)-methyl]-cyclohexyl}-amide
(257) 2-(4-chloro-phenoxy)-N-[4-(dimethylamino-thiophen-2-yl-methyl)-cyclohexyl]-nicotinamide
(258) N-[4-(1-dimethylamino-3-phenyl-propyl)-cyclohexyl]-4-fluoro-benzamide
(259) 5-bromo-N-[4-(dimethylamino-phenyl-methyl)-cyclohexyl]-nicotinamide
(260) 4-bromo-2-ethyl-5-methyl-2H-pyrazole-3-carboxylic acid [4-(dimethylamino-thiophen-2-yl-methyl)-cyclohexyl]-amide
(261) 3-cyano-N-[4-(dimethylamino-phenyl-methyl)-cyclohexyl]-benzamide
(262) N-{4-[dimethylamino-(4-fluoro-phenyl)-methyl]-cyclohexyl}-4-fluoro-benzamide
(263) 3-bromo-N-{4-[dimethylamino-(4-fluoro-phenyl)-methyl]-cyclohexyl}-benzamide
(264) 2-phenyl-thiazole-4-carboxylic acid {4-[dimethylamino-(3-fluoro-phenyl)-methyl]-cyclohexyl}-amide
(265) 2,5-dimethyl-furan-3-carboxylic acid {4-[dimethylamino-(3-fluoro-phenyl)-methyl]-cyclohexyl}-amide
(266) 2-methyl-5-phenyl-furan-3-carboxylic acid {4-[dimethylamino-(3-fluoro-phenyl)-methyl]-cyclohexyl}-amide
(267) 5-pyridin-2-yl-thiophene-2-carboxylic acid {4-[dimethylamino-(3-fluoro-phenyl)-methyl]-cyclohexyl}-amide
(268) 4-bromo-2-ethyl-5-methyl-2H-pyrazole-3-carboxylic acid [4-(dimethylamino-phenyl-methyl)-cyclohexyl]-amide
(269) 3-chloro-N-{4-[dimethylamino-(3-fluoro-phenyl)-methyl]-cyclohexyl}-4-fluoro-benzamide
(270) 3,4-dichloro-N-{4-[dimethylamino-(4-fluoro-phenyl)-methyl]-cyclohexyl}-benzamide
(271) N-{4-[dimethylamino-(4-fluoro-phenyl)-methyl]-cyclohexyl}-2,4,5-trifluoro-benzamide
(272) cyclohexanecarboxylic acid [4-(dimethylamino-phenyl-methyl)-cyclohexyl]-amide
(273) N-{4-[dimethylamino-(3-fluoro-phenyl)-methyl]-cyclohexyl}-2-phenyl-butyramide
(274) 2-(4-chloro-phenyl)-N-{4-[dimethylamino-(3-fluoro-phenyl)-methyl]-cyclohexyl}-acetamide
(275) N-[4-(dimethylamino-phenyl-methyl)-cyclohexyl]-3-nitro-benzamide
(276) N-[4-(1-dimethylamino-3-phenyl-propyl)-cyclohexyl]-2,5-difluoro-benzamide
(277) 3-bromo-N-[4-(1-dimethylamino-3-phenyl-propyl)-cyclohexyl]-benzamide
(278) N-{4-[dimethylamino-(3-fluoro-phenyl)-methyl]-cyclohexyl}-2,6-difluoro-benzamide
(279) 2,5-dimethyl-furan-3-carboxylic acid [4-(dimethylamino-phenyl-methyl)-cyclohexyl]-amide
(280) 3-chloro-N-{4-[dimethylamino-(4-fluoro-phenyl)-methyl]-cyclohexyl}-4-fluoro-benzamide
(281) N-[4-(dimethylamino-phenyl-methyl)-cyclohexyl]-5-fluoro-2-trifluoromethyl-benzamide
(282) 5-methyl-isoxazole-3-carboxylic acid [4-(dimethylamino-phenyl-methyl)-cyclohexyl]-amide (283) 2-(2,3-dihydro-benzofuran-5-yl)-4-methyl-thiazole-5-carboxylic acid [4-(dimethylamino-thiophen-2-yl-methyl)-cyclohexyl]-amide
(284) 2-(4-chloro-phenoxy)-N-[4-(dimethylamino-phenyl-methyl)-cyclohexyl]-acetamide
(285) 5-(4-chloro-phenyl)-2-methyl-furan-3-carboxylic acid {4-[dimethylamino-(3-fluoro-phenyl)-methyl]-cyclohexyl}-amide
(286) 2-bromo-N-[4-(dimethylamino-phenyl-methyl)-cyclohexyl]-benzamide
(287) N-[4-(dimethylamino-phenyl-methyl)-cyclohexyl]-2,6-dimethoxy-benzamide
(288) cyclopentanecarboxylic acid [4-(dimethylamino-phenyl-methyl)-cyclohexyl]-amide
(289) 2-(2,3-dihydro-benzofuran-5-yl)-thiazole-4-carboxylic acid [4-(dimethylamino-phenyl-methyl)-cyclohexyl]-amide
(290) benzo[1,2,5]thiadiazole-5-carboxylic acid {4-[dimethylamino-(3-fluoro-phenyl)-methyl]-cyclohexyl}-amide
(291) N-[4-(dimethylamino-thiophen-2-yl-methyl)-cyclohexylmethyl]-2-thiophen-2-yl-acetamide
(292) benzo[b]thiophene-3-carboxylic acid [4-(dimethylamino-phenyl-methyl)-cyclohexylmethyl]-amide
(293) 5-chloro-4-methoxy-thiophene-3-carboxylic acid [4-(dimethylamino-phenyl-methyl)-cyclohexylmethyl]-amide
(294) N-[4-(dimethylamino-phenyl-methyl)-cyclohexylmethyl]-3,4-difluoro-benzamide (less polar diastereoisomer)
(295) N-{4-[dimethylamino-(3-fluoro-phenyl)-methyl]-cyclohexylmethyl}-3,3-dimethyl-butyramide
(296) 2-bromo-N-[4-(dimethylamino-thiophen-2-yl-methyl)-cyclohexylmethyl]-benzamide
(297) N-[4-(dimethylamino-thiophen-2-yl-methyl)-cyclohexylmethyl]-2,2-diphenyl-acetamide
(298) N-[4-(dimethylamino-phenyl-methyl)-cyclohexylmethyl]-3,3-dimethyl-butyramide
(299) N-[4-(dimethylamino-phenyl-methyl)-cyclohexylmethyl]-2-methylsulfanyl-nicotinamide
(300) N-[4-(dimethylamino-thiophen-2-yl-methyl)-cyclohexylmethyl]-2,6-dimethoxy-benzamide
(301) N-[4-(dimethylamino-thiophen-2-yl-methyl)-cyclohexylmethyl]-3,3-dimethyl-butyramide
(302) benzo[b]thiophene-3-carboxylic acid [4-(dimethylamino-thiophen-2-yl-methyl)-cyclohexylmethyl]-amide
(303) 5-chloro-4-methoxy-thiophene-3-carboxylic acid {4-[dimethylamino-(3-fluoro-phenyl)-methyl]-cyclohexylmethyl}-amide
(304) N-[4-(dimethylamino-thiophen-2-yl-methyl)-cyclohexylmethyl]-2-phenoxy-propionamide
(305) N-[4-(dimethylamino-thiophen-2-yl-methyl)-cyclohexylmethyl]-2-methoxy-benzamide
(306) N-[4-(dimethylamino-phenyl-methyl)-cyclohexylmethyl]-2-phenyl-acetamide
(307) 3-bromo-N-[4-(dimethylamino-thiophen-2-yl-methyl)-cyclohexylmethyl]-benzamide
(308) N-[4-(dimethylamino-thiophen-2-yl-methyl)-cyclohexylmethyl]-3-fluoro-5-trifluoromethyl-benzamide
(309) N-{4-[(4-chloro-phenyl)-dimethylamino-methyl]-cyclohexylmethyl}-3,3-dimethyl-butyramide
(310) N-[4-(dimethylamino-phenyl-methyl)-cyclohexylmethyl]-2-ethylsulfanyl-nicotinamide
(311) 2-(4-chloro-phenyl)-N-[4-(dimethylamino-thiophen-2-yl-methyl)-cyclohexyl-methyl]-acetamide
(312) N-{4-[(4-chloro-phenyl)-dimethylamino-methyl]-cyclohexylmethyl}-2,2-diphenyl-acetamide
(313) N-[4-(dimethylamino-thiophen-2-yl-methyl)-cyclohexylmethyl]-2,6-difluoro-benzamide
(314) benzo[b]thiophene-3-carboxylic acid {4-[dimethylamino-(3-fluoro-phenyl)-methyl]-cyclohexylmethyl}-amide
(315) N-{4-[(4-chloro-phenyl)-dimethylamino-methyl]-cyclohexylmethyl}-2-methyl-sulfanyl-nicotinamide
(316) N-{4-[(4-chloro-phenyl)-dimethylamino-methyl]-cyclohexylmethyl}-2-thiophen-2-yl-acetamide
(317) N-[4-(dimethylamino-phenyl-methyl)-cyclohexylmethyl]-2-methyl-benzamide (less polar diastereoisomer)
(318) 1-(4-chloro-phenyl)-cyclopentane-carboxylic acid [4-(dimethylamino-phenyl-methyl)-cyclohexylmethyl]-amide
(319) N-{4-[dimethylamino-(3-fluoro-phenyl)-methyl]-cyclohexylmethyl}-2-phenyl-acetamide (more polar diastereoisomer)
(320) N-{4-[(4-chloro-phenyl)-dimethylamino-methyl]-cyclohexylmethyl}-2-(3-methoxy-phenyl)-acetamide
(321) N-[4-(dimethylamino-phenyl-methyl)-cyclohexylmethyl]-2-phenyl-butyramide
(322) N-{4-[dimethylamino-(4-fluoro-phenyl)-methyl]-cyclohexylmethyl}-3,3-dimethyl-butyramide
(323) N-[4-(dimethylamino-phenyl-methyl)-cyclohexylmethyl]-2-phenoxy-propionamide
(324) 2-(4-chloro-phenyl)-N-[4-(dimethylamino-phenyl-methyl)-cyclohexylmethyl]-acetamide
(325) N-[4-(dimethylamino-phenyl-methyl)-cyclohexylmethyl]-2-methyl-benzamide (more polar diastereoisomer)
(326) N-[4-(dimethylamino-phenyl-methyl)-cyclohexylmethyl]-3-trifluoromethyl-benzamide (less polar diastereoisomer)
(327) 1-(4-chloro-phenyl)-cyclopentane-carboxylic acid {4-[dimethylamino-(3-fluoro-phenyl)-methyl]-cyclohexylmethyl}-amide
(328) thiophene-2-carboxylic acid [4-(dimethylamino-phenyl-methyl)-cyclohexyl-methyl]-amide
(329) 3,5-dichloro-N-[4-(dimethylamino-phenyl-methyl)-cyclohexylmethyl]-benzamide
(330) 2-methyl-5-phenyl-furan-3-carboxylic acid {4-[(4-chloro-phenyl)-dimethylamino-methyl]-cyclohexylmethyl}-amide
(331) 3-chloro-N-[4-(dimethylamino-phenyl-methyl)-cyclohexylmethyl]-benzamide
(332) N-{4-[dimethylamino-(3-fluoro-phenyl)-methyl]-cyclohexylmethyl}-2-phenoxy-propionamide (more polar diastereoisomer)
(333) N-[4-(dimethylamino-phenyl-methyl)-cyclohexylmethyl]-3-trifluoromethyl-benzamide (more polar diastereoisomer)
(334) thiophene-2-carboxylic acid {4-[dimethylamino-(3-fluoro-phenyl)-methyl]-cyclohexylmethyl}-amide (more polar diastereoisomer)
(335) 2-phenyl-thiazole-4-carboxylic acid [4-(dimethylamino-phenyl-methyl)-cyclohexylmethyl]-amide
(336) benzo[b]thiophene-3-carboxylic acid {4-[(4-chloro-phenyl)-dimethylamino-methyl]-cyclohexylmethyl}-amide (less polar diastereoisomer)
(337) N-{4-[dimethylamino-(3-fluoro-phenyl)-methyl]-cyclohexylmethyl}-2-p-tolyloxy-nicotinamide
(338) 2,4,6-trichloro-N-[4-(dimethylamino-phenyl-methyl)-cyclohexylmethyl]-benzamide
(339) 1-(4-chloro-phenyl)-cyclopentane-carboxylic acid [4-(dimethylamino-phenyl-methyl)-cyclohexylmethyl]-amide (340) thiophene-2-carboxylic acid {4-[dimethylamino-(3-fluoro-phenyl)-methyl]-cyclohexylmethyl}-amide (less polar diastereoisomer)
(341) N-{4-[dimethylamino-(3-fluoro-phenyl)-methyl]-cyclohexylmethyl}-2-phenoxy-propionamide (less polar diastereoisomer)
(342) N-{4-[dimethylamino-(3-fluoro-phenyl)-methyl]-cyclohexylmethyl}-2-methyl-butyramide (more polar diastereoisomer)
(343) N-{4-[dimethylamino-(3-fluoro-phenyl)-methyl]-cyclohexylmethyl}-2-thiophen-2-yl-acetamide
(344) benzo[b]thiophene-3-carboxylic acid {4-[dimethylamino-(4-fluoro-phenyl)-methyl]-cyclohexylmethyl}-amide
(345) 2-methyl-5-phenyl-furan-3-carboxylic acid [4-(dimethylamino-phenyl-methyl)-cyclohexylmethyl]-amide
(346) N-{4-[dimethylamino-(3-fluoro-phenyl)-methyl]-cyclohexylmethyl}-2-phenoxy-propionamide
(347) 3-cyano-N-[4-(dimethylamino-thiophen-2-yl-methyl)-cyclohexylmethyl]-benzamide
(348) N-{4-[dimethylamino-(3-fluoro-phenyl)-methyl]-cyclohexylmethyl}-2-phenyl-acetamide (less polar diastereoisomer)
(349) N-[4-(dimethylamino-phenyl-methyl)-cyclohexylmethyl]-2-(3-methoxy-phenyl)-acetamide
(350) N-{4-[dimethylamino-(3-fluoro-phenyl)-methyl]-cyclohexylmethyl}-4-fluoro-3-trifluoromethyl-benzamide
(351) N-{4-[(4-chloro-phenyl)-dimethylamino-methyl]-cyclohexylmethyl}-2-ethyl-sulfanyl-nicotinamide
(352) N-[4-(dimethylamino-thiophen-2-yl-methyl)-cyclohexylmethyl]-2-p-tolyloxy-nicotinamide (more polar diastereoisomer)
(353) 2-methyl-5-phenyl-furan-3-carboxylic acid {4-[dimethylamino-(3-fluoro-phenyl)-methyl]-cyclohexylmethyl}-amide
(354) 2-chloro-N-{4-[(4-chloro-phenyl)-dimethylamino-methyl]-cyclohexylmethyl}-benzamide
(355) 2-chloro-N-[4-(dimethylamino-phenyl-methyl)-cyclohexylmethyl]-nicotinamide
(356) N-[4-(dimethylamino-thiophen-2-yl-methyl)-cyclohexylmethyl]-4-propyl-benzamide
(357) N-[4-(dimethylamino-phenyl-methyl)-cyclohexylmethyl]-3,4-difluoro-benzamide (more polar diastereoisomer)
(358) 3-bromo-N-[4-(dimethylamino-phenyl-methyl)-cyclohexylmethyl]-benzamide
(359) N-{4-[dimethylamino-(4-fluoro-phenyl)-methyl]-cyclohexylmethyl}-2-thiophen-2-yl-acetamide
(360) 2-(4-chloro-phenoxy)-N-[4-(dimethylamino-phenyl-methyl)-cyclohexylmethyl]-nicotinamide (less polar diastereoisomer)
(361) 2,4-dichloro-N-[4-(dimethylamino-phenyl-methyl)-cyclohexylmethyl]-benzamide
(362) N-[4-(dimethylamino-phenyl-methyl)-cyclohexylmethyl]-3-methyl-benzamide
(363) 2-bromo-N-{4-[dimethylamino-(3-fluoro-phenyl)-methyl]-cyclohexylmethyl}-benzamide
(364) N-{4-[dimethylamino-(3-fluoro-phenyl)-methyl]-cyclohexylmethyl}-3-trifluoro-methyl-benzamide
(365) 2-phenyl-thiazole-4-carboxylic acid {4-[dimethylamino-(3-fluoro-phenyl)-methyl]-cyclohexylmethyl}-amide
(366) 2-tert-butyl-5-methyl-2H-pyrazole-3-carboxylic acid [4-(dimethylamino-thiophen-2-yl-methyl)-cyclohexylmethyl]-amide
(367) 3-chloro-4-(propane-2-sulfonyl)-thiophene-2-carboxylic acid [4-(dimethylamino-thiophen-2-yl-methyl)-cyclohexylmethyl]-amide
(368) N-{4-[dimethylamino-(3-fluoro-phenyl)-methyl]-cyclohexylmethyl}-2-methoxy-benzamide
(369) N-{4-[(4-chloro-phenyl)-dimethylamino-methyl]-cyclohexylmethyl}-3-trifluoromethyl-benzamide
(370) 1-(4-chloro-phenyl)-cyclopentane-carboxylic acid {4-[dimethylamino-(4-fluoro-phenyl)-methyl]-cyclohexylmethyl}-amide
(371) 3,5-dichloro-N-{4-[dimethylamino-(3-fluoro-phenyl)-methyl]-cyclohexylmethyl}-benzamide
(372) benzo[b]thiophene-3-carboxylic acid {4-[(4-chloro-phenyl)-dimethylamino-methyl]-cyclohexylmethyl}-amide (more polar diastereoisomer)
(373) 2-methyl-5-phenyl-furan-3-carboxylic acid {4-[dimethylamino-(3-fluoro-phenyl)-methyl]-cyclohexylmethyl}-amide
(374) 2-(4-chloro-phenylsulfanyl)-N-[4-(dimethylamino-phenyl-methyl)-cyclohexyl-methyl]-nicotinamide
(375) 4-bromo-2-ethyl-5-methyl-2H-pyrazole-3-carboxylic acid [4-(dimethylamino-thiophen-2-yl-methyl)-cyclohexylmethyl]-amide
(376) 5-chloro-4-methoxy-thiophene-3-carboxylic acid {4-[dimethylamino-(4-fluoro-phenyl)-methyl]-cyclohexylmethyl}-amide
(378) N-{4-[dimethylamino-(3-fluoro-phenyl)-methyl]-cyclohexylmethyl}-2-methyl-butyramide (less polar diastereoisomer)
(379) 5-methyl-isoxazole-3-carboxylic acid [4-(dimethylamino-phenyl-methyl)-cyclohexylmethyl]-amide
(380) benzo[b]thiophene-3-carboxylic acid [4-(1-dimethylamino-3-phenyl-propyl)-cyclohexylmethyl]-amide
(381) N-{4-[dimethylamino-(4-fluoro-phenyl)-methyl]-cyclohexylmethyl}-2-methyl-sulfanyl-nicotinamide
(382) N-{4-[(4-chloro-phenyl)-dimethylamino-methyl]-cyclohexylmethyl}-2-p-tolyloxy-nicotinamide
(383) 2-(4-chloro-phenoxy)-N-[4-(dimethylamino-phenyl-methyl)-cyclohexylmethyl]-nicotinamide (more polar diastereoisomer)
(384) N-{4-[dimethylamino-(3-fluoro-phenyl)-methyl]-cyclohexylmethyl}-2-methyl-benzamide
(385) 5-methyl-isoxazole-3-carboxylic acid {4-[(4-chloro-phenyl)-dimethylamino-methyl]-cyclohexylmethyl}-amide
(386) 5-bromo-N-[4-(dimethylamino-phenyl-methyl)-cyclohexylmethyl]-nicotinamide
(387) N-[4-(dimethylamino-phenyl-methyl)-cyclohexylmethyl]-2-methyl-butyramide
(388) N-{4-[dimethylamino-(3-fluoro-phenyl)-methyl]-cyclohexylmethyl}-2-ethylsulfanyl-nicotinamide
(389) N-[4-(dimethylamino-thiophen-2-yl-methyl)-cyclohexyl methyl]-2-p-tolyloxy-nicotinamide (less polar diastereoisomer)
(390) 4-bromo-2-ethyl-5-methyl-2H-pyrazole-3-carboxylic acid [4-(dimethylamino-phenyl-methyl)-cyclohexylmethyl]-amide
(391) N-{4-[(4-chloro-phenyl)-dimethylamino-methyl]-cyclohexylmethyl}-2-phenoxy-propionamide
(392) N-[4-(dimethylamino-phenyl-methyl)-cyclohexylmethyl]-3,5-dinitro-benzamide
(393) N-{4-[(4-chloro-phenyl)-dimethylamino-methyl]-cyclohexylmethyl}-3-methoxy-benzamide
(394) 2-bromo-N-{4-[(4-chloro-phenyl)-dimethylamino-methyl]-cyclohexylmethyl}-benzamide
(395) 2-bromo-N-(2-{4-[(4-chloro-phenyl)-dimethylamino-methyl]-cyclohexyl}-ethyl)-benzamide (396) 2-bromo-N-(2-{4-[dimethylamino-(3-fluoro-phenyl)-methyl]-cyclohexyl}-ethyl)-benzamide
(397) 3-chloro-N-{2-[4-(dimethylamino-phenyl-methyl)-cyclohexyl]-ethyl}-benzamide (more polar diastereoisomer)
(398) 3-chloro-N-{2-[4-(dimethylamino-phenyl-methyl)-cyclohexyl]-ethyl}-benzamide (less polar diastereoisomer)
(399) 3-chloro-N-(2-{4-[(4-chloro-phenyl)-dimethylamino-methyl]-cyclohexyl}-ethyl)-benzamide
(400) 3-chloro-N-(2-{4-[dimethylamino-(3-fluoro-phenyl)-methyl]-cyclohexyl}-ethyl)-benzamide (less polar diastereoisomer)
(401) 3-chloro-N-(2-{4-[dimethylamino-(3-fluoro-phenyl)-methyl]-cyclohexyl}-ethyl)-benzamide (more polar diastereoisomer)
(402) 2-chloro-N-{2-[4-(dimethylamino-phenyl-methyl)-cyclohexyl]-ethyl}-benzamide
(403) 2-chloro-N-(2-{4-[(4-chloro-phenyl)-dimethylamino-methyl]-cyclohexyl}-ethyl)-benzamide
(404) 2-chloro-N-(2-{4-[dimethylamino-(3-fluoro-phenyl)-methyl]-cyclohexyl}-ethyl)-benzamide
(405) 4-chloro-N-{2-[4-(dimethylamino-phenyl-methyl)-cyclohexyl]-ethyl}-benzamide
(406) 4-chloro-N-(2-{4-[dimethylamino-(3-fluoro-phenyl)-methyl]-cyclohexyl}-ethyl)-benzamide
(407) N-{2-[4-(dimethylamino-phenyl-methyl)-cyclohexyl]-ethyl}-4-fluoro-benzamide
(408) N-(2-{4-[(4-chloro-phenyl)-dimethylamino-methyl]-cyclohexyl}-ethyl)-4-fluoro-benzamide
(409) N-(2-{4-[dimethylamino-(3-fluoro-phenyl)-methyl]-cyclohexyl}-ethyl)-4-fluoro-benzamide
(410) N-{2-[4-(dimethylamino-phenyl-methyl)-cyclohexyl]-ethyl}-2-fluoro-benzamide
(411) N-(2-{4-[dimethylamino-(3-fluoro-phenyl)-methyl]-cyclohexyl}-ethyl)-2-fluoro-benzamide
(412) N-(2-{4-[dimethylamino-(3-fluoro-phenyl)-methyl]-cyclohexyl}-ethyl)-3-methyl-benzamide
(413) 2,6-dichloro-N-{2-[4-(dimethylamino-phenyl-methyl)-cyclohexyl]-ethyl}-benzamide
(414) N-{2-[4-(dimethylamino-phenyl-methyl)-cyclohexyl]-ethyl}-2-methoxy-benzamide
(415) N-(2-{4-[dimethylamino-(3-fluoro-phenyl)-methyl]-cyclohexyl}-ethyl)-2-methoxy-benzamide
(416) 3,4-dichloro-N-{2-[4-(dimethylamino-phenyl-methyl)-cyclohexyl]-ethyl}-benzamide
(417) N-{2-[4-(dimethylamino-phenyl-methyl)-cyclohexyl]-ethyl}-2-methyl-benzamide (more polar diastereoisomer)
(418) N-{2-[4-(dimethylamino-phenyl-methyl)-cyclohexyl]-ethyl}-2-methyl-benzamide (less polar diastereoisomer)
(419) N-(2-{4-[(4-chloro-phenyl)-dimethylamino-methyl]-cyclohexyl}-ethyl)-2-methyl-benzamide
(420) N-(2-{4-[dimethylamino-(3-fluoro-phenyl)-methyl]-cyclohexyl}-ethyl)-2-methyl-benzamide
(421) 4-cyano-N-{2-[4-(dimethylamino-phenyl-methyl)-cyclohexyl]-ethyl}-benzamide
(422) 3-chloro-N-(2-{4-[dimethylamino-(4-fluoro-phenyl)-methyl]-cyclohexyl}-ethyl)-benzamide (more polar diastereoisomer)
(423) 3-chloro-N-(2-{4-[dimethylamino-(4-fluoro-phenyl)-methyl]-cyclohexyl}-ethyl)-benzamide (less polar diastereoisomer)
(424) 3-chloro-N-{2-[4-(dimethylamino-thiophen-2-yl-methyl)-cyclohexyl]-ethyl}-benzamide
(425) 2-chloro-N-{2-[4-(dimethylamino-thiophen-2-yl-methyl)-cyclohexyl]-ethyl}-benzamide
(426) N-{2-[4-(dimethylamino-thiophen-2-yl-methyl)-cyclohexyl]-ethyl}-4-fluoro-benzamide
(427) N-(2-{4-[dimethylamino-(4-fluoro-phenyl)-methyl]-cyclohexyl}-ethyl)-2-fluoro-benzamide
(428) N-{2-[4-(dimethylamino-thiophen-2-yl-methyl)-cyclohexyl]-ethyl}-2-fluoro-benzamide
(429) N-(2-{4-[dimethylamino-(4-fluoro-phenyl)-methyl]-cyclohexyl}-ethyl)-3-methyl-benzamide
(430) N-{2-[4-(dimethylamino-thiophen-2-yl-methyl)-cyclohexyl]-ethyl}-3-methyl-benzamide
(431) 2,6-dichloro-N-{2-[4-(dimethylamino-thiophen-2-yl-methyl)-cyclohexyl]-ethyl}-benzamide
(432) N-(2-{4-[dimethylamino-(4-fluoro-phenyl)-methyl]-cyclohexyl}-ethyl)-2-methoxy-benzamide
(433) N-{2-[4-(dimethylamino-phenyl-methyl)-cyclohexyl]-ethyl}-3,5-difluoro-benzamide
(434) N-(2-{4-[(4-chloro-phenyl)-dimethylamino-methyl]-cyclohexyl}-ethyl)-3,5-difluoro-benzamide
(435) N-(2-{4-[dimethylamino-(3-fluoro-phenyl)-methyl]-cyclohexyl}-ethyl)-3,5-difluoro-benzamide
(436) N-(2-{4-[(4-chloro-phenyl)-dimethylamino-methyl]-cyclohexyl}-ethyl)-2,4-difluoro-benzamide
(437) 2,4-dichloro-N-(2-{4-[(4-chloro-phenyl)-dimethylamino-methyl]-cyclohexyl}-ethyl)-5-fluoro-benzamide
(438) 2,4-dichloro-N-(2-{4-[dimethylamino-(3-fluoro-phenyl)-methyl]-cyclohexyl}-ethyl)-5-fluoro-benzamide (more polar diastereoisomer)
(439) 2,4-dichloro-N-(2-{4-[dimethylamino-(3-fluoro-phenyl)-methyl]-cyclohexyl}-ethyl)-5-fluoro-benzamide (less polar diastereoisomer)
(440) 2,4-dichloro-N-{2-[4-(dimethylamino-thiophen-2-yl-methyl)-cyclohexyl]-ethyl}-5-fluoro-benzamide
(441) 2-chloro-N-(2-{4-[(4-chloro-phenyl)-dimethylamino-methyl]-cyclohexyl}-ethyl)-nicotinamide
(442) naphthalene-2-carboxylic acid (2-{4-[dimethylamino-(4-fluoro-phenyl)-methyl]-cyclohexyl}-ethyl)-amide
(443) N-{2-[4-(dimethylamino-thiophen-2-yl-methyl)-cyclohexyl]-ethyl}-4-propyl-benzamide
(444) N-{2-[4-(dimethylamino-phenyl-methyl)-cyclohexyl]-ethyl}-3,4-difluoro-benzamide
(445) N-(2-{4-[(4-chloro-phenyl)-dimethylamino-methyl]-cyclohexyl}-ethyl)-3,4-difluoro-benzamide
(446) N-{2-[4-(dimethylamino-thiophen-2-yl-methyl)-cyclohexyl]-ethyl}-3,4-difluoro-benzamide
(447) N-(2-{4-[dimethylamino-(4-fluoro-phenyl)-methyl]-cyclohexyl}-ethyl)-3-methoxy-benzamide
(448) N-{2-[4-(dimethylamino-phenyl-methyl)-cyclohexyl]-ethyl}-2,2-diphenyl-acetamide
(449) 1-(4-chloro-phenyl)-cyclopentane-carboxylic acid {2-[4-(dimethylamino-phenyl-methyl)-cyclohexyl]-ethyl}-amide
(450) 2-benzyloxy-N-{2-[4-(dimethylamino-phenyl-methyl)-cyclohexyl]-ethyl}-acetamide
(451) N-{2-[4-(dimethylamino-phenyl-methyl)-cyclohexyl]-ethyl}-2-phenyl-acetamide
(452) thiophene-2-carboxylic acid {2-[4-(dimethylamino-phenyl-methyl)-cyclohexyl]-ethyl}-amide
(453) N-(2-{4-[dimethylamino-(3-fluoro-phenyl)-methyl]-cyclohexyl}-ethyl)-2-(3-methoxy-phenyl)-acetamide
(454) N-{2-[4-(dimethylamino-thiophen-2-yl-methyl)-cyclohexyl]-ethyl}-2-(3-methoxy-phenyl)-acetamide
(455) N-(2-{4-[(4-chloro-phenyl)-dimethylamino-methyl]-cyclohexyl}-ethyl)-2-phenyl-butyramide
(456) N-{2-[4-(dimethylamino-thiophen-2-yl-methyl)-cyclohexyl]-ethyl}-2-phenyl-butyramide (457) benzo[b]thiophene-2-carboxylic acid {2-[4-(dimethylamino-phenyl-methyl)-cyclohexyl]-ethyl}-amide
(458) N-{2-[4-(dimethylamino-phenyl-methyl)-cyclohexyl]-ethyl}-4-nitro-benzamide
(459) 3-bromo-N-(2-{4-[dimethylamino-(4-fluoro-phenyl)-methyl]-cyclohexyl}-ethyl)-benzamide
(460) N-{2-[4-(dimethylamino-phenyl-methyl)-cyclohexyl]-ethyl}-2,3,4,5,6-pentafluoro-benzamide
(461) N-{2-[4-(dimethylamino-phenyl-methyl)-cyclohexyl]-ethyl}-2,6-difluoro-benzamide
(462) N-(2-{4-[dimethylamino-(3-fluoro-phenyl)-methyl]-cyclohexyl}-ethyl)-2,6-difluoro-benzamide
(463) 2-phenyl-thiazole-4-carboxylic acid {2-[4-(dimethylamino-phenyl-methyl)-cyclohexyl]-ethyl}-amide
(464) 2-phenyl-thiazole-4-carboxylic acid (2-{4-[dimethylamino-(4-fluoro-phenyl)-methyl]-cyclohexyl}-ethyl)-amide
(465) benzo[b]thiophene-3-carboxylic acid {2-[4-(dimethylamino-thiophen-2-yl-methyl)-cyclohexyl]-ethyl}-amide
(466) N-{2-[4-(dimethylamino-phenyl-methyl)-cyclohexyl]-ethyl}-2-methylsulfanyl-nicotinamide
(467) 2-methyl-5-phenyl-furan-3-carboxylic acid {2-[4-(dimethylamino-phenyl-methyl)-cyclohexyl]-ethyl}-amide
(468) 2-(2,3-dihydro-benzofuran-5-yl)-thiazole-4-carboxylic acid {2-[4-(dimethylamino-phenyl-methyl)-cyclohexyl]-ethyl}-amide
(469) 3-(2,6-dichloro-phenyl)-5-methyl-isoxazole-4-carboxylic acid {2-[4-(dimethylamino-thiophen-2-yl-methyl)-cyclohexyl]-ethyl}-amide
(470) 2-(4-chloro-phenylsulfanyl)-N-{2-[4-(dimethylamino-phenyl-methyl)-cyclohexyl]-ethyl}-nicotinamide (more polar diastereoisomer)
(471) 2-(4-chloro-phenylsulfanyl)-N-{2-[4-(dimethylamino-phenyl-methyl)-cyclohexyl]-ethyl}-nicotinamide (less polar diastereoisomer)
(472) benzo[1,2,3]thiadiazole-5-carboxylic acid {2-[4-(dimethylamino-phenyl-methyl)-cyclohexyl]-ethyl}-amide
(473) 5-bromo-N-{2-[4-(dimethylamino-phenyl-methyl)-cyclohexyl]-ethyl}-nicotinamide
(474) 5-chloro-4-methoxy-thiophene-3-carboxylic acid {2-[4-(dimethylamino-phenyl-methyl)-cyclohexyl]-ethyl}-amide
(475) 5-chloro-4-methoxy-thiophene-3-carboxylic acid (2-{4-[dimethylamino-(4-fluoro-phenyl)-methyl]-cyclohexyl}-ethyl)-amide
(476) 5-chloro-4-methoxy-thiophene-3-carboxylic acid {2-[4-(1-dimethylamino-3-phenyl-propyl)-cyclohexyl]-ethyl}-amide
(477) 3-cyano-N-{2-[4-(dimethylamino-phenyl-methyl)-cyclohexyl]-ethyl}-benzamide
(478) N-{2-[4-(dimethylamino-phenyl-methyl)-cyclohexyl]-ethyl}-2,4-dimethoxy-benzamide
(479) 2-chloro-N-((4-((dimethylamino)(phenyl)methyl)cyclohexyl)methyl)-benzamide
(480) N-((4-((dimethylamino)(phenyl)methyl)cyclohexyl)methyl)-4-fluoro-benzamide
(481) N-(2-(4-((dimethylamino)(phenyl)methyl)cyclohexyl)ethyl)-4-fluoro-benzamide
(482) N-((4-((dimethylamino)(phenyl)methyl)cyclohexyl)methyl)-2-fluoro-benzamide
(483) N-((4-((dimethylamino)(phenyl)methyl)cyclohexyl)methyl)-3-methyl-benzamide
(484) N-((4-((dimethylamino)(phenyl)methyl)cyclohexyl)methyl)-2-methoxy-benzamide
(485) N-(2-(4-((dimethylamino)(phenyl)methyl)cyclohexyl)ethyl)-3,5-dimethoxy-benzamide
(486) N-((4-((dimethylamino)(3-fluorophenyl)methyl)cyclohexyl)methyl)-2,6-dimethoxybenzamide
(487) N-((4-((dimethylamino)(phenyl)methyl)cyclohexyl)methyl)-2,4-difluoro-benzamide
(488) N-((4-((dimethylamino)(thiophen-2-yl)methyl)cyclohexyl)methyl)-3-methoxy-benzamide
(489) N-((4-((dimethylamino)(thiophen-2-yl)methyl)cyclohexyl)methyl)-3,4,5-trimethoxybenzamide
(490) 4-((dimethylamino)(phenyl)methyl)-1-(4-fluoro-3-methylphenyl)cyclohexanol
(491) N-cyclohexyl-2-(4-(2-phenyl-1-(pyrrolidin-1-yl)ethyl)cyclohexyl)acetamide
(492) N-(3-methoxyphenyl)-2-(4-(2-phenyl-1-(pyrrolidin-1-yl)ethyl)cyclohexyl)-acetamide
(493) N-(4-methoxyphenyl)-2-(4-(piperidin-1-yl(p-tolyl)methyl)cyclohexylidene)-acetamide
(494) N-phenethyl-2-(4-(piperidin-1-yl(p-tolyl)methyl)cyclohexylidene)acetamide
(495) 2-(4-(2-phenyl-1-(pyrrolidin-1-yl)ethyl)cyclohexylidene)-N-(pyridin-2-ylmethyl)acetamide
(496) N-benzyl-N-methyl-2-(4-(piperidin-1-yl(p-tolyl)methyl)cyclohexylidene)-acetamide
(497) 3-thiophen-2-yl-[1,2,4]oxadiazole-5-carboxylic acid [4-(dimethylamino-phenyl-methyl)-cyclohexyl]-amide
(498) 3-methyl-[1,2,4]oxadiazole-5-carboxylic acid {2-[4-(dimethylamino-phenyl-methyl)-cyclohexyl]-ethyl}-amide
(499) 3-phenyl-[1,2,4]oxadiazole-5-carboxylic acid {4-[dimethylamino-(3-fluoro-phenyl)-methyl]-cyclohexyl}-amide
(500) 3-cyclopropylmethyl-[1,2,4]oxadiazole-5-carboxylic acid {4-[dimethylamino-(3-fluoro-phenyl)-methyl]-cyclohexyl}-amide
(501) 3-methoxymethyl-[1,2,4]oxadiazole-5-carboxylic acid {2-[4-(1-dimethylamino-3-phenyl-propyl)-cyclohexyl]-ethyl}-amide in the form of the racemate; of the enantiomers, diastereoisomers, mixtures of the enantiomers or diastereoisomers or of an individual enantiomer or diastereoisomer; of the bases and/or salts of physiologically acceptable acids.

EXAMPLES

Synthesis of the Cyclohexanones Used

The cyclohexanones form the starting point for further derivatisations. The ketones were obtained from commercially available 4-oxo-cyclohexane-carboxylic acid ethyl ester in a multistage synthesis in the manner described hereinbelow. The yields of the prepared compounds are not optimised. All temperatures are uncorrected.

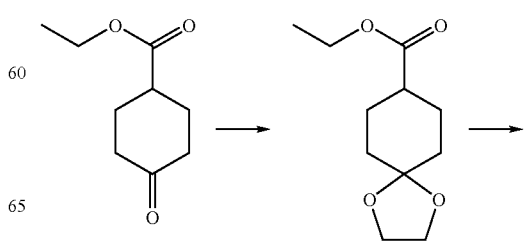

-continued

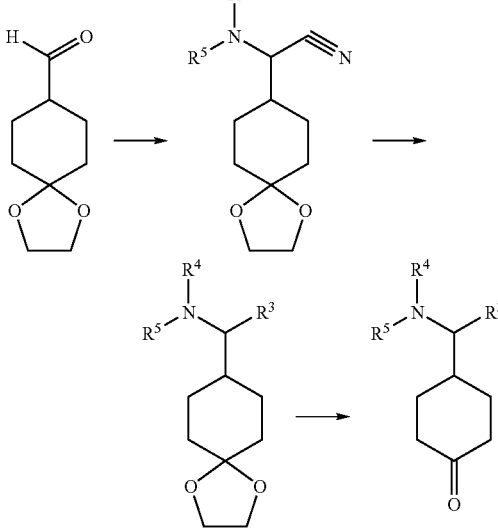

1,4-Dioxa-spiro[4.5]decane-8-carboxylic acid ethyl ester 1

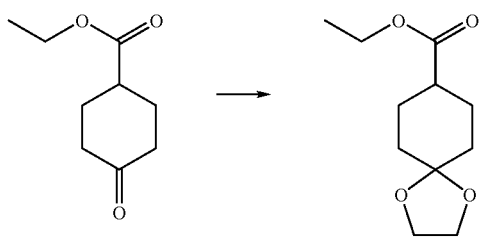

4-Oxo-cyclohexanecarboxylic acid ethyl ester (52.8 g, 0.31 mol, Merck, Order No. 814249), ethylene glycol (67.4 g, 1.08 mol) and p-toluenesulfonic acid (0.7 g) in toluene (160 ml) were stirred for 20 h at RT; the reaction solution was poured into diethyl ether (300 ml) and washed with water, sodium hydrogen carbonate solution and sodium chloride solution. The solution was dried ($Na_2SO_4$) and concentrated in vacuo, and the colourless liquid that remained was processed further without being purified.

Yield: 66.5 g (100%)

$^1$H-NMR (CDCl$_3$): 1.24 (t, 3 H); 1.53 (m, 2 H); 1.76 (m, 4 H); 1.92 (m, 2 H); 2.31 (m, 1 H); 3.91 (s, 4 H); 4.11 (q, 2 H).

$^{13}$C-NMR (CDCl$_3$): 14.28 (q); 26.32 (t); 33.76 (t); 41.59 (d); 60.14 (t); 64.21 (t); 107.90 (d); 174.77 (s).

1,4-Dioxa-spiro[4.5]decane-8-carbaldehyde 2

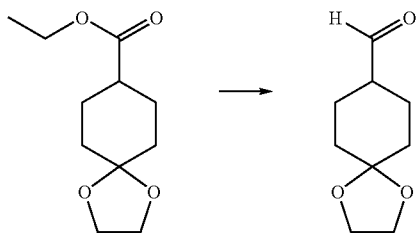

Diisobutylaluminium hydride (1.5 M solution in toluene, 102 ml, 153 mmol) was added dropwise at from −70 to −65° C., under argon, to a solution of 1,4-dioxa-spiro[4.5]decane-8-carboxylic acid ethyl ester 1 (32.13 g, 150 mmol) in abs. toluene (160 ml), and stirring was carried out for 30 minutes. The mixture was then quenched at from −70 to −60° C. by addition of methanol (80 ml). The reaction solution was heated to RT, saturated sodium chloride solution (100 ml) was added, and the reaction solution was filtered off with suction over kieselguhr. Kieselguhr was washed twice with ethyl acetate and the aqueous solution was separated off and extracted twice with ethyl acetate. The combined organic extracts were washed with saturated sodium chloride solution, dried over sodium sulfate and concentrated in vacuo.

Yield: 24.01 g (94%), yellow oil $^1$H-NMR (CDCl$_3$): 1.54 (m, 2 H); 1.74 (m, 4 H); 1.91 (m, 2 H); 2.21 (m, 1 H); 3.91 (s, 4 H); 9.60 (s, 1 H).

$^{13}$C-NMR (CDCl$_3$): 23.35 (t); 33.37 (t); 48.18 (d); 64.30 (t); 107.89 (d); 203.51 (s).

Dimethylamino-(1,4-dioxa-spiro[4.5]dec-8-yl)-acetonitrile 3

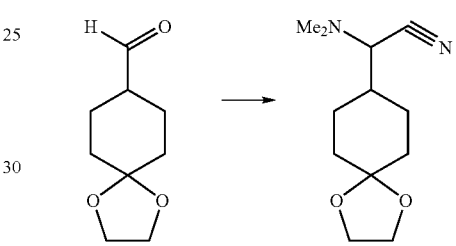

40% aqueous dimethylamine solution (85 ml, 0.67 mol), 1,4-dioxa-spiro[4.5]decane-8-carbaldehyde 2 (240 g, 0.141 mol) and potassium cyanide (22.05 g, 0.338 mol) were added, while cooling with ice, to a mixture of 4N hydrochloric acid (37 ml) and methanol (22 ml). The mixture was stirred for 4 d at room temperature and then, after addition of water (80 ml), extracted with diethyl ether (4×100 ml). The organic phase was dried over sodium sulfate and concentrated in vacuo, and the product was obtained in the form of a white solid.

Yield: 25.2 g (81%)

Melting point: 48-51° C.

$^1$H-NMR (CDCl$_3$): 1.23-2.03 (m, 9 H); 2.28 (s, 6 H); 3.16 (d, 1 H); 3.93 (m, 4 H).

$^{13}$C-NMR (CDCl$_3$): 26.67 (t); 27.93 (t); 33.87 (t); 36.94 (d); 41.90 (q); 64.30 (t); 64.36 (t); 108.33 (d); 115.94 (s).

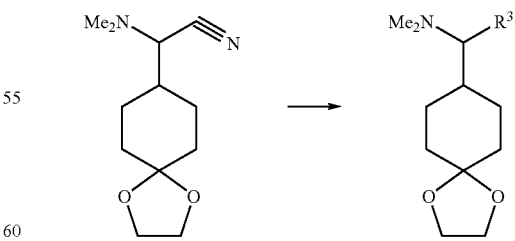

[(1,4-Dioxa-spiro[4.5]dec-8-yl)-phenyl-methyl]-dimethyl-amine 4 ($R^3$=phenyl)

A solution of the aminonitrile 3 (23.56 g, 105 mmol) in abs. THF (100 ml) was added dropwise, under argon and while cooling with ice, to a 25% solution of phenylmagnesium chloride (144 ml, 262.5 mmol) in THF, and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried (Na$_2$SO$_4$) and concentrated.

Yield: 28.9 g (100%).

$^{13}$C-NMR (CDCl$_3$): 27.05; 28.13; 34.48; 34.57; 36.94 (C$_8$); 41.64 (N(CH$_3$)$_2$); 64.15; 74.33 (CH); 109.02 (C$_5$); 126.70 (C$_{arom}$); 127.49 (C$_{arom}$); 129.12 (C$_{arom}$); 136.57 (C$_{arom}$).

[(1,4-Dioxa-spiro[4.5]dec-8-yl)-4-fluorophenyl-methyl]-dimethylamine 5 (R$^3$=4-fluorophenyl)

A solution of the aminonitrile 3 (19.89 g, 88 mmol) in abs. THF (160 ml) was added dropwise, under argon and while cooling with ice, to a 1M solution of 4-fluorophenylmagnesium bromide in THF (220 ml, 220 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried (Na$_2$SO$_4$) and concentrated.

Yield: 31 g (>100%)

$^{13}$C-NMR (CDCl$_3$): 26.68 (t); 28.11 (t); 34.43 (t); 34.55 (t); 37.37 (d); 41.68 (q); 64.12 (t); 73.65 (d); 108.88 (d); 114.23 (d); 114.44 (d); 130.27; 130.35; 132.43; 160.36 (s); 162.78 (s).

[(1,4-Dioxa-spiro[4.5]dec-8-yl)-3-fluorophenyl-methyl]-dimethyl-amine 6 (R$^3$=3-fluorophenyl)

A solution of the aminonitrile 3 (23.45 g, 104 mmol) in abs. THF (100 ml) was added dropwise, under argon and while cooling with ice, to a 1M solution of 3-fluorophenylmagnesium bromide in THF (208 ml, 208 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried and concentrated.

Yield: 30.33 g (99%).

$^1$H-NMR (CDCl$_3$): 1.12 (m, 1 H); 1.26 (m, 1 H); 1.46-1.81 (m, 7 H); 2.10 (s, 6 H); 3.10 (d, 1 H); 3.90 (m, 4 H); 6.85 (m, 3 H); 7.27 (m, 1 H).

$^{13}$C-NMR (CDCl$_3$): 26.80 (t); 28.08 (t); 34.48 (t); 34.45 (t); 34.59 (t); 37.26 (d); 41.71 (q); 64.19 (t); 74.04 (t); 108.91 (d); 113.51 (d); 113.71 (d); 115.52 (d); 115.72 (d); 124.83 (d); 128.82 (d); 128.90 (d); 139.66 (s); 161.15 (s); 163.58 (s).

[(4-Chlorophenyl)-(1,4-dioxa-spiro[4.5]dec-8-yl)-methyl]-dimethyl-amine 7 (R$^3$=4-chlorophenyl)

A solution of the aminonitrile 3 (22.43 g, 100 mmol) in abs. ether (100 ml) was added dropwise, under argon and while cooling with ice, to a 1M solution of 4-chlorophenylmagnesium bromide in ether (200 ml, 200 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried and concentrated.

Yield: 30.9 g (100%)

$^{13}$C-NMR (CDCl$_3$): 26.65 (t); 28.11 (t); 34.46 (t); 34.60 (t); 37.28 (d); 41.76 (q); 64.17 (t); 73.80 (d); 108.88 (s); 127.72 (d); 129.53 (d); 132.39 (d); 135.33 (d).

[(1,4-Dioxa-spiro[4.5]dec-8-yl)-thiophen-2-yl-methyl]-dimethylamine 8 (R$^3$=2-thienyl)

A solution of the aminonitrile 3 (2.24 g, 10 mmol) in abs. THF (10 ml) was added dropwise, under argon and while cooling with ice, to a 1M solution of thiophen-2-yl-magnesium bromide in THF (20 ml, 20 mmol), and stirring was carried out for 20 h at RT. For working up the reaction mixture, saturated ammonium chloride solution (10 ml) and water (10 ml) were added, while cooling with ice, and extraction with diethyl ether (3×10 ml) was carried out. The organic phase was washed with water and saturated sodium chloride solution, dried and concentrated.

Yield: 2.8 g (100%)

$^{13}$C-NMR (CDCl$_3$): 27.72 (t); 27.88 (t); 34.27 (t); 39.28 (d); 41.10 (q); 64.11 (t); 68.89 (d); 108.88 (s); 123.55 (d); 125.88 (d); 127.53 (d); 139.50 (s).

[1-(1,4-Dioxa-spiro[4.5]dec-8-yl)-3-phenyl-propyl]-dimethylamine 9 (R$^3$=phenethyl)

A solution of the aminonitrile 3 (21.93 g, 97 mmol) in abs. THF (180 ml) was added dropwise, under argon and while cooling with ice, to a 1M solution of phenylethylmagnesium chloride in THF (242 ml, 242 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried and concentrated.

Yield: 34 g (>100%).

$^{13}$C-NMR (CDCl$_3$): 27.43 (t); 28.95 (t); 29.42 (t); 34.82 (t); 35.40 (t); 38.76 (d); 41.16 (q); 64.17 (t); 67.41 (d); 108.86 (s); 125.41 (d); 127.66 (d); 128.11 (d); 142.69 (s).

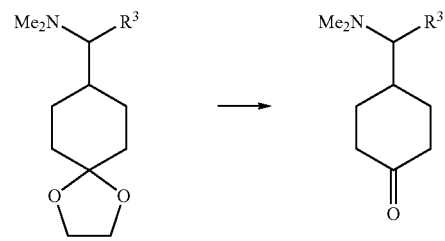

4-(Dimethylamino-phenyl-methyl)-cyclohexanone 10 (R$^3$=phenyl)

The ketal 4 (28.9 g, 0.105 mol) was dissolved in water (44 ml); conc. hydrochloric acid (64 ml) was added and stirring was carried out for 20 h at RT. The reaction mixture was extracted by shaking with diethyl ether (2×100 ml) and the aqueous phase was rendered alkaline with 5N NaOH, while cooling with ice, extracted with dichloromethane (3×100 ml), dried and concentrated. The ketone was isolated in the form of a colourless oil.

Yield: 18.2 g (75%)

$^1$H-NMR (CDCl$_3$): 1.20 (1 H, m); 1.33 (1 H, m); 1.74 (1 H, m); 2.17 (6 H, s, N(CH$_3$)$_2$); 2.70 (6 H, m); 3.10 (1 H, d, C$_8$—H); 7.07 (2H, m, C$_{arom}$—H); 7.23 (3 H, m, C$_{arom}$—H).

$^{13}$C-NMR (CDCl$_3$): 29.13; 30.56; 36.90 (C$_4$); 40.61; 40.82; 41.89 (N(CH$_3$)$_2$); 73.79 (CH); 127.05 (C$_{arom}$); 127.67 (C$_{arom}$); 129.00 (C$_{arom}$); 136.13 (C$_{arom}$); 211.79 (C=O).

4-[Dimethylamino-(4-fluorophenyl)-methyl]-cyclohexanone 11 (R$^3$=4-fluorophenyl)

The crude product of the ketal 5 (26 g, 88 mmol) was dissolved in water (40 ml); conc. hydrochloric acid (59 ml) was added and stirring was carried out for 20 h at RT. The reaction mixture was extracted with diethyl ether (2×100 ml) and the aqueous phase was rendered alkaline with 5N NaOH, while cooling with ice, extracted with dichloromethane (3×100 ml), dried and concentrated.

Yield: 21.36 g (98%)

$^{13}$C-NMR (CDCl$_3$): 28.90 (t); 30.48 (t); 37.00 (t); 40.49 (t); 40.72 (t); 41.79 (q); 72.98 (d); 114.42 (d); 114.62 (d); 130.20 (d); 130.28 (d); 131.88 (s); 160.50 (s); 162.93 (s); 211.44 (s).

4-[Dimethylamino-(3-fluorophenyl)-methyl]-cyclohexanone 12 (R$^3$=3-fluorophenyl)

The ketal 6 (30.3 g, 103 mmol) was dissolved in water (44 ml); conc. hydrochloric acid (64 ml) was added and stirring was carried out for 20 h at RT. The reaction mixture was extracted by shaking with diethyl ether (2×100 ml) and the aqueous phase was rendered alkaline with 5N NaOH, while cooling with ice, extracted with dichloromethane (3×100 ml), dried and concentrated. The ketone was isolated in the form of a colourless solid.

Yield: 22.4 g (87%)

Melting point: 72-75° C.

$^{13}$C-NMR (CDCl$_3$): 28.97 (t); 30.44 (t); 36.90 (t); 40.52 (t); 40.75 (t); 41.82 (q); 73.37 (d); 113.84; 114.06; 115.42; 115.62; 124.71; 129.03; 129.11; 139.00; 139.06; 161.16; 163.60; 211.40 (s).

4-[(4-Chloro-phenyl)-dimethylamino-methyl]-cyclohexanone 13 (R$^3$=4-chlorophenyl)

The ketal 7 (30.98 g, 100 mmol) was dissolved in water (44 ml); conc. hydrochloric acid (64 ml) was added and stirring was carried out for 20 h at RT. The reaction mixture was extracted by shaking with diethyl ether (2×100 ml) and the aqueous phase was rendered alkaline with 5N NaOH, while cooling with ice, extracted with dichloromethane (3×100 ml), dried and concentrated. The ketone was isolated in the form of an oil.

Yield: 21.9 g (82%)

$^{13}$C-NMR (CDCl$_3$): 28.88 (t); 30.45 (t); 36.89 (t); 40.49 (t); 40.74 (t); 41.83 (q); 73.12 (d); 127.87 (d); 130.16 (d); 132.75 (d); 134.70 (s); 211.35 (s).

4-(Dimethylamino-thiophen-2-yl-methyl)-cyclohexanone 14 (R$^3$=2-thienyl)

The ketal 8 (2.80 g, 10 mmol) was dissolved in water (4.4 ml); conc. hydrochloric acid (6.4 ml) was added and stirring was carried out for 20 h at RT. The reaction mixture was extracted by shaking with diethyl ether (2×10 ml) and the aqueous phase was rendered alkaline with 5N NaOH, while cooling with ice, extracted with dichloromethane (3×10 ml), dried and concentrated. The ketone was isolated in the form of an oil.

Yield: 1.79 g (75%)

$^{13}$C-NMR (CDCl$_3$): 30.02 (t); 30.18 (t); 38.84 (t); 40.29 (t); 39.28 (d); 41.17 (q); 68.24 (d); 123.88 (d); 126.01 (d); 126.34 (d); 138.77 (d); 211.49 (s).

4-(1-Dimethylamino-3-phenyl-propyl)-cyclohexanone 15 (R$^3$=phenethyl)

The crude product of the ketal 9 (29.6 g, 97 mmol) was dissolved in water (44 ml); conc. hydrochloric acid (64 ml) was added and stirring was carried out for 20 h at RT. The reaction mixture was extracted by shaking with diethyl ether (2×100 ml) and the aqueous phase was rendered alkaline with 5N NaOH, while cooling with ice, extracted with dichloromethane (3×100 ml), dried and concentrated. The ketone was isolated in the form of a colourless oil.

Yield: 16.9 g (58%)

$^{13}$C-NMR (CDCl$_3$): 29.40 (t); 30.02 (t); 30.97 (t); 35.34 (t); 38.71 (t); 40.79 (t); 41.01 (t); 41.23 (q); 66.65 (d); 125.66 (d); 128.12 (d); 128.19 (d); 142.27 (s); 211.70 (s).

Synthesis of the Amino-, Aminomethyl- and Aminoethyl-cyclohexyls

The corresponding amines can then be obtained from the cyclohexanone derivatives by simple transformation.

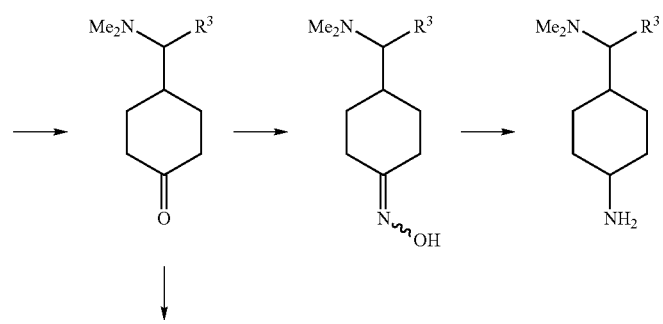

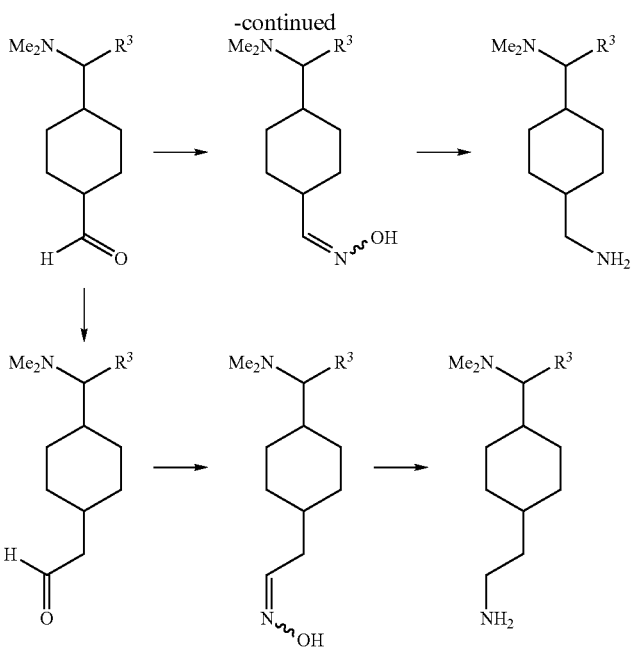

Synthesis of the Aminocyclohexanes ($R^1=(CH_2)_n NH_2$, n=0)

The aminocyclohexanes were prepared from the correspondingly substituted cyclohexanones by two-stage reactions with hydroxylamine hydrochloride and subsequent cleavage with lithium aluminium hydride.

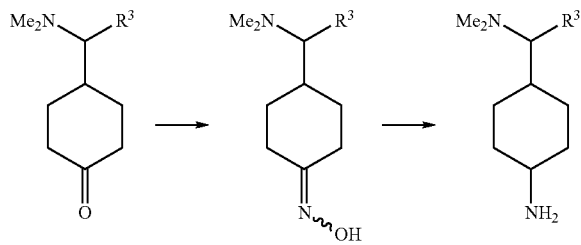

4-(Dimethylamino-phenyl-methyl)-cyclohexanone oxime 16 ($R^3$=phenyl)

The ketone 10 (9.25 g, 40 mmol) and hydroxylamine hydrochloride (4.17 g, 60 mmol) were dissolved in abs. ethanol (150 ml); basic ion exchanger Amberlyst A21 (28 g) was added and stirring was carried out overnight at RT. The ion exchanger was filtered off and washed with ethanol (2×50 ml). The solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 9.54 g (97%)

Melting point: 110-115° C. (colourless crystals)

$^{13}$C-NMR (CDCl$_3$): 23.53; 23.70; 27.87; 29.04; 29.48; 30.70; 31.26; 31.40; 37.89 ($C_4$); 42.02 (N(CH$_3$)$_2$); 74.36 (CH); 126.87 ($C_{arom}$); 127.56 ($C_{arom}$); 129.09 ($C_{arom}$); 136.57 ($C_{arom}$); 160.12 (C=N—O).

4-(Dimethylamino-phenyl-methyl)-cyclohexylamine 17 ($R^3$=phenyl)

LiAlH$_4$ (2.92 g, 77 mmol) was added, under argon, to absolute THF (400 ml); the mixture was heated to 60° C., and the oxime 16 (9.5 g, 38.5 mmol) dissolved in THF (90 ml) was added dropwise. After 4 hours' stirring at 60° C., water (100 ml) was added dropwise, while cooling with an ice bath (10° C.), and the solution was filtered off with suction over kieselguhr. The filter residue was washed with THF. The THF was removed in vacuo and the residue was adjusted to pH 11 with 5N NaOH and extracted with ethyl acetate (4×40 ml). The organic phase was dried over sodium sulfate and concentrated by evaporation, and the residue was purified over a silica gel column (300 g) with MeCN/MeOH/0.5 M NH$_4$Cl (9:1:1).

The individual fractions were dissolved in water and methylene chloride and rendered alkaline with ammonia, and the aqueous phase was extracted (twice) with CH$_2$Cl$_2$.

Total yield: 6.33 g (71%), oil $^{13}$C-NMR (CDCl$_3$): 24.22; 24.80; 28.24; 29.96; 32.39; 32.45; 36.03; 36.58; 36.79; 37.93 ($C_4$); 41.33; 41.89 (N(CH$_3$)$_2$); 47.42; 50.85; 71.95; 75.22 (CH); 126.52 ($C_{arom}$); 127.29 ($C_{arom}$); 127.33 ($C_{arom}$); 129.04 ($C_{arom}$); 129.11 ($C_{arom}$); 136.22 ($C_{arom}$); 137.03 ($C_{arom}$).

4-[Dimethylamino-(4-fluorophenyl)-methyl]-cyclohexanone oxime 18 ($R^3$=4-fluorophenyl)

The ketone 11 (10.68 g, 43 mmol) and hydroxylamine hydrochloride (4.52 g, 65 mmol) were dissolved in abs. ethanol (160 ml); basic ion exchanger Amberlyst A21 (30 g) was added and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml) and the organic phase was dried over sodium sulfate and concentrated in vacuo.

Yield: 10.49 g (93%)

$^{13}$C-NMR (CDCl$_3$): 23.76; 23.66; 27.69; 28.87; 29.50; 30.73; 31.22; 31.38; 38.06 ($C_4$); 42.01 (N(CH$_3$)$_2$); 73.66

(CH); 114.36 ($C_{arom}$); 114.57 ($C_{arom}$); 130.32 ($C_{arom}$); 130.40 ($C_{arom}$); 132.40 ($C_{arom}$); 160.03 (C=N—O); 160.49 ($C_{arom}$); 162.93 ($C_{arom}$).

4-[Dimethylamino-(4-fluorophenyl)-methyl]-cyclohexylamine 19 ($R^3$=4-fluorophenyl)

LiAlH$_4$ (3.04 g, 82 mmol) was added, under argon, to absolute THF (435 ml); the mixture was heated to 60° C., and the oxime 18 (10.49 g, 40 mmol) dissolved in THF (90 ml) was added dropwise. After 4 hours' stirring at 60° C., water (100 ml) was added dropwise, while cooling with an ice bath (10° C.), and the solution was filtered off with suction over kieselguhr. The filter residue was washed with THF. The THF was removed in vacuo and the residue was adjusted to pH 11 with 5N NaOH and extracted with ethyl acetate (4×50 ml). The organic phase was dried over sodium sulfate and concentrated by evaporation, and the residue was purified by flash chromatography with MeCN/MeOH/0.5M NH$_4$Cl (9:1:1). The individual fractions were dissolved in water and methylene chloride and rendered alkaline with ammonia, and the aqueous phase was extracted twice with CH$_2$Cl$_2$.

Yield: 6.95 g (70%), oil $^{13}$C-NMR (CDCl$_3$): 24.01; 24.76; 27.99; 29.92; 32.32; 36.26; 36.51; 36.73; 38.07; 41.26 (C$_4$); 41.85 (N(CH$_3$)$_2$); 47.31; 50.81; 71.25; 74.44 (CH); 114.01 ($C_{arom}$); 114.08 ($C_{arom}$); 130.20 ($C_{arom}$); 130.27 ($C_{arom}$); 132.02 ($C_{arom}$); 132.85 ($C_{arom}$); 160.22 ($C_{arom}$); 162.64 ($C_{arom}$).

4-[Dimethylamino-(3-fluorophenyl)-methyl]-cyclohexanone oxime 20 ($R^3$=3-fluorophenyl)

The ketone 12 (10 g, 40 mmol) and hydroxylamine hydrochloride (4.17 g, 60 mmol) were dissolved in abs. ethanol (150 ml); basic ion exchanger Amberlyst A21 (28 g) was added and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml) and the organic phase was dried over sodium sulfate and concentrated in vacuo.

Yield: 10.05 g (95%)

$^{13}$C-NMR (CDCl$_3$): 23.48; 23.66; 27.69; 28.87; 29.39; 30.61; 31.18; 31.33; 37.91 (C$_4$); 41.99 (N(CH$_3$)$_2$); 74.00 (CH); 113.70 ($C_{arom}$); 113.90 ($C_{arom}$); 115.51 ($C_{arom}$); 124.80 ($C_{arom}$); 128.90 ($C_{arom}$); 128.98 ($C_{arom}$); 139.48 ($C_{arom}$); 139.54 ($C_{arom}$); 159.89 (C=N—O); 161.13 ($C_{arom}$); 163.57 ($C_{arom}$).

4-[Dimethylamino-(3-fluorophenyl)-methyl]-cyclohexylamine 21 ($R^3$=3-fluorophenyl)

LiAlH$_4$ (2.83 g, 75 mmol) was added, under argon, to absolute THF (400 ml); the mixture was heated to 60° C., and the oxime 20 (9.86 g, 37.3 mmol) dissolved in THF (90 ml) was added dropwise. After 4 hours' stirring at 60° C., water (100 ml) was added dropwise, while cooling with an ice bath (10° C.), and the solution was filtered off with suction over kieselguhr. The filter residue was washed with THF. The THF was removed in vacuo and the residue was adjusted to pH 11 with 5N NaOH and extracted with ethyl acetate (4×40 ml). The organic phase was dried over sodium sulfate and concentrated by evaporation, and the residue was purified over a silica gel column (300 g) with MeCN/MeOH/0.5 M NH$_4$Cl (9:1:1). The individual fractions were dissolved in water and methylene chloride and rendered alkaline with ammonia, and the aqueous phase was extracted twice with CH$_2$Cl$_2$.

Yield: 6.81 g (73%), oil $^{13}$C-NMR (CDCl$_3$): 24.08; 24.69; 28.05; 29.84; 32.33; 32.37; 36.10; 36.48; 36.69; 37.95; 41.27 (C$_4$); 41.85 (N(CH$_3$)$_2$); 47.32; 50.81; 71.63; 74.81 (CH); 113.29 ($C_{arom}$); 115.43 ($C_{arom}$); 124.74 ($C_{arom}$); 128.58 ($C_{arom}$); 139.19 ($C_{arom}$); 139.99 ($C_{arom}$); 160.97 ($C_{arom}$); 163.41 ($C_{arom}$).

4-[(4-Chlorophenyl)-dimethylamino-methyl]-cyclohexanone oxime 22 ($R^3$=4-chlorophenyl)

The ketone 13 (15.76 g, 59.2 mmol) and hydroxylamine hydrochloride (6.25 g, 90 mmol) were dissolved in abs. ethanol (200 ml); basic ion exchanger Amberlyst A21 (42 g) was added and stirring was carried out overnight at RT. The ion exchanger was filtered off and washed with ethanol (2×70 ml). The solution was concentrated, the residue was adjusted to pH 11 with 5N NaOH, the aqueous phase was extracted with ethyl acetate (3×70 ml) and the organic phase was dried over sodium sulfate and concentrated in vacuo.

Yield: 16.6 g (100%)

$^{13}$C-NMR (CDCl$_3$): 23.46; 23.66; 27.65; 28.81; 29.44; 30.67; 31.21; 31.37; 37.93 (C$_4$); 42.05 (N(CH$_3$)$_2$); 73.76 (CH); 127.80 ($C_{arom}$); 130.27 ($C_{arom}$); 132.62 ($C_{arom}$); 135.20 159.90 (C=N—O).

4-[(4-Chlorophenyl)-dimethylamino-methyl]-cyclohexylamine 23 ($R^3$=4-chlorophenyl)

LiAlH$_4$ (4.48 g, 118 mmol) was added, under argon, to absolute THF (600 ml); the mixture was heated to 60° C., and the oxime 22 (16.6 g, 59 mmol) dissolved in THF (120 ml) was added dropwise. After 4 hours' stirring at 60° C., water (150 ml) was added dropwise, while cooling with an ice bath (10° C.), and the solution was filtered off with suction over kieselguhr. The filter residue was washed with THF. The THF was removed in vacuo and the residue was adjusted to pH 11 with 5N NaOH and extracted with ethyl acetate (4×100 ml). The organic phase was dried over sodium sulfate and concentrated by evaporation, and the residue was purified over a silica gel column (400 g) with MeCN/MeOH/0.5M NH$_4$Cl (8:2:1).

The individual fractions were dissolved in water and methylene chloride and rendered alkaline with ammonia, and the aqueous phase was extracted twice with CH$_2$Cl$_2$.

Yield: 12.02 g (76%), oil $^{13}$C-NMR (CDCl$_3$): 24.06; 24.80; 27.99; 29.96; 32.41; 36.24; 36.58; 36.81; 38.06; 41.39 (C$_4$); 42.00 (N(CH$_3$)$_2$); 47.36; 50.89; 71.51; 74.66 (CH); 127.58 ($C_{arom}$); 127.65 ($C_{arom}$); 130.30 ($C_{arom}$); 130.35 ($C_{arom}$); 132.27 ($C_{arom}$); 134.94 ($C_{arom}$); 135.80 ($C_{arom}$).

4-(Dimethylamino-thiophen-2-yl-methyl)-cyclohexanone oxime 24 ($R^3$=2-thiophene)

The ketone 14 (9.49 g, 40 mmol) and hydroxylamine hydrochloride (4.17 g, 60 mmol) were dissolved in abs. ethanol (150 ml); basic ion exchanger Amberlyst A21 (28 g) was added and stirring was carried out overnight at RT. The ion exchanger was filtered off and washed with ethanol (2×50 ml). The solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 9.21 g (91%)

Melting point: 118-121° C., yellow crystals

4-(Dimethylamino-thiophen-2-yl-methyl)-cyclohexylamine 25 (R³=2-thiophene)

LiAlH₄ (2.73 g, 72 mmol) was added, under argon, to absolute THF (300 ml); the mixture was heated to 60° C., and the oxime 24 (9.08 g, 35.9 mmol) dissolved in THF (80 ml) was added dropwise. After 4 hours' stirring at 60° C., water (80 ml) was added dropwise, while cooling with an ice bath (10° C.), and the solution was filtered off with suction over kieselguhr. The filter residue was washed with THF. The THF was removed in vacuo and the residue was adjusted to pH 11 with 5N NaOH and extracted with ethyl acetate (3×50 ml). The organic phase was dried over sodium sulfate and concentrated by evaporation, and the residue was purified over a silica gel column (300 g) with MeCN/MeOH/0.5M NH₄Cl (8:2:1). The individual fractions were dissolved in water and methylene chloride and rendered alkaline with ammonia, and the aqueous phase was extracted twice with CH₂Cl₂.

Total yield: 5.66 g (66%), oil
¹³C-NMR (CDCl₃): 24.81; 24.96; 29.26; 29.76; 32.18; 32.22; 36.46; 36.58; 38.10; 39.99; 40.86; 41.20 (N(CH₃)₂); 47.66; 50.80; 64.27; 69.82; 123.43; 125.71; 125.75; 125.95; 126.07; 139.34; 139.79.

4-(1-Dimethylamino-3-phenyl-propyl)-cyclohexanone oxime 26 (R³=phenethyl)

The ketone 15 (10.2 g, 40 mmol) and hydroxylamine hydrochloride (4.17 g, 60 mmol) were dissolved in abs. ethanol (150 ml); basic ion exchanger Amberlyst A21 (28 g) was added and stirring was carried out overnight at RT. The ion exchanger was filtered off and washed with ethanol (2×50 ml), the solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 10.8 g (100%), oil
¹³C-NMR (CDCl₃): 23.80; 23.96; 28.80; 29.27; 30.00; 31.21; 31.49; 31.58; 35.89 (C₄); 39.29; 41.26 (N(CH₃)₂); 67.24 (CH); 125.58 (C_arom); 128.13 (C_arom); 142.40 (C_arom); 159.99; 160.04 (C=N—O).

4-(1-Dimethylamino-3-phenyl-propyl)-cyclohexylamine 27 (R³=phenethyl)

LiAlH₄ (3.04 g, 82 mmol) was added, under argon, to absolute THF (435 ml); the mixture was heated to 60° C., and the oxime 26 (11.14 g, 40 mmol) dissolved in THF (90 ml) was added dropwise. After 4 hours' stirring at 60° C., water (100 ml) was added dropwise, while cooling with an ice bath (10° C.), and the solution was filtered off with suction over kieselguhr. The filter residue was washed with THF. The THF was removed in vacuo and the residue was adjusted to pH 11 with 5N NaOH and extracted with ethyl acetate (4×50 ml). The organic phase was dried over sodium sulfate and concentrated by evaporation, and the residue was purified over a silica gel column (300 g) with MeCN/MeOH/0.5M NH₄Cl (9:1:1) and (9:4:1).

The individual fractions were dissolved in water and methylene chloride and rendered alkaline with ammonia, and the aqueous phase was extracted twice with CH₂Cl₂.

Yield: 5.02 g (50%), oil
¹³C-NMR (CDCl₃): 24.70; 25.36; 29.22; 29.35; 30.42; 32.98; 35.46; 35.72; 36.95; 37.07; 38.89 (C₄); 39.32; 41.04; 41.26 (N(CH₃)₂); 46.98; 50.85; 66.01; 68.05 (CH); 125.49 (C_arom); 128.11 (C_arom); 128.14 (C_arom); 142.75 (C_arom).

Synthesis of the Aminomethylcyclohexanes (R¹=(CH₂)_nNH₂, n=1)

The aminomethylcyclohexanes were prepared from the correspondingly substituted cyclohexanones via the stage of the cyclohexylaldehydes by three-stage reactions by reaction with hydroxylamine hydrochloride and subsequent cleavage with lithium aluminium hydride.

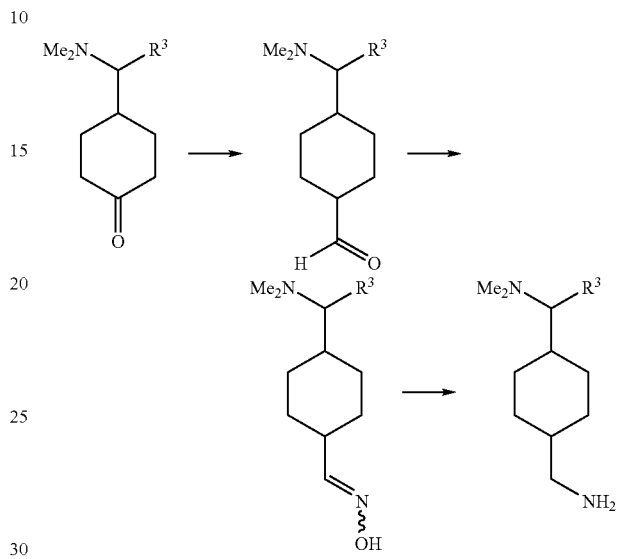

4-(Dimethylamino-phenyl-methyl)-cyclohexane-carbaldehyde 28 (R³=phenyl)

(Methoxymethyl)triphenylphosphonium chloride (31.5 g, 0.092 mol) was suspended, under argon, in abs. THF (150 ml); potassium tert-butylate (10.38 g, 0.092 mol) dissolved in abs. THF (100 ml) was added dropwise at 0° C., and stirring was then carried out for 15 minutes at 0° C. (the solution turned deep-orange in colour).

The ketone 10 (14.2 g, 0.061 mol) dissolved in abs. THF (100 ml) was then added dropwise to the above solution at RT, and stirring was carried out overnight at RT. Hydrolysis was carried out dropwise with water (50 ml) and 6N HCl (150 ml), while cooling with ice-water. After 1 hour's stirring at RT, extraction with ether (10×50 ml) was carried out and the aqueous phase was adjusted to pH 11 with 5N NaOH, extracted by shaking with ethyl acetate (3×50 ml), dried over Na₂SO₄ and concentrated in vacuo. The crude product was purified over a silica gel column (300 g) with ethyl acetate/cyclohexane (1:1).

Yield: 12.2 g (82%)
¹³C-NMR (CDCl₃): 24.01; 24.22; 25.90; 26.06; 26.40; 27.33; 28.21; 29.92; 37.00; 38.19 (C₄); 41.51; 41.98; (N(CH₃)₂); 47.45; 50.60; 73.37; 75.24 (CH); 126.72 (C_arom); 126.76 (C_arom); 127.48 (C_arom); 129.13 (C_arom); 136.14 (C_arom); 136.79 (C_arom); 204.22; 205.05 (CHO).

4-(Dimethylamino-phenyl-methyl)-cyclohexane-carbaldehyde oxime 29 (R³=phenyl)

The carbaldehyde 28 (7.36 g, 30 mmol) and hydroxylamine hydrochloride (3.12 g, 45 mmol) were dissolved in abs. ethanol (100 ml); basic ion exchanger Amberlyst A21 (21 g) was added and stirring was carried out overnight at RT. The ion exchanger was filtered off and washed with ethanol (2×50 ml). The solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 7.81 g (100%)

$^{13}$C-NMR (CDCl$_3$): 25.83; 26.34; 27.10; 27.55; 28.25; 29.41; 30.12; 30.32; 34.20; 36.45; 36.74; 37.00; 38.19 (C$_4$); 41.37; 41.03; (N(CH$_3$)$_2$); 72.28; 75.59 (CH); 126.77 (C$_{arom}$); 127.50 (C$_{arom}$); 129.22 (C$_{arom}$); 136.14 (C$_{arom}$); 136.94 (C$_{arom}$); 137.05 (C$_{arom}$); 154.84; 155.55; 156.35.

[(4-Aminomethyl-cyclohexyl)-phenyl-methyl]-dimethylamine 30 (R$^3$=phenyl)

LiAlH$_4$ (2.27 g, 60 mmol) was added, under argon, to absolute THF (300 ml); the mixture was heated to 60° C. and the oxime 29 (7.81 g, 30 mmol) dissolved in THF (60 ml) was added dropwise. After 4 hours' stirring at 60° C., water (70 ml) was added dropwise, while cooling with an ice bath (10° C.), and the reaction solution was filtered off with suction over kieselguhr. The filter residue was washed with THF. The combined organic phases were concentrated in vacuo and the residue was adjusted to pH 11 with 5N NaOH and extracted with ethyl acetate (4×40 ml). The organic phase was dried over sodium sulfate and concentrated.

Yield: 6.4 g (87%), oil $^{13}$C-NMR (CDCl$_3$): 25.53; 26.03; 26.64; 26.68; 29.06; 30.37; 30.51; 30.67; 30.74; 36.01; 38.83; 38.93; (C$_4$); 41.50; 41.94; (N(CH$_3$)$_2$); 72.28; 75.59 (CH); 126.77 (C$_{arom}$); 127.50 (C$_{arom}$); 129.22 (C$_{arom}$); 136.14 (C$_{arom}$); 136.94 (C$_{arom}$); 137.05 (C$_{arom}$); 154.84; 155.55; 156.35.

4-[Dimethylamino-(4-fluorophenyl)-methyl]-cyclohexane-carbaldehyde 31 (R$^3$=4-fluorophenyl)

(Methoxymethyl)triphenylphosphonium chloride (25.7 g, 75 mmol) was suspended, under argon, in abs. THF (100 ml); potassium tert-butylate (8.42 g, 75 mmol) dissolved in abs. THF (70 ml) was added dropwise at 0° C., and stirring was then carried out for 15 minutes at 0° C.

The ketone 11 (12.44 g, 50 mmol) dissolved in abs. THF (75 ml) was then added dropwise to the above solution at RT, and stirring was carried out overnight at RT. Hydrolysis was carried out dropwise with water (38 ml) and 6N HCl (112 ml), while cooling with ice-water. After 1 hour's stirring at RT, extraction with ether (10×50 ml) was carried out and the aqueous phase was adjusted to pH 11 with 5N NaOH, extracted by shaking with ethyl acetate (3×50 ml), dried over Na$_2$SO$_4$ and concentrated in vacuo. The crude product was purified by flash chromatography with ethyl acetate/cyclohexane (1:1).

Yield: 9.13 g (70%).

$^1$H-NMR (DMSO, 600 MHz, selected signals): δ=1.97 (s, 3 H); 1.99 (s, 3 H); 3.08 (d, 1 H, J=9.06 Hz); 3.14 (d, 1 H, J=9.82 Hz); 9.53 (s, 1 H); 9.56 (s, 1 H).

$^{13}$C-NMR (CDCl$_3$, both diastereoisomers): δ=23.97; 24.21; 25.85; 26.02; 26.17; 27.35; 28.00; 29.90; 37.26; 38.34; 41.50; 41.95; 47.36; 50.55; 72.75; 75.84; 114.25; 114.45; 130.33; 130.40; 132.61; 160.41; 162.83; 204.10; 204.93.

4-[Dimethylamino-(4-fluorophenyl)-methyl]-cyclohexane-carbaldehyde oxime 32 (R$^3$=4-fluorophenyl)

The aldehyde 31 (6.50 g, 25 mmol) and hydroxylamine hydrochloride (2.6 g, 37.5 mmol) were dissolved in abs. ethanol (80 ml); basic ion exchanger Amberlyst A21 (16.5 g) was added and stirring was carried out overnight at RT. The ion exchanger was filtered off and washed with ethanol (2×50 ml). The solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 6.9 g (99%)

[(4-Aminomethyl-cyclohexyl)-(4-fluorophenyl)-methyl]-dimethylamine 33 (R$^3$=4-fluorophenyl)

LiAlH$_4$ (1.9 g, 50 mmol) was added, under argon, to absolute THF (360 ml); the mixture was heated to 60° C. and the oxime 32 (6.9 g, 25 mmol) dissolved in THF (60 ml) was added dropwise. After 4 hours' stirring at 60° C., water (93 ml) was added dropwise, while cooling with an ice bath (10° C.), and the reaction solution was filtered off with suction over kieselguhr. The filter residue was washed with THF. The combined organic phases were concentrated in vacuo and the residue was adjusted to pH 11 with 5N NaOH and extracted three times with ethyl acetate (100 ml each time). The organic phase was dried over sodium sulfate and concentrated.

Yield: 5.4 g (82%), oil $^{13}$C-NMR (CDCl$_3$): 25.25; 25.93; 26.60; 28.75; 30.30; 30.40; 30.67; 36.20; 38.78; 38.93; (C$_4$); 41.24; 41.43 (N(CH$_3$)$_2$); 48.71; 70.62; 74.69 (CH); 113.97 (C$_{arom}$); 114.04 (C$_{arom}$); 130.24 (C$_{arom}$); 130.31 (C$_{arom}$); 132.94 (C$_{arom}$); 160.19; 162.62; (C$_{arom}$).

4-[Dimethylamino-(3-fluorophenyl)-methyl]-cyclohexane-carbaldehyde (R$^3$=3-fluorophenyl) 34

(Methoxymethyl)triphenylphosphonium chloride (15.42 g, 45 mmol) was suspended, under argon, in abs. THF (50 ml); potassium tert-butylate (5.05 g, 45 mmol) dissolved in abs. THF (50 ml) was added dropwise at 0° C., and stirring was then carried out for 15 minutes at 0° C.

The ketone 12 (7.48 g, 0.30 mmol) dissolved in abs. THF (50 ml) was then added dropwise to the above solution at RT, and stirring was carried out overnight at RT. Hydrolysis was carried out dropwise with water (25 ml) and 6N HCl (75 ml), while cooling with ice-water. After 1 hour's stirring at RT, extraction with ether (10×50 ml) was carried out and the aqueous phase was adjusted to pH 11 with 5N NaOH, extracted with ethyl acetate (3×50 ml), dried over Na$_2$SO$_4$ and concentrated in vacuo. The crude product was purified by flash chromatography with ethyl acetate/cyclohexane (1:1).

Yield: 6.55 g (83%).

Melting point: 40-43° C.

$^1$H-NMR (DMSO, 600 MHz, selected signals): δ=1.99 (s, 3 H); 2.01 (s, 3 H); 3.10 (d, 1 H, J=9.06 Hz); 3.18 (d, 1 H, J=9.82 Hz); 9.54 (s, 1 H); 9.56 (s, 1 H).

$^{13}$C-NMR (CDCl$_3$): 23.93; 24.12; 25.79; 25.95; 26.19; 27.19; 27.99; 29.77; 37.05; 38.16; 41.45; 41.91; 47.30; 50.49; 71.50; 74.78; 113.50; 115.37; 124.78; 128.24; 130.59; 131.24; 131.67; 139.14; 139.76; 160.06; 163.50; 204.01; 204.85.

4-[Dimethylamino-(3-fluorophenyl)-methyl]-cyclohexane-carbaldehyde oxime 35 (R$^3$=3-fluorophenyl)

The carbaldehyde 34 (6.32 g, 24 mmol) and hydroxylamine hydrochloride (2.5 g, 36 mmol) were dissolved in abs. ethanol (90 ml); basic ion exchanger Amberlyst A21 (17 g) was added and stirring was carried out for 3.5 h at RT. The ion exchanger was filtered off and washed with ethanol (2×50 ml). The solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 6.68 g (100%)

$^{13}$C-NMR (CDCl$_3$): 25.59; 26.21; 27.38; 28.02; 28.36; 29.27; 29.45; 30.00; 34.14; 35.58; 36.56; 38.19 (C$_4$); 41.33; 41.99; (N(CH$_3$)$_2$); 72.02; 75.05; 75.19 (CH); 113.55 (C$_{arom}$); 115.62 (C$_{arom}$); 124.88 (C$_{arom}$); 128.78 (C$_{arom}$); 128.86 (C$_{arom}$); 139.84 (C$_{arom}$); 139.90 (C$_{arom}$); 154.38; 155.13; 161.10 (C$_{arom}$); 163.54 (C$_{arom}$).

[(4-Aminomethyl-cyclohexyl)-(3-fluorophenyl)-methyl]-dimethylamine 36 (R$^3$=3-fluorophenyl)

LiAlH$_4$ (1.82 g, 48 mmol) was added, under argon, to absolute THF (300 ml); the mixture was heated to 60° C. and the oxime 35 (6.68 g, 24 mmol) dissolved in THF (60 ml) was added dropwise. After 4 hours' stirring at 60° C., water (70 ml) was added dropwise, while cooling with an ice bath (10° C.), and the reaction solution was filtered over kieselguhr. The filter residue was washed with THF, the organic phases were combined, the THF was removed in vacuo and the residue was adjusted to pH 11 with 5N NaOH and extracted with ethyl acetate (4×40 ml). The organic phase was dried over sodium sulfate and concentrated.

Yield: 5.7 g (90%), oil $^{13}$C-NMR (CDCl$_3$): 25.38; 25.93; 26.44; 28.89; 30.36; 30.45; 30.65; 30.87; (C$_4$); 41.33; 41.49; 41.93 (N(CH$_3$)$_2$); 71.05; 75.11 (CH); 113.94 (C$_{arom}$); 115.53 (C$_{arom}$); 124.86 (C$_{arom}$); 128.59 (C$_{arom}$); 128.67 (C$_{arom}$); 140.14 (C$_{arom}$); 141.21 (C$_{arom}$); 161.03 (C$_{arom}$); 163.46 (C$_{arom}$).

4-[(4-Chloro-phenyl)-dimethylamino-methyl]-cyclohexane-carbaldehyde 37 (R$^3$=4-chlorophenyl)

(Methoxymethyl)triphenylphosphonium chloride (68.55 g, 200 mmol) was suspended, under argon, in abs. THF (200 ml); potassium tert-butylate (22.44 g, 200 mmol) dissolved in abs. THF (300 ml) was added dropwise at 0° C., and stirring was then carried out for 15 minutes at 0° C.

The ketone 13 (38 g, 143 mmol) dissolved in abs. THF (200 ml) was then added dropwise to the above solution at RT, and stirring was carried out overnight at RT. Hydrolysis was carried out dropwise with water (150 ml) and 6N HCl (450 ml), while cooling with ice-water. After 1 hour's stirring at RT, extraction with ether (10×100 ml) was carried out and the aqueous phase was adjusted to pH 11 with 5N NaOH, extracted by shaking with ethyl acetate (3×100 ml), dried over Na$_2$SO$_4$ and concentrated in vacuo. The crude product was purified over two silica gel columns (400 g) with ethyl acetate/cyclohexane (1:1).

Yield: 32.17 g (80%).

$^1$H-NMR (DMSO, 600 MHz, selected signals): δ=1.97 (s, 3 H); 1.99 (s, 3 H); 3.07 (d, 1 H, J=9.07 Hz); 3.14 (d, 1 H, J=9.82 Hz); 9.53 (s, 1 H, 9.55 (s, 1 H).

$^{13}$C-NMR (CDCl$_3$): δ=23.92; 24.16; 25.80; 25.97; 26.13; 27.25; 27.90; 29.81; 37.08; 38.19; 41.47; 41.96; 47.29; 50.48; 72.81; 74.54; 127.65; 130.28; 132.40; 134.78; 135.43; 203.98; 204.82.

4-[(4-Chlorophenyl)-dimethylamino-methyl]-cyclohexanecarbaldehyde oxime 38 (R$^3$=4-chlorophenyl)

The carbaldehyde 37 (7.55 g, 27 mmol) and hydroxylamine hydrochloride (2.81 g, 40 mmol) were dissolved in abs. ethanol (100 ml); basic ion exchanger Amberlyst A21 (19 g) was added and stirring was carried out for 3.5 h at RT.

The ion exchanger was filtered off and washed with ethanol (2×50 ml). The solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 7.57 g (96%)

[(4-Aminomethyl-cyclohexyl)-(4-chlorophenyl)-methyl]-dimethylamine 39 (R$^3$=4-chlorophenyl)

LiAlH$_4$ (1.89 g, 50 mmol) was added, under argon, to absolute THF (300 ml); the mixture was heated to 60° C. and the oxime 38 (7.5 g, 25 mmol) dissolved in THF (60 ml) was added dropwise. After 4 hours' stirring at 60° C., water (70 ml) was added dropwise, while cooling with an ice bath (10° C.), and the reaction solution was filtered over kieselguhr. The filter residue was washed with THF, the organic phases were combined, the THF was removed in vacuo and the residue was adjusted to pH 11 with 5N NaOH and extracted with ethyl acetate (4×40 ml). The organic phase was dried over sodium sulfate and concentrated.

Yield: 6.3 g (90%), oil $^{13}$C-NMR (CDCl$_3$): 25.22; 25.87; 26.58; 28.70; 30.36; 30.53; 30.59; 36.02; 38.76 (C$_4$); 41.29; 41.39; 41.91 (N(CH$_3$)$_2$); 45.64; 48.72; 70.72; 74.77 (CH); 127.46 (C$_{arom}$); 127.52 (C$_{arom}$); 130.27 (C$_{arom}$); 132.11 (C$_{arom}$); 132.15 (C$_{arom}$); 134.80 (C$_{arom}$); 135.72 (C$_{arom}$).

4-(Dimethylamino-thiophen-2-yl-methyl)-cyclohexanecarbaldehyde 40 (R$^3$=2-thienyl)

(Methoxymethyl)triphenylphosphonium chloride (20.56 g, 60 mmol) was suspended, under argon, in abs. THF (70 ml); potassium tert-butylate (6.73 g, 60 mmol) dissolved in abs. THF (70 ml) was added dropwise at 0° C., and stirring was then carried out for 15 minutes at 0° C. The ketone 14 (9.4 g, 40 mmol) dissolved in abs. THF (70 ml) was then added dropwise to the above solution at RT, and stirring was carried out overnight at RT. Hydrolysis was carried out dropwise with water (60 ml) and 6N HCl (180 ml), while cooling with ice-water. After 1 hour's stirring at RT, extraction with ether (5×50 ml) was carried out and the aqueous phase was adjusted to pH 11 with 5N NaOH, extracted by shaking with ethyl acetate (3×50 ml), dried over Na$_2$SO$_4$ and concentrated in vacuo. The crude product was purified by flash chromatography with ethyl acetate/-cyclohexane (1:1).

Yield: 7.66 g (77%).

$^1$H-NMR (DMSO, 600 MHz, selected signals): δ=2.03 (s, 3 H); 2.05 (s, 3 H); 3.44 (d, 1 H, J=9.82 Hz); 3.52 (d, 1 H, J=10.58 Hz); 9.54 (s, 1 H); 9.58 (s, 1 H).

$^{13}$C-NMR (CDCl$_3$): δ=23.74; 23.83; 25.80; 25.84; 26.98; 27.09; 29.15; 29.68; 39.13; 40.20; 40.98; 41.29 (N(CH$_3$)$_2$); 47.48; 50.49; 67.81; 69.79; 123.61; 123.70; 125.89; 126.20; 126.24; 139.14; 139.48; 204.07; 204.82.

4-(Dimethylamino-thiophen-2-yl-methyl)-cyclohexanecarbaldehyde oxime 41 (R$^3$=2-thiophene)

The carbaldehyde 40 (7.54 g, 30 mmol) and hydroxylamine hydrochloride (3.12 g, 45 mmol) were dissolved in abs. ethanol (100 ml); basic ion exchanger Amberlyst A21 (21 g) was added and stirring was carried out overnight at RT. The ion exchanger was filtered off and washed with ethanol (2×50 ml). The solution was concentrated and the residue was adjusted to pH 11 with 5N NaOH. The aqueous phase was extracted with ethyl acetate (3×50 ml) and the organic phase was dried over sodium sulfate and concentrated in vacuo.

Yield: 7.99 g (100%)

[(4-Aminomethyl-cyclohexyl)-thiophen-2-yl-methyl]-dimethylamine 42 ($R^3$=2-thiophene)

LiAlH$_4$ (2.27 g, 60 mmol) was added, under argon, to absolute THF (300 ml); the mixture was heated to 60° C. and the oxime 41 (7.99 g, 30 mmol) dissolved in THF (60 ml) was added dropwise. After 4 hours' stirring at 60° C., water (70 ml) was added dropwise, while cooling with an ice bath (10° C.), and the reaction solution was filtered over kieselguhr. The filter residue was washed with THF, the organic phases were combined, the THF was removed in vacuo and the residue was adjusted to pH 11 with 5N NaOH and extracted with ethyl acetate (3×50 ml). The organic phase was dried over sodium sulfate and concentrated.

Yield: 6.72 g (89%), oil $^{13}$C-NMR (CDCl$_3$): 25.93; 26.11; 26.24; 26.30; 29.97; 30.34; 30.42; 38.03; 40.65; 40.82; 41.18; 41.34 (N(CH$_3$)$_2$); 46.19; 48.67; 65.58; 70.06; 123.61; 125.88; 126.23; 140.08.

4-(1-Dimethylamino-3-phenyl-propyl)-cyclohexane-carbaldehyde 43 ($R^3$=phenethyl)

(Methoxymethyl)triphenylphosphonium chloride (20.56 g, 60 mmol) was suspended, under argon, in abs. THF (85 ml); potassium tert-butylate (6.73 g, 60 mmol) dissolved in abs. THF (70 ml) was added dropwise at 0° C., and stirring was then carried out for 15 minutes at 0° C.

The ketone 15 (10.2 g, 40 mmol) dissolved in abs. THF (60 ml) was then added dropwise to the above solution at RT, and stirring was carried out overnight at RT. Hydrolysis was carried out dropwise with water (35 ml) and 6N HCl (90 ml), while cooling with ice-water. After 1 hour's stirring at RT, extraction with ether (10×50 ml) was carried out and the aqueous phase was adjusted to pH 11 with 5N NaOH, extracted with ethyl acetate (3×50 ml), dried over Na$_2$SO$_4$ and concentrated in vacuo. The crude product was purified by flash chromatography with ethyl acetate/cyclohexane (1:1).

Yield: 6.73 g (63%).

$^1$H-NMR (DMSO, 600 MHz, selected signals): δ=2.18 (s, 3 H); 2.20 (s, 3 H); 9.54 (s, 1 H); 9.61 (s, 1 H).

$^{13}$C-NMR (CDCl$_3$): δ=24.35; 24.49; 26.00; 26.09; 26.85; 27.79; 29.07; 29.13; 35.27; 39.02; 40.98; 41.19; 46.99; 50.33; 66.85; 67.85; 70.54; 71.42; 125.40; 125.44; 128.02; 128.13; 131.15; 131.17; 142.45; 204.10; 205.01.

4-(1-Dimethylamino-3-phenyl-propyl)-cyclohexan-ecarbaldehyde oxime 44 ($R^3$=phenethyl)

The aldehyde 43 (6.55 g, 24 mmol) and hydroxylamine hydrochloride (2.5 g, 36 mmol) were dissolved in abs. ethanol (90 ml); basic ion exchanger Amberlyst A21 (15.6 g) was added and stirring was carried out overnight at RT. The ion exchanger was filtered off and washed twice with ethanol (50 ml each time). The solution was concentrated and the residue was adjusted to pH 11 with 5N NaOH. The aqueous phase was extracted three times with ethyl acetate (50 ml each time) and the organic phase was dried over sodium sulfate and concentrated in vacuo.

Yield: 6.90 g (100%)

[1-(4-Aminomethyl-cyclohexyl)-3-phenyl-propyl]-dimethylamine 45 ($R^3$=phenethyl)

LiAlH$_4$ (1.82 g, 48 mmol) was added, under argon, to absolute THF (360 ml); the mixture was heated to 60° C. and the oxime 44 (6.90 g, 24 mmol) dissolved in THF (60 ml) was added dropwise. After 4 hours' stirring at 60° C., water (90 ml) was added dropwise, while cooling with an ice bath (10° C.), and the reaction solution was filtered over kieselguhr. The filter residue was washed with THF, the organic phases were combined, the THF was removed in vacuo and the residue was adjusted to pH 11 with 5N NaOH and extracted with ethyl acetate (4×40 ml). The organic phase was dried over sodium sulfate and concentrated.

Yield: 5.6 g (85%), oil $^{13}$C-NMR (CDCl$_3$): 25.93; 26.58; 27.09; 29.21; 29.90; 30.32; 30.73; 30.77; 35.38; 35.66; 38.73; (C$_4$); 40.06; 40.90; 41.19 (N(CH$_3$)$_2$); 48.78; 65.15; 68.22 (CH); 125.36; 127.99; 128.05; 142.69.

Synthesis of the Aminoethylcyclohexanes ($R^1$=(CH$_2$)$_n$NH$_2$, n=2)

The aminoethylcyclohexanes were prepared from the correspondingly substituted cyclohexylaldehydes by three-stage reactions by chain extension (Wittig) and reaction with hydroxylamine hydrochloride and subsequent cleavage with lithium aluminium hydride.

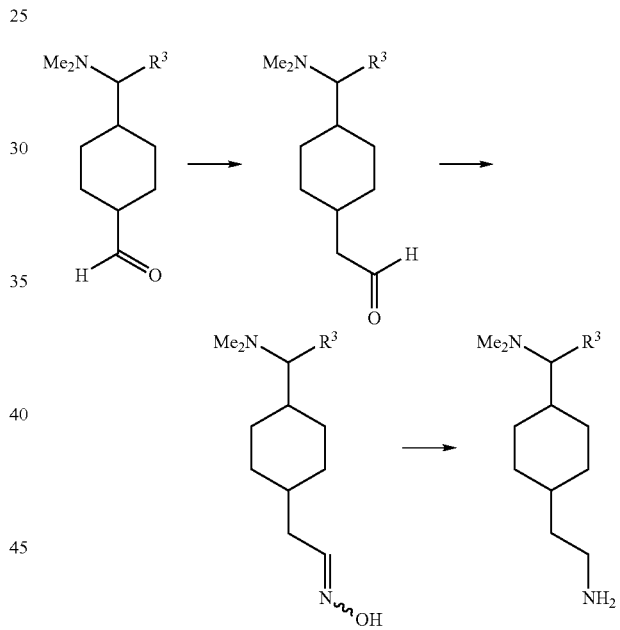

[4-(Dimethylamino-phenyl-methyl)-cyclohexyl]-acetaldehyde 46 ($R^3$=phenyl)

(Methoxymethyl)triphenylphosphonium chloride (38.39 g, 0.112 mol) was suspended, under argon, in abs. THF (150 ml); potassium tert-butylate (12.56 g, 0.112 mol) dissolved in abs. THF (120 ml) was added dropwise at 0° C., and stirring was then carried out for 15 minutes at 0° C. (the solution turned deep-orange in colour).

The aldehyde 28 (18.4 g, 0.075 mol) dissolved in abs. THF (120 ml) was then added dropwise at RT, and stirring was carried out overnight at RT. Hydrolysis was carried out dropwise with water (50 ml) and 6N HCl (150 ml), while cooling with ice-water. After 1 hour's stirring at RT, extraction with ether (10×100 ml) was carried out. The aqueous phase was adjusted to pH 11 with 5N NaOH, extracted by shaking with ethyl acetate (3×80 ml), dried over Na$_2$SO$_4$ and concentrated in vacuo. The crude product was purified by flash chromatography with ethyl acetate/cyclohexane (1:1).

Yield: 16.31 g (84%), oil $^{13}$C-NMR (CDCl$_3$): 25.30; 25.92; 29.04; 29.19; 29.74; 30.86; 32.99; 33.02; 35.98; 38.31 (C$_4$); 41.42; 42.06; (N(CH$_3$)$_2$); 48.04; 51.24; 71.82; 75.47 (CH); 126.64 (C$_{arom}$); 126.68 (C$_{arom}$); 127.39 (C$_{arom}$); 127.46 (C$_{arom}$); 129.15 (C$_{arom}$); 136.20 (C$_{arom}$); 137.11 (C$_{arom}$); 202.27; 202.37 (CHO).

[4-(Dimethylamino-phenyl-methyl)-cyclohexyl]-acetaldehyde oxime 47 (R$^3$=phenyl)

The carbaldehyde 46 (11.04 g, 42.5 mmol) and hydroxylamine hydrochloride (4.44 g, 64 mmol) were dissolved in abs. ethanol (150 ml); basic ion exchanger Amberlyst A21 (30 g) was added and stirring was carried out for 4 hours at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml) and the organic phase was dried over sodium sulfate and concentrated in vacuo.

Yield: 11.66 (100%)

$^{13}$C-NMR (CDCl$_3$): 25.41; 25.57; 28.87; 29.11; 30.92; 30.97; 32.33; 32.99; 33.67; 35.99; 36.10; 38.59 (C$_4$); 41.31; 41.40; 42.11; 42.14 (N(CH$_3$)$_2$); 71.74; 75.63 (CH); 126.71 (C$_{arom}$); 127.46 (C$_{arom}$); 129.26 (C$_{arom}$); 137.26 (C$_{arom}$); 150.95; 151.37; 151.56 (C=N—O).

2-[4-Dimethylamino-phenyl-methyl)-cyclohexyl]-ethylamine 48 (R$^3$=phenyl)

LiAlH$_4$ (3.22 g, 85 mmol) was added, under argon, to absolute THF (400 ml); the mixture was heated to 60° C. and the oxime 47 (11.66 g, 42.5 mmol) dissolved in THF (80 ml) was added dropwise. After 4 hours' stirring at 60° C., water (100 ml) was added dropwise, while cooling with an ice bath (10° C.), the reaction solution was filtered off with suction over kieselguhr and the kieselguhr was washed with THF. The combined THF solutions were concentrated in vacuo and the residue was adjusted to pH 11 with 5N NaOH and extracted with ethyl acetate (4×50 ml). The organic phase was dried over sodium sulfate and concentrated by evaporation.

Yield: 9.15 g (83%), oil $^{13}$C-NMR (CDCl$_3$): 25.58; 26.08; 29.16; 29.21; 30.39; 31.10; 32.49; 33.16; 33.33; 35.54; 36.22; 38.80 (C$_4$); 40.32; 41.36; 41.50; 42.11; (N(CH$_3$)$_2$); 71.77; 75.66 (CH); 126.52 (C$_{arom}$); 127.31 (C$_{arom}$); 127.38 (C$_{arom}$); 129.18 (C$_{arom}$); 139.39 (C$_{arom}$); 137.41 (C$_{arom}$).

{4-[Dimethylamino-(4-fluorophenyl)-methyl]-cyclohexyl}-acetaldehyde 49 (R$^3$=4-fluorophenyl)

(Methoxymethyl)triphenylphosphonium chloride (43.53 g, 127 mmol) was suspended, under argon, in abs. THF (200 ml); potassium tert-butylate (14.25 g, 127 mmol) dissolved in abs. THF (130 ml) was added dropwise at 0° C., and stirring was then carried out for 15 minutes at 0° C.

The aldehyde 31 (22.3 g, 85 mmol) dissolved in abs. THF (130 ml) was then added dropwise at RT, and stirring was carried out overnight at RT. Hydrolysis was carried out dropwise with water (80 ml) and 6N HCl (200 ml), while cooling with ice-water. After 1 hour's stirring at RT, extraction with ether was carried out ten times (100 ml each time). The aqueous phase was adjusted to pH 11 with 5N NaOH, extracted by shaking three times with ethyl acetate (100 ml each time), dried over Na$_2$SO$_4$ and concentrated in vacuo. The crude product was purified by flash chromatography with ethyl acetate/cyclohexane (1:1). Yield: 15.8 g (67%).

$^{13}$C-NMR (CDCl$_3$): δ=25.08; 25.87; 28.80; 29.10; 29.13; 29.62; 30.82; 32.90; 33.08; 36.19; 38.43; 41.36; 42.01; 47.94; 51.17; 71.11; 74.69; 114.11; 114.20; 114.32; 130.32; 130.40; 132.00; 132.92; 160.31; 162.74; 202.15; 202.23.

{4-[Dimethylamino-(4-fluorophenyl)-methyl]-cyclohexyl}-acetaldehyde oxime 50 (R$^3$=4-fluorophenyl)

The carbaldehyde 49 (5.30 g, 20.0 mmol) and hydroxylamine hydrochloride (2.08 g, 30 mmol) were dissolved in abs. ethanol (90 ml); basic ion exchanger Amberlyst A21 (14.8 g) was added and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×100 ml) and the organic phase was dried over sodium sulfate and concentrated in vacuo. The residue was purified by flash chromatography with EA/cyclohexane (2:1).

Yield: 3.50 (60%)

2-{4-[Dimethylamino-(4-fluorophenyl)-methyl]-cyclohexyl}-ethylamine 51 (R$^3$=4-fluorophenyl)

LiAlH$_4$ (2.35 g, 62 mmol) was added, under argon, to absolute THF (450 ml); the mixture was heated to 60° C. and the oxime 50 (9.10 g, 31.0 mmol) dissolved in THF (75 ml) was added dropwise. After 4 hours' stirring at 60° C., water (116 ml) was added dropwise, while cooling with an ice bath (10° C.), the reaction solution was filtered off with suction over kieselguhr and the kieselguhr was washed with THF. The combined THF solutions were concentrated in vacuo and the residue was adjusted to pH 11 with 5N NaOH and extracted with ethyl acetate (4×50 ml). The organic phase was dried over sodium sulfate and concentrated in vacuo.

Yield: 6.80 g (79%), oil $^{13}$C-NMR (CDCl$_3$): 25.32; 26.03; 28.94; 29.08; 30.37; 31.06; 32.39; 32.90; 33.07; 33.26; 35.50; 37.81; 38.80; 39.78 (C$_4$); 41.33; 41.42; 42.09 (N(CH$_3$)$_2$); 71.11; 74.89 (CH); 114.03; 114.11; 130.32; 130.40; 132.19; 133.18; 133.21; 160.27; 162.69.

{4-[Dimethylamino-(3-fluorophenyl)-methyl]-cyclohexyl}-acetaldehyde 52 (R$^3$=3-fluorophenyl)

(Methoxymethyl)triphenylphosphonium chloride (26.73 g, 78 mmol) was suspended, under argon, in abs. THF (90 ml); potassium tert-butylate (8.75 g, 78 mmol) dissolved in abs. THF (90 ml) was added dropwise at 0° C., and stirring was then carried out for 15 minutes at 0° C.

The aldehyde 34 (13.69 g, 52 mmol) dissolved in abs. THF (90 ml) was then added dropwise at RT, and stirring was carried out overnight at RT. Hydrolysis was carried out dropwise with water (50 ml) and 6N HCl (150 ml), while cooling with ice-water. After 1 hour's stirring at RT, extraction with ether was carried out ten times (50 ml each time). The aqueous phase was adjusted to pH 11 with 5N NaOH, extracted by shaking three times with ethyl acetate (100 ml each time), dried over Na$_2$SO$_4$ and concentrated in vacuo. The crude product was purified by flash chromatography with ethyl acetate/cyclohexane (1:1).

Yield: 12.61 g (87%)

$^{13}$C-NMR (CDCl$_3$): δ=25.19; 25.83; 28.90; 29.06; 29.14; 29.68; 30.77; 32.92; 32.98; 33.10; 36.05; 38.36; 41.39; 42.04; 48.02; 51.20; 71.48; 75.07; 113.43; 113.49; 113.64; 113.69;

115.55; 115.76; 124.89; 128.70; 128.78; 128.88; 139.24; 140.08; 140.14; 161.09; 163.52; 202.19; 202.27.

{4-[Dimethylamino-(3-fluorophenyl)-methyl]-cyclohexyl}-acetaldehyde oxime 53 ($R^3$=3-fluorophenyl)

The carbaldehyde 52 (7.18 g, 25.8 mmol) and hydroxylamine hydrochloride (2.71 g, 39 mmol) were dissolved in abs. ethanol (90 ml); basic ion exchanger Amberlyst A21 (20 g) was added and stirring was carried out for 20 h at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml) and the organic phase was dried over sodium sulfate and concentrated in vacuo.

Yield: 7.54 (100%)

2-{4-[Dimethylamino-(3-fluorophenyl)-methyl]-cyclohexyl}-ethylamine 54 ($R^3$=3-fluorophenyl)

$LiAlH_4$ (1.97 g, 52 mmol) was added, under argon, to absolute THF (300 ml); the mixture was heated to 60° C. and the oxime 53 (7.54 g, 25.8 mmol) dissolved in THF (70 ml) was added dropwise. After 4 hours' stirring at 60° C., water (100 ml) was added dropwise, while cooling with an ice bath (10° C.), the reaction solution was filtered off with suction over kieselguhr and the kieselguhr was washed with THF. The combined THF solutions were concentrated in vacuo and the residue was adjusted to pH 11 with 5N NaOH and extracted with ethyl acetate (3×50 ml). The organic phase was dried over sodium sulfate and concentrated in vacuo.

Yield: 6.3 g (88%), oil $^{13}$C-NMR ($CDCl_3$): 25.28; 25.84; 28.87; 28.98; 30.28; 32.30; 32.93; 33.13; 35.38; 36.16; 37.81; 38.69 ($C_4$); 39.69; 41.20; 41.37; 41.94 (N($CH_3$)$_2$); 71.29; 75.11 (CH); 113.14; 113.18; 113.38; 115.41; 115.62; 124.73; 128.44; 128.53; 139.25; 140.27; 140.33; 160.91; 163.34.

{4-[(4-Chlorophenyl)-dimethylamino-methyl]-cyclohexyl}-acetaldehyde 55 ($R^3$=4-chlorophenyl)

(Methoxymethyl)triphenylphosphonium chloride (25.02 g, 73 mmol) was suspended, under argon, in abs. THF (90 ml); potassium tert-butylate (8.19 g, 73 mmol) dissolved in abs. THF (90 ml) was added dropwise at 0° C., and stirring was then carried out for 15 minutes at 0° C.

The aldehyde 37 (13.86 g, 49 mmol) dissolved in abs. THF (90 ml) was then added dropwise at RT, and stirring was carried out overnight at RT. Hydrolysis was carried out dropwise with water (50 ml) and 6N HCl (150 ml), while cooling with ice-water. After 1 hour's stirring at RT, extraction with ether was carried out ten times (50 ml each time). The aqueous phase was adjusted to pH 11 with 5N NaOH, extracted by shaking three times with ethyl acetate (100 ml each time), dried over $Na_2SO_4$ and concentrated in vacuo. The crude product was purified by flash chromatography with ethyl acetate/cyclohexane (1:1). Yield: 12.07 g (84%).

$^{13}$C-NMR ($CDCl_3$): δ=25.06; 25.82; 28.74; 29.00; 29.13; 29.60; 30.77; 32.87; 32.94; 33.07; 36.06; 38.32; 41.38; 42.05; 47.95; 51.17; 71.23; 74.80; 127.58; 127.66; 130.31; 132.28; 132.34; 134.81; 135.77; 202.12; 202.20.

{4-[Dimethylamino-(4-chlorophenyl)-methyl]-cyclohexyl}-acetaldehyde oxime 65 ($R^3$=4-chlorophenyl)

The carbaldehyde 55 (6.72 g, 22.8 mmol) and hydroxylamine hydrochloride (2.36 g, 34 mmol) were dissolved in abs. ethanol (90 ml); basic ion exchanger Amberlyst A21 (16 g) was added and stirring was carried out for 20 h at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml) and the organic phase was dried over sodium sulfate and concentrated in vacuo.

Yield: 7.04 (100%)

2-{4-[Dimethylamino-(4-chlorophenyl)-methyl]-cyclohexyl}-ethylamine 66 ($R^3$=4-chlorophenyl)

$LiAlH_4$ (1.73 g, 45.6 mmol) was added, under argon, to absolute THF (300 ml); the mixture was heated to 60° C. and the oxime 65 (7.04 g, 22.8 mmol) dissolved in THF (60 ml) was added dropwise. After 4 hours' stirring at 60° C., water (100 ml) was added dropwise, while cooling with an ice bath (10° C.), the reaction solution was filtered off with suction over kieselguhr and the kieselguhr was washed with THF. The combined THF solutions were concentrated in vacuo and the residue was adjusted to pH 11 with 5N NaOH and extracted with ethyl acetate (3×50 ml). The organic phase was dried over sodium sulfate and concentrated in vacuo.

Yield: 5.76 g (86%), oil $^{13}$C-NMR ($CDCl_3$): 25.67; 26.35; 29.23; 29.44; 30.74; 31.39; 33.41; 33.61; 35.86; 36.71; 38.20; 39.18; 40.17; 40.67; 41.72; 41.81; 42.50 (N($CH_3$)$_2$); 71.59; 75.37; 127.86; 127.95; 130.70; 132.52; 135.38; 136.45.

{4-[Dimethylamino-thiophen-2-yl-methyl]-cyclohexyl}-acetaldehyde 67 ($R^3$=2-thiophene)

(Methoxymethyl)triphenylphosphonium chloride (28.79 g, 84 mmol) was suspended, under argon, in abs. THF (100 ml); potassium tert-butylate (9.42 g, 84 mmol) dissolved in abs. THF (100 ml) was added dropwise at 0° C., and stirring was then carried out for 15 minutes at 0° C.

The aldehyde 40 (14.08 g, 56 mmol) dissolved in abs. THF (100 ml) was then added dropwise at RT, and stirring was carried out overnight at RT. Hydrolysis was carried out dropwise with water (50 ml) and 6N HCl (150 ml), while cooling with ice-water. After 1 hour's stirring at RT, extraction with ether was carried out ten times (50 ml each time). The aqueous phase was adjusted to pH 11 with 5N NaOH, extracted by shaking three times with ethyl acetate (100 ml each time), dried over $Na_2SO_4$ and concentrated in vacuo. The crude product was purified by flash chromatography with ethyl acetate/cyclohexane (1:2). Yield: 11.48 g (77%).

$^{13}$C-NMR ($CDCl_3$): δ=25.80; 25.88; 28.73; 29.95; 30.49; 32.23; 32.76; 37.89; 40.21; 40.88; 41.23; 48.36; 51.09; 66.02; 69.97; 123.19; 123.72; 125.95; 126.31; 139.42; 139.91; 202.61.

[4-(Dimethylamino-thiophen-2-yl-methyl)-cyclohexyl]-acetaldehyde oxime 68 ($R^3$=2-thiophene)

The carbaldehyde 67 (6.3 g, 23.7 mmol) and hydroxylamine hydrochloride (2.5 g, 36 mmol) were dissolved in abs. ethanol (90 ml); basic ion exchanger Amberlyst A21 (20 g) was added and stirring was carried out for 20 h at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml) and the organic phase was dried over sodium sulfate and concentrated in vacuo.

Yield: 6.64 (100%)

2-[4-(Dimethylamino-thiophen-2-yl-methyl)-cyclohexyl]-ethylamine 69 ($R^3$=2-thiophene)

LiAlH$_4$ (1.78 g, 47 mmol) was added, under argon, to absolute THF (250 ml); the mixture was heated to 60° C. and the oxime 68 (6.64 g, 23.7 mmol) dissolved in THF (60 ml) was added dropwise. After 4 hours' stirring at 60° C., water (100 ml) was added dropwise, while cooling with an ice bath (10° C.), the reaction solution was filtered off with suction over kieselguhr and the kieselguhr was washed with THF. The combined THF solutions were concentrated in vacuo and the residue was adjusted to pH 11 with 5N NaOH and extracted with ethyl acetate (3×50 ml). The organic phase was dried over sodium sulfate and concentrated in vacuo.

Yield: 5.62 g (89%), oil $^{13}$C-NMR (CDCl$_3$): 25.97; 26.13; 28.72; 28.79; 30.15; 30.23; 30.74; 32.61; 32.90; 35.32; 38.22; 39.70; 40.09; 40.69; 40.84; 41.26 (N(CH$_3$)$_2$); 70.14; 123.56; 123.60; 125.86; 126.21; 126.23; 139.70; 140.24.

[4-(1-Dimethylamino-3-phenyl-propyl)-cyclohexyl]-acetaldehyde 70 ($R^3$=phenethyl)

(Methoxymethyl)triphenylphosphonium chloride (50.3 g, 147 mmol) was suspended, under argon, in abs. THF (150 ml); potassium tert-butylate (16.5 g, 147 mmol) dissolved in abs. THF (140 ml) was added dropwise at 0° C., and stirring was then carried out for 15 minutes at 0° C.

The aldehyde 43 (27.0 g, 98 mmol) dissolved in abs. THF (150 ml) was then added dropwise at RT, and stirring was carried out overnight at RT. Hydrolysis was carried out dropwise with water (102 ml) and 6N HCl (240 ml), while cooling with ice-water. After 1 hour's stirring at RT, extraction with ether was carried out five times (200 ml each time). The aqueous phase was adjusted to pH 11 with 5N NaOH, while cooling with ice, extracted by shaking three times with ethyl acetate (200 ml each time), dried over Na$_2$SO$_4$ and concentrated in vacuo. The crude product was purified by flash chromatography with ethyl acetate/cyclohexane (1:1).

Yield: 18.1 g (64%)

$^{13}$C-NMR (CDCl$_3$): δ=25.55; 26.19; 29.04; 29.15; 29.35; 29.85; 31.00; 32.87; 32.68; 33.04; 35.33; 38.49; 40.86; 41.13; 47.51; 51.15; 65.48; 68.09.

[4-(1-Dimethylamino-3-phenyl-propyl)-cyclohexyl]-acetaldehyde oxime 71 ($R^3$=phenethyl)

The carbaldehyde 70 (12.6 g, 44.0 mmol) and hydroxylamine hydrochloride (4.60 g, 66.0 mmol) were dissolved in abs. ethanol (200 ml); basic ion exchanger Amberlyst A21 (32 g) was added and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml) and the organic phase was dried over sodium sulfate and concentrated in vacuo.

Yield: 13.3 (100%)

{1-[4-(2-Amino-ethyl)-cyclohexyl]-3-phenyl-propyl}-dimethylamine 72 ($R^3$=phenethyl)

LiAlH$_4$ (4.25 g, 112 mmol) was added, under argon, to absolute THF (600 ml); the mixture was heated to 60° C. and the oxime 71 (17.1 g, 56.0 mmol) dissolved in THF (150 ml) was added dropwise. After 4 hours' stirring at 60° C., water (360 ml) was added dropwise, while cooling with an ice bath (10° C.), the reaction solution was filtered off with suction over kieselguhr and the kieselguhr was washed with THF. The combined THF solutions were concentrated in vacuo and the residue was adjusted to pH 11 with 5N NaOH and extracted with ethyl acetate (5×100 ml). The organic phase was dried over sodium sulfate and concentrated in vacuo.

Yield: 16.2 g (100%), oil $^{13}$C-NMR (CDCl$_3$): 25.67; 26.44; 29.07; 29.16; 30.05; 30.22; 31.32; 31.80; 33.30; 35.24; 35.37; 37.26; 39.77; 40.30; 40.85; 41.15; 41.40 (N(CH$_3$)$_2$); 65.61; 68.29; 125.53; 127.68; 128.16; 128.200; 142.91.

Synthesis of the Urea Derivatives ($R^1$=(CH$_2$)$_n$NH-CONHR$^9$)

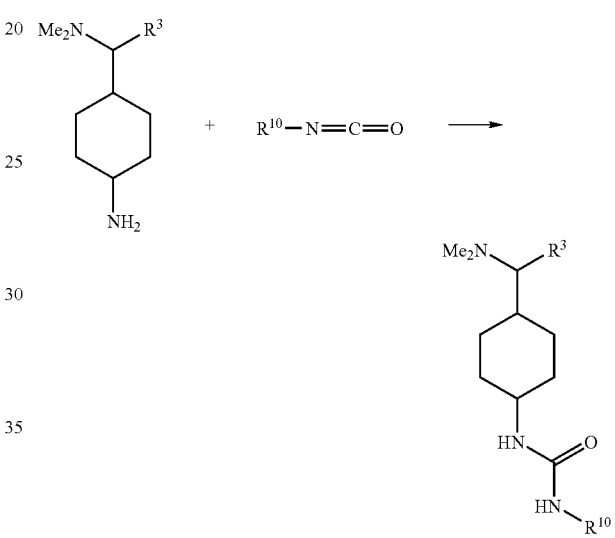

1-(4-((Dimethylamino)(phenyl)methyl)cyclohexyl)-3-(naphthalen-1-yl)urea 73 ($R^3$=phenyl)

The amine 17 (0.5 g, 2.15 mmol) was placed in toluene (21 ml), and 1-naphthyl isocyanate (0.36 g, 2.15 mmol) was added, with stirring. The mixture was then stirred for 4 h at 115° C. and subsequently allowed to stand overnight at room temperature, whereupon a solid precipitated. The resulting solid was filtered off and washed with ethyl acetate. The mother liquor was concentrated to dryness using a rotary evaporator, and ethyl acetate was added. The solid thereby obtained was separated off, washed with ethyl acetate and combined with the first precipitation.

$^1$H NMR (600 MHz, DMSO) 0.76-1.00 (m, 2 H) 1.05-1.31 (m, 2 H) 1.32-1.44 (m, 1 H) 1.78-2.06 (m, 10 H) 2.06-2.16 (m, 1 H) 3.07 (d, J=9.06 Hz, 1 H) 6.50 (d, J=7.55 Hz, 1 H) 7.16 (d, J=7.55 Hz, 2 H) 7.26 (t, J=7.18 Hz, 2 H) 7.34 (t, J=7.55 Hz, 1 H) 7.39 (t, J=7.55 Hz, 1 H) 7.52 (td, J=13.60, 6.80 Hz, 3 H) 7.88 (d, J=7.55 Hz, 1 H) 8.01 (d, J=7.55 Hz, 1 H) 8.05 (d, J=8.31 Hz, 1 H) 8.39 (s, 1 H).

1-(2,4-Difluorophenyl)-3-(4-((dimethylamino)(phenyl)methyl)cyclohexyl)urea hydrochloride 74 ($R^3$=phenyl)

The amine 17 (0.5 g, 2.15 mmol) was placed in toluene (21 ml), and 2,4-difluoro-phenyl isocyanate (0.33 g, 2.15 mmol)

was added, with stirring. The mixture was then stirred for 4 h at 115° C. and subsequently allowed to stand overnight at room temperature, whereupon a solid precipitated. The reaction solution was concentrated to dryness using a rotary evaporator and purified by flash chromatography (ethyl acetate/methanol 20:1).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

$^1$H NMR (600 MHz, DMSO) 0.89-0.97 (m, 2 H) 1.10-1.17 (m, 1 H) 1.19-1.26 (m, 1 H) 1.45-1.52 (m, 1 H) 1.81 (d, J=12.84 Hz, 1 H) 1.93 (t, J=12.84 Hz, 2 H) 2.23-2.30 (m, 1 H) 2.57-2.62 (m, 3 H) 2.62-2.67 (m, 3 H) 3.22-3.28 (m, 1 H) 4.22-4.27 (m, 1 H) 6.59 (d, J=6.80 Hz, 1 H) 6.93-6.98 (m, J=5.29 Hz, 1 H) 7.20-7.25 (m, 1 H) 7.47-7.52 (m, 5 H) 8.01-8.07 (m, 1 H) 8.13-8.18 (m, 1 H) 10.00 (s, 1 H).

1-(4-((Dimethylamino)(phenyl)methyl)cyclohexyl)-3-(3-(trifluoromethyl)-phenyl)-urea hydrochloride 75 ($R^3$=phenyl)

The amine 17 (0.5 g, 2.15 mmol) was placed in toluene (21 ml), and 3-(trifluoro-methyl)phenyl isocyanate (0.40 g, 2.15 mmol) was added, with stirring. The mixture was then stirred for 4 h at 115° C. and subsequently allowed to stand overnight at room temperature, whereupon a solid precipitated. The resulting solid was filtered off and washed with ethyl acetate. The product was dissolved in methyl ethyl ketone (2 ml), and then water (0.01 ml/1 mmol) and trimethyl-chlorosilane (1.3 ml/1 mmol) were added. Filtering off with suction and washing with ether yielded white crystals, which were dried in vacuo.

1H NMR (600 MHz, DMSO) 0.84-1.00 (m, 2 H) 1.11-1.34 (m, 2 H) 1.50-1.63 (m, 1 H) 1.76-1.88 (m, 1 H) 1.89-2.01 (m, 2 H) 2.19-2.32 (m, 1 H) 2.54-2.62 (m, 3 H) 2.63-2.72 (m, 3 H) 3.18-3.31 (m, 1 H) 4.20-4.29 (m, 1 H) 7.10 (t, J=7.55 Hz, 1 H) 7.42-7.57 (m, 6 H) 7.62 (t, J=7.93 Hz, 1 H) 8.03 (d, J=8.31 Hz, 1 H) 8.28 (d, J=8.31 Hz, 1 H) 9.30 (s, 1 H), 10.35 (s, 1 H).

1-(4-((Dimethylamino)(phenyl)methyl)cyclohexyl)-3-(2-nitrophenyl)urea hydrochloride 76 ($R^3$=phenyl)

The amine 17 (0.5 g, 2.15 mmol) was placed in toluene (21 ml), and 2-nitro-phenyl isocyanate (0.35 g, 2.15 mmol) was added, with stirring. The mixture was then stirred for 4 h at 115° C. and subsequently allowed to stand overnight at room temperature, whereupon a solid precipitated. The reaction solution was concentrated to dryness using a rotary evaporator and purified by flash chromatography (ethyl acetate/methanol 20:1).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

1H NMR (600 MHz, 0.89-0.97 (m, 2 H) 1.13-1.20 (m, 1 H) 1.22-1.30 (m, 1 H) 1.45-1.52 (m, 1 H) 1.79-1.85 (m, 1 H) 1.91-1.98 (m, 2 H) 2.22-2.29 (m, 1 H) 2.57-2.62 (m, 3 H) 2.63-2.67 (m, 3 H) 3.23-3.31 (m, 1 H) 4.22-4.29 (m, 1 H) 6.39-6.45 (m, 1 H) 7.17-7.23 (m, 1 H) 7.41-7.46 (m, 2 H) 7.47-7.53 (m, 5 H) 7.95 (s, 1 H) 8.98 (s, 1 H) 10.01 (s, 1 H).

1-(3-Bromophenyl)-3-(4-((dimethylamino)(phenyl)methyl)cyclohexyl)urea hydrochloride 77 ($R^3$=phenyl)

The amine 17 (0.5 g, 2.15 mmol) was placed in toluene (21 ml), and 3-bromo-phenyl isocyanate (0.43 g, 2.15 mmol) was added, with stirring. The mixture was then stirred for 4 h at 115° C. and subsequently allowed to stand overnight at room temperature, whereupon a solid precipitated. The reaction solution was concentrated to dryness using a rotary evaporator and purified by flash chromatography (ethyl acetate/methanol 20:1).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

$^1$H NMR (600 MHz, DMSO-$d_6$) d ppm 0.85 (t, J=7.55 Hz, 2H) 1.04-1.26 (m, 2 H) 1.43-1.61 (m, 1 H) 1.67-1.80 (m, 1 H) 1.81-1.94 (m, 1 H) 2.11-2.23 (m, 1 H) 2.37 (q, J=7.30 Hz, 1 H) 2.48-2.55 (m, 3 H) 2.56-2.64 (m, 3 H) 3.10-3.23 (m, 1 H) 4.19 (t, J=6.04 Hz, 1 H) 6.36-6.48 (m, 1 H) 6.96 (d, J=7.55 Hz, 1 H) 7.08 (t, J=7.93 Hz, 1 H) 7.14 (d, 1 H) 7.31-7.58 (m, J=5.29 Hz, 4 H) 7.71 (s, 1 H) 8.93 (s, 1 H); 10.28 (s, 1 H).

1-(4-((Dimethylamino)(phenyl)methyl)cyclohexyl)-3-phenylurea hydrochloride 78 ($R^3$=phenyl)

The amine 17 (0.5 g, 2.15 mmol) was placed in toluene (21 ml), and phenyl isocyanate (0.43 g, 2.15 mmol) was added, with stirring. The mixture was then stirred for 4 h at 115° C. and subsequently allowed to stand overnight at room temperature, whereupon a solid precipitated. The solid was purified by flash chromatography (ethyl acetate/methanol 20:1).

1-Benzyl-3-(4-((dimethylamino)(phenyl)methyl)cyclohexyl)urea 79 ($R^3$=phenyl)

The amine 17 (0.35 g, 1.5 mmol) was placed in toluene (15 ml), and benzyl isocyanate (0.20 g, 1.5 mmol) was added, with stirring. The mixture was then stirred for 4 h at 115° C. and subsequently allowed to stand overnight at room temperature. The reaction solution was concentrated to dryness using a rotary evaporator, and ethyl acetate was added. The resulting solid was filtered off with suction and washed with ethyl acetate.

1-Cyclohexyl-3-(4-((dimethylamino)(phenyl)methyl)cyclohexyl)urea 80 ($R^3$=phenyl)

The amine 17 (0.35 g, 1.5 mmol) was placed in toluene (15 ml), and cyclohexyl isocyanate (0.19 g, 1.5 mmol) was added, with stirring. The mixture was then stirred for 4 h at 115° C. and subsequently allowed to stand overnight at room temperature. The reaction solution was concentrated to dryness using a rotary evaporator, and ethyl acetate was added. The resulting solid was filtered off with suction and washed with ethyl acetate.

1-(4-Bromophenyl)-3-(4-((dimethylamino)(phenyl)methyl)cyclohexyl)urea 81 ($R^3$=phenyl)

The amine 17 (0.35 g, 1.5 mmol) was placed in toluene (15 ml), and 4-bromo-phenyl isocyanate (0.30 g, 1.5 mmol) was added, with stirring. The mixture was then stirred for 4 h at 115° C. and subsequently allowed to stand overnight at room temperature. The reaction solution was concentrated to dryness using a rotary evaporator, and ethyl acetate was added. The resulting solid was filtered off with suction and washed with ethyl acetate.

1-(4-((Dimethylamino)(phenyl)methyl)cyclohexyl)-3-(4-methoxyphenyl)urea 82 ($R^3$=phenyl)

The amine 17 (0.35 g, 1.5 mmol) was placed in toluene (15 ml), and 4-methoxy-phenyl isocyanate (0.22 g, 1.5 mmol)

was added, with stirring. The mixture was then stirred for 4 h at 115° C. and subsequently allowed to stand overnight at room temperature. The reaction solution was concentrated to dryness using a rotary evaporator, and ethyl acetate was added. The resulting solid was filtered off with suction and washed with ethyl acetate.

Synthesis of the Thiourea Derivatives ($R^1$=(CH$_2$)$_n$ NHCSNHR$^9$)

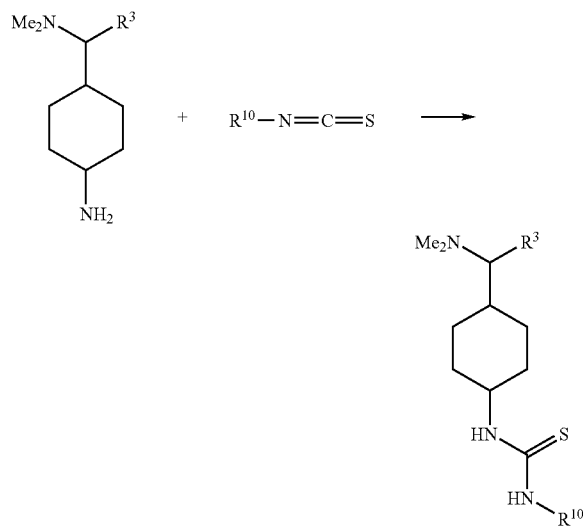

The thiourea derivatives are obtained analogously to the described methods of urea derivative synthesis, the corresponding isothiocyanates being used instead of isocyanates.

Reductive Amination of the Primary Amines ($R^1$= (CH$_2$)$_n$NR$^6$R$^7$)

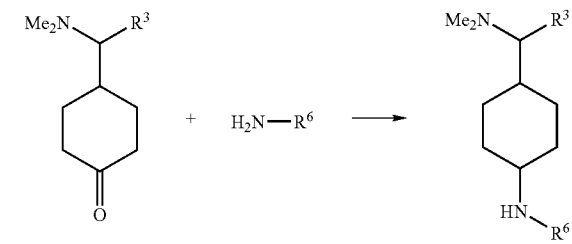

N-(2-(1H-Indol-3-yl)ethyl)-4-((dimethylamino)(phenyl)methyl)cyclohexan-amine hydrochloride 83 ($R^3$=phenyl)

The ketone 10 (1.0 g, 4.3 mmol) was placed in THF (40 ml), and tryptamine (0.69 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

4-((Dimethylamino)(phenyl)methyl)-N-phenethylcyclohexanamine hydrochloride 84 ($R^3$=phenyl)

The ketone 10 (1.0 g, 4.3 mmol) was placed in THF (40 ml), and phenethyl-amine (0.52 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

4-((Dimethylamino)(phenyl)methyl)-N-(3-phenylpropyl)cyclohexanamine dihydrochloride 85 ($R^3$=phenyl)

The ketone 10 (1.0 g, 4.3 mmol) was placed in THF (40 ml), and 3-phenylpropyl-amine (0.58 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

N-Benzyl-4-((dimethylamino)(phenyl)methyl)cyclohexanamine hydrochloride 86 ($R^3$=phenyl)

The ketone 10 (1.0 g, 4.3 mmol) was placed in THF (40 ml), and benzylamine (0.46 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

4-((Dimethylamino)(phenyl)methyl)-N-(4-phenylbutyl)cyclohexanamine hydrochloride 87 ($R^3$=phenyl)

The ketone 10 (1.0 g, 4.3 mmol) was placed in THF (40 ml), and butylphenyl-amine (0.65 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

N-(1-(1H-Indol-3-yl)propan-2-yl)-4-((dimethylamino)(phenyl)methyl)cyclo-hexanamine hydrochloride 88 ($R^3$=phenyl)

The ketone 10 (1.3 g, 5.6 mmol) was placed in THF (40 ml), and DL-alpha-methyl-tryptamine (0.98 g, 5.6 mmol) was added, while cooling with an ice bath. Glacial acetic acid (0.48 ml, 8.4 mmol) was then added dropwise. After 15 minutes' stirring, sodium triacetoxyborohydride (1.67 g, 7.9 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (1 ml), and then water (0.01 ml/1 mmol) and trimethylchlorosilane (1.3 ml/1 mmol) were added. Filtering off with suction and washing with ether yielded white crystals, which were dried in vacuo.

$^{13}$C NMR (600 MHz, DMSO) 7.57; 15.20; 21.33; 21.90; 22.41; 23.22; 23.29; 24.99; 25.13; 28.46; 28.59; 29.27; 31.11; 31.18; 35.97; 43.38; 50.05; 50.12; 50.65; 50.70; 67.50; 67.55; 108.87; 111.45; 118.20; 118.46; 120.99; 124.01; 127.06; 128.93; 129.75; 130.29; 136.09.

N-(4-((Dimethylamino)(phenyl)methyl)cyclohexyl)-4-methoxybenzenamine hydrochloride 89 ($R^3$=phenyl)

The ketone 10 (1.0 g, 4.3 mmol) was placed in THF (40 ml), and p-anisidine (0.53 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

4-((Dimethylamino)(phenyl)methyl)-N-(4-methoxybenzyl)cyclohexanamine dihydrochloride 90 ($R^3$=phenyl)

The ketone 10 (1.0 g, 4.3 mmol) was placed in THF (40 ml), and 4-methoxy-benzylamine (0.59 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

4-((Dimethylamino)(phenyl)methyl)-N-(4-fluorobenzyl)cyclohexanamine hydrochloride 91 ($R^3$=phenyl, $R^{12}$=4-fluorobenzyl)

The ketone 10 (1.0 g, 4.3 mmol) was placed in THF (40 ml), and 4-fluorobenzyl-amine (0.54 g, 4.3 mmol) was added, while cooling with an ice bath. Glacial acetic acid (0.37 ml, 6.6 mmol) was then added dropwise. After 15 minutes' stirring, sodium triacetoxyborohydride (1.28 g, 6.1 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl)benzenamine hydrochloride 92 ($R^3$=phenyl)

The ketone 10 (3.95 g, 17.1 mmol) was placed in THF (60 ml), and aniline (1.59 g, 17.1 mmol) was added, while cooling with an ice bath. Glacial acetic acid (1.46 ml, 25.6 mmol) was then added dropwise. After 15 minutes' stirring, sodium triacetoxyborohydride (5.07 g, 23.9 mmol) was added rapidly in portions, and the reaction mixture was stirred overnight at RT. For working up, hydrolysis was first carefully carried out at 15° C. with NaHCO$_3$, and the yellow suspension was then extracted with ether. The combined organic phases were washed first with water and then with saturated NaCl and were dried over MgSO$_4$.

The crude product was purified by means of flash chromatography (diethyl ether).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

Synthesis Specification for Automated Synthesis

140 μmol of triacetoxy borohydride resin (0.078 g, 140 μmol of triacetoxy borohydride) were weighed at RT into a dry screw-cap jar with a septum cap, and THF (1 ml) was added. There were subsequently added first a solution of the cyclohexanone derivative (100 μmol, 1 ml, 0.1 M in THF) and then a solution of the amine (100 μmol, 1 ml, 0.1 M in THF). The reaction solution was agitated for 16 h at RT in a Synthesis 1 Solid from Heidolph.

For working up, the mixtures were filtered off with suction via the filtering unit, the resin was rinsed with 1.5 ml of THF, and the filtrate was then concentrated in a GeneVac.

Methyl 2-(4-((dimethylamino)(phenyl)methyl)cyclohexylamino)-3-(1H-indol-3-yl)-propanoate, more polar diastereoisomer 174 and less polar diastereoisomer 175 were prepared in an analogous manner.

Amidation of the Primary Amines ($R^1$=$(CH_2)_n$NH-$COR^{13}$)

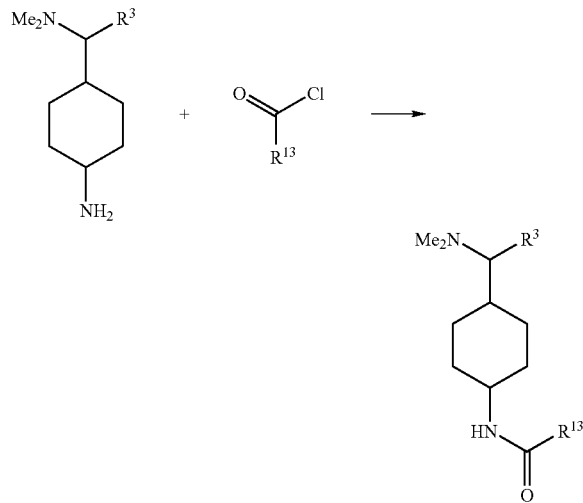

N-(4-((Dimethylamino)(phenyl)methyl)cyclohexyl)-2-ethylbutanamide hydrochloride 93 ($R^3$=phenyl)

The amine 17 (0.43 g, 1.9 mmol) was dissolved in DCM (2 ml), and a spatula tip of DMAP was added. 2-Ethylbutyl chloride (0.27 g, 2.0 mmol) was then added dropwise at −10° C., and the reaction mixture was stirred overnight at RT. 2 ml of 5N KOH were added to the suspension, and extraction with DCM was then carried out. The combined organic phases were washed with saturated NaCl solution, dried over $Na_2SO_4$ and concentrated.

Purification was carried out by column chromatography (eluant: ethyl acetate/-methanol: 20:1).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl) benzamide hydrochloride 94 ($R^3$=phenyl)

The amine 17 (0.40 g, 1.7 mmol) was dissolved in DCM (2 ml), and a spatula tip of DMAP was added. Benzoyl chloride (0.27 g, 1.9 mmol) was then added dropwise at −10° C., and the reaction mixture was stirred overnight at RT. 2 ml of 5N KOH were added to the suspension, and extraction with DCM was then carried out. The combined organic phases were washed with saturated NaCl solution, dried over $Na_2SO_4$ and concentrated.

Purification was carried out by column chromatography (eluant: ethyl acetate/-methanol: 20:1).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

Synthesis Specification for Automated Synthesis

A solution of the amine (100 μmol, 1 ml, 0.1 M in pyridine) is placed at RT in a dry screw-cap jar with a septum cap, and there are added 100 μmol of triethylamine solution (to which DMAP has been added: 1 mg/10 ml of solution) (100 μmol, 1 ml, 0.1 M in pyridine) and acid chloride derivative (300 μmol, 1 ml, 0.3 M in pyridine). The reaction solution was stirred for 24 h at RT. 3 ml of dichloromethane were then added at RT, and 9.5% $NaHCO_3$ solution (1 ml) was added. The solution was mixed thoroughly for 30 minutes.

The phases were separated. DCM (2 ml) was added to the aqueous phase, and the mixture was mixed intensively for 15 minutes in a spin reactor. After centrifugation, the organic phase was separated off and combined with the first fraction. The aqueous phase was extracted a second time with DCM in an analogous manner. The combined organic phases were then dried over a $MgSO_4$ cartridge and concentrated.

The following examples were synthesised in that manner. Analysis was by HPLC-MS (ESI). In all the cases listed here, the mass was found as M+1:

| No. | Name | Mass |
|---|---|---|
| 176 | N-(4-((Dimethylamino)(phenyl)methyl)cyclohexyl)-N-(4-methoxybenzyl)acetamide | 394.26 |
| 177 | N-(1-(1H-indol-3-yl)propan-2-yl)-N-(4-((dimethylamino)(phenyl)methyl)cyclohexyl)acetamide (more polar diastereoisomer) | 431.29 |
| 178 | N-(1-(1H-indol-3-yl)propan-2-yl)-N-(4-((dimethylamino)(phenyl)methyl)cyclohexyl)acetamide (less polar diastereoisomer) | 431.29 |
| 179 | N-(4-((Dimethylamino)(phenyl)methyl)cyclohexyl)-N-(4-fluorobenzyl)acetamide | 382.24 |
| 180 | N-(4-((Dimethylamino)(phenyl)methyl)cyclohexyl)-N-phenylbutyramide | 378.27 |
| 181 | N-(2-(1H-indol-3-yl)ethyl)-N-(4-((dimethylamino)(phenyl)methyl)cyclohexyl)butyramide | 445.31 |

-continued

| No. | Name | Mass |
|---|---|---|
| 182 | N-(2-(1H-indol-3-yl)ethyl)-N-(4-((dimethylamino)(phenyl)methyl)-cyclohexyl)acetamide | 417.28 |
| 183 | Benzo[b]thiophene-3-carboxylic acid [4-(dimethylamino-phenyl-methyl)-cyclohexyl]-amide | 392.19 |
| 184 | 1-(4-Chloro-phenyl)-cyclopentanecarboxylic acid [4-(dimethylamino-phenyl-methyl)-cyclohexyl]-amide | 438.24 |
| 185 | N-[4-(Dimethylamino-thiophen-2-yl-methyl)-cyclohexyl]-4-propyl-benzamide | 384.22 |
| 186 | 3-Cyano-N-[4-(dimethylamino-thiophen-2-yl-methyl)-cyclohexyl]-benzamide | 367.17 |
| 187 | 3-Chloro-N-[4-(dimethylamino-phenyl-methyl)-cyclohexyl]-benzamide | 370.18 |
| 188 | 5-Chloro-4-methoxy-thiophene-3-carboxylic acid [4-(dimethylamino-phenyl-methyl)-cyclohexyl]-amide | 406.15 |
| 189 | 3.4-Dichloro-N-[4-(dimethylamino-phenyl-methyl)-cyclohexyl]-benzamide | 404.14 |
| 190 | N-[4-(Dimethylamino-phenyl-methyl)-cyclohexyl]-3-fluoro-5-trifluoro-methyl-benzamide | 422.20 |
| 191 | 5-Chloro-4-methoxy-thiophene-3-carboxylic acid {4-[dimethylamino-(3-fluoro-phenyl)-methyl]-cyclohexyl}-amide | 424.14 |
| 192 | N-[4-(Dimethylamino-thiophen-2-yl-methyl)-cyclohexyl]-4-fluoro-3-trifluoromethyl-benzamide | 428.15 |
| 193 | Thiophene-2-carboxylic acid [4-(dimethylamino-thiophen-2-yl-methyl)-cyclohexyl]-amide | 348.13 |
| 194 | 3.5-Dichloro-N-[4-(dimethylamino-thiophen-2-yl-methyl)-cyclohexyl]-benzamide | 410.10 |
| 195 | 5-Chloro-4-methoxy-thiophene-3-carboxylic acid [4-(dimethylamino-thiophen-2-yl-methyl)-cyclohexyl]-amide | 412.10 |
| 196 | N-[4-(Dimethylamino-phenyl-methyl)-cyclohexyl]-2,4,5-trifluoro-benzamide | 390.19 |
| 197 | 3-Bromo-N-[4-(dimethylamino-phenyl-methyl)-cyclohexyl]-benzamide | 414.13 |
| 198 | N-[4-(Dimethylamino-thiophen-2-yl-methyl)-cyclohexyl]-4-methyl-benzamide | 356.19 |
| 199 | N-[4-(Dimethylamino-thiophen-2-yl-methyl)-cyclohexyl]-3-methoxy-benzamide | 372.19 |
| 200 | N-[4-(Dimethylamino-thiophen-2-yl-methyl)-cyclohexyl]-3.3-dimethyl-butyramide | 336.22 |
| 201 | 2-tert-Butyl-5-methyl-2H-pyrazole-3-carboxylic acid [4-(dimethyl-amino-thiophen-2-yl-methyl)-cyclohexyl]-amide | 402.25 |
| 202 | N-[4-(Dimethylamino-thiophen-2-yl-methyl)-cyclohexyl]-2,4-dimethoxy-benzamide | 402.20 |
| 203 | N-[4-(Dimethylamino-phenyl-methyl)-cyclohexyl]-3-trifluoromethyl-benzamide | 404.21 |
| 204 | N-{4-[Dimethylamino-(3-fluoro-phenyl)-methyl]-cyclohexyl}-3.5-difluoro-benzamide | 390.19 |
| 205 | N-[4-(Dimethylamino-phenyl-methyl)-cyclohexyl]-2-fluoro-5-trifluoro-methyl-benzamide | 422.20 |
| 206 | 2-(4-Chloro-phenyl)-N-[4-(dimethylamino-phenyl-methyl)-cyclohexyl]-acetamide | 384.20 |
| 207 | N-[4-(Dimethylamino-thiophen-2-yl-methyl)-cyclohexyl]-2-methoxy-benzamide | 372.19 |
| 208 | N-[4-(Dimethylamino-thiophen-2-yl-methyl)-cyclohexyl]-2-methyl-sulfanyl-nicotinamide | 389.16 |
| 209 | 3.4-Dichloro-N-{4-[dimethylamino-(3-fluoro-phenyl)-methyl]-cyclo-hexyl}-benzamide | 422.13 |
| 210 | N-[4-(1-Dimethylamino-3-phenyl-propyl)-cyclohexyl]-4-fluoro-3-trifluoromethyl-benzamide (more polar diastereoisomer) | 450.23 |
| 211 | 5-Chloro-4-methoxy-thiophene-3-carboxylic acid {4-[dimethylamino-(4-fluoro-phenyl)-methyl]-cyclohexyl}-amide | 424.14 |
| 212 | N-[4-(Dimethylamino-thiophen-2-yl-methyl)-cyclohexyl]-3,4,5-trimethoxy-benzamide | 432.21 |
| 213 | N-[4-(Dimethylamino-thiophen-2-yl-methyl)-cyclohexyl]-2-ethyl-sulfanyl-nicotinamide | 403.18 |
| 214 | 2-Methyl-5-phenyl-furan-3-carboxylic acid [4-(dimethylamino-phenyl-methyl)-cyclohexyl]-amide | 416.25 |
| 215 | N-{4-[Dimethylamino-(3-fluoro-phenyl)-methyl]-cyclohexyl}-2-phenoxy-propionamide (less polar diastereoisomer) | 398.24 |
| 216 | N-[4-(Dimethylamino-phenyl-methyl)-cyclohexyl]-2,4-dimethoxy-benzamide | 396.24 |
| 217 | 4-tert-Butyl-N-[4-(dimethylamino-phenyl-methyl)-cyclohexyl]-benzamide | 392.28 |
| 218 | 2-(4-Chloro-phenylsulfanyl)-N-[4-(dimethylamino-thiophen-2-yl-methyl)-cyclohexyl]-nicotinamide | 485.14 |
| 219 | 2-(4-Chloro-phenyl)-N-[4-(dimethylamino-thiophen-2-yl-methyl)-cyclohexyl]-acetamide | 390.15 |
| 220 | N-[4-(Dimethylamino-thiophen-2-yl-methyl)-cyclohexyl]-2-p-tolyloxy-nicotinamide | 449.21 |
| 221 | 3-Chloro-4-(propane-2-sulfonyl)-thiophene-2-carboxylic acid [4-(dimethylamino-thiophen-2-yl-methyl)-cyclohexyl]-amide | 488.10 |

-continued

| No. | Name | Mass |
|---|---|---|
| 222 | N-{4-[Dimethylamino-(3-fluoro-phenyl)-methyl]-cyclohexyl}-2-phenoxy-propionamide (more polar diastereoisomer) | 398.24 |
| 223 | 2-tert-Butyl-5-methyl-2H-pyrazole-3-carboxylic acid [4-(dimethyl-amino-phenyl-methyl)-cyclohexyl]-amide | 396.29 |
| 224 | 5-Methyl-isoxazole-3-carboxylic acid [4-(dimethylamino-thiophen-2-yl-methyl)-cyclohexyl]-amide | 347.17 |
| 225 | 5-Bromo-N-[4-(dimethylamino-thiophen-2-yl-methyl)-cyclohexyl]-nicotinamide | 421.08 |
| 226 | Naphthyl-1-carboxylic acid [4-(dimethylamino-phenyl-methyl)-cyclo-hexyl]-amide | 386.24 |
| 227 | N-[4-(1-Dimethylamino-3-phenyl-propyl)-cyclohexyl]-4-fluoro-3-trifluoromethyl-benzamide (less polar diastereoisomer) | 450.23 |
| 228 | N-[4-(Dimethylamino-phenyl-methyl)-cyclohexyl]-3,3-dimethyl-butyramide (more polar diastereoisomer) | 330.27 |
| 229 | 5-(4-Chloro-phenyl)-2-methyl-furan-3-carboxylic acid [4-(dimethyl-amino-thiophen-2-yl-methyl)-cyclohexyl]-amide | 456.16 |
| 230 | N-[4-(Dimethylamino-phenyl-methyl)-cyclohexyl]-2-phenoxy-propionamide | 380.25 |
| 231 | Benzo[b]thiophene-2-carboxylic acid {4-[dimethylamino-(3-fluoro-phenyl)-methyl]-cyclohexyl}-amide | 410.18 |
| 232 | 5-(4-Chloro-phenyl)-2-methyl-furan-3-carboxylic acid [4-(dimethyl-amino-phenyl-methyl)-cyclohexyl]-amide | 450.21 |
| 233 | 4-(4-Chloro-benzenesulfonyl)-3-methyl-thiophene-2-carboxylic acid [4-(dimethylamino-phenyl-methyl)-cyclohexyl]-amide | 530.15 |
| 234 | 4-[4-(Dimethylamino-phenyl-methyl)-cyclohexyl]-2-phenyl-butyramide (less polar diastereoisomer) | 378.27 |
| 235 | 5-Bromo-N-[4-(dimethylamino-phenyl-methyl)-cyclohexyl]-nicotinamide | 415.13 |
| 236 | Adamantane-1-carboxylic acid [4-(dimethylamino-phenyl-methyl)-cyclohexyl]-amide | 394.30 |
| 237 | 2-Phenyl-thiazole-4-carboxylic acid [4-(dimethylamino-phenyl-methyl)-cyclohexyl]-amide | 419.20 |
| 238 | 4-Methyl-2-phenyl-thiazole-5-carboxylic acid [4-(dimethylamino-phenyl-methyl)-cyclohexyl]-amide | 433.22 |
| 239 | 2-(2,3-Dihydro-benzofuran-5-yl)-thiazole-4-carboxylic acid [4-(dimethylamino-thiophen-2-yl-methyl)-cyclohexyl]-amide | 467.17 |
| 240 | N-{4-[Dimethylamino-(3-fluoro-phenyl)-methyl]-cyclohexyl}-2-phenyl-acetamide | 368.23 |
| 241 | 3-Chloro-N-[4-(1-dimethylamino-3-phenyl-propyl)-cyclohexyl]-benzamide | 398.21 |
| 242 | N-[4-(Dimethylamino-phenyl-methyl)-cyclohexyl]-4-methyl-benzamide | 350.24 |
| 243 | 3,5-Dichloro-N-{4-[dimethylamino-(3-fluoro-phenyl)-methyl]-cyclo-hexyl}-benzamide | 422.13 |
| 244 | N-[4-(Dimethylamino-phenyl-methyl)-cyclohexyl]-2,3,6-trifluoro-benzamide | 390.19 |
| 245 | Thiophene-2-carboxylic acid [4-(dimethylamino-phenyl-methyl)-cyclohexyl]-amide (less polar diastereoisomer) | 342.18 |
| 246 | N-[4-(Dimethylamino-phenyl-methyl)-cyclohexyl]-3,3-dimethyl-butyramide (less polar diastereoisomer) | 330.27 |
| 247 | 2-tert-Butyl-5-methyl-2H-pyrazole-3-carboxylic acid [4-(dimethyl-amino-phenyl-methyl)-cyclohexyl]-amide | 396.29 |
| 248 | N-[4-(1-Dimethylamino-3-phenyl-propyl)-cyclohexyl]-3-methyl-benzamide | 378.27 |
| 249 | Thiophene-2-carboxylic acid [4-(dimethylamino-phenyl-methyl)-cyclohexyl]-amide (more polar diastereoisomer) | 342.18 |
| 250 | N-[4-(Dimethylamino-phenyl-methyl)-cyclohexyl]-2-phenyl-butyramide (more polar diastereoisomer) | 378.27 |
| 251 | N-{4-[Dimethylamino-(3-fluoro-phenyl)-methyl]-cyclohexyl}-3,3-dimethyl-butyramide | 348.26 |
| 252 | 3-Chloro-4-methanesulfonyl-thiophene-2-carboxylic acid [4-(dimethylamino-phenyl-methyl)-cyclohexyl]-amide | 454.12 |
| 253 | 4-(4-Chloro-benzenesulfonyl)-3-methyl-thiophene-2-carboxylic acid [4-(dimethylamino-phenyl-methyl)-cyclohexyl]-amide | 530.15 |
| 254 | 2-Benzyloxy-N-[4-(dimethylamino-phenyl-methyl)-cyclohexyl]-acetamide | 380.25 |
| 255 | N-[4-Dimethylamino-phenyl-methyl)-cyclohexyl]-2-thiophen-2-yl-acetamide | 356.19 |
| 256 | 4-Methyl-2-phenyl-thiazole-5-carboxylic acid {4-[dimethylamino-(3-fluoro-phenyl)-methyl]-cyclohexyl}-amide | 451.21 |
| 257 | 2-(4-Chloro-phenoxy)-N-[4-(dimethylamino-thiophen-2-yl-methyl)-cyclohexyl]-nicotinamide | 469.16 |
| 258 | N-[4-(1-Dimethylamino-3-phenyl-propyl)-cyclohexyl]-4-fluoro-benzamide | 382.24 |
| 259 | 5-Bromo-N-[4-(dimethylamino-phenyl-methyl)-cyclohexyl]-nicotinamide | 415.13 |
| 260 | 4-Bromo-2-ethyl-5-methyl-2H-pyrazole-3-carboxylic acid [4-(dimethyl-amino-thiophen-2-yl-methyl)-cyclohexyl]-amide | 452.12 |

| No. | Name | Mass |
|---|---|---|
| 261 | 3-Cyano-N-[4-(dimethylamino-phenyl-methyl)-cyclohexyl]-benzamide | 361.22 |
| 262 | N-{4-[Dimethylamino-(4-fluoro-phenyl)-methyl]-cyclohexyl}-4-fluoro-benzamide | 372.20 |
| 263 | 3-Bromo-N-{4-[dimethylamino-(4-fluoro-phenyl)-methyl]-cyclohexyl}-benzamide | 432.12 |
| 264 | 2-Phenyl-thiazole-4-carboxylic acid {4-[dimethylamino-(3-fluoro-phenyl)-methyl]-cyclohexyl}-amide | 437.19 |
| 265 | 2,5-Dimethyl-furan-3-carboxylic acid {4-[dimethylamino-(3-fluoro-phenyl)-methyl]-cyclohexyl}-amide | 372.22 |
| 266 | 2-Methyl-5-phenyl-furan-3-carboxylic acid {4-[dimethylamino-(3-fluoro-phenyl)-methyl]-cyclohexyl}-amide | 434.24 |
| 267 | 5-Pyridin-2-yl-thiophene-2-carboxylic acid {4-[dimethylamino-(3-fluoro-phenyl)-methyl]-cyclohexyl}-amide | 437.19 |
| 268 | 4-Bromo-2-ethyl-5-methyl-2H-pyrazole-3-carboxylic acid [4-(dimethylamino-phenyl-methyl)-cyclohexyl]-amide | 446.17 |
| 269 | 3-Chloro-N-{4-[dimethylamino-(3-fluoro-phenyl)-methyl]-cyclohexyl}-4-fluoro-benzamide | 406.16 |
| 270 | 3,4-Dichloro-N-{4-[dimethylamino-(4-fluoro-phenyl)-methyl]-cyclohexyl}-benzamide | 422.13 |
| 271 | N-{4-[Dimethylamino-(4-fluoro-phenyl)-methyl]-cyclohexyl}-2,4,5-trifluoro-benzamide | 408.18 |
| 272 | Cyclohexanecarboxylic acid [4-(dimethylamino-phenyl-methyl)-cyclohexyl]-amide | 342.27 |
| 273 | N-{4-[Dimethylamino-(3-fluoro-phenyl)-methyl]-cyclohexyl}-2-phenyl-butyramide | 396.26 |
| 274 | 2-(4-Chloro-phenyl)-N-{4-[dimethylamino-(3-fluoro-phenyl)-methyl]-cyclohexyl}-acetamide | 402.19 |
| 275 | N-[4-(Dimethylamino-phenyl-methyl)-cyclohexyl]-3-nitro-benzamide | 381.21 |
| 276 | N-[4-(1-Dimethylamino-3-phenyl-propyl)-cyclohexyl]-2,5-difluoro-benzamide | 400.23 |
| 277 | 3-Bromo-N-[4-(1-dimethylamino-3-phenyl-propyl)-cyclohexyl]-benzamide | 442.16 |
| 278 | N-{4-[Dimethylamino-(3-fluoro-phenyl)-methyl]-cyclohexyl}-2,6-difluoro-benzamide | 390.19 |
| 279 | 2,5-Dimethyl-furan-3-carboxylic acid [4-(dimethylamino-phenyl-methyl)-cyclohexyl]-amide | 354.23 |
| 280 | 3-Chloro-N-{4-[dimethylamino-(4-fluoro-phenyl)-methyl]-cyclohexyl}-4-fluoro-benzamide | 406.16 |
| 281 | N-[4-(Dimethylamino-phenyl-methyl)-cyclohexyl]-5-fluoro-2-trifluoromethyl-benzamide | 422.20 |
| 282 | 5-Methyl-isoxazole-3-carboxylic acid [4-(dimethylamino-phenyl-methyl)-cyclohexyl]-amide | 341.21 |
| 283 | 2-(2,3-Dihydro-benzofuran-5-yl)-4-methyl-thiazole-5-carboxylic acid [4-(dimethylamino-thiophen-2-yl-methyl)-cyclohexyl]-amide | 481.19 |
| 284 | 2-(4-Chloro-phenoxy)-N-[4-(dimethylamino-phenyl-methyl)-cyclohexyl]-acetamide | 400.19 |
| 285 | 5-(4-Chloro-phenyl)-2-methyl-furan-3-carboxylic acid {4-[dimethylamino-(3-fluoro-phenyl)-methyl]-cyclohexyl}-amide | 468.20 |
| 286 | 2-Bromo-N-[4-(dimethylamino-phenyl-methyl)-cyclohexyl]-benzamide | 414.13 |
| 287 | N-[4-(Dimethylamino-phenyl-methyl)-cyclohexyl]-2,6-dimethoxy-benzamide | 396.24 |
| 288 | Cyclopentanecarboxylic acid [4-(dimethylamino-phenyl-methyl)-cyclohexyl]-amide | 328.25 |
| 289 | 2-(2,3-Dihydro-benzofuran-5-yl)-thiazole-4-carboxylic acid [4-(dimethylamino-phenyl-methyl)-cyclohexyl]-amide | 461.21 |
| 290 | Benzo[1,2,5]thiadiazole-5-carboxylic acid {4-[dimethylamino-(3-fluoro-phenyl)-methyl]-cyclohexyl}-amide | 412.17 |
| 291 | N-[4-(Dimethylamino-thiophen-2-yl-methyl)-cyclohexylmethyl]-2-thiophen-2-yl-acetamide | 376.16 |
| 292 | Benzo[b]thiophene-3-carboxylic acid [4-(dimethylamino-phenyl-methyl)-cyclohexylmethyl]-amide | 406.21 |
| 293 | 5-Chloro-4-methoxy-thiophene-3-carboxylic acid [4-(dimethylamino-phenyl-methyl)-cyclohexylmethyl]-amide | 420.16 |
| 294 | N-[4-(Dimethylamino-phenyl-methyl)-cyclohexylmethyl]-3,4-difluoro-benzamide (less polar diastereoisomer) | 386.22 |
| 295 | N-{4-[Dimethylamino-(3-fluoro-phenyl)-methyl]-cyclohexylmethyl}-3,3-dimethyl-butyramide | 362.27 |
| 296 | 2-Bromo-N-[4-(dimethylamino-thiophen-2-yl-methyl)-cyclohexylmethyl]-benzamide | 434.10 |
| 297 | N-[4-(Dimethylamino-thiophen-2-yl-methyl)-cyclohexylmethyl]-2,2-diphenyl-acetamide | 446.24 |
| 298 | N-[4-(Dimethylamino-phenyl-methyl)-cyclohexylmethyl]-3,3-dimethyl-butyramide | 344.28 |
| 299 | N-[4-(Dimethylamino-phenyl-methyl)-cyclohexylmethyl]-2-methylsulfanyl-nicotinamide | 397.22 |
| 300 | N-[4-(Dimethylamino-thiophen-2-yl-methyl)-cyclohexylmethyl]-2,6-dimethoxy-benzamide | 416.21 |

-continued

| No. | Name | Mass |
|---|---|---|
| 301 | N-[4-(Dimethylamino-thiophen-2-yl-methyl)-cyclohexylmethyl]-3,3-dimethyl-butyramide | 350.24 |
| 302 | Benzo[b]thiophene-3-carboxylic acid [4-(dimethylamino-thiophen-2-yl-methyl)-cyclohexylmethyl]-amide | 412.16 |
| 303 | 5-Chloro-4-methoxy-thiophene-3-carboxylic acid {4-[dimethylamino-(3-fluoro-phenyl)-methyl]-cyclohexylmethyl}-amide | 438.15 |
| 304 | N-[4-(Dimethylamino-thiophen-2-yl-methyl)-cyclohexylmethyl]-2-phenoxy-propionamide | 400.22 |
| 305 | N-[4-(Dimethylamino-thiophen-2-yl-methyl)-cyclohexylmethyl]-2-methoxy-benzamide | 386.20 |
| 306 | N-[4-(Dimethylamino-phenyl-methyl)-cyclohexylmethyl]-2-phenyl-acetamide | 364.25 |
| 307 | 3-Bromo-N-[4-(dimethylamino-thiophen-2-yl-methyl)-cyclohexyl-methyl]-benzamide | 434.10 |
| 308 | N-[4-(Dimethylamino-thiophen-2-yl-methyl)-cyclohexylmethyl]-3-fluoro-5-trifluoromethyl-benzamide | 442.17 |
| 309 | N-{4-[(4-Chloro-phenyl)-dimethylamino-methyl]-cyclohexylmethyl}-3,3-dimethyl-butyramide | 378.24 |
| 310 | N-[4-(Dimethylamino-phenyl-methyl)-cyclohexylmethyl]-2-ethyl-sulfanyl-nicotinamide | 411.23 |
| 311 | 2-(4-Chloro-phenyl)-N-[4-(dimethylamino-thiophen-2-yl-methyl)-cyclohexylmethyl]-acetamide | 404.17 |
| 312 | N-{4-[(4-Chloro-phenyl)-dimethylamino-methyl]-cyclohexylmethyl}-2.2-diphenyl-acetamide | 474.24 |
| 313 | N-[4-(Dimethylamino-thiophen-2-yl-methyl)-cyclohexylmethyl]-2.6-difluoro-benzamide | 392.17 |
| 314 | Benzo[b]thiophene-3-carboxylic acid {4-[dimethylamino-(3-fluoro-phenyl)-methyl]-cyclohexylmethyl}-amide | 424.20 |
| 315 | N-{4-[(4-Chloro-phenyl)-dimethylamino-methyl]-cyclohexylmethyl}-2-methylsulfanyl-nicotinamide | 431.18 |
| 316 | N-{4-[(4-Chloro-phenyl)-dimethylamino-methyl]-cyclohexylmethyl}-2-thiophen-2-yl-acetamide | 404.17 |
| 317 | N-[4-(Dimethylamino-phenyl-methyl)-cyclohexylmethyl]-2-methyl-benzamide (less polar diastereoisomer) | 364.25 |
| 318 | 1-(4-Chloro-phenyl)-cyclopentane-carboxylic acid [4-(dimethylamino-phenyl-methyl)-cyclohexylmethyl]-amide | 452.26 |
| 319 | N-{4-[Dimethylamino-(3-fluoro-phenyl)-methyl]-cyclohexylmethyl}-2-phenyl-acetamide (more polar diastereoisomer) | 382.24 |
| 320 | N-{4-[(4-Chloro-phenyl)-dimethylamino-methyl]-cyclohexylmethyl}-2-(3-methoxy-phenyl)-acetamide | 428.22 |
| 321 | N-[4-(Dimethylamino-phenyl-methyl)-cyclohexylmethyl]-2-phenyl-butyramide | 392.28 |
| 322 | N-{4-[Dimethylamino-(4-fluoro-phenyl)-methyl]-cyclohexylmethyl}-3.3-dimethyl-butyramide | 362.27 |
| 323 | N-[4-(Dimethylamino-phenyl-methyl)-cyclohexylmethyl]-2-phenoxy-propionamide | 394.26 |
| 324 | 2-(4-Chloro-phenyl)-N-[4-(dimethylamino-phenyl-methyl)-cyclohexyl-methyl]-acetamide | 398.21 |
| 325 | N-[4-(Dimethylamino-phenyl-methyl)-cyclohexylmethyl]-2-methyl-benzamide (more polar diastereoisomer) | 364.25 |
| 326 | N-[4-(Dimethylamino-phenyl-methyl)-cyclohexylmethyl]-3-trifluoro-methyl-benzamide (less polar diastereoisomer) | 418.22 |
| 327 | 1-(4-Chloro-phenyl)-cyclopentane-carboxylic acid {4-[dimethylamino-(3-fluoro-phenyl)-methyl]-cyclohexylmethyl}-amide | 470.25 |
| 328 | Thiophene-2-carboxylic acid [4-(dimethylamino-phenyl-methyl)-cyclo-hexylmethyl]-amide | 356.19 |
| 329 | 3,5-Dichloro-N-[4-(dimethylamino-phenyl-methyl)-cyclohexylmethyl]-benzamide | 418.16 |
| 330 | 2-Methyl-5-phenyl-furan-3-carboxylic acid {4-[(4-chloro-phenyl)-dimethylamino-methyl]-cyclohexylmethyl}-amide | 464.22 |
| 331 | 3-Chloro-N-[4-(dimethylamino-phenyl-methyl)-cyclohexylmethyl]-benzamide | 384.20 |
| 332 | N-{4-[Dimethylamino-(3-fluoro-phenyl)-methyl]-cyclohexylmethyl}-2-phenoxy-propionamide (more polar diastereoisomer) | 412.25 |
| 333 | N-[4-(Dimethylamino-phenyl-methyl)-cyclohexylmethyl]-3-trifluoro-methyl-benzamide (more polar diastereoisomer) | 418.22 |
| 334 | Thiophene-2-carboxylic acid {4-[dimethylamino-(3-fluoro-phenyl)-methyl]-cyclohexylmethyl}-amide (more polar diastereoisomer) | 374.18 |
| 335 | 2-Phenyl-thiazole-4-carboxylic acid [4-(dimethylamino-phenyl-methyl)-cyclohexylmethyl]-amide | 433.22 |
| 336 | Benzo[b]thiophene-3-carboxylic acid {4-[(4-chloro-phenyl)-dimethyl-amino-methyl]-cyclohexylmethyl}-amide (less polar diastereoisomer) | 440.17 |
| 337 | N-{4-[Dimethylamino-(3-fluoro-phenyl)-methyl]-cyclohexylmethyl}-2-p-tolyloxy-nicotinamide | 475.26 |
| 338 | 2,4,6-Trichloro-N-[4-(dimethylamino-phenyl-methyl)-cyclohexyl-methyl]-benzamide | 452.12 |
| 339 | 1-(4-Chloro-phenyl)-cyclopentane-carboxylic acid [4-(dimethylamino-phenyl-methyl)-cyclohexylmethyl]-amide | 452.26 |

-continued

| No. | Name | Mass |
|---|---|---|
| 340 | Thiophene-2-carboxylic acid {4-[dimethylamino-(3-fluoro-phenyl)-methyl]-cyclohexylmethyl}-amide (less polar diastereoisomer) | 374.18 |
| 341 | N-{4-[Dimethylamino-(3-fluoro-phenyl)-methyl]-cyclohexylmethyl}-2-phenoxy-propionamide (less polar diastereoisomer) | 412.25 |
| 342 | N-{4-[Dimethylamino-(3-fluoro-phenyl)-methyl]-cyclohexylmethyl}-2-methyl-butyramide (more polar diastereoisomer) | 348.26 |
| 343 | N-{4-[Dimethylamino-(3-fluoro-phenyl)-methyl]-cyclohexylmethyl}-2-thiophen-2-yl-acetamide | 388.20 |
| 344 | Benzo[b]thiophene-3-carboxylic acid {4-[dimethylamino-(4-fluoro-phenyl)-methyl]-cyclohexylmethyl}-amide | 424.20 |
| 345 | 2-Methyl-5-phenyl-furan-3-carboxylic acid [4-(dimethylamino-phenyl-methyl)-cyclohexylmethyl]-amide | 430.26 |
| 346 | N-{4-[Dimethylamino-(3-fluoro-phenyl)-methyl]-cyclohexylmethyl}-2-phenoxy-propionamide | 412.25 |
| 347 | 3-Cyano-N-[4-(dimethylamino-thiophen-2-yl-methyl)-cyclohexyl-methyl]-benzamide | 381.19 |
| 348 | N-{4-[Dimethylamino-(3-fluoro-phenyl)-methyl]-cyclohexylmethyl}-2-phenyl-acetamide (less polar diastereoisomer) | 382.24 |
| 349 | N-[4-(Dimethylamino-phenyl-methyl)-cyclohexylmethyl]-2-(3-methoxy-phenyl)-acetamide | 394.26 |
| 350 | N-{4-[Dimethylamino-(3-fluoro-phenyl)-methyl]-cyclohexylmethyl}-4-fluoro-3-trifluoromethyl-benzamide | 454.20 |
| 351 | N-{4-[(4-Chloro-phenyl)-dimethylamino-methyl]-cyclohexylmethyl}-2-ethylsulfanyl-nicotinamide | 445.20 |
| 352 | N-[4-(Dimethylamino-thiophen-2-yl-methyl)-cyclohexylmethyl]-2-p-tolyloxy-nicotinamide (more polar diastereoisomer) | 463.23 |
| 353 | 2-Methyl-5-phenyl-furan-3-carboxylic acid {4-[dimethylamino-(3-fluoro-phenyl)-methyl]-cyclohexylmethyl}-amide | 448.25 |
| 354 | 2-Chloro-N-{4-[(4-chloro-phenyl)-dimethylamino-methyl]-cyclohexyl-methyl}-benzamide | 418.16 |
| 355 | 2-Chloro-N-[4-(dimethylamino-phenyl-methyl)-cyclohexylmethyl]-nicotinamide | 385.19 |
| 356 | N-[4-(Dimethylamino-thiophen-2-yl-methyl)-cyclohexylmethyl]-4-propyl-benzamide | 398.24 |
| 357 | N-[4-(Dimethylamino-phenyl-methyl)-cyclohexylmethyl]-3,4-difluoro-benzamide (more polar diastereoisomer) | 386.22 |
| 358 | 3-Bromo-N-[4-(dimethylamino-phenyl-methyl)-cyclohexylmethyl]-benzamide | 428.15 |
| 359 | N-{4-[Dimethylamino-(4-fluoro-phenyl)-methyl]-cyclohexylmethyl}-2-thiophen-2-yl-acetamide | 388.20 |
| 360 | 2-(4-Chloro-phenoxy)-N-[4-(dimethylamino-phenyl-methyl)-cyclohexyl-methyl]-nicotinamide (less polar diastereoisomer) | 477.22 |
| 361 | 2,4-Dichloro-N-[4-(dimethylamino-phenyl-methyl)-cyclohexylmethyl]-benzamide | 418.16 |
| 362 | N-[4-(Dimethylamino-phenyl-methyl)-cyclohexylmethyl]-3-methyl-benzamide | 364.25 |
| 363 | 2-Bromo-N-{4-[dimethylamino-(3-fluoro-phenyl)-methyl]-cyclohexyl-methyl}-benzamide | 446.14 |
| 364 | N-{4-[Dimethylamino-(3-fluoro-phenyl)-methyl]-cyclohexylmethyl}-3-trifluoromethyl-benzamide | 436.21 |
| 365 | 2-Phenyl-thiazole-4-carboxylic acid {4-[dimethylamino-(3-fluoro-phenyl)-methyl]-cyclohexylmethyl}-amide | 451.21 |
| 366 | 2-tert-Butyl-5-methyl-2H-pyrazole-3-carboxylic acid [4-(dimethyl-amino-thiophen-2-yl-methyl)-cyclohexylmethyl]-amide | 416.26 |
| 367 | 3-Chloro-4-(propane-2-sulfonyl)-thiophene-2-carboxylic acid [4-(dimethylamino-thiophen-2-yl-methyl)-cyclohexylmethyl]-amide | 502.12 |
| 368 | N-{4-[Dimethylamino-(3-fluoro-phenyl)-methyl]-cyclohexylmethyl}-2-methoxy-benzamide | 398.24 |
| 369 | N-{4-[(4-Chloro-phenyl)-dimethylamino-methyl]-cyclohexylmethyl}-3-trifluoromethyl-benzamide | 452.18 |
| 370 | 1-(4-Chloro-phenyl)-cyclopentane-carboxylic acid {4-[dimethylamino-(4-fluoro-phenyl)-methyl]-cyclohexylmethyl}-amide | 470.25 |
| 371 | 3,5-Dichloro-N-{4-[dimethylamino-(3-fluoro-phenyl)-methyl]-cyclo-hexylmethyl}-benzamide | 436.15 |
| 372 | Benzo[b]thiophene-3-carboxylic acid {4-[(4-chloro-phenyl)-dimethyl-amino-methyl]-cyclohexylmethyl}-amide (more polar diastereoisomer) | 440.17 |
| 373 | 2-Methyl-5-phenyl-furan-3-carboxylic acid {4-[dimethylamino-(3-fluoro-phenyl)-methyl]-cyclohexylmethyl}-amide | 448.25 |
| 374 | 2-(4-Chloro-phenylsulfanyl)-N-[4-(dimethylamino-phenyl-methyl)-cyclohexylmethyl]-nicotinamide | 493.20 |
| 375 | 4-Bromo-2-ethyl-5-methyl-2H-pyrazole-3-carboxylic acid [4-(dimethyl-amino-thiophen-2-yl-methyl)-cyclohexylmethyl]-amide | 466.14 |
| 376 | 5-Chloro-4-methoxy-thiophene-3-carboxylic acid {4-[dimethylamino-(4-fluoro-phenyl)-methyl]-cyclohexylmethyl}-amide | 438.15 |
| 378 | N-{4-[Dimethylamino-(3-fluoro-phenyl)-methyl]-cyclohexylmethyl}-2-methyl-butyramide (less polar diastereoisomer) | 348.26 |
| 379 | 5-Methyl-isoxazole-3-carboxylic acid [4-(dimethylamino-phenyl-methyl)-cyclohexylmethyl]-amide | 355.23 |

-continued

| No. | Name | Mass |
|---|---|---|
| 380 | Benzo[b]thiophene-3-carboxylic acid [4-(1-dimethylamino-3-phenyl-propyl)-cyclohexylmethyl]-amide | 434.24 |
| 381 | N-{4-[Dimethylamino-(4-fluoro-phenyl)-methyl]-cyclohexylmethyl}-2-methylsulfanyl-nicotinamide | 415.21 |
| 382 | N-{4-[(4-Chloro-phenyl)-dimethylamino-methyl]-cyclohexylmethyl}-2-p-tolyloxy-nicotinamide | 491.23 |
| 383 | 2-(4-Chloro-phenoxy)-N-[4-(dimethylamino-phenyl-methyl)-cyclohexyl-methyl]-nicotinamide (more polar diastereoisomer) | 477.22 |
| 384 | N-{4-[Dimethylamino-(3-fluoro-phenyl)-methyl]-cyclohexylmethyl}-2-methyl-benzamide | 382.24 |
| 385 | 5-Methyl-isoxazole-3-carboxylic acid {4-[(4-chloro-phenyl)-dimethyl-amino-methyl]-cyclohexylmethyl}-amide | 389.19 |
| 386 | 5-Bromo-N-[4-(dimethylamino-phenyl-methyl)-cyclohexylmethyl]-nicotinamide | 429.14 |
| 387 | N-[4-(Dimethylamino-phenyl-methyl)-cyclohexylmethyl]-2-methyl-butyramide | 330.27 |
| 388 | N-{4-[Dimethylamino-(3-fluoro-phenyl)-methyl]-cyclohexylmethyl}-2-ethylsulfanyl-nicotinamide | 429.22 |
| 389 | N-[4-(Dimethylamino-thiophen-2-yl-methyl)-cyclohexylmethyl]-2-p-tolyloxy-nicotinamide (less polar diastereoisomer) | 463.23 |
| 390 | 4-Bromo-2-ethyl-5-methyl-2H-pyrazole-3-carboxylic acid [4-(dimethyl-amino-phenyl-methyl)-cyclohexylmethyl]-amide | 460.18 |
| 391 | N-{4-[(4-Chloro-phenyl)-dimethylamino-methyl]-cyclohexylmethyl}-2-phenoxy-propionamide | 428.22 |
| 392 | N-[4-(Dimethylamino-phenyl-methyl)-cyclohexylmethyl]-3,5-dinitro-benzamide | 440.21 |
| 393 | N-{4-[(4-Chloro-phenyl)-dimethylamino-methyl]-cyclohexylmethyl}-3-methoxy-benzamide | 414.21 |
| 394 | 2-Bromo-N-{4-[(4-chloro-phenyl)-dimethylamino-methyl]-cyclohexyl-methyl}-benzamide | 462.11 |
| 395 | 2-Bromo-N-(2-{4-[(4-chloro-phenyl)-dimethylamino-methyl]-cyclo-hexyl}-ethyl)-benzamide | 476.12 |
| 396 | 2-Bromo-N-(2-{4-[dimethylamino-(3-fluoro-phenyl)-methyl]-cyclo-hexyl}-ethyl)-benzamide | 460.15 |
| 397 | 3-Chloro-N-{2-[4-(dimethylamino-phenyl-methyl)-cyclohexyl]-ethyl}-benzamide (more polar diastereoisomer) | 398.21 |
| 398 | 3-Chloro-N-{2-[4-(dimethylamino-phenyl-methyl)-cyclohexyl]-ethyl}-benzamide (less polar diastereoisomer) | 398.21 |
| 399 | 3-Chloro-N-(2-{4-[(4-chloro-phenyl)-dimethylamino-methyl]-cyclo-hexyl}-ethyl)-benzamide | 432.17 |
| 400 | 3-Chloro-N-(2-{4-[dimethylamino-(3-fluoro-phenyl)-methyl]-cyclo-hexyl}-ethyl)-benzamide (less polar diastereoisomer) | 416.20 |
| 401 | 3-Chloro-N-(2-{4-[dimethylamino-(3-fluoro-phenyl)-methyl]-cyclo-hexyl}-ethyl)-benzamide (more polar diastereoisomer) | 416.20 |
| 402 | 2-Chloro-N-{2-[4-(dimethylamino-phenyl-methyl)-cyclohexyl]-ethyl}-benzamide | 398.21 |
| 403 | 2-Chloro-N-(2-{4-[(4-chloro-phenyl)-dimethylamino-methyl]-cyclo-hexyl}-ethyl)-benzamide | 432.17 |
| 404 | 2-Chloro-N-(2-{4-[dimethylamino-(3-fluoro-phenyl)-methyl]-cyclo-hexyl}-ethyl)-benzamide | 416.20 |
| 405 | 4-Chloro-N-{2-[4-(dimethylamino-phenyl-methyl)-cyclohexyl]-ethyl}-benzamide | 398.21 |
| 406 | 4-Chloro-N-(2-{4-[dimethylamino-(3-fluoro-phenyl)-methyl]-cyclo-hexyl}-ethyl)-benzamide | 416.20 |
| 407 | N-{2-[4-(Dimethylamino-phenyl-methyl)-cyclohexyl]-ethyl}-4-fluoro-benzamide | 382.24 |
| 408 | N-(2-{4-[(4-Chloro-phenyl)-dimethylamino-methyl]-cyclohexyl}-ethyl)-4-fluoro-benzamide | 416.20 |
| 409 | N-(2-{4-[Dimethylamino-(3-fluoro-phenyl)-methyl]-cyclohexyl}-ethyl)-4-fluoro-benzamide | 400.23 |
| 410 | N-{2-[4-(Dimethylamino-phenyl-methyl)-cyclohexyl]-ethyl}-2-fluoro-benzamide | 382.24 |
| 411 | N-(2-{4-[Dimethylamino-(3-fluoro-phenyl)-methyl]-cyclohexyl}-ethyl)-2-fluoro-benzamide | 400.23 |
| 412 | N-(2-{4-[Dimethylamino-(3-fluoro-phenyl)-methyl]-cyclohexyl}-ethyl)-3-methyl-benzamide | 396.26 |
| 413 | 2,6-Dichloro-N-{2-[4-(dimethylamino-phenyl-methyl)-cyclohexyl]-ethyl}-benzamide | 432.17 |
| 414 | N-{2-[4-(Dimethylamino-phenyl-methyl)-cyclohexyl]-ethyl}-2-methoxy-benzamide | 394.26 |
| 415 | N-(2-{4-[Dimethylamino-(3-fluoro-phenyl)-methyl]-cyclohexyl}-ethyl)-2-methoxy-benzamide | 412.25 |
| 416 | 3,4-Dichloro-N-{2-[4-(dimethylamino-phenyl-methyl)-cyclohexyl]-ethyl}-benzamide | 432.17 |
| 417 | N-{2-[4-(Dimethylamino-phenyl-methyl)-cyclohexyl]-ethyl}-2-methyl-benzamide (more polar diastereoisomer) | 378.27 |
| 418 | N-{2-[4-(Dimethylamino-phenyl-methyl)-cyclohexyl]-ethyl}-2-methyl-benzamide (less polar diastereoisomer) | 378.27 |

-continued

| No. | Name | Mass |
|---|---|---|
| 419 | N-(2-{4-[(4-Chloro-phenyl)-dimethylamino-methyl]-cyclohexyl}-ethyl)-2-methyl-benzamide | 412.23 |
| 420 | N-(2-{4-[Dimethylamino-(3-fluoro-phenyl)-methyl]-cyclohexyl}-ethyl)-2-methyl-benzamide | 396.26 |
| 421 | 4-Cyano-N-{2-[4-(dimethylamino-phenyl-methyl)-cyclohexyl]-ethyl}-benzamide | 389.25 |
| 422 | 3-Chloro-N-(2-{4-[dimethylamino-(4-fluoro-phenyl)-methyl]-cyclohexyl}-ethyl)-benzamide | 416.20 |
| 423 | 3-Chloro-N-(2-{4-[dimethylamino-(4-fluoro-phenyl)-methyl]-cyclohexyl}-ethyl)-benzamide (less polar diastereoisomer) | 416.20 |
| 424 | 3-Chloro-N-{2-[4-(dimethylamino-thiophen-2-yl-methyl)-cyclohexyl]-ethyl}-benzamide | 404.17 |
| 425 | 2-Chloro-N-{2-[4-(dimethylamino-thiophen-2-yl-methyl)-cyclohexyl]-ethyl}-benzamide | 404.17 |
| 426 | N-{2-[4-(Dimethylamino-thiophen-2-yl-methyl)-cyclohexyl]-ethyl}-4-fluoro-benzamide | 388.20 |
| 427 | N-(2-{4-[Dimethylamino-(4-fluoro-phenyl)-methyl]-cyclohexyl}-ethyl)-2-fluoro-benzamide | 400.23 |
| 428 | N-{2-[4-(Dimethylamino-thiophen-2-yl-methyl)-cyclohexyl]-ethyl}-2-fluoro-benzamide | 388.20 |
| 429 | N-(2-{4-[Dimethylamino-(4-fluoro-phenyl)-methyl]-cyclohexyl}-ethyl)-3-methyl-benzamide | 396.26 |
| 430 | N-{2-[4-(Dimethylamino-thiophen-2-yl-methyl)-cyclohexyl]-ethyl}-3-methyl-benzamide | 384.22 |
| 431 | 2,6-Dichloro-N-{2-[4-(dimethylamino-thiophen-2-yl-methyl)-cyclohexyl]-ethyl}-benzamide | 438.13 |
| 432 | N-(2-{4-[Dimethylamino-(4-fluoro-phenyl)-methyl]-cyclohexyl}-ethyl)-2-methoxy-benzamide | 412.25 |
| 433 | N-{2-[4-(Dimethylamino-phenyl-methyl)-cyclohexyl]-ethyl}-3,5-difluoro-benzamide | 400.23 |
| 434 | N-(2-{4-[(4-Chloro-phenyl)-dimethylamino-methyl]-cyclohexyl}-ethyl)-3,5-difluoro-benzamide | 434.19 |
| 435 | N-(2-{4-[Dimethylamino-(3-fluoro-phenyl)-methyl]-cyclohexyl}-ethyl)-3,5-difluoro-benzamide | 418.22 |
| 436 | N-(2-{4-[(4-Chloro-phenyl)-dimethylamino-methyl]-cyclohexyl}-ethyl)-2,4-difluoro-benzamide | 434.19 |
| 437 | 2,4-Dichloro-N-(2-{4-[(4-chloro-phenyl)-dimethylamino-methyl]-cyclohexyl}-ethyl)-5-fluoro-benzamide | 484.13 |
| 438 | 2,4-Dichloro-N-(2-{4-[dimethylamino-(3-fluoro-phenyl)-methyl]-cyclohexyl}-ethyl)-5-fluoro-benzamide (more polar diastereoisomer) | 468.15 |
| 439 | 2,4-Dichloro-N-(2-{4-[dimethylamino-(3-fluoro-phenyl)-methyl]-cyclohexyl}-ethyl)-5-fluoro-benzamide (less polar diastereoisomer) | 468.15 |
| 440 | 2,4-Dichloro-N-{2-[4-(dimethylamino-thiophen-2-yl-methyl)-cyclohexyl]-ethyl}-5-fluoro-benzamide | 456.12 |
| 441 | 2-Chloro-N-(2-{4-[(4-chloro-phenyl)-dimethylamino-methyl]-cyclohexyl}-ethyl)-nicotinamide | 433.17 |
| 442 | Naphthalene-2-carboxylic acid (2-{4-[dimethylamino-(4-fluoro-phenyl)-methyl]-cyclohexyl}-ethyl)-amide | 432.26 |
| 443 | N-{2-[4-(Dimethylamino-thiophen-2-yl-methyl)-cyclohexyl]-ethyl}-4-propyl-benzamide | 412.25 |
| 444 | N-{2-[4-(Dimethylamino-phenyl-methyl)-cyclohexyl]-ethyl}-3,4-difluoro-benzamide | 400.23 |
| 445 | N-(2-{4-[(4-Chloro-phenyl)-dimethylamino-methyl]-cyclohexyl}-ethyl)-3,4-difluoro-benzamide | 434.19 |
| 446 | N-{2-[4-(Dimethylamino-thiophen-2-yl-methyl)-cyclohexyl]-ethyl}-3,4-difluoro-benzamide | 406.19 |
| 447 | N-(2-{4-[Dimethylamino-(4-fluoro-phenyl)-methyl]-cyclohexyl}-ethyl)-3-methoxy-benzamide | 412.25 |
| 448 | N-{2-[4-(Dimethylamino-phenyl-methyl)-cyclohexyl]-ethyl}-2,2-diphenyl-acetamide | 454.30 |
| 449 | 1-(4-Chloro-phenyl)-cyclopentane-carboxylic acid {2-[4-(dimethylamino-phenyl-methyl)-cyclohexyl]-ethyl}-amide | 466.28 |
| 450 | 2-Benzyloxy-N-{2-[4-(dimethylamino-phenyl-methyl)-cyclohexyl]-ethyl}-acetamide | 408.28 |
| 451 | N-{2-[4-(Dimethylamino-phenyl-methyl)-cyclohexyl]-ethyl}-2-phenyl-acetamide | 378.27 |
| 452 | Thiophene-2-carboxylic acid {2-[4-(dimethylamino-phenyl-methyl)-cyclohexyl]-ethyl}-amide | 370.21 |
| 453 | N-(2-{4-[Dimethylamino-(3-fluoro-phenyl)-methyl]-cyclohexyl}-ethyl)-2-(3-methoxy-phenyl)-acetamide | 426.27 |
| 454 | N-{2-[4-(Dimethylamino-thiophen-2-yl-methyl)-cyclohexyl]-ethyl}-2-(3-methoxy-phenyl)-acetamide | 414.23 |
| 455 | N-(2-{4-[(4-Chloro-phenyl)-dimethylamino-methyl]-cyclohexyl}-ethyl)-2-phenyl-butyramide | 440.26 |
| 456 | N-{2-[4-(Dimethylamino-thiophen-2-yl-methyl)-cyclohexyl]-ethyl}-2-phenyl-butyramide | 412.25 |
| 457 | Benzo[b]thiophene-2-carboxylic acid {2-[4-(dimethylamino-phenyl-methyl)-cyclohexyl]-ethyl}-amide | 420.22 |

-continued

| No. | Name | Mass |
|---|---|---|
| 458 | N-{2-[4-(Dimethylamino-phenyl-methyl)-cyclohexyl]-ethyl}-4-nitro-benzamide | 409.24 |
| 459 | 3-Bromo-N-(2-{4-[dimethylamino-(4-fluoro-phenyl)-methyl]-cyclohexyl}-ethyl)-benzamide | 460.15 |
| 460 | N-{2-[4-(Dimethylamino-phenyl-methyl)-cyclohexyl]-ethyl}-2,3,4,5,6-pentafluoro-benzamide | 454.20 |
| 461 | N-{2-[4-(Dimethylamino-phenyl-methyl)-cyclohexyl]-ethyl}-2,6-difluoro-benzamide | 400.23 |
| 462 | N-(2-{4-[Dimethylamino-(3-fluoro-phenyl)-methyl]-cyclohexyl}-ethyl)-2,6-difluoro-benzamide | 418.22 |
| 463 | 2-Phenyl-thiazole-4-carboxylic acid {2-[4-(dimethylamino-phenyl-methyl)-cyclohexyl]-ethyl}-amide | 447.23 |
| 464 | 2-Phenyl-thiazole-4-carboxylic acid (2-{4-[dimethylamino-(4-fluoro-phenyl)-methyl]-cyclohexyl}-ethyl)-amide | 465.22 |
| 465 | Benzo[b]thiophene-3-carboxylic acid {2-[4-(dimethylamino-thiophen-2-yl-methyl)-cyclohexyl]-ethyl}-amide | 426.18 |
| 466 | N-{2-[4-(Dimethylamino-phenyl-methyl)-cyclohexyl]-ethyl}-2-methylsulfanyl-nicotinamide | 411.23 |
| 467 | 2-Methyl-5-phenyl-furan-3-carboxylic acid {2-[4-(dimethylamino-phenyl-methyl)-cyclohexyl]-ethyl}-amide | 444.28 |
| 468 | 2-(2,3-Dihydro-benzofuran-5-yl)-thiazole-4-carboxylic acid {2-[4-(dimethylamino-phenyl-methyl)-cyclohexyl]-ethyl}-amide | 489.24 |
| 469 | 3-(2,6-Dichloro-phenyl)-5-methyl-isoxazole-4-carboxylic acid {2-[4-(dimethylamino-thiophen-2-yl-methyl)-cyclohexyl]-ethyl}-amide | 519.15 |
| 470 | 2-(4-Chloro-phenylsulfanyl)-N-{2-[4-(dimethylamino-phenyl-methyl)-cyclohexyl]-ethyl}-nicotinamide (more polar diastereoisomer) | 507.21 |
| 471 | 2-(4-Chloro-phenylsulfanyl)-N-{2-[4-(dimethylamino-phenyl-methyl)-cyclohexyl]-ethyl}-nicotinamide (less polar diastereoisomer) | 507.21 |
| 472 | Benzo[1,2,3]thiadiazole-5-carboxylic acid {2-[4-(dimethylamino-phenyl-methyl)-cyclohexyl]-ethyl}-amide | 422.21 |
| 473 | 5-Bromo-N-{2-[4-(dimethylamino-phenyl-methyl)-cyclohexyl]-ethyl}-nicotinamide | 443.16 |
| 474 | 5-Chloro-4-methoxy-thiophene-3-carboxylic acid {2-[4-(dimethylamino-phenyl-methyl)-cyclohexyl]-ethyl}-amide | 434.18 |
| 475 | 5-Chloro-4-methoxy-thiophene-3-carboxylic acid (2-{4-[dimethylamino-(4-fluoro-phenyl)-methyl]-cyclohexyl}-ethyl)-amide | 452.17 |
| 476 | 5-Chloro-4-methoxy-thiophene-3-carboxylic acid {2-[4-(1-dimethylamino-3-phenyl-propyl)-cyclohexyl]-ethyl}-amide | 462.21 |
| 477 | 3-Cyano-N-{2-[4-(dimethylamino-phenyl-methyl)-cyclohexyl]-ethyl}-benzamide | 389.25 |
| 478 | N-{2-[4-(Dimethylamino-phenyl-methyl)-cyclohexyl]-ethyl}-2,4-dimethoxy-benzamide | 424.27 |
| 479 | 2-Chloro-N-((4-((dimethylamino)(phenyl)methyl)cyclohexyl)methyl)-benzamide | 384.20 |
| 480 | N-((4-((Dimethylamino)(phenyl)methyl)cyclohexyl)methyl)-4-fluoro-benzamide | 368.23 |
| 481 | N-(2-(4-((Dimethylamino)(phenyl)methyl)cyclohexyl)ethyl)-4-fluoro-benzamide | 382.24 |
| 482 | N-((4-((Dimethylamino)(phenyl)methyl)cyclohexyl)methyl)-2-fluoro-benzamide | 368.23 |
| 483 | N-((4-((Dimethylamino)(phenyl)methyl)cyclohexyl)methyl)-3-methyl-benzamide | 364.25 |
| 484 | N-((4-((Dimethylamino)(phenyl)methyl)cyclohexyl)methyl)-2-methoxy-benzamide | 380.25 |
| 485 | N-(2-(4-((dimethylamino)(phenyl)methyl)cyclohexyl)ethyl)-3,5-dimethoxybenzamide | 424.27 |
| 486 | N-((4-((Dimethylamino)(3-fluorophenyl)methyl)cyclohexyl)methyl)-2,6-dimethoxybenzamide | 428.25 |
| 487 | N-((4-((Dimethylamino)(phenyl)methyl)cyclohexyl)methyl)-2,4-difluoro-benzamide | 386.22 |
| 488 | N-((4-((Dimethylamino)(thiophen-2-yl)methyl)cyclohexyl)methyl)-3-methoxybenzamide | 386.20 |
| 489 | N-((4-((Dimethylamino)(thiophen-2-yl)methyl)cyclohexyl)methyl)-3,4,5-trimethoxybenzamide | 446.22 |
| 497 | 3-Thiophen-2-yl-[1,2,4]oxadiazole-5-carboxylic acid [4-(dimethylamino-phenyl-methyl)-cyclohexyl]-amide | 410.18 |
| 498 | 3-Methyl-[1,2,4]oxadiazole-5-carboxylic acid {2-[4-(dimethylamino-phenyl-methyl)-cyclohexyl]-ethyl}-amide | 370.24 |
| 499 | 3-Phenyl-[1,2,4]oxadiazole-5-carboxylic acid {4-[dimethylamino-(3-fluoro-phenyl)-methyl]-cyclohexyl}-amide | 422.21 |
| 500 | 3-Cyclopropylmethyl-[1,2,4]oxadiazole-5-carboxylic acid {4-[dimethylamino-(3-fluoro-phenyl)-methyl]-cyclohexyl}-amide | 400.23 |
| 501 | 3-Methoxymethyl-[1,2,4]oxadiazole-5-carboxylic acid {2-[4-(1-dimethylamino-3-phenyl-propyl)-cyclohexyl]-ethyl}-amide | 428.28 |

Amidation of the Secondary Amines ($R^1$=(CH$_2$)$_n$ NR$^6$R$^7$, R$^7$=COR$^{13}$)

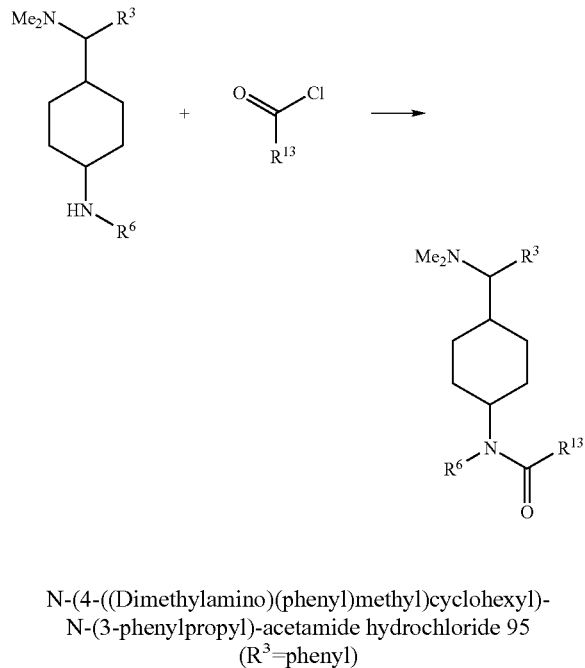

N-(4-((Dimethylamino)(phenyl)methyl)cyclohexyl)-N-(3-phenylpropyl)-acetamide hydrochloride 95 ($R^3$=phenyl)

The amine 85 (1.1 g, 3.1 mmol) was dissolved in anhydrous pyridine (20 ml), and acetic anhydride (3.2 g, 31.4 mmol) was added at room temperature. The reaction mixture was stirred overnight at RT. In order to remove the excess acetic anhydride, toluene (20 ml) was added to the reaction mixture and concentration was carried out using a rotary evaporator. This operation was repeated twice more. 1N NaOH was added to the residue, and the product was extracted with ethyl acetate. After drying over Na$_2$SO$_4$, the organic phase was concentrated using a rotary evaporator. Purification of the crude product was carried out by flash chromatography (eluant: diethyl ether).

The product was dissolved in methyl ethyl ketone (3 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl)-N-phenylacetamide hydrochloride 96 ($R^3$=phenyl)

The amine 92 (0.9 g, 2.9 mmol) was dissolved in anhydrous pyridine (20 ml), and acetic anhydride (2.98 g, 29.2 mmol) was added at room temperature. The reaction mixture was stirred overnight at RT. In order to remove the excess acetic anhydride, toluene (20 ml) was added to the reaction mixture and concentration was carried out using a rotary evaporator. This operation was repeated twice more. 1N NaOH was added to the residue and the product was extracted with ethyl acetate. After drying over Na$_2$SO$_4$, the organic phase was concentrated using a rotary evaporator. Purification of the crude product was carried out by column chromatography (eluant: ethyl acetate/methanol 20:1). The product was dissolved in methyl ethyl ketone (5 ml), and then water (0.01 ml/1 mmol) and trimethylchlorosilane (1.3 ml/1 mmol) were added. Filtering off with suction and washing with ether yielded white crystals, which were dried in vacuo.

$^{13}$C NMR (75 MHz, DMSO) 23.20; 25.16; 25.89; 25.58; 25.64; 31.45; 37.09; 42.93; 52.97; 68.87; 127.93; 128.73; 129.17; 129.81; 130.08; 130.92; 140.02; 168.62.

N-(4-((Dimethylamino)(phenyl)methyl)cyclohexyl)-N-(4-phenylbutyl)-propionamide hydrochloride 97 ($R^3$=phenyl)

The amine 87 (0.49 g, 1.3 mmol) was dissolved in DCM (1 ml); triethylamine (0.27 g, 2.7 mmol) and a spatula tip of DMAP were added and the mixture was cooled to −10° C. Propionyl chloride (0.19 g, 2.7 mmol) dissolved in DCM (2 ml) was added, and the reaction mixture was stirred for 5 h at RT. For working up, KOH (5 N, 2 ml) was added, the phases were separated, and the aqueous phase was then extracted twice with 5 ml of dichloromethane each time. The combined organic phases were washed with saturated NaCl solution, dried over Na$_2$SO$_4$ and concentrated. The crude product was purified by column chromatography (diethyl ether/methanol: 40:1).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl)-N-(4-phenylbutyl)-acetamide hydrochloride 98 ($R^3$=phenyl)

The amine 87 (0.50 g, 1.4 mmol) was dissolved in DCM (1 ml); triethylamine (0.28 g, 2.8 mmol) and a spatula tip of DMAP were added and the mixture was cooled to −10° C. Acetyl chloride (0.16 g, 2.1 mmol) dissolved in DCM (2 ml) was added, and the reaction mixture was stirred for 5 h at RT. For working up, KOH (5 N, 2 ml) was added, the phases were separated, and the aqueous phase was then extracted twice with 5 ml of DCM each time. The combined organic phases were washed with saturated NaCl solution, dried over Na$_2$SO$_4$ and concentrated. The crude product was purified by column chromatography (diethyl ether/-methanol: 20:1).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl)-N-(4-methoxyphenyl)-acetamide hydrochloride 99 ($R^3$=phenyl)

The amine 89 (0.68 g, 2.0 mmol) was dissolved in DCM (2 ml); triethylamine (0.41 g, 4.0 mmol) and a spatula tip of DMAP were added and the mixture was cooled to −10° C. Acetyl chloride (0.24 g, 3.0 mmol) dissolved in DCM (2 ml) was added, and the reaction mixture was stirred for 5 h at RT. For working up, KOH (5 N, 2 ml) was added, the phases were separated, and the aqueous phase was then extracted twice with 5 ml of DCM each time. The combined organic phases were washed with saturated NaCl solution, dried over Na$_2$SO$_4$ and concentrated. The crude product was purified by column chromatography (diethyl ether/-methanol: 20:1).

The product was dissolved in methyl ethyl ketone (4 ml), and then water (0.01 ml/1 mmol) and trimethylchlorosilane (1.3 ml/1 mmol) were added. Filtering off with suction and washing with ether yielded white crystals, which were dried in vacuo.

$^{13}$C NMR (75 MHz, DMSO) 21.21; 23.16; 23.64; 23.77; 24.01; 29.65; 35.24; 41.02; 50.71; 53.27; 67.02; 112.32; 126.83; 127.53; 128.95; 130.65; 156.49; 167.10.

N-Benzyl-N-(4-((dimethylamino)(phenyl)methyl) cyclohexyl)acetamide hydrochloride 100 (R$^3$=phenyl)

The amine 86 (0.9 g, 2.8 mmol) was dissolved in anhydrous pyridine (18 ml), and acetic anhydride (2.85 g, 27.9 mmol) was added at room temperature. The reaction mixture was stirred overnight at RT. In order to remove the excess acetic anhydride, toluene (20 ml) was added to the reaction mixture and concentration was carried out using a rotary evaporator. This operation was repeated twice more. 1N NaOH was added to the residue and the product was extracted with ethyl acetate. After drying over Na$_2$SO$_4$, the organic phase was concentrated using a rotary evaporator. Purification of the crude product was carried out by column chromatography (eluant: ethyl acetate/methanol: 20:1). The product was dissolved in methyl ethyl ketone (5 ml), and then water (0.01 ml/1 mmol) and trimethylchlorosilane (1.3 ml/1 mmol) were added. Filtering off with suction and washing with ether yielded white crystals, which were dried in vacuo.

N-Benzyl-N-(4-((dimethylamino)(phenyl)methyl) cyclohexyl)-2-ethyl-butanamide hydrochloride 101 (R$^3$=phenyl)

The amine 86 (0.5 g, 1.6 mmol) was dissolved in DCM (1.6 ml); triethylamine (0.31 g, 3.1 mmol) and a spatula tip of DMAP were added, and the mixture was cooled to −10° C. 2-Ethylbutyl chloride (0.31 g, 2.3 mmol) dissolved in DCM (2.8 ml) was added, and the reaction mixture was stirred for 16 h at RT. For working up, KOH (5N, 10 ml) was added, the phases were separated, and the aqueous phase was then extracted twice with 5 ml of DCM each time. The combined organic phases were washed with saturated NaCl solution, dried over Na$_2$SO$_4$ and concentrated. The crude product was purified by column chromatography (diethyl ether).

The product was dissolved in methyl ethyl ketone (3 ml), and then water (0.01 ml/1 mmol) and trimethylchlorosilane (1.3 ml/1 mmol) were added. Filtering off with suction and washing with ether yielded white crystals, which were dried in vacuo.

N-Benzyl-N-(4-((dimethylamino)(phenyl)methyl) cyclohexyl)butyramide hydrochloride 102 (R$^3$=phenyl)

The amine 86 (0.5 g, 1.6 mmol) was dissolved in DCM (1.6 ml); triethylamine (0.31 g, 3.1 mmol) and a spatula tip of DMAP were added, and the mixture was cooled to −10° C. Butyric acid chloride (0.25 g, 2.3 mmol) dissolved in DCM (2.8 ml) was added, and the reaction mixture was stirred for 16 h at RT. For working up, KOH (5N, 10 ml) was added, the phases were separated, and the aqueous phase was then extracted twice with 5 ml of DCM each time. The combined organic phases were washed with saturated NaCl solution, dried over Na$_2$SO$_4$ and concentrated. The crude product was purified by column chromatography (diethyl ether).

The product was dissolved in methyl ethyl ketone (3 ml), and then water (0.01 ml/1 mmol) and trimethylchlorosilane (1.3 ml/1 mmol) were added. Filtering off with suction and washing with ether yielded white crystals, which were dried in vacuo.

N-Benzyl-N-(4-((dimethylamino)(phenyl)methyl) cyclohexyl)-4-fluoro-benzamide hydrochloride 103 (R$^3$=phenyl)

The amine 86 (0.5 g, 1.6 mmol) was dissolved in DCM (1.6 ml); triethylamine (0.31 g, 3.1 mmol) and a spatula tip of DMAP were added, and the mixture was cooled to −10° C. 4-Fluorobenzoyl chloride (0.37 g, 2.3 mmol) dissolved in DCM (2.8 ml) was added, and the reaction mixture was stirred for 16 h at RT. For working up, KOH (5N, 10 ml) was added, the phases were separated, and the aqueous phase was then extracted twice with 5 ml of DCM each time. The combined organic phases were washed with saturated NaCl solution, dried over Na$_2$SO$_4$ and concentrated. The crude product was purified by column chromatography (diethyl ether).

The product was dissolved in methyl ethyl ketone (4 ml), and then water (0.01 ml/1 mmol) and trimethylchlorosilane (1.3 ml/1 mmol) were added. Filtering off with suction and washing with ether yielded white crystals, which were dried in vacuo.

N-Benzyl-N-(4-((dimethylamino)(phenyl)methyl) cyclohexyl)benzamide hydrochloride 104 (R$^3$=phenyl)

The amine 86 (0.5 g, 1.6 mmol) was dissolved in DCM (1.6 ml); triethylamine (0.31 g, 3.1 mmol) and a spatula tip of DMAP were added, and the mixture was cooled to −10° C. Benzoyl chloride (0.33 g, 2.3 mmol) dissolved in DCM (2.8 ml) was added, and the reaction mixture was stirred for 16 h at RT. For working up, KOH (5N, 10 ml) was added, the phases were separated, and the aqueous phase was then extracted twice with 5 ml of DCM each time. The combined organic phases were washed with saturated NaCl solution, dried over Na$_2$SO$_4$ and concentrated. The crude product was purified by column chromatography (diethyl ether).

The product was dissolved in methyl ethyl ketone (5 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl)-2-ethyl-N-phenyl-butanamide hydrochloride 105 (R$^3$=phenyl)

The amine 92 (0.55 g, 1.8 mmol) was dissolved in DCM (1.8 ml); triethylamine (0.36 g, 3.6 mmol) and a spatula tip of DMAP were added, and the mixture was cooled to −10° C. 2-Ethylbutyl chloride (0.36 g, 2.7 mmol) dissolved in DCM (3.2 ml) was added, and the reaction mixture was stirred for 16 h at RT. For working up, KOH (5N, 10 ml) was added, the phases were separated, and the aqueous phase was then extracted twice with 5 ml of DCM each time. The combined organic phases were washed with saturated NaCl solution, dried over $Na_2SO_4$ and concentrated. The product was purified by preparative HPLC.

Sulfonylation of the Primary Amines ($R^1$=$(CH_2)_n$ $NHSO_2R^{12}$)

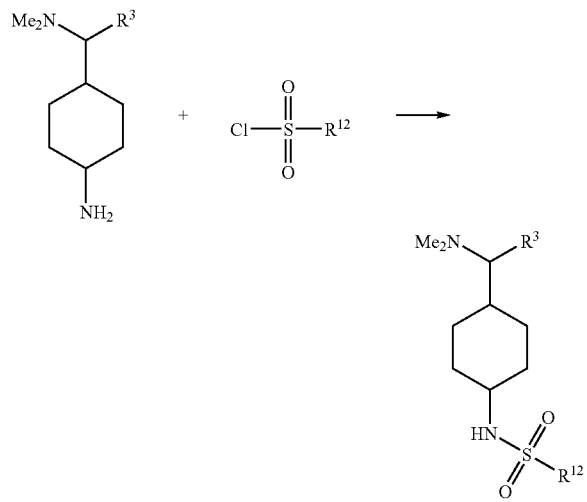

4-Chloro-N-(4-((dimethylamino)(phenyl)methyl) cyclohexyl)benzene-sulfonamide hydrochloride 106 ($R^3$=phenyl)

The amine 17 (0.24 g, 1 mmol) was dissolved in DCM (6.9 ml); first triethylamine (0.13 g, 1.2 mmol) and then 4-chlorobenzenesulfonic acid chloride (0.44 g, 2.1 mmol) were added and stirring was carried out for 22 h at room temperature. When the reaction was complete, the mixture was first hydrolysed with water and then rendered alkaline with $Na_2CO_3$ solution. The product was extracted with DCM, dried over $Na_2SO_4$ and concentrated. Purification was carried out by column chromatography (ethyl acetate/methanol 20:1).

The product was dissolved in methyl ethyl ketone (5 ml), and then water (0.01 ml/1 mmol) and trimethylchlorosilane (1.3 ml/1 mmol) were added. Filtering off with suction and washing with ether yielded a reddish-brown resin, which was dried in vacuo.

N-(4-((Dimethylamino)(phenyl)methyl)cyclohexyl)-4-methoxybenzene-sulfonamide hydrochloride 107 ($R^3$=phenyl)

The amine 17 (0.24 g, 1 mmol) was dissolved in DCM (6.9 ml); first triethylamine (0.13 g, 1.2 mmol) and then 4-methoxybenzenesulfonic acid chloride (0.43 g, 2.1 mmol) were added and stirring was carried out for 22 h at room temperature. When the reaction was complete, the mixture was first hydrolysed with water and then rendered alkaline with $Na_2CO_3$ solution. The product was extracted with DCM, dried over $Na_2SO_4$ and concentrated. Purification was carried out by column chromatography (ethyl acetate/methanol 20:1).

The product was dissolved in methyl ethyl ketone (5 ml), and then water (0.01 ml/1 mmol) and trimethylchlorosilane (1.3 ml/1 mmol) were added. Filtering off with suction and washing with ether yielded a reddish-brown resin, which was dried in vacuo.

4-tert-Butyl-N-(4-((dimethylamino)(phenyl)methyl) cyclohexyl)benzene-sulfonamide hydrochloride 108 ($R^3$=phenyl)

The amine 17 (0.24 g, 1 mmol) was dissolved in DCM (6.9 ml); first triethylamine (0.13 g, 1.2 mmol) and then 4-tert-butylbenzenesulfonic acid chloride (0.48 g, 2.1 mmol) were added and stirring was carried out for 22 h at room temperature. When the reaction was complete, the mixture was first hydrolysed with water and then rendered alkaline with $Na_2CO_3$ solution. The product was extracted with DCM, dried over $Na_2SO_4$ and concentrated. Purification was carried out by column chromatography (ethyl acetate/methanol 20:1).

The product was dissolved in methyl ethyl ketone (5 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl)-2-nitrobenzene-sulfonamide hydrochloride 109 ($R^3$=phenyl)

The amine 17 (0.24 g, 1 mmol) was dissolved in DCM (6.9 ml); first triethylamine (0.13 g, 1.2 mmol) and then 2-nitrobenzenesulfonic acid chloride (0.46 g, 2.1 mmol) were added and stirring was carried out for 22 h at room temperature. When the reaction was complete, the mixture was first hydrolysed with water and then rendered alkaline with $Na_2CO_3$ solution. The product was extracted with DCM, dried over $Na_2SO_4$ and concentrated. Purification was carried out by column chromatography (ethyl acetate/methanol 20:1).

The product was dissolved in methyl ethyl ketone (5 ml), and then water (0.01 ml/1 mmol) and trimethylchlorosilane (1.3 ml/1 mmol) were added. Filtering off with suction and washing with ether yielded white crystals, which were dried in vacuo.

N-(4-((Dimethylamino)(phenyl)methyl)cyclohexyl) benzenesulfonamide hydrochloride 110 ($R^3$=phenyl)

The amine 17 (0.24 g, 1 mmol) was dissolved in DCM (6.9 ml); first triethylamine (0.13 g, 1.2 mmol) and then benzenesulfonic acid chloride (0.36 g, 2.1 mmol) were added and stirring was carried out for 22 h at room temperature. When the reaction was complete, the mixture was first hydrolysed with water and then rendered alkaline with $Na_2CO_3$ solution. The product was extracted with DCM, dried over $Na_2SO_4$ and concentrated. Purification was carried out by column chromatography (ethyl acetate/methanol 20:1).

The product was dissolved in methyl ethyl ketone (3 ml), and then water (0.01 ml/1 mmol) and trimethylchlorosilane (1.3 ml/1 mmol) were added. Filtering off with suction and washing with ether yielded white crystals, which were dried in vacuo.

Synthesis of the Cyclohexanols, Hydroxymethyl-, Hydroxyethyl- and Hydroxypropyl-cyclohexanes The corresponding alcohols are obtained from the corresponding cyclohexanones, cyclohexylaldehydes and cyclohexylacetaldehydes by reduction.

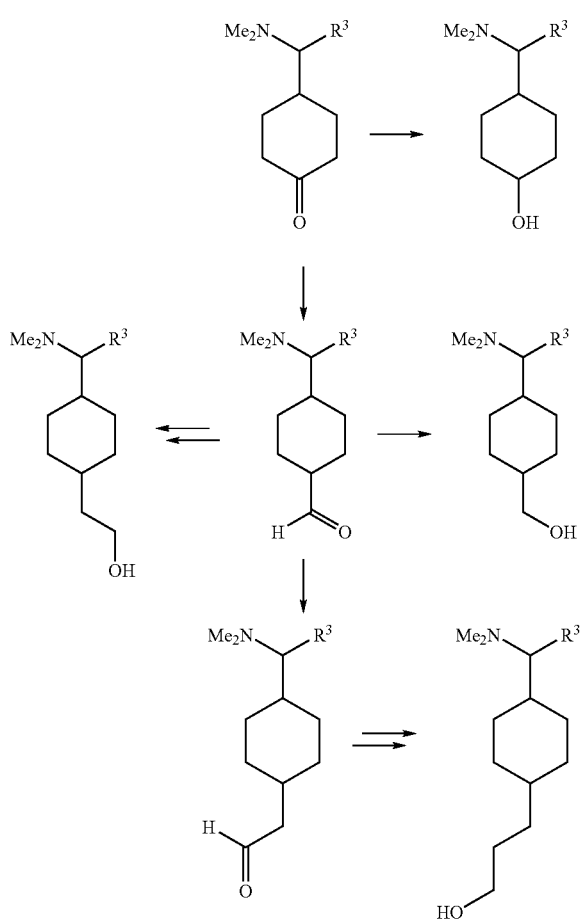

Synthesis of the Cyclohexanols ($R^1$=(CH$_2$)$_n$OH, n=0)

The cyclohexanols were prepared by reduction of the correspondingly substituted cyclohexanones with sodium borohydride.

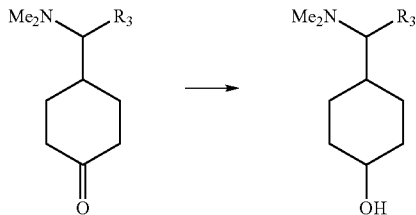

4-[Dimethylamino-phenyl-methyl]-cyclohexanol 111 ($R^3$=phenyl)

LiAlH$_4$ (2.8 ml, 6.5 mmol, 2.3 M in THF) is added dropwise to a solution of the ketone 10 (1.5 g, 6.5 mmol) in THF (6.5 ml) in such a manner that the THF boils gently. When the addition is complete, stirring is carried out for 15 h at RT. The mixture is quenched carefully with water (10 ml), while cooling with an ice bath. NaOH solution (10 ml, 5N) is then added to the mixture. After 1 hour's stirring, the mixture is filtered off over filtering earth and then washed with ether. Extraction is carried out 3× with 40 ml of ether, followed by drying over Na$_2$SO$_4$ and concentration.

Yield: 1.42 g (93%) oil $^{13}$C-NMR (CDCl$_3$): 27.50; 24.73; 35.40; 35.60; 37.71; 41.59 (N(CH$_3$)$_2$); 71.13; 75.11; 126.90; 127.65; 129.32; 137.14.

4-[Dimethylamino-(4-fluorophenyl)-methyl]-cyclohexanol 112 ($R^3$=4-fluorophenyl)

The ketone 11 (6.22 g, 25 mmol) was dissolved in ethanol (250 ml); sodium borohydride (1.89 g, 50 mmol) was added, and stirring was carried out for 3 h at RT. The reaction mixture was concentrated in vacuo, water was added to the residue, and extraction with ethyl acetate (3×70 ml) was carried out. The combined extracts were washed with water and saturated sodium chloride solution, dried (Na$_2$SO$_4$) and concentrated in vacuo.

Yield: 5.92 g (94%), oil $^{13}$C-NMR (CDCl$_3$): 23.47; 24.73; 27.36; 29.27; 32.28; 35.42; 37.39; 37.97; 41.68; 41.99 (N(CH$_3$)$_2$); 60.39; 66.91 (CH); 71.04; 74.34; 114.23; 114.44; 130.33; 130.40; 130.48; 132.79; 160.41; 162.83.

4-[Dimethylamino-(3-fluorophenyl)-methyl]-cyclohexanol 113 ($R^3$=3-fluorophenyl)

The ketone 12 (6.22 g, 25 mmol) was dissolved in ethanol (250 ml); sodium borohydride (1.89 g, 50 mmol) was added and stirring was carried out for 3 h at RT. The reaction mixture was concentrated in vacuo, water was added to the residue, and extraction with ethyl acetate (3×70 ml) was carried out. The combined extracts were washed with water and saturated sodium chloride solution, dried (Na$_2$SO$_4$) and concentrated in vacuo.

Yield: 6.00 g (96%), oil $^{13}$C-NMR (CDCl$_3$): 23.46; 24.55; 27.32; 29.12; 32.15; 35.25; 37.77; 41.55; 41.63; 41.89 (N(CH$_3$)$_2$); 64.06; 66.66 (CH); 70.76; 74.62; 113.42; 113.64; 115.47; 115.68; 124.75; 124.89; 128.70; 128.78; 139.47; 139.52; 161.02; 163.45.

4-[(4-Chlorophenyl)-dimethylamino-methyl]-cyclohexanol 114 ($R^3$=4-chlorophenyl)

The ketone 13 (5.84 g, 22 mmol) was dissolved in ethanol (200 ml); sodium borohydride (1.66 g, 44 mmol) was added and stirring was carried out for 3 h at RT. The reaction mixture was concentrated in vacuo, water was added to the residue, and extraction with ethyl acetate (3×70 ml) was carried out. The combined extracts were washed with water and saturated sodium chloride solution, dried over sodium sulfate and concentrated in vacuo.

Yield: 5.89 g (100%), oil $^{13}$C-NMR (CDCl$_3$): 23.39; 24.67; 27.26; 29.21; 32.26; 32.42; 35.38; 35.59; 37.29; 37.85; 41.71; 42.03 (N(CH$_3$)$_2$); 66.86; 71.01; 73.21; 74.45 (CH); 127.69; 130.31; 132.43; 135.26; 135.66.

4-(Dimethylamino-thiophen-2-yl-methyl)-cyclohexanol 115 ($R^3$=2-thiophene)

The ketone 14 (5.93 g, 25 mmol) was dissolved in ethanol (200 ml); sodium borohydride (1.89 g, 50 mmol) was added and stirring was carried out for 20 h at RT. The reaction mixture was concentrated in vacuo, water was added to the residue, and extraction with ethyl acetate (3×70 ml) was carried out. The combined extracts were washed with water and saturated sodium chloride solution, dried ($Na_2SO_4$) and concentrated in vacuo.

Yield: 5.71 g (95%), reddish oil $^{13}$C-NMR (CDCl$_3$): 24.40; 24.48; 28.50; 28.98; 32.07; 35.26; 35.34; 39.11; 39.76; 41.05; 41.27; 67.12; 68.09; 69.69; 71.06; 123.83; 126.06; 126.35; 126.49; 139.89.

4-(1-Dimethylamino-3-phenyl-propyl)-cyclohexanol 116 (R$^3$=phenethyl)

The ketone 15 (5.7 g, 22 mmol) was dissolved in ethanol (200 ml); sodium borohydride (1.66 g, 44 mmol) was added and stirring was carried out for 3 h at RT. The reaction mixture was concentrated in vacuo, water was added to the residue, and extraction with ethyl acetate (3×70 ml) was carried out. The combined extracts were washed with water and saturated sodium chloride solution, dried over sodium sulfate and concentrated in vacuo.

Yield: 5.56 g (97%), oil $^{13}$C-NMR (CDCl$_3$): 24.21; 25.16; 28.48; 29.28; 29.64; 32.68; 35.58; 39.20; 41.23; 41.29; (N(CH$_3$)$_2$); 66.68; 67.24; 67.82 (CH); 71.04; 125.57; 128.17; 142.68.

Synthesis of the Hydroxymethylcyclohexanes (R$^1$= (CH$_2$)$_n$OH, n=1)

The hydroxymethylcyclohexanes were obtained by reduction of the corresponding cyclohexylaldehydes with sodium borohydride.

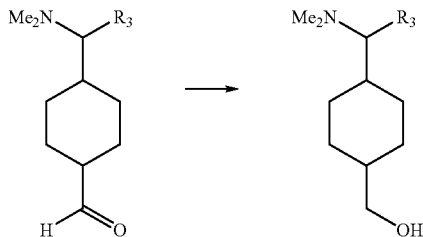

[4-(Dimethylamino-phenyl-methyl)-cyclohexyl]-methanol 117 (R$^3$=phenyl)

The aldehyde 28 (6.13 g, 25 mmol) was dissolved, under argon, in ethanol (100 ml), water (50 ml) and 1N NaOH (25 ml, 25 mmol) and stirred for 30 minutes at RT. A solution of NaBH$_4$ (1.82 g, 50 mmol) in water (160 ml) was then slowly added dropwise and the mixture was stirred overnight. The ethanol was removed in vacuo, the aqueous residue was extracted three times with ethyl acetate (100 ml each time), and the organic phase was washed with water (100 ml) and saturated NaCl solution (100 ml), dried (Na$_2$SO$_4$) and concentrated in vacuo.

Yield: 5.86 g (95%)

$^{13}$C-NMR (CDCl$_3$): 28.84; 29.35; 29.50; 30.53; 38.78; 40.69; 41.95 (N(CH$_3$)$_2$); 68.39; 75.11; 126.56; 127.33; 129.14; 137.08.

{4-[Dimethylamino-(4-fluorophenyl)-methyl]-cyclohexyl}-methanol 118 (R$^3$=4-fluorophenyl)

The aldehyde 31 (6.2 g, 24 mmol) was dissolved, under argon, in ethanol (105 ml), water (53 ml) and 1N NaOH (24 ml, 24 mmol) and stirred for 30 minutes at RT. A solution of NaBH$_4$ (1.82 g, 48 mmol) in water (158 ml) was then slowly added dropwise and the mixture was stirred overnight. The ethanol was removed in vacuo, the aqueous residue was extracted three times with ethyl acetate (100 ml each time), and the organic phase was washed with water (100 ml) and saturated NaCl solution (100 ml), dried (Na$_2$SO$_4$) and concentrated in vacuo.

Yield: 5.99 g (94%)

$^{13}$C-NMR (CDCl$_3$): 21.04; 25.56; 25.64; 26.02; 28.63; 29.47; 30.54; 38.95; 40.70; 41.40; 41.97 (N(CH$_3$)$_2$); 60.34; 68.39 (CH); 74.80; 114.10; 114.30; 130.33; 130.41; 132.91; 160.31; 162.73.

{4-[Dimethylamino-(3-fluorophenyl)-methyl]-cyclohexyl}-methanol 119 (R$^3$=3-fluorophenyl)

The aldehyde 34 (7.11 g, 27 mmol) was dissolved, under argon, in ethanol (120 ml), water (60 ml) and 1N NaOH (27 ml, 27 mmol) and stirred for 30 minutes at RT. A solution of NaBH$_4$ (2.04 g, 54 mmol) in water (200 ml) was then slowly added dropwise and the mixture was stirred overnight. Ethanol was removed in vacuo, the aqueous residue was extracted three times with ethyl acetate (100 ml each time), and the organic phase was washed with water (100 ml) and saturated NaCl solution (100 ml), dried (Na$_2$SO$_4$) and concentrated in vacuo.

Yield: 7.1 g (99%)

$^{13}$C-NMR (CDCl$_3$): 25.32; 25.57; 25.61; 28.71; 29.28, 29.45; 30.46; 37.86; 38.83; 40.70; 41.41; 41.96 (N(CH$_3$)$_2$); 65.72; 68.43; 71.20; 75.15; 113.38; 113.59; 115.56; 115.77; 124.89; 128.67; 128.75; 140.09; 140.15; 161.06; 163.50.

{4-[(4-Chlorophenyl)-dimethylamino-methyl]-cyclohexyl}-methanol 120 (R$^3$=4-chlorophenyl)

The aldehyde 37 (5.59 g, 20 mmol) was dissolved, under argon, in ethanol (100 ml), water (50 ml) and 1N NaOH (20 ml, 20 mmol) and stirred for 30 minutes at RT. A solution of NaBH$_4$ (1.51 g, 40 mmol) in water (160 ml) was then slowly added dropwise and the mixture was stirred overnight. Ethanol was removed in vacuo, the aqueous residue was extracted three times with ethyl acetate (100 ml each time), and the organic phase was washed with water (100 ml) and saturated NaCl solution (100 ml), dried (Na$_2$SO$_4$) and concentrated in vacuo.

Yield: 5.5 g (97%)

$^{13}$C-NMR (CDCl$_3$): 25.24; 25.55; 26.00; 28.61; 29.29; 29.46; 30.51; 37.86; 38.85 40.71; 41.45; 42.03 (N(CH$_3$)$_2$); 68.47; 74.92; 127.59; 130.64; 132.28; 135.82.

[4-(Dimethylamino-thiophen-2-yl-methyl)-cyclohexyl]-methanol 121 (R$^3$=2-thiophene)

The aldehyde 40 (6.66 g, 26.4 mmol) was dissolved, under argon, in ethanol (120 ml), water (60 ml) and 1N NaOH (26.4 ml, 27 mmol) and stirred for 30 minutes at RT. A solution of NaBH$_4$ (1.89 g, 50 mmol) in water (200 ml) was then slowly added dropwise and the mixture was stirred overnight. Ethanol was removed in vacuo, the aqueous residue was extracted three times with ethyl acetate (100 ml each time), and the organic phase was washed with water (100 ml) and saturated NaCl solution (100 ml), dried (Na$_2$SO$_4$) and concentrated in vacuo.

Yield: 6.56 g (98%)

$^{13}$C-NMR (CDCl$_3$): 25.19; 25.26; 25.92; 26.06; 29.16; 29.78; 30.23; 38.16; 40.56; 40.79; 40.91; 41.21 (N(CH$_3$)$_2$); 68.41; 70.07; 123.67; 123.71; 125.95; 126.00; 126.35; 140.03.

[4-(1-Dimethylamino-3-phenyl-propyl)-cyclohexyl]-methanol 122 (R$^3$=phenethyl)

The aldehyde 43 (7.20 g, 26 mmol) was dissolved, under argon, in ethanol (121 ml), water (61 ml) and 1N NaOH (26 ml, 26 mmol) and stirred for 30 minutes at RT. A solution of NaBH$_4$ (1.97 g, 52 mmol) in water (209 ml) was then slowly added dropwise and the mixture was stirred overnight. The ethanol was removed in vacuo, the aqueous residue was extracted three times with ethyl acetate (100 ml each time), and the organic phase was washed with water (100 ml) and saturated NaCl solution (100 ml), dried (Na$_2$SO$_4$) and concentrated in vacuo.

Yield: 6.99 g (98%)

$^{13}$C-NMR (CDCl$_3$): 21.03; 25.92; 26.12; 26.63; 29.00; 29.32; 29.60; 29.67; 30.93; 35.45; 38.77; 40.02; 40.56; 41.25 (N(CH$_3$)$_2$); 60.32; 68.30; 68.43 (CH); 125.44; 128.05; 128.09; 142.67.

Synthesis of the Hydroxymethylcyclohexanes (R$^1$=(CH$_2$)$_n$OH, n=2)

Hydroxyethylcyclohexanes were prepared from the corresponding cyclohexyl acetates by reduction with lithium aluminium hydride. The cyclohexyl acetates are obtained by hydrogenation from the corresponding cyclohexylidene acetates, which are obtained form the cyclohexanones, in the presence of Pd/C.

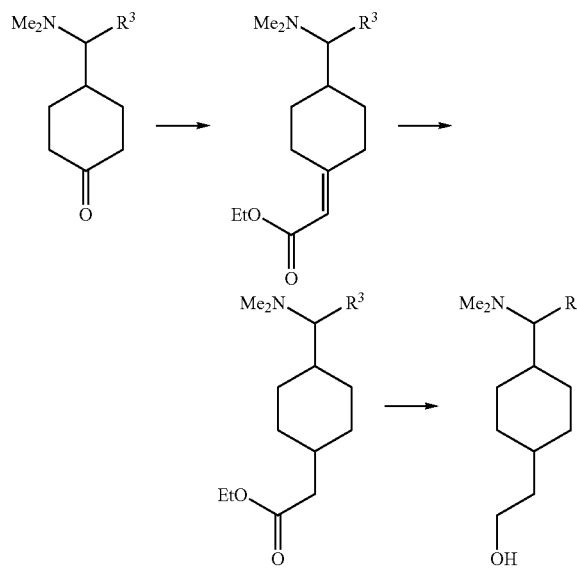

[4-(Dimethylamino-phenyl-methyl)-cyclohexylidene]-acetic acid ethyl ester 123 (R$^3$=phenyl)

Potassium tert-butylate (15.15 g, 0.135 mol) was added, under argon, to a solution of phosphonoacetic acid triethyl ester (30.26 g, 0.135 mol) in abs. DMF (200 ml), and the mixture was stirred for 10 minutes. The ketone 10 (20.82 g, 0.09 mol) dissolved in DMF (200 ml) was then added dropwise. After about 20 minutes, a solid precipitates. For better mixing, the mixture was diluted by addition of DMF (200 ml), stirred for 3 h at RT and then poured onto ice. The reaction mixture was extracted with diethyl ether (3×100 ml) and the organic phase was washed with water and saturated sodium chloride solution, dried and concentrated in vacuo. The crude product was purified by flash chromatography with ethyl acetate/cyclohexane (1:2).

Yield: 21.83 g (80%), oil $^{13}$C-NMR (CDCl$_3$): 25.93; 26.58; 27.09; 29.21; 29.90; 30.32; 30.73; 30.77; 35.38; 35.66; 38.73; (C$_4$); 40.06; 40.90; 41.19 (N(CH$_3$)$_2$); 48.78; 65.15; 68.22 (CH); 125.36; 127.99; 128.05; 142.69.

[4-(Dimethylamino-phenyl-methyl)-cyclohexyl]-acetic acid ethyl ester 124 (R$^3$=phenyl)

The cyclohexylidene acetate 123 (16.4 g, 0.0544 mol) was dissolved in methanol (200 ml); 10% palladium/carbon (1.64 g) was added and hydrogenation was carried out for 24 h at 3 bar (RT). The Pd/C was filtered off with suction over kieselguhr and the solvent was removed in vacuo. The residue was dissolved in 1N NaOH (100 ml) and ethyl acetate (100 ml) and the organic phase was separated off, washed with water, dried and concentrated.

Yield: 15.73 g (95%), colourless oil $^{13}$C-NMR (CDCl$_3$): 14.22; 25.41; 25.77; 28.71; 28.88; 30.69; 32.17; 32.84; 35.08; 35.75; 38.26; 38.94; 41.20; 41.98; 42.04 (N(CH$_3$)$_2$); 60.01; 71.53; 75.48; 126.73; 126.78; 127.49; 127.57; 129.08; 129.31; 136.23; 137.31; 172.79; 173.30.

2-[4-(Dimethylamino-phenyl-methyl)-cyclohexyl]-ethanol 125 (R$^3$=phenyl)

The cyclohexyl acetate 124 (9.86 g, 32.4 mmol) and LiAlH$_4$ (1.25 g, 33 mmol) were boiled for 7 h under reflux in abs. THF (200 ml). Water (50 ml) and 5N NaOH (40 ml) were carefully added dropwise, while cooling with an ice bath (10° C.); the mixture was stirred for 1 h at RT and then filtered off with suction over kieselguhr. The filter residue was washed with ether, the aqueous phase was extracted with ether (2×50 ml) and the combined organic solutions were dried and concentrated in vacuo.

Yield: 8.33 g (98%)

$^{13}$C-NMR (CDCl$_3$): 25.33; 25.89; 29.00; 29.06; 30.89; 31.19; 33.00; 33.16; 34.37; 36.14; 36.57; 38.60; 40.18; 41.32; 41.99 (N(CH$_3$)$_2$); 60.66; 61.12; 75.60 (CH); 126.69; 126.73; 127.46; 127.53; 127.81; 136.49; 137.41.

{4-[Dimethylamino-(4-fluorophenyl)-methyl]-cyclohexylidene}-acetic acid ethyl ester 126 (R$^3$=4-fluorophenyl)

Potassium tert-butylate (13.46 g, 0.12 mol) was added, under argon, to a solution of phosphonoacetic acid triethyl ester (26.9 g, 0.12 mol) in abs. DMF (250 ml), and the mixture was stirred for 10 minutes. The ketone 11 (19.95 g, 0.08 mol) dissolved in DMF (200 ml) was then added dropwise. After about 20 minutes, a solid precipitates. For better mixing, the mixture was diluted by addition of DMF (200 ml), stirred for 3 h at RT and then poured onto ice. The reaction mixture was extracted with diethyl ether (3×100 ml) and the organic phase was washed with water and saturated NaCl solution, dried and concentrated in vacuo. The crude product was purified by flash chromatography with ethyl acetate/cyclohexane (1:2).

Yield: 19.7 g (77%), oil $^{13}$C-NMR (CDCl$_3$): 14.18; 28.56; 28.76; 29.69; 30.17; 31.51; 32.24; 37.03; 38.07; 38.11; 41.80; 41.93; 59.34; 73.80; 73.84; 113.12; 114.24; 114.53; 130.35; 130.45; 132.48; 132.65; 160.11; 162.53; 162.59; 163.35; 166.54.

{4-[Dimethylamino-(4-fluorophenyl)-methyl]-cyclohexyl}-acetic acid ethyl ester 127 (R$^3$=4-fluorophenyl)

The cyclohexylidene acetate 126 (14.0 g, 0.044 mol) was dissolved in methanol (200 ml); 10% palladium/carbon (1.4 g) was added and hydrogenation was carried out for 24 h at 3 bar (RT). The Pd/C was filtered off with suction over kieselguhr and the solvent was removed in vacuo. The residue was dissolved in 1N NaOH (100 ml) and EA (100 ml) and the organic phase was separated off, washed with water, dried and concentrated.

Yield: 136 g (96%), colourless oil $^{13}$C-NMR (CDCl$_3$): 14.19; 25.17; 25.72; 28.64; 28.76; 30.65; 32.06; 32.58; 32.77; 35.02; 35.99; 38.39; 38.83; 41.14; 41.93; 59.98; 70.82; 74.70; 114.15; 114.24; 114.43; 130.44; 130.54; 132.00; 133.05; 133.09; 160.10; 163.64; 172.90; 173.19.

2-{4-[Dimethylamino-(4-fluorophenyl)-methyl]-cyclohexyl}-ethanol 128 (R$^3$=4-fluorophenyl)

The cyclohexyl acetate 127 (8.26 g, 25.7 mmol) and LiAlH$_4$ (0.986 g, 26 mmol) were boiled for 7 h under reflux in abs. THF (150 ml). Water (50 ml) and 5N NaOH (25 ml) were carefully added dropwise, while cooling with an ice bath (10° C.); the mixture was stirred for 1 h at RT and then filtered off with suction over kieselguhr. The filter residue was washed with ether, the aqueous phase was extracted with ether (3×50 ml) and the combined organic solutions were dried and concentrated in vacuo.

Yield: 87.2 g (100%)

$^{13}$C-NMR (CDCl$_3$): 25.11; 25.87; 28.83; 28.97; 30.89; 31.12; 32.94; 33.12; 34.38; 36.43; 36.48; 38.76; 40.15; 41.31; 42.00; 60.63; 61.09; 71.22; 74.87; 114.15; 114.23; 114.42; 114.50; 130.48; 130.58; 132.28; 133.20; 133.24; 160.10; 163.34.

{4-[Dimethylamino-(3-fluorophenyl)-methyl]-cyclohexylidene}-acetic acid ethyl ester 129 (R$^3$=3-fluorophenyl)

Potassium tert-butylate (15.15 g, 0.135 mol) was added, under argon, to a solution of phosphonoacetic acid triethyl ester (30.26 g, 0.135 mol) in abs. DMF (200 ml), and the mixture was stirred for 10 minutes. The ketone 12 (22.43 g, 0.09 mol) dissolved in DMF (200 ml) was then added dropwise. After about 20 minutes, a solid precipitates. For better mixing, the mixture was diluted by addition of DMF (200 ml), stirred for 3 h at RT and then poured onto ice. The reaction mixture was extracted with diethyl ether (3×100 ml) and the organic phase was washed with water and saturated NaCl solution, dried and concentrated in vacuo. The crude product was purified by flash chromatography with ethyl acetate/cyclohexane (1:2).

Yield: 24.78 g (86%), oil $^{13}$C-NMR (CDCl$_3$): 14.36; 28.72; 28.92; 29.90; 30.39; 31.76; 30.06; 32.31; 36.96; 37.13; 38.12; 38.17; 41.91; 42.04 (N(CH$_3$)$_2$); 59.40; 74.21; 74.25; 113.15; 113.17; 113.53; 113.56; 113.74; 113.77; 115.47; 115.68; 124.78; 128.79; 128.86; 139.59; 139.66; 139.78; 139.83; 161.09; 162.18; 162.22; 163.52; 166.34; 171.55.

{4-[Dimethylamino-(3-fluorophenyl)-methyl]-cyclohexyl}-acetic acid ethyl ester 130 (R$^3$=3-fluorophenyl)

The cyclohexylidene acetate 129 (17.5 g, 0.054 mol) was dissolved in methanol (200 ml); 10% palladium/carbon (1.75 g) was added and hydrogenation was carried out for 24 h at 3 bar (RT). The Pd/C was filtered off with suction over kieselguhr and the solvent was removed in vacuo. The residue was dissolved in 1N NaOH (100 ml) and EA (100 ml) and the organic phase was separated off, washed with water, dried and concentrated.

Yield: 15.5 g (90%), colourless oil $^{13}$C-NMR (CDCl$_3$): 14.37; 25.39; 25.82; 28.85; 30.74; 32.23; 32.721; 32.91; 35.17; 38.45; 39.00; 41.27; 41.68; 42.04 (N(CH$_3$)$_2$); 60.04; 71.24; 75.11; 113.37; 113.42; 113.58; 113.63; 115.55; 115.76; 124.89; 128.65; 128.74; 128.82; 139.12; 139.18; 140.18; 140.24; 161.09; 163.51; 172.64; 172.93.

2-{4-[Dimethylamino-(3-fluorophenyl)-methyl]-cyclohexyl}-ethanol 131 (R$^3$=3-fluorophenyl)

The cyclohexyl acetate 130 (9.46 g, 29 mmol) and LiAlH$_4$ (1.13 g, 30 mmol) were boiled for 7 h under reflux in abs. THF (150 ml). Water (50 ml) and 5N NaOH (25 ml) were carefully added dropwise, while cooling with an ice bath (10° C.); the mixture was stirred for 1 h at RT and then filtered off with suction over kieselguhr. The filter residue was washed with ether, the aqueous phase was extracted with ether (3×50 ml) and the combined organic solutions were dried and concentrated in vacuo.

Yield: 8.0 g (99%)

$^{13}$C-NMR (CDCl$_3$): 25.37; 25.98; 29.06; 29.14; 30.98; 31.35; 33.08; 33.26; 34.40; 34.55; 36.37; 38.81; 40.28; 40.69; 41.72 (N(CH$_3$)$_2$); 60.29; 60.76; 61.21; 71.57; 75.27 (CH); 113.36; 113.40; 113.57; 115.60; 115.81; 124.93; 128.65; 128.81; 139.41; 139.47; 140.33; 140.39; 161.09; 163.52.

Synthesis of the Hydroxypropylcyclohexanes (R$^1$=(CH$_2$)$_n$OH, n=3)

The hydroxypropylcyclohexanes were prepared from the corresponding cyclohexylpropionic acid esters by reduction with lithium aluminium hydride. The described cyclohexylpropionic acid esters were synthesised from the corresponding cyclohexylacrylic acid esters by hydrogenation in the presence of Pd/C.

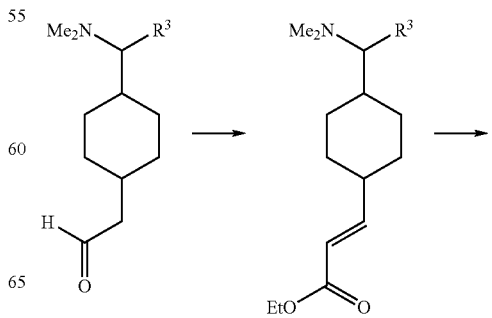

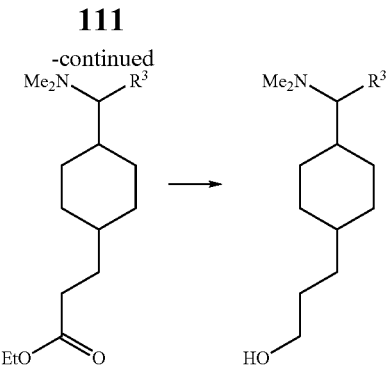

3-[4-(Dimethylamino-phenyl-methyl)-cyclohexyl]-acrylic acid ethyl ester 132 (R³=phenyl)

Potassium tert-butylate (16.83 g, 0.15 mol) was added, under argon, to a solution of phosphonoacetic acid triethyl ester (33.62 g, 0.15 mol) in abs. DMF (250 ml), and the mixture was stirred for 10 minutes. The aldehyde 28 (24.27 g, 0.099 mol) dissolved in DMF (250 ml) was then added dropwise. The mixture was stirred for 3 h at RT and then poured onto ice. The reaction mixture was extracted with diethyl ether (3×200 ml) and the organic phase was washed with water and saturated NaCl solution, dried and concentrated in vacuo. The crude product was purified by flash chromatography with ethyl acetate/cyclohexane (1:2).

Yield: 27.2 g (87%), oil $^{13}$C-NMR (CDCl$_3$): 14.22; 25.94; 27.92; 28.23; 28.33; 28.65; 30.18; 30.45; 30.60; 31.45; 31.63; 32.15; 33.03; 37.74; 38.10; 38.55; 40.71; 41.04; 41.30; 41.97; 59.67; 60.05; 71.34; 74.89; 75.61; 117.96; 118.97; 120.02; 126.81; 127.55; 137.20; 153.31; 153.90; 155.25; 166.28; 166.99.

3-[4-(Dimethylamino-phenyl-methyl)-cyclohexyl]-propionic acid ethyl ester 133 (R³=phenyl)

The cyclohexylacrylic acid ester 132 (20.9 g, 0.066 mol) was dissolved in methanol (150 ml); 10% palladium/carbon (2.0 g) was added and hydrogenation was carried out for 24 h at 3 bar (RT). The Pd/C was filtered off with suction over kieselguhr and the solvent was removed in vacuo. The residue was dissolved in 1N NaOH (100 ml) and ethyl acetate (100 ml) and the organic phase was separated off, washed with water, dried and concentrated.

Yield: 18.6 g (89%), colourless oil $^{13}$C-NMR (CDCl$_3$): 14.15; 25.49; 25.79; 28.54; 29.00; 30.84; 31.62; 31.91; 32.15; 32.35; 32.59; 32.76; 34.62; 35.80; 37.18; 37.37; 38.57; 41.14; 41.96; 60.05; 71.33; 75.55; 126.65; 127.43; 127.50; 127.95; 129.06; 129.27; 136.25; 137.40; 173.97.

3-[4-(Dimethylamino-phenyl-methyl)-cyclohexyl]-propan-1-ol 134 (R³=phenyl)

The cyclohexylpropionic acid ester 133 (9.7 g, 30.5 mmol) and LiAlH$_4$ (1.18 g, 31 mmol) were boiled for 7 h under reflux in abs. THF (150 ml). Water (50 ml) and 5N NaOH (25 ml) were carefully added dropwise, while cooling with an ice bath (10° C.), and the mixture was stirred for 1 h at RT and then filtered off with suction over kieselguhr. The filter residue was washed with ether, the aqueous phase was extracted with ether (2×50 ml) and the combined organic solutions were dried and concentrated in vacuo.

Yield: 8.4 g (100%)

$^{13}$C-NMR (CDCl$_3$): 25.53; 28.91; 29.14; 29.78; 30.14; 31.00; 32.99; 33.16; 33.27; 34.80; 36.02; 37.63; 38.75; 41.20; 42.01; 63.16; 71.55; 75.69; 126.67; 127.46; 129.32; 137.53.

3-{4-[Dimethylamino-(4-fluorophenyl)-methyl]-cyclohexyl}-acrylic acid ethyl ester 135 (R³=4-fluorophenyl)

Potassium tert-butylate (12.56 g, 0.112 mol) was added, under argon, to a solution of phosphonoacetic acid triethyl ester (25.1 g, 0.112 mol) in abs. DMF (150 ml), and the mixture was stirred for 10 minutes. The aldehyde 31 (19.9 g, 0.075 mol) dissolved in DMF (225 ml) was then added dropwise. The mixture was stirred for 3 h at RT and then poured onto ice. The reaction mixture was extracted with diethyl ether (3×200 ml) and the organic phase was washed with water and saturated NaCl solution, dried and concentrated in vacuo. The crude product was purified by flash chromatography with ethyl acetate/cyclohexane (1:2).

Yield: 23.7 g (95%), oil $^{13}$C-NMR (CDCl$_3$): 14.30; 25.78; 26.06; 28.15; 28.32; 28.48; 30.23; 30.48; 31.45; 31.64; 32.32; 37.57; 37.63; 38.28 (C$_4$); 41.03; 41.80; 41.96 (N(CH$_3$)$_2$); 59.62; 60.01; 74.64; 74.80; 114.12; 114.29; 117.86; 118.87; 119.94; 130.28; 132.78; 152.84; 153.46; 154.85; 160.31; 162.73; 165.91; 166.61.

3-{4-[Dimethylamino-(4-fluorophenyl)-methyl]-cyclohexyl}-propionic acid ethyl ester 136 (R³=4-fluorophenyl)

The cyclohexylacrylic acid ester 135 (12.3 g, 0.050 mol) was dissolved in methanol (100 ml); 10% palladium/carbon (1.63 g) was added and hydrogenation was carried out for 24 h at 3 bar (RT). The Pd/C was filtered off with suction over kieselguhr and the solvent was removed in vacuo. The residue was dissolved in 1N NaOH (100 ml) and EA (100 ml) and the organic phase was separated off, washed with water, dried and concentrated.

Yield: 16.7 g (100%), colourless oil $^{13}$C-NMR (CDCl$_3$): 14.32; 25.43; 25.93; 28.67; 28.72; 28.93; 31.00; 32.05; 32.50; 32.70; 32.88; 34.69; 36.26; 38.90 (C$_4$); 41.24; 42.08 (N(CH$_3$)$_2$); 60.11; 70.79 74.87; 114.08; 114.16; 114.27; 130.35; 130.43; 132.03; 133.17; 160.32; 162.74; 173.71.

3-{4-[Dimethylamino-(4-fluorophenyl)-methyl]-cyclohexyl}-propan-1-ol 137 (R³=4-fluorophenyl)

The cyclohexylpropionic acid ester 136 (8.08 g, 24.1 mmol) and LiAlH$_4$ (0.952 g, 25 mmol) were boiled for 8 h under reflux in abs. THF (150 ml). Water (50 ml) and 5N NaOH (25 ml) were carefully added dropwise, while cooling with an ice bath (10° C.), and the mixture was stirred for 1 h at RT and then filtered off with suction over kieselguhr. The filter residue was washed with ether, the aqueous phase was extracted with ether (2×50 ml) and the combined organic solutions were dried and concentrated in vacuo.

Yield: 5.62 g (79%)

$^{13}$C-NMR (CDCl$_3$): 25.26; 25.80; 28.83; 30.06; 30.56; 30.92; 32.87; 33.06; 33.21; 34.65; 36.23; 37.56; 38.82 (C$_4$); 41.20; 41.97 (N(CH$_3$)$_2$); 63.00; 70.84; 114.13; 114.20; 130.45; 130.52; 132.11; 133.22; 133.24; 160.45; 162.88.

3-{4-[Dimethylamino-(3-fluorophenyl)-methyl]-cyclohexyl}-acrylic acid ethyl ester 138 (R³=3-fluorophenyl)

Potassium tert-butylate (12.34 g, 0.11 mol) was added, under argon, to a solution of phosphonoacetic acid triethyl ester (24.66 g, 0.11 mol) in abs. DMF (200 ml), and the mixture was stirred for 10 minutes. The aldehyde 34 (19.3 g, 0.073 mol) dissolved in DMF (200 ml) was then added dropwise. The mixture was stirred for 3 h at RT and then poured onto ice. The reaction mixture was extracted with diethyl ether (3×200 ml) and the organic phase was washed with water and saturated NaCl solution, dried and concentrated in vacuo. The crude product was purified by flash chromatography with ethyl acetate/cyclohexane (1:2).

Yield: 21.9 g (90%), oil
$^{13}$C-NMR (CDCl$_3$): 14.26; 25.82; 28.28; 28.49; 30.09; 30.35; 31.38; 31.56; 32.07; 35.80; 37.54; 38.12; 40.68; 41.05; 41.31; 41.98; 59.75; 60.14; 75.07; 113.57; 113.84; 115.67; 115.94; 118.02; 119.04; 120.12; 125.03; 128.88; 140.13; 153.18; 153.80; 155.20; 160.92; 164.17; 167.03.

3-{4-[Dimethylamino-(3-fluorophenyl)-methyl]-cyclohexyl}-propionic acid ethyl ester 139 (R³=3-fluorophenyl)

The cyclohexylacrylic acid ester 138 (14.98 g, 0.045 mol) was dissolved in methanol (100 ml); 10% palladium/carbon (1.5 g) was added and hydrogenation was carried out for 24 h at 3 bar (RT). The Pd/C was filtered off with suction over kieselguhr and the solvent was removed in vacuo. The residue was dissolved in 1N NaOH (100 ml) and EA (100 ml) and the organic phase was separated off, washed with water, dried and concentrated.

Yield: 14.3 g (95%), colourless oil
$^{13}$C-NMR (CDCl$_3$): 14.18; 25.36; 25.72; 28.55; 28.86; 30.77; 31.94; 32.14; 32.38; 32.54; 32.73; 34.58; 35.94; 37.38; 38.64; 41.16; 41.98; 60.12; 71.08; 75.19; 113.41; 113.68; 115.64; 115.91; 125.03; 128.75; 128.86; 140.40; 160.86; 164.11; 174.02.

3-{4-[Dimethylamino-(3-fluorophenyl)-methyl]-cyclohexyl}-propan-1-ol 140 (R³=3-fluorophenyl)

The cyclohexylpropionic acid ester 139 (8.51 g, 25 mmol) and LiAlH$_4$ (0.986 g, 26 mmol) were boiled for 7 h under reflux in abs. THF (150 ml). Water (50 ml) and 5N NaOH (25 ml) were carefully added dropwise, while cooling with an ice bath (10° C.), and the mixture was stirred for 1 h at RT and then filtered off with suction over kieselguhr. The filter residue was washed with ether, the aqueous phase was extracted with ether (2×50 ml) and the combined organic solutions were dried and concentrated in vacuo.

Yield: 7.33 g (100%)
$^{13}$C-NMR (CDCl$_3$): 25.43; 25.57; 28.85; 29.00; 29.78; 30.15; 30.92; 32.93; 33.11; 33.24; 34.77; 36.05; 37.63; 38.76; 41.20; 42.01; 63.27; 67.93; 71.18; 75.27; 113.41; 113.68; 115.66; 115.94; 125.07; 128.76; 128.86; 140.48; 140.56; 160.87; 164.12.

3-[4-(1-Dimethylamino-3-phenyl-propyl)-cyclohexyl]-acrylic acid ethyl ester 141 (R³=phenethyl)

Potassium tert-butylate (13.46 g, 0.120 mol) was added, under argon, to a solution of phosphonoacetic acid triethyl ester (26.9 g, 0.120 mol) in abs. DMF (150 ml), and the mixture was stirred for 10 minutes. The aldehyde 43 (21.34 g, 0.080 mol) dissolved in DMF (225 ml) was then added dropwise. The mixture was stirred for 3 h at RT and then poured onto ice. The reaction mixture was extracted with diethyl ether (3×200 ml) and the organic phase was washed with water and saturated NaCl solution, dried and concentrated in vacuo. The crude product was purified by flash chromatography with ethyl acetate/cyclohexane (1:2).

Yield: 19.1 g (71%), oil
$^{13}$C-NMR (CDCl$_3$): 14.14; 28.99; 29.53; 30.56; 31.53; 31.59; 35.26; 39.26; 40.46; 40.72; 41.09; 41.03 (N(CH$_3$)$_2$); 59.95; 68.01; 118.84; 125.54; 128.14; 128.17; 142.70; 153.83; 166.86.

3-[4-(1-Dimethylamino-3-phenyl-propyl)-cyclohexyl]-propionic acid ethyl ester 142 (R³=phenethyl)

The cyclohexylacrylic acid ester 141 (14.04 g, 0.041 mol) was dissolved in methanol (100 ml); 10% palladium/carbon (1.4 g) was added and hydrogenation was carried out for 48 h at 3 bar (RT). The Pd/C was filtered off with suction over kieselguhr and the solvent was removed in vacuo. The residue was dissolved in 1N NaOH (100 ml) and EA (100 ml) and the organic phase was separated off, washed with water, dried and concentrated.

Yield: 11.7 g (82%), colourless oil
$^{13}$C-NMR (CDCl$_3$): 14.18; 25.68; 26.37; 28.36; 29.11; 30.01; 31.23; 31.65; 32.18; 32.50; 32.85; 32.90; 34.12; 35.37; 37.25; 38.73; 39.78; 40.84; 41.17; 60.07; 65.41; 68.25; 125.56; 128.24; 142.93; 174.01.

3-[4-(1-Dimethylamino-3-phenyl-propyl)-cyclohexyl]-propan-1-ol 143 (R³=phenethyl)

The cyclohexylpropionic acid ester 142 (6.58 g, 19 mmol) and LiAlH$_4$ (0.76 g, 20 mmol) were boiled for 7 h under reflux in abs. THF (100 ml). Water (50 ml) and 5N NaOH (25 ml) were carefully added dropwise, while cooling with an ice bath (10° C.), and the mixture was stirred for 1 h at RT and then filtered off with suction over kieselguhr. The filter residue was washed with ether, the aqueous phase was extracted with ether (2×50 ml) and the combined organic solutions were dried and concentrated in vacuo.

Yield: 5.56 g (96%)
$^{13}$C-NMR (CDCl$_3$): 29.15; 29.25; 30.09; 30.16; 31.42; 33.23; 33.32; 33.24; 35.40; 37.54; 39.92; 40.88; 41.20; 63.13; 68.39; 125.55; 128.19; 128.24; 142.93.

Synthesis of the Ethers (R¹=(CH$_2$)$_n$OR⁸)

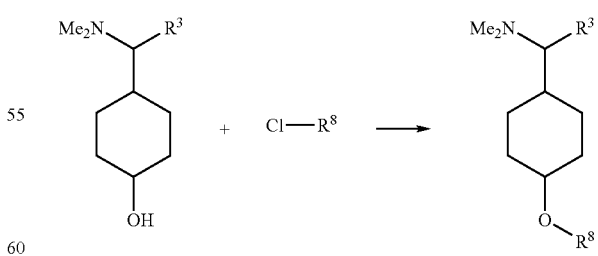

4-(Benzyloxy)cyclohexyl)-N,N-dimethyl(phenyl)methanamine hydrochloride 144 (R³=phenyl)

To a suspension of NaH (0.15 g, 6.4 mmol) in THF (10 ml) there were slowly added at RT the alcohol 111 (1.5 g; 6.4 mmol) dissolved in THF (10 ml) and then benzyl chloride (0.9 g, 7.1 mmol), and heating was then carried out for 21 h under reflux. While cooling with an ice bath, the mixture was carefully quenched with water (10 ml), and NaOH solution (10 ml, 5N) was added. After 1 hour's stirring, the mixture was filtered off over filtering earth and then washed with diethyl ether. Extraction with diethyl ether (3×40 ml) was carried out, followed by drying over $Na_2SO_4$ and concentration.

The crude product was purified by column chromatography with diethyl ether.

Yield: 451 mg (27.6%) yellow solid

The product was dissolved in methyl ethyl ketone (4 ml), and then water (0.014 ml) and trimethylchlorosilane (0.197 ml) were added.

After some time, a solid formed. Filtering off with suction and washing with ether yielded white crystals, which were dried in vacuo.

$^1$H NMR (600 MHz, DMSO) 0.83-0.88 (m, 2 H); 1.17-1.24 (m, 1 H); 1.25-1.32 (m, 1 H); 1.56-1.63 (m, 1 H); 1.90-1.98 (m, 2 H); 2.03-2.10 (m, 1 H); 2.21-2.28 (m, 1 H); 2.52-2.59 (m, 3 H); 2.64-2.70 (m, 3 H); 3.10-3.17 (m, 1 H); 4.20-4.25 (m, 1 H); 4.46 (s, 2 H); 7.24-7.29 (m, 2 H); 7.30-7.33 (m, 2 H); 7.45-7.52 (m, 5 H); 10.35 (s, 1 H).

4-(4-Fluorobenzyloxy)cyclohexyl)-N,N-dimethyl (phenyl)methanamine hydrochloride 145 ($R^3$=phenyl)

To a suspension of NaH (0.15 g, 6.4 mmol) in THF (10 ml) there were slowly added at RT the alcohol 111 (1.5 g; 6.4 mmol) dissolved in THF (10 ml) and then p-fluorobenzyl chloride (1.02 g, 7.1 mmol), and heating was then carried out for 21 h under reflux.

While cooling with an ice bath, the mixture was carefully quenched with water (10 ml), and NaOH solution (10 ml, 5N) was added. After 1 hour's stirring, the mixture was filtered off over filtering earth and then washed with diethyl ether. Extraction with diethyl ether (3×40 ml) was carried out, followed by drying over $Na_2SO_4$ and concentration.

The crude product was purified by column chromatography with diethyl ether/-hexane (1:1). It was possible to isolate the cis-diastereoisomer homogeneously. The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

$^1$H NMR (600 MHz, DMSO) 0.80-0.88 (m, 2 H); 1.16-1.23 (m, 1 H); 1.25-1.32 (m, 1 H); 1.53-1.61 (m, 1 H); 1.89-1.97 (m, 2 H); 2.03-2.09 (m, 1 H); 2.21-2.28 (m, 1 H); 2.53-2.59 (m, 3 H); 2.64-2.70 (m, 3 H); 3.10-3.18 (m, 1 H); 4.20-4.26 (m, 1 H); 4.44 (s, 2 H); 7.11-7.17 (m, 2 H); 7.30-7.36 (m, 2 H); 7.45-7.52 (m, 5 H); 10.25 (s, 1 H).

Synthesis of the Grignard Compounds ($R^2$=OH)

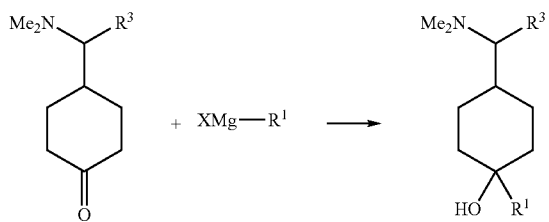

N,N-Dimethyl(4-phenethylcyclohexyl)(phenyl) methanamine hydrochloride 146 ($R^3$=phenyl)

The phenethylmagnesium chloride solution (9.1 ml, 9.1 mmol, 1.0 M in THF) was placed in a reaction vessel, under a nitrogen atmosphere, and cooled to about 10° C. with an ice bath. The ketone 10 was dissolved in THF (9 ml) and added dropwise. The reaction mixture was stirred overnight at RT. For working up, the mixture was hydrolysed with $NH_4Cl$ solution (20%, 9 ml), while cooling with ice, and extracted with diethyl ether (3×40 ml). The combined organic phases were dried ($Na_2SO_4$) and concentrated.

Purification was carried out by column chromatography (ether).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

$^{13}$C NMR (75 MHz, DMSO) 22.58; 24.58; 25.28; 26.00; 28.66; 29.08; 35.38; 35.51; 35.62; 35.70; 36.16; 36.70; 38.19; 38.50; 39.12; 39.40; 39.45; 42.20; 42.58; 46.04; 72.26; 74.00; 125.29; 125.30; 128.02; 128.05; 128.08; 128.12; 128.60; 128.56; 129.06; 129.24; 129.95; 142.93.

1-Benzyl-4-((dimethylamino)(phenyl)methyl)cyclohexanol hydrochloride 147 ($R^3$=phenyl)

The benzylmagnesium chloride solution (4.5 ml, 9.1 mmol, 2.0 M in THF) was placed in a reaction vessel, under a nitrogen atmosphere, and cooled to about 10° C. with an ice bath. The ketone 10 was dissolved in THF (9 ml) and added dropwise. The reaction mixture was stirred overnight at RT. For working up, the mixture was hydrolysed with $NH_4Cl$ solution (20%, 9 ml), while cooling with ice, and extracted with diethyl ether ml (3×40 ml). The combined organic phases were dried ($Na_2SO_4$) and concentrated.

Purification was carried out by flash chromatography (ether). The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

4-((Dimethylamino)(phenyl)methyl)-1-(4-fluorobenzyl)cyclohexanol hydrochloride 148 ($R^3$=phenyl)

Magnesium turnings (0.19 g, 7.8 mmol) were placed in a flask, and a small amount of THF (3 ml) was added. ¹/₂₀ of the 4-fluorobenzyl chloride (1.12 g, 7.8 mmol) was first added in pure form to the magnesium so that the reaction started. When the reaction had begun, the halide was diluted with THF (14 ml) and added dropwise in such a manner that the solvent boiled gently. When the dropwise addition was complete, stirring was carried out for about 1 h at boiling temperature. The ketone 10 (1.5 g, 6.5 mmol) was then added dropwise at RT and stirring was carried out overnight at RT.

While cooling with ice, the mixture was then hydrolysed with $NH_4Cl$ solution (20%, 10 ml) and extracted with ether (3×40 ml). The combined organic phases were dried ($Na_2SO_4$) and concentrated.

Purification was carried out by flash chromatography (diethyl ether).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

1-(2,5-Dimethoxyphenyl)-4-((dimethylamino)(phenyl)methyl)cyclohexanol hydrochloride 149 ($R^3$=phenyl)

Magnesium turnings (0.15 g, 6.2 mmol) were placed in a flask, and a small amount of THF (3 ml) was added. 1/20 of the 1-bromo-2,5-dimethoxybenzene (1.35 g, 6.2 mmol) was first added dropwise in pure form to the magnesium so that the reaction started. When the reaction had begun, the halide was diluted with THF (10 ml) and added dropwise in such a manner that the solvent boiled gently. When the dropwise addition was complete, stirring was carried out for about 1 h at boiling temperature. The ketone 10 (1.2 g, 5.2 mmol) was then added dropwise at RT and stirring was carried out overnight at RT.

While cooling with ice, the mixture was then hydrolysed with $NH_4Cl$ solution (20%, 10 ml) and extracted with ether (3×40 ml). The combined organic phases were dried ($Na_2SO_4$) and concentrated.

Purification was carried out by flash chromatography (diethyl ether).

The product was dissolved in methyl ethyl ketone (2 ml), and then water (0.01 ml/1 mmol) and trimethylchlorosilane (1.3 ml/1 mmol) were added. Filtering off with suction and washing with ether yielded white crystals, which were dried in vacuo.

Synthesis Procedure for Automated Synthesis a) Use of Grignard Reagent Solutions The cyclohexanone derivative (200 µmol, 400 µl, 0.5 mol/l in THF) was placed at 0° C. in a thoroughly heated reactor block flushed with $N_2$ [ACT Vantage], and the corresponding Grignard reagent (400 µmol, 800 µl, 0.5 mol/l in THF or diethyl ether) was added. The reaction mixture was agitated for 2.5 h at room temperature and then quenched by addition of 2 ml of a semi-saturated $NH_4Cl$ solution at 0° C. The solution was then agitated for about 30 minutes at room temperature, and 1 ml of ethyl acetate was added.

For working up, the organic phase was removed [MYRIAD Allex] and transferred to a tared vessel. The aqueous phase was then extracted once again with 2.5 ml of ethyl acetate and the organic phases were collected. The combined organic phases are concentrated to dryness and weighed again to determine the yield. Purification was carried out by HPLC.

b) Use of GRIGNARD Reagents from Iodoaromatic Compounds

The solution of the iodoaromatic compound (325 µmol, 650 µl, 0.5 mol/l in/THF) was placed at 0° C. in a thoroughly heated reactor block flushed with $N_2$ [ACT Vantage], and isopropylmagnesium chloride (275 µmol, 550 µl, 0.5 mol/l in THF) was added. After about 30 minutes' agitation at 0° C., the cyclohexanone derivative (200 µmol, 400 µl, 0.5 mol/l in THF) was pipetted into the reaction solution. The reaction mixture was agitated for 5 h at room temperature and then quenched by addition of 2 ml of a semi-saturated $NH_4Cl$ solution at 0° C. The solution was then agitated for about 30 minutes at room temperature, and 1 ml of ethyl acetate was added.

For working up, the organic phase was removed [MYRIAD Allex]. The aqueous phase was then extracted once again with 3 ml of ethyl acetate. The combined organic phases were concentrated to dryness. Purification was carried out by HPLC.

The following examples were synthesised in this manner. Analysis was by HPLC-MS (ESI). In all the cases listed here, the mass was found as M+1:

| No. | Name | Mass |
|---|---|---|
| 150 | 4-((Dimethylamino)(phenyl)methyl)-1-(4-fluoro-3-methylphenyl)-cyclohexanol | 337.24 |
| 151 | 4-(Dimethylamino-phenyl-methyl)-1-(4-fluoro-3-methyl-phenyl)-cyclohexanol | 341.22 |
| 152 | 1-Benzyl-4-[dimethylamino-(3-fluoro-phenyl)-methyl]-cyclohexanol | 341.22 |
| 153 | 4-[Dimethylamino-(3-fluoro-phenyl)-methyl]-1-phenethyl-cyclohexanol | 355.23 |
| 154 | 4-[Dimethylamino-(3-fluoro-phenyl)-methyl]-1-pentyl-cyclohexanol | 321.25 |
| 155 | 1-(3,5-Dichloro-phenyl)-4-[dimethylamino-(3-fluoro-phenyl)-methyl]-cyclohexanol | 395.12 |
| 156 | 4-[Dimethylamino-(3-fluoro-phenyl)-methyl]-1-(3-methoxy-benzyl)-cyclohexanol | 371.23 |
| 157 | 1-(4-Chloro-3-trifluoromethyl-phenyl)-4-[dimethylamino-(3-fluoro-phenyl)-methyl]-cyclohexanol | 429.15 |
| 158 | 4-[(4-Chloro-phenyl)-dimethylamino-methyl]-1-phenyl-cyclohexanol | 343.17 |
| 159 | 1-Benzyl-4-[(4-chloro-phenyl)-dimethylamino-methyl]-cyclohexanol | 357.19 |
| 160 | 4-[(4-Chloro-phenyl)-dimethylamino-methyl]-1-(4-fluoro-3-methyl-phenyl)-cyclohexanol | 375.18 |
| 161 | 4-[(4-Chloro-phenyl)-dimethylamino-methyl]-1-o-tolyl-cyclohexanol | 357.19 |
| 162 | 4-[(4-Chloro-phenyl)-dimethylamino-methyl]-1-(4-fluoro-phenyl)-cyclohexanol | 361.16 |
| 163 | 4-[(4-Chloro-phenyl)-dimethylamino-methyl]-1-phenethyl-cyclohexanol | 371.20 |
| 164 | 4-[(4-Chloro-phenyl)-dimethylamino-methyl]-1-(3-methoxy-phenyl)-cyclohexanol | 373.18 |
| 165 | 4-[(4-Chloro-phenyl)-dimethylamino-methyl]-1-p-tolyl-cyclohexanol | 357.19 |
| 166 | 4-[(4-Chloro-phenyl)-dimethylamino-methyl]-1-(3,5-difluoro-phenyl)-cyclohexanol | 379.15 |
| 167 | 1-Butyl-4-[(4-chloro-phenyl)-dimethylamino-methyl]-cyclohexanol | 323.20 |
| 168 | 4-[(4-Chloro-phenyl)-dimethylamino-methyl]-1-hexyl-cyclohexanol | 351.23 |
| 169 | 4-[(4-Chloro-phenyl)-dimethylamino-methyl]-1-pentyl-cyclohexanol (more polar diastereoisomer) | 337.22 |
| 170 | 4-[(4-Chloro-phenyl)-dimethylamino-methyl]-1-pentyl-cyclohexanol (less polar diastereoisomer) | 337.22 |

-continued

| No. | Name | Mass |
|---|---|---|
| 171 | 4-[(4-Chloro-phenyl)-dimethylamino-methyl]-1-(3-fluoro-phenyl)-cyclohexanol | 361.16 |
| 172 | 4-[(4-Chloro-phenyl)-dimethylamino-methyl]-1-(4-fluoro-benzyl)-cyclohexanol | 375.18 |
| 173 | 4-[(4-Chloro-phenyl)-dimethylamino-methyl]-1-(3-methoxy-benzyl)-cyclohexanol | 387.20 |

Synthesis of Amides from Esters ($R^1=(CH_2)_n CONR^{10}R^{11}$ or $R^1=XCONR^{10}R^{11}$)

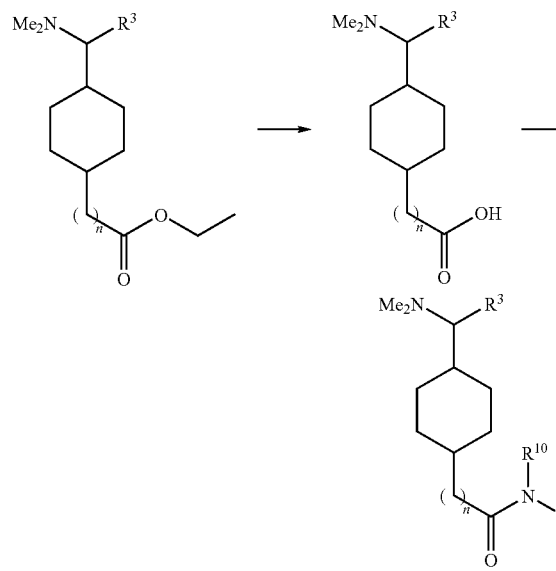

or

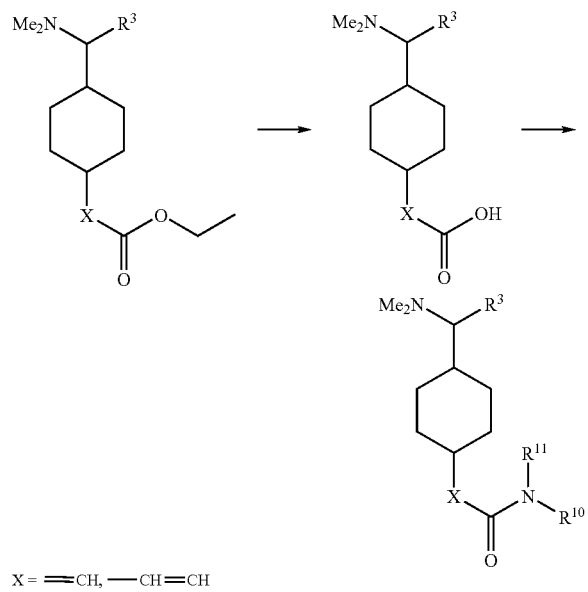

$X = =CH, \text{—}CH=CH$

General Method for Hydrolysis of the Esters

Sodium hydroxide solution (6 M, 40 ml) was added to a solution of the cyclohexylacetic acid, cyclohexylideneacetic acid, cyclohexylacrylic acid or cyclohexylpropionic acid ester (20 mmol) in THF (130 ml) and water (80 ml), and stirring was carried out for 4-16 hours at room temperature. The solvent was then largely removed by distillation, and conc. hydrochloric acid was added slowly until a pH value of 7 was achieved. The solvent was removed completely by distillation and the residue was washed with 2-propanol (3×200 ml).

Automated Synthesis for Formation of the Amides

Cyclohexylacetic acid, cyclohexylideneacetic acid, cyclohexylacrylic acid or cyclohexylpropionic acid (100 µmol, 0.05 M solution in $CH_2Cl_2$) was placed at RT in a dry screw-cap jar, and carbonyldiimidazole solution (105 µmol, 0.1 M solution in $CH_2Cl_2$) was added. After a stirring time of 1 hour at RT, the amine (100 µmol, 0.1 M solution in $CH_2Cl_2$) was added to the reaction solution and the mixture was stirred for 16 h at RT. After the addition of water (3 ml) and extraction, the organic phase was separated off and washed with saturated NaCl solution (3 ml). The organic phase which had been separated off was dried over $MgSO_4$ and the solvent was removed by distillation.

Alternative Synthesis Process

General synthesis scheme

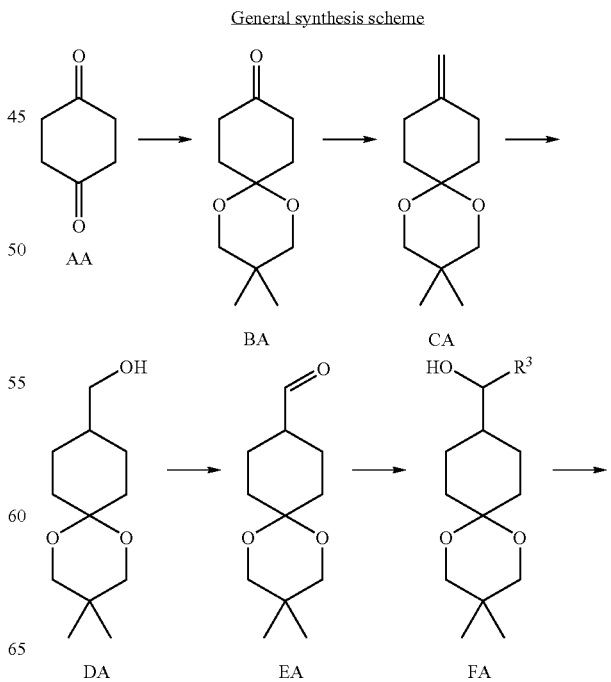

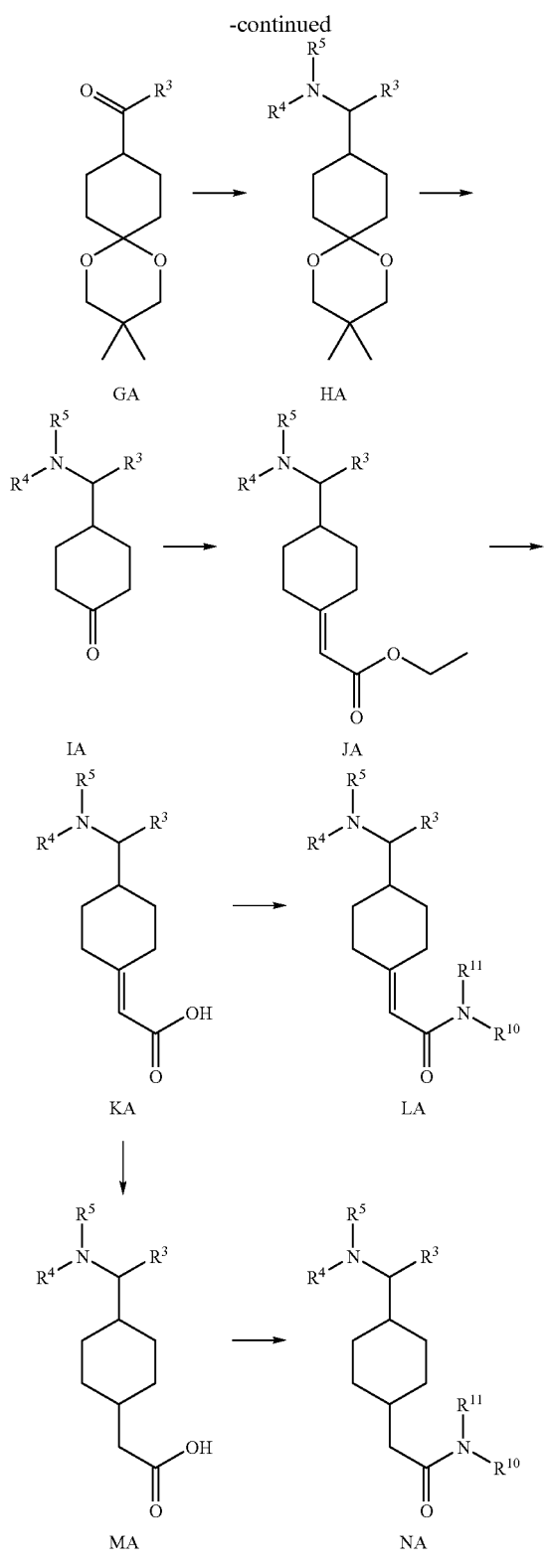

General Process 1,4-Cyclohexanedione AA is converted into the acetal BA under conditions known to the person skilled in the art in an acetal-forming reaction with a glycol derivative in an organic solvent such as dichloromethane, cyclohexane, toluene, benzene, ethanol, methanol or xylene, possibly also in the presence of a water-removing reagent, such as sulfuric acid, sodium or magnesium sulfate, molecular sieve or phosphorus oxides, optionally also with the addition of catalytic amounts of p-toluenesulfonic acid, at a temperature of from RT to the reflux temperature of the organic solvent in question.

Acetal ketones BA are converted into the products CA by methods known to the person skilled in the art in a Wittig reaction using phosphorylidene in organic solvents, such as THF, DME or diethyl ether, in the presence of organometallic bases, such as n-BuLi, tert-BuLi, LDA, metal hydrides such as NaH, KH, at a temperature of from −10° C. to the reflux temperature of the organic solvent in question.

The compound CA is converted into the alcohols DA in a hydroxylation reaction in the presence of boron trifluoride etherate and metal hydrides such as sodium borohydride or lithium aluminium hydride in an organic solvent such as THF or diethyl ether, also with the addition of diglyme, at a temperature of from −10° C. to RT.

The alcohols DA can be converted into the aldehyde EA under conditions known to the person skilled in the art by the use of reagents such as PCC, periodinane, IBX, TPAP, NMO, $MnO_2$ or oxalyl chloride, optionally also in the presence of molecular sieve or of a base, such as triethylamine, in an organic solvent such as dichloromethane, DMSO, methanol, ethanol, diethyl ether, THF, DMF, DME, at a temperature of from −78° C. to the reflux temperature of the organic solvent in question.

The alcohols FA are obtained under conditions known to the person skilled in the art by the addition of metal organyls, such as magnesium, copper, zinc or lithium organyls, in organic solvents, such as ether, THF, methanol, ethanol or dichloromethane, at a temperature of from −78° C. to RT.

The alcohols F can be converted into the aldehydes GA under conditions known to the person skilled in the art by the use of reagents such as chromium trioxide, PCC, periodinane, PDC, IBX, TPAP, NMO, $MnO_2$ or oxalyl chloride, optionally also in the presence of molecular sieve or of a base, such as triethylamine, or of an acid, such as aqueous sulfuric acid, in an organic solvent such as dichloromethane, DMSO, acetone, methanol, ethanol, diethyl ether, THF, DMF, DME, at a temperature of from −78° C. to the reflux temperature of the organic solvent in question.

The ketones GA are converted into the compounds HA with amines in a reductive amination using reducing agents, such as sodium cyanoborohydride or sodium triacetoxyborohydride or borane-pyridine complex, in an organic solvent, such as dichloromethane, diethyl ether, 1,2-dichloroethane, DME, DMF, methanol, ethanol or THF, at a temperature of from 0° C. to reflux temperature. The amine ketones IA are obtained under conditions known to the person skilled in the art in an acetal cleavage reaction in an organic solvent such as THF, methanol, ethanol, dichloromethane or diethyl ether, with the addition of inorganic acids, such as sulfuric acid, hydrochloric acid, ammonium chloride or hydrogen sulfate, or in the presence of organic acids, such as p-toluenesulfonic acid or trifluoroacetic acid, at a temperature of from −10° C. to RT.

The compounds IA are converted into the products JA under conditions known to the person skilled in the art with triethyl phosphonoacetate, in an organic solvent, such as DME, THF, diethyl ether or dichloromethane, in the presence of bases such as n-BuLi, tert-BuLi, LDA, metal hydrides such as NaH, KH, at a temperature of from −10° C. to the reflux temperature of the organic solvent in question.

The compounds JA are converted into the acids KA in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents such as methanol, ethanol, dioxane, dichloromethane, THF, diethyl ether or these solvents in the form of mixtures, at a temperature of from −10° C. to RT.

The compounds KA can be converted into the compounds MA by methods known to the person skilled in the art in a hydrogenation reaction in the presence of a catalyst, such as Raney/nickel or palladium, in each case using hydrogen, sodium borohydride, magnesium or palladium, in the presence of ammonium formate, in organic solvents, such as ethanol or methanol, at a temperature of from 0° C. to RT.

The acids KA or MA can be converted into the final products of the general formulae LA or NA under conditions known to the person skilled in the art in an amide formation using primary or secondary amines in the presence of water-removing agents, such as sodium or magnesium sulfate, phosphorus oxide or reagents such as, for example, CDI, DCC (optionally polymer-bonded), TBTU, EDCI, PyBOP or PFPTFA, also in the presence of HOAt or HOBt and of an organic base, for example DIPEA or pyridine, in an organic solvent such as THF, dichloromethane, diethyl ether, dioxane, DMF or acetonitrile.

Preparation of Example Compounds 491-496

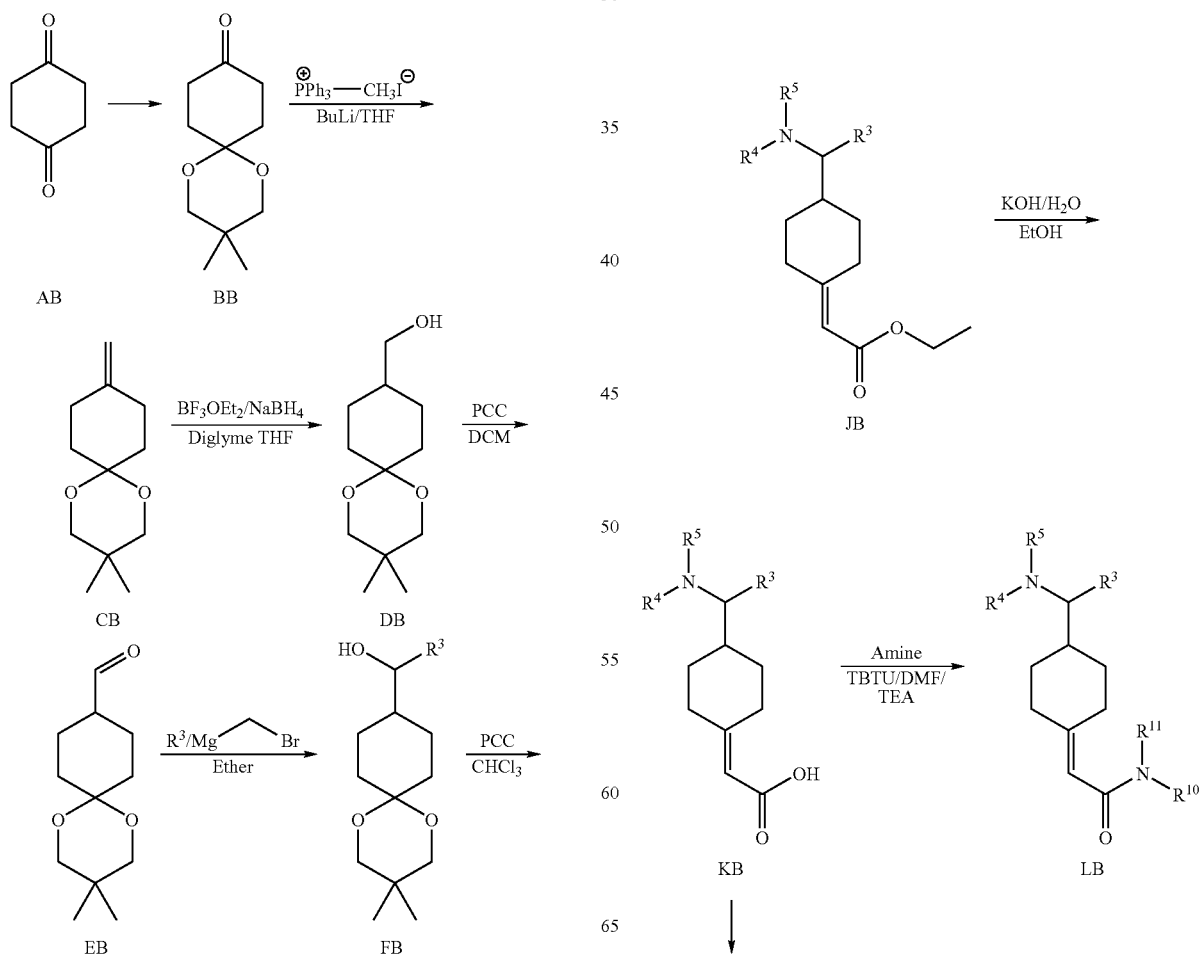

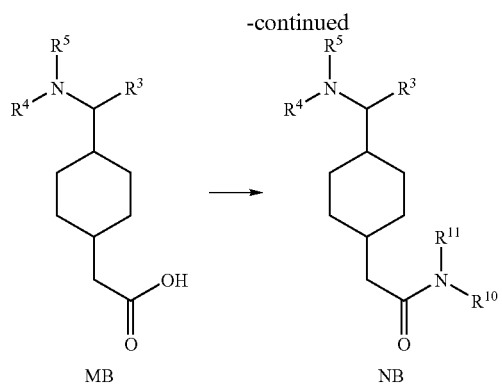

Preparation of BB

Neopentyl glycol (47 g, 1 equivalent) and $H_2SO_4$ (8 g, 0.2 equivalent) were added to a solution of 1,4-cyclohexanedione AB (50 g, 1 equivalent) in DCM (400 ml), and the reaction solution was stirred overnight at RT. The reaction solution was added to a saturated aqueous $Na_2CO_3$ solution, while cooling with ice, and the organic phase was separated off. After drying the organic phase over $Na_2SO_4$ and filtration, the solvent was removed in vacuo. Heptane (200 ml) was added to the residue, and the mixture was filtered off with suction. The product BB was obtained in a yield of 71% (51 g).

Preparation of CB:

n-BuLi (236 ml, 1.5 equivalents) was added dropwise at 0° C. to the Wittig reagent (122 g, 1.2 equivalents) in absolute THF (600 ml), and stirring was carried out for 1 h at 0° C. and for a further 2 h at from −5° C. to 0° C. After the dropwise addition of a solution of BB (50 g, 1 equivalent) in THF (150 ml), the reaction mixture was stirred for 1 h at from −5° C. to 0° C. After heating to RT, the reaction solution was stirred for a further 4 h at RT.

Saturated aqueous $NH_4Cl$ solution (250 ml) was added to the reaction solution, and extraction with ethyl acetate (3×200 ml) was carried out. The organic phase was separated off, dried over $Na_2SO_4$ and filtered, and the solvent was removed in vacuo. The residue was purified by column chromatography (5% EtOAc/heptane). The product CB was obtained in a yield of 75% (40 g).

Preparation of DB:

$NaBH_4$ (13 g, 1.5 equivalents) and diglyme (135 ml) were stirred for 10 minutes in a three-necked flask, and then $BF_3OEt_2$ (65 g, 2 equivalents) was added dropwise thereto over a period of 30 minutes. The $BH_3$ gas that formed thereby was introduced into a solution of CB (45 g, 1 equivalent) in THF (450 ml) which had been cooled to 0° C. Sodium hydroxide solution was added to the reaction mixture and extraction with ethyl acetate (3×150 ml) was carried out. The organic phase was separated off and the solvent was removed in vacuo. The product EB was obtained in an amount of 45 g.

Preparation of EB:

A reaction mixture of PCC (105.4 g, 2 equivalents), DCM (550 ml) and Celite was stirred for 10 minutes at 0° C. A solution of DB (45 g, 1 equivalent) in DCM (125 ml) was then added dropwise over a period of 15 minutes. The reaction mixture was heated for 1 h at 60° C.

After filtering the reaction mixture over Celite, washing with DCM (125 ml) was carried out. The solvent was removed in vacuo and the crude product was purified by column chromatography (10% EtOAc/heptane). The product E was obtained in a yield of 40% (18 g).

Preparation of FB:

In order to prepare solution 1, absolute diethyl ether (100 ml), Mg (4.52 g, 4 equivalents) and alkyl halide (2 equivalents) were brought together in succession and stirred for 10 minutes at RT. Solution 1 was added dropwise under an inert gas atmosphere to a solution of the aldehyde EB (47 mmol, 1 equivalent) in absolute THF (100 ml), and stirring was carried out for 4 h at RT. Saturated aqueous $NH_4Cl$ solution (100 ml) was added to the reaction solution and extraction with ethyl acetate (3×100 ml) was carried out. The solvent was removed in vacuo and the product FB was purified by column chromatography (5% EtOAc/heptane).

Preparation of GB:

Celite and PCC (2 equivalents) were added to a solution of FB (23 mmol, 1 equivalent) in $CHCl_3$ (140 ml), and the reaction mixture was stirred for 2 h at RT. The reaction mixture was filtered off over Celite and washed with $CHCl_3$. After removal of the solvent in vacuo, the crude product GB was purified by column chromatography (7% EtOAc/heptane).

Preparation of HB:

An amine (1.5 equivalents), $NaCNBH_4$ (2 equivalents) and ACOH (16 ml) were added to a solution of GB (18 mmol, 1 equivalent) in methanol (5 ml) and the mixture was stirred for 12 h at RT.

Saturated aqueous $Na_2CO_3$ solution (50 ml) was added to the reaction solution, and extraction with ethyl acetate (3×100 ml) was carried out. The solvent was removed in vacuo and the residue HB was purified by column chromatography (10% EtOAc/heptane).

Preparation of IB:

10% HCl (80 ml) was added at 0° C. to a solution of GB (12 mmol, 1 equivalent) in methanol (45 ml) and the mixture was stirred for 10 minutes. Sodium hydroxide solution (20 ml) was added to the reaction mixture and extraction with ethyl acetate (3×50 ml) was carried out. The solvent was removed in vacuo and the product was used in the next stage without being purified further.

Preparation of JB:

NaH (1.4 equivalents) was added to a solution of triethyl phosphonoacetate (1.2 equivalents) in DME (35 ml) and the mixture was stirred for 2 h at RT under an inert gas atmosphere. A solution of IB (12 mmol) in DME (33 ml) was then added dropwise and stirring was carried out for a further 3 h at RT. Ice-water (100 ml) was added slowly to the reaction mixture, and the reaction mixture was extracted with ethyl acetate (3×50 ml). The ethyl acetate was removed in vacuo and the crude product was purified by column chromatography (15% EtOAc/heptane).

Preparation of KB:

KOH (2 equivalents) and water (3 ml) were added to a solution of JB (2 mmol) in ethanol (14 ml). The reaction mixture was then stirred for 3 h at RT.

The reaction mixture was neutralised with HCl and extracted with ethyl acetate (3×50 ml). Removal of the ethyl acetate in vacuo yielded the product KB, which was used in the next stage without being purified further.

Preparation of MB:

A catalytic amount of Raney/Ni was added, under a hydrogen atmosphere, to a solution of KB (0.5 g) in ethanol (15 ml) and the reaction solution was stirred for 30 minutes at RT. After filtration over Celite, the solvent was removed in vacuo.

Preparation of the Example Compounds

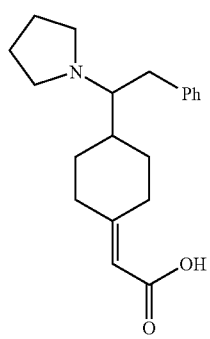

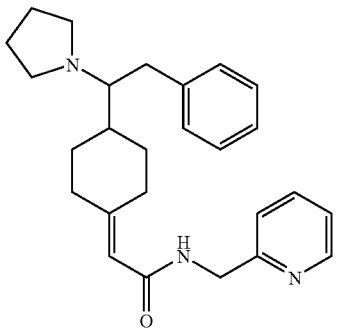

Preparation of 2-(4-(2-phenyl-1-(pyrrolidin-1-yl) ethyl)cyclohexylidene)-N-(pyridin-2-ylmethyl)acetamide (Example 495)

TBTU (0.1 g, 1 equivalent) and triethylamine (64 mg, 2 equivalents) were added to a solution of KB (0.3 mmol, 100 mg) in DMF (1 ml) and the mixture was stirred for 10 minutes at RT. After the addition of 2-(aminomethyl)-pyridine (34 mg, 1 equivalent), stirring was carried out for 2 h at RT.

The reaction mixture was added to ice-water and extracted with ethyl acetate (3×10 ml). The organic phase was separated off, dried over Na$_2$SO$_4$ and filtered. The ethyl acetate was removed in vacuo and the residue was purified by column chromatography (50% EtOAc/heptane). The product was obtained in a yield of 18% (22 mg).

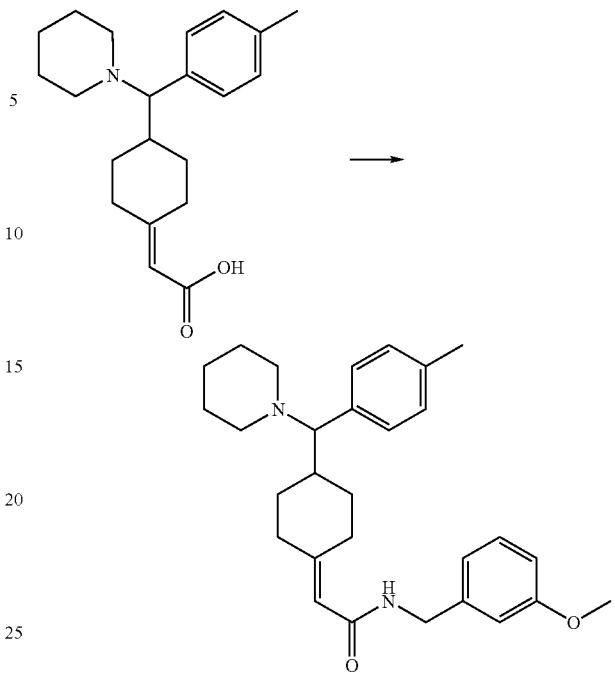

Preparation of N-(4-methoxyphenyl)-2-(4-(piperidin-1-yl(p-tolyl)methyl)-cyclohexylidene)acetamide (Example 493)

TBTU (20 mg, 1 equivalent) and triethylamine (6 mg, 2 equivalents) were added to a solution of KB (0.06 mmol, 20 mg) in DMF (0.5 ml) and the mixture was stirred for 10 minutes at RT. After the addition of p-methoxyaniline (30 mg, 1 equivalent), stirring was carried out for 45 minutes at RT.

The reaction mixture was added to ice-water and the product was filtered off.

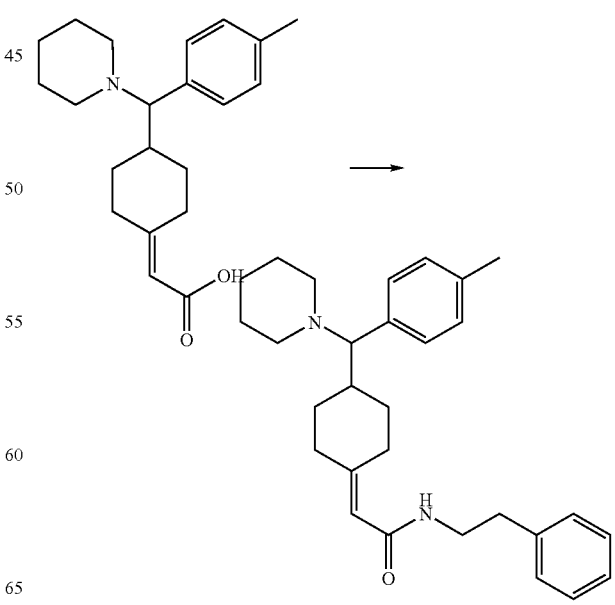

Preparation of N-phenethyl-2-(4-(piperidin-1-yl(p-tolyl)methyl)-cyclohexylidene)acetamide (Example 494)

TBTU (20 mg, 1 equivalent) and triethylamine (6 mg, 2 equivalents) were added to a solution of KB (20 mg) in DMF (3 ml) and the mixture was stirred for 10 minutes at RT. After the addition of phenylethylamine (7 mg, 1 equivalent), stirring was carried out for 3 h at RT.

The reaction mixture was extracted with ethyl acetate (2×100 ml). The organic phase was separated off, dried over $Na_2SO_4$ and filtered. The ethyl acetate was removed in vacuo and the residue was purified by column chromatography (10% EtOAc/heptane).

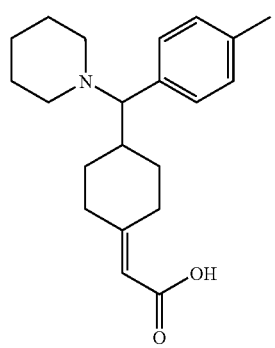

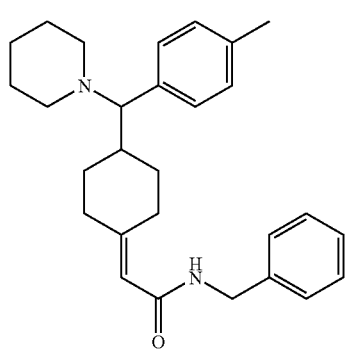

Preparation of N-benzyl-N-methyl-2-(4-(piperidin-1-yl(p-tolyl)methyl)cyclo-hexylidene)acetamide (Example 496)

TBTU (20 mg, 1 equivalent) and triethylamine (6 mg, 2 equivalents) were added to a solution of MB (20 mg) in DMF (3 ml) and the mixture was stirred for 10 minutes at RT. After the addition of N-methylbenzylamine (7 mg, 1 equivalent), stirring was carried out for 3 h at RT.

The reaction mixture was added to ice-water (100 ml) and extracted with ethyl acetate (2×100 ml). The organic phase was separated off, dried over $Na_2SO_4$ and filtered. The ethyl acetate was removed in vacuo and the residue was purified by column chromatography (10% EtOAc/heptane). The product was obtained in a yield of 22% (13 mg).

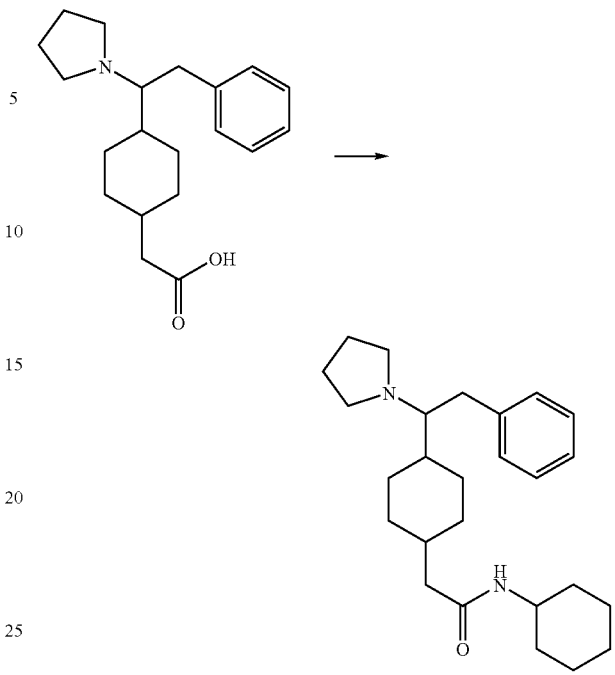

Preparation of N-cyclohexyl-2-(4-(2-phenyl-1-(pyrrolidin-1-yl)ethyl)cyclohexyl)acetamide (Example 491)

TBTU (0.1 g, 1 equivalent) and triethylamine (30 mg, 2 equivalents) were added to a solution of MB (0.3 mmol, 100 mg) in DMF (1 ml) and the mixture was stirred for 10 minutes at RT. After the addition of cyclohexylamine (30 mg, 1 equivalent), stirring was carried out for 30 minutes at RT.

The reaction mixture was added to ice-water (20 ml) and the product was filtered off. The product was obtained in a yield of 96% (32 mg).

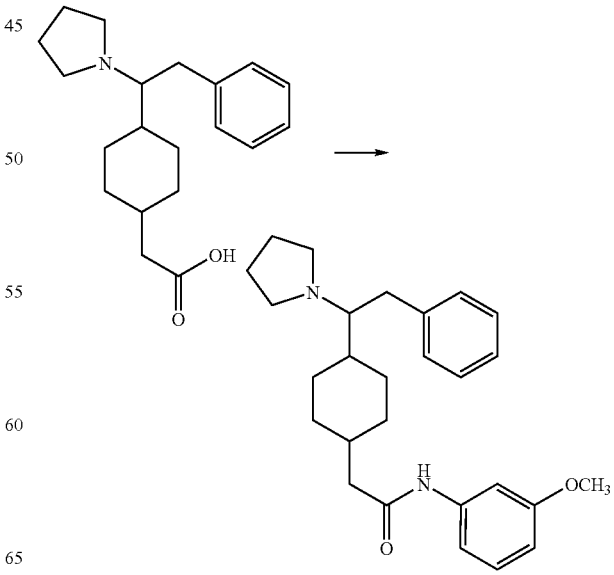

Preparation of N-(3-methoxyphenyl)-2-(4-(2-phenyl-1-(pyrrolidin-1-yl)ethyl)-cyclohexyl)acetamide (Example 492)

TBTU (0.1 g, 1 equivalent) and triethylamine (30 mg, 2 equivalents) were added to a solution of KB (0.3 mmol, 100 mg) in DMF (1 ml) and the mixture was stirred for 10 minutes at RT. After the addition of m-methoxyaniline (30 mg, 1 equivalent), stirring was carried out for 30 minutes at RT.

The reaction mixture was added to ice-water (20 ml) and the product was filtered off. The product was obtained in a yield of 96% (32 mg).

Separation of the Diastereoisomers

In cases in which diastereoisomers were separated, this was carried out by the following method:

The crude product was applied to a HPLC column VP 100/21 Nucleodur C 18 (5 µm), 100 mm, 21 mm inside diameter, from Macherey-Nagel with the aid of a Waters 600 HPLC pump with a starting eluant of 60% water and 40% methanol at 25° C. and a flow of 20 ml/minute. The methanol content of the eluant was increased continuously to 100% in the course of 14 minutes. Elution with 100% methanol was carried out for a further 5.5 minutes. Detection was effected by means of a Waters 2487 UV detector at 220 and 254 nm and ES-MS. The separated fractions were collected, concentrated and analysed by means of ES mass spectroscopy. In the present invention, the example compounds eluted in the first fraction are referred to as the "more polar diastereoisomer" and those eluted in the second fraction are referred to as the "less polar diastereoisomer".

Studies of the Effectiveness of the Compounds According to the Invention

Method for Determining the Affinity for the Human µ-Opiate Receptor

The receptor affinity for the human µ-opiate receptor is determined in a homogeneous batch on microtitre plates. To this end, serial dilutions of the substances to be tested are incubated for 90 minutes at room temperature with a receptor membrane preparation (15-40 µg of protein/250 µl of incubation batch) of CHO-K1 cells, which express the human µ-opiate receptor (RB-HOM receptor membrane preparation from PerkinElmer Life Sciences, Zaventem, Belgium), in the presence of 1 nmol/l of the radioactive ligand [$^3$H]-naloxone (NET719, PerkinElmer Life Sciences, Zaventem, Belgium) and 1 mg of WGA-SPA beads (wheatgerm agglutinin SPA beads from Amersham/Pharmacia, Freiburg, Germany) in a total volume of 250 µl. The incubation buffer used is 50 mmol/l of Tris-HCl supplemented with 0.06 wt. % bovine serum albumin. In order to determine non-specific binding, 100 µmol/l of naloxone are additionally added. When the ninety-minute incubation time has ended, the microtitre plates are centrifuged off for 20 minutes at 1000 g and the radioactivity is measured in a β-counter (Microbeta-Trilux, PerkinElmer Wallac, Freiburg, Germany). The percentage displacement of the radioactive ligand from its binding to the human µ-opiate receptor at a concentration of the test substances of 1 µmol/l is determined and stated as the percentage inhibition of specific binding.

Noradrenaline (NA) and Serotonin (5HT) Reuptake Inhibition

In order to be able to carry out these studies in vitro, synaptosomes are freshly isolated from areas of rat brain. A so-called "$P_2$" fraction prepared by the method of Gray and Whittaker (E. G. Gray and V. P. Whittaker (1962) J. Anat. 76, 79-88) is used in each case. For the NA uptake, these vesicular particles are isolated from the hypothalamus of male rat brains.

A detailed description of the method will be found in the literature (M. Ch. Frink, H. H. Hennies, W. Englberger, M. Haurand and B. Wilffert (1996) Arzneim.-Forsch./Drug Res. 46 (III), 11, 1029-1036).

Tables.

TABLE 1

Monoamine reuptake inhibition of the aldehydes

| Comp. | NA reuptake, % inhibition [10 µM] | Serotonin reuptake, % inhibition [10 µM] |
|---|---|---|
| 28 | 84 | 85 |
| 34 | 87 | 87 |
| 37 | 97 | 75 |
| 40 | 77 | 78 |
| 43 | 98 | 80 |
| 46 | 95 | 92 |
| 49 | 97 | 93 |
| 52 | 96 | 94 |
| 55 | 95 | 88 |
| 67 | 86 | 95 |
| 70 | 93 | 70 |

TABLE 2

µ affinity of the aldehydes

| Comp. | µ-Opioid receptor, % inhibition [1 µM] | µ-Opioid receptor, $K_i$ [µM] |
|---|---|---|
| 28 | 69 | n.d. |
| 34 | 34 | n.d. |
| 37 | 45 | n.d. |
| 40 | 69 | n.d. |
| 46 | 75 | n.d. |
| 49 | 34 | n.d. |
| 52 | 67 | n.d. |
| 55 | 50 | n.d. |
| 67 | 79 | 0.2 |

TABLE 3

NA reuptake inhibition of the esters

| Comp. | NA reuptake, % inhibition [10 µM] | NA reuptake, $K_i$ [µM] |
|---|---|---|
| 123 | 66 | n.d. |
| 124 | 76 | n.d. |
| 125 | 86 | n.d. |
| 126 | 81 | n.d. |
| 127 | 89 | n.d. |
| 129 | 81 | n.d. |
| 130 | 82 | n.d. |
| 132 | 84 | 0.59 |
| 133 | 87 | n.d. |
| 135 | 90 | 0.49 |
| 136 | 89 | 0.58 |
| 138 | 96 | 0.62 |
| 139 | 94 | 0.79 |
| 141 | 98 | n.d. |
| 142 | 99 | n.d. |

TABLE 4

Serotonin reuptake inhibition of the esters

| Comp. | Serotonin reuptake, % inhibition [10 μM] | Serotonin reuptake, $K_i$ [μM] |
|---|---|---|
| 123 | 92 | |
| 124 | 85 | 0.097000 |
| 125 | 82 | n.d. |
| 126 | 86 | n.d. |
| 127 | 90 | n.d. |
| 129 | 91 | 0.086 |
| 130 | 93 | 0.016 |
| 132 | 86 | 0.42 |
| 133 | 89 | 0.099 |
| 135 | 78 | 0.22 |
| 136 | 86 | 0.083 |
| 138 | 84 | 0.31 |
| 139 | 89 | 0.058 |
| 141 | 83 | n.d. |
| 142 | 84 | n.d. |

TABLE 5

μ affinity of the esters

| Comp. | μ-Opioid receptor, % inhibition [1 μM] | μ-Opioid receptor, $K_i$ [μM] |
|---|---|---|
| 123 | 75 | 0.19 |
| 124 | 79 | 0.079 |
| 125 | 62 | n.d. |
| 126 | 35 | n.d. |
| 127 | 34 | n.d. |
| 129 | 47 | 0.54 |
| 130 | 82 | 0.23 |
| 132 | 91 | 0.12 |
| 133 | 81 | 0.096 |
| 135 | 70 | 0.38 |
| 136 | 73 | 0.23 |
| 138 | 73 | 0.092 |
| 139 | 90 | 0.044 |

TABLE 6

Alcohols

| Comp. | NA reuptake, % inhibition [10 μM] | Serotonin reuptake, % inhibition [10 μM] | μ-Opioid receptor, % inhibition [1 μM] |
|---|---|---|---|
| 112 | 74 | 82 | 66 |
| 113 | 82 | 83 | 46 |
| 114 | 93 | 64 | 43 |
| 115 | 47 | 63 | 61 |
| 116 | 95 | 74 | 37 |
| 117 | 82 | 85 | 57 |
| 118 | 91 | 90 | 33 |
| 119 | 91 | 88 | 43 |
| 120 | 93 | 79 | 51 |
| 121 | 66 | 74 | 61 |
| 122 | 97 | 77 | 32 |
| 125 | 86 | 82 | 62 |
| 128 | 88 | 84 | 18 |
| 131 | 89 | 91 | 68 |
| 134 | 90 | 86 | 45 |
| 137 | 93 | 89 | 13 |
| 140 | 94 | 85 | 31 |
| 143 | 100 | 90 | 24 |

TABLE 7

Ether derivatives

| Comp. | NA reuptake, % inhibition [10 μM] | Serotonin reuptake, % inhibition [10 μM] | Serotonin reuptake, $K_i$ [μM] | μ-Opioid receptor, % inhibition [1 μM] | μ-Opioid receptor, $K_i$ [μM] |
|---|---|---|---|---|---|
| 144 | 75 | 80 | n.d. | 81 | 0.12 |
| 145 | 84 | 83 | 0.29 | 73 | 0.31 |

TABLE 8

NA reuptake inhibition of the Grignard compounds

| Comp. | NA reuptake, % inhibition [10 μM] | $K_i$ [μM] |
|---|---|---|
| 146 | 94 | 0.6 |
| 147 | 12 | n.d. |
| 148 | 97 | n.d. |
| 149 | 75 | n.d. |

TABLE 9

5HT uptake inhibition of the Grignard derivatives

| Comp. | Serotonin reuptake, % inhibition [10 μM] | Serotonin reuptake, $K_i$ [μM] |
|---|---|---|
| 146 | 92 | 0.15 |
| 148 | 90 | 0.37 |
| 149 | 85 | n.d. |

TABLE 10

μ affinity of the Grignard compounds

| Comp. | μ-Opioid receptor, % inhibition [1 μM] |
|---|---|
| 146 | 97 |
| 148 | 91 |
| 149 | 82 |
| 150 | 74 |
| 151 | 71 |
| 152 | 63 |
| 153 | 87 |

TABLE 10-continued

µ affinity of the Grignard compounds

| Comp. | µ-Opioid receptor, % inhibition [1 µM] |
|---|---|
| 154 | 50 |
| 155 | 77 |
| 156 | 73 |
| 157 | 72 |
| 158 | 58 |
| 159 | 83 |
| 160 | 67 |
| 161 | 60 |
| 162 | 59 |
| 163 | 81 |
| 164 | 58 |
| 165 | 52 |
| 166 | 62 |
| 167 | 58 |
| 168 | 58 |
| 169 | 71 |
| 170 | 63 |
| 171 | 67 |
| 172 | 77 |
| 173 | 84 |

TABLE 11

Primary amines

| Comp. | Serotonin reuptake, % inhibition [10 µM] | Serotonin reuptake, $K_i$ [µM] | NA reuptake, % inhibition [10 µM] | NA reuptake, $K_i$ [µM] |
|---|---|---|---|---|
| 17 | 86 | 0.86 | 92 | 0.87 |
| 19 | 87 | n.d. | 93 | n.d. |
| 21 | 80 | n.d. | 90 | n.d. |
| 23 | 64 | n.d. | 97 | n.d. |
| 25 | 71 | n.d. | 84 | n.d. |
| 27 | 78 | n.d. | 95 | n.d. |
| 30 | 89 | n.d. | 89 | n.d. |
| 33 | 95 | n.d. | 94 | n.d. |
| 36 | 89 | 0.096 | 93 | 0.11 |
| 39 | 87 | n.d. | 97 | n.d. |
| 42 | 86 | n.d. | 83 | n.d. |
| 45 | 90 | n.d. | 96 | n.d. |
| 48 | 95 | n.d. | 100 | n.d. |
| 51 | 97 | n.d. | 98 | n.d. |
| 54 | 94 | n.d. | 102 | n.d. |
| 66 | 96 | n.d. | 96 | n.d. |
| 69 | 83 | n.d. | 98 | n.d. |
| 72 | 79 | n.d. | 91 | n.d. |

TABLE 12

µ affinity of the primary amines

| | µ-Opioid receptor, % inhibition [1 µM] | µ-Opioid receptor, $K_i$ [µM] |
|---|---|---|
| 17 | 83 | 0.44 |
| 21 | 48 | n.d. |
| 23 | 58 | n.d. |
| 25 | 74 | 0.26 |
| 30 | 94 | 0.21 |
| 36 | 68 | n.d. |
| 39 | 56 | n.d. |
| 42 | 80 | 0.24 |
| 48 | 67 | n.d. |
| 54 | 62 | n.d. |
| 66 | 62 | n.d. |
| 69 | 61 | n.d. |

TABLE 13

Secondary amines

| | Serotonin reuptake, % inhibition [10 µM] | NA reuptake, % inhibition [10 µM] |
|---|---|---|
| 83 | 93 | 100 |
| 84 | 76 | 93 |
| 85 | 77 | 103 |
| 86 | 88 | 95 |
| 87 | 95 | 106 |
| 88 | 88 | 84 |
| 89 | 73 | 85 |
| 90 | 87 | 98 |
| 91 | 76 | 93 |
| 92 | 69 | 75 |

TABLE 14

µ affinity of the secondary amines

| | µ-Opioid receptor, % inhibition [1 µM] | µ-Opioid receptor, $K_i$ [µM] |
|---|---|---|
| 83 | 95 | 0.007 |
| 84 | 95 | 0.012 |
| 85 | 98 | 0.0028 |
| 86 | 98 | 0.0038 |
| 87 | 85 | 0.0037 |
| 88 | 99 | 0.0024 |
| 89 | 95 | 0.059 |
| 90 | 94 | 0.045 |
| 91 | 90 | 0.0081 |
| 92 | 91 | 0.017 |
| 174 | 95 | 0.004900 |
| 175 | 86 | 0.011000 |

TABLE 15

Ureas

| | Serotonin reuptake, % inhibition [10 µM] | Serotonin reuptake, $K_i$ [µM] | NA reuptake, % inhibition [10 µM] | NA reuptake, $K_i$ [µM] |
|---|---|---|---|---|
| 73 | 90 | 0.061 | 94 | 0.18 |
| 75 | 80 | 0.013 | 88 | 0.55 |
| 74 | 86 | 0.12 | 93 | 0.22 |
| 76 | 84 | n.d. | 100 | n.d. |
| 77 | 84 | n.d. | 93 | n.d. |
| 78 | 87 | 0.16 | 98 | 0.29 |
| 79 | 97 | 0.091 | 96 | 0.12 |
| 80 | 97 | 0.25 | 97 | 0.49 |
| 81 | 97 | n.d. | 97 | n.d. |
| 82 | 98 | 0.11 | 98 | 0.12 |

TABLE 16

µ affinity of the ureas

| | µ-Opioid receptor, % inhibition [1 µM] | µ-Opioid receptor, $K_i$ [µM] |
|---|---|---|
| 73 | 96 | 0.046 |
| 75 | 88 | 0.098 |
| 74 | 88 | 0.16 |
| 76 | 61 | n.d. |
| 77 | 88 | 0.078 |
| 78 | 91 | 0.054 |
| 79 | 103 | 0.0083 |
| 80 | 95 | 0.02 |

TABLE 16-continued

μ affinity of the ureas

| | μ-Opioid receptor, % inhibition [1 μM] | μ-Opioid receptor, K$_i$ [μM] |
|---|---|---|
| 81 | 95 | 0.033 |
| 82 | 92 | 0.19 |

TABLE 17

Sulfonamides

| | Serotonin reuptake, % inhibition [10 μM] | NA reuptake, % inhibition [10 μM] | μ-Opioid receptor, % inhibition [1 μM] | μ-Opioid receptor, K$_i$ [μM] |
|---|---|---|---|---|
| 106 | 83 | 68 | 96 | 0.0037 |
| 107 | 90 | 78 | 99 | 0.015 |
| 108 | 75 | 75 | 92 | 0.022 |
| 109 | 93 | 76 | 92 | 0.077 |
| 110 | 86 | 62 | 93 | 0.025 |

TABLE 18

Acylated amines

| Comp. | Serotonin reuptake, % inhibition [10 μM] | Serotonin reuptake, K$_i$ [μM] | Na reuptake, % inhibition [10 μM] | NA reuptake, K$_i$ [μM] |
|---|---|---|---|---|
| 95 | 66 | n.d. | 80 | n.d. |
| 96 | 83 | 0.66 | 88 | 0.8 |
| 97 | 76 | 0.99 | 94 | 0.7 |
| 98 | 74 | 0.63 | 95 | 0.7 |
| 99 | 83 | 0.54 | 75 | |
| 93 | 75 | 0.66 | 48 | |
| 100 | 86 | 0.52 | 91 | 0.32 |
| 101 | 81 | 0.88 | 86 | 0.67 |
| 102 | 85 | 0.45 | 92 | 0.13 |
| 103 | 93 | 0.56 | 87 | 0.4 |
| 104 | 90 | 0.44 | 92 | 0.32 |
| 105 | 85 | | 88 | |

TABLE 19

μ affinity of acylated amines

| Comp. | μ-Opioid receptor, % inhibition [1 μM] | μ-Opioid receptor, K$_i$ [μM] |
|---|---|---|
| 95 | 95 | 0.0025 |
| 96 | 99 | 0.086 |
| 97 | 97 | 0.0037 |
| 98 | 104 | |
| 99 | 77 | 0.47 |
| 93 | 94 | 0.094 |
| 100 | 100 | 0.0035 |
| 101 | 101 | 0.0023 |
| 102 | 94 | 0.0015 |
| 103 | 99 | 0.0088 |
| 104 | 92 | 0.014 |
| 105 | 100 | 0.02 |
| 176 | 86 | 0.019 |
| 177 | 86 | 0.0072 |
| 178 | 96 | 0.0012 |
| 179 | 99 | 0.003 |
| 180 | 90 | 0.02 |
| 181 | 95 | 0.0039 |
| 182 | 95 | 0.0021 |

TABLE 20

μ affinity of the acylated amines

| Comp. | μ-Opioid receptor, % inhibition [1 μM] | μ-Opioid receptor, K$_i$ [μM] |
|---|---|---|
| 183 | 103 | 0.0039 |
| 184 | 101 | 0.0052 |
| 185 | 100 | 0.037 |
| 186 | 100 | 0.018 |
| 187 | 100 | 0.0085 |
| 188 | 100 | 0.0052 |
| 189 | 99 | 0.011 |
| 190 | 99 | 0.025 |
| 191 | 99 | |
| 192 | 98 | 0.018 |
| 193 | 96 | 0.023 |
| 194 | 96 | 0.0053 |
| 195 | 96 | 0.015 |
| 196 | 96 | 0.019 |
| 197 | 96 | 0.016 |
| 198 | 95 | 0.015 |
| 199 | 94 | 0.021 |
| 200 | 94 | 0.029 |
| 201 | 94 | 0.016 |
| 202 | 94 | 0.031 |
| 203 | 94 | 0.051 |
| 204 | 94 | 0.018 |
| 205 | 94 | 0.022 |
| 206 | 93 | 0.056 |
| 207 | 92 | 0.028 |
| 208 | 92 | 0.13 |
| 209 | 92 | 0.047 |
| 210 | 92 | 0.024 |
| 211 | 92 | |
| 212 | 91 | 0.019 |
| 213 | 91 | 0.096 |
| 214 | 91 | 0.028 |
| 215 | 90 | 0.034 |
| 216 | 90 | 0.056 |
| 217 | 90 | 0.062 |
| 218 | 89 | |
| 219 | 89 | 0.056 |
| 220 | 88 | 0.15 |
| 221 | 88 | 0.029 |
| 222 | 88 | 0.02 |
| 223 | 88 | 0.02 |
| 224 | 87 | |
| 225 | 87 | 0.02 |
| 226 | 87 | 0.058 |
| 227 | 87 | 0.058 |
| 228 | 87 | 0.019 |
| 229 | 86 | 0.039 |
| 230 | 86 | 0.021 |
| 231 | 86 | 0.045 |
| 232 | 84 | 0.074 |
| 233 | 84 | 0.071 |
| 234 | 84 | 0.046 |
| 235 | 84 | 0.061 |
| 236 | 83 | 0.063 |
| 237 | 83 | 0.048 |
| 238 | 83 | 0.038 |
| 239 | 82 | 0.08 |
| 240 | 82 | 0.051 |
| 241 | 82 | 0.068 |
| 242 | 82 | 0.046 |
| 243 | 82 | 0.025 |
| 244 | 82 | 0.03 |
| 245 | 82 | 0.066 |
| 246 | 82 | 0.039 |
| 247 | 82 | 0.036 |
| 248 | 81 | 0.088 |
| 249 | 81 | 0.064 |
| 250 | 81 | 0.036 |
| 251 | 81 | 0.091 |
| 252 | 81 | 0.02 |
| 253 | 80 | 0.079 |
| 254 | 80 | 0.056 |
| 255 | 80 | 0.046 |
| 256 | 80 | 0.08 |

TABLE 20-continued

μ affinity of the acylated amines

| Comp. | μ-Opioid receptor, % inhibition [1 μM] | μ-Opioid receptor, $K_i$ [μM] |
|---|---|---|
| 257 | 79 | 0.081 |
| 258 | 79 | 0.068 |
| 259 | 79 | 0.062 |
| 260 | 78 | |
| 261 | 78 | 0.13 |
| 262 | 78 | 0.096 |
| 263 | 78 | 0.028 |
| 264 | 78 | 0.11 |
| 265 | 78 | 0.14 |
| 266 | 78 | 0.036 |
| 267 | 77 | 0.15 |
| 268 | 76 | 0.086 |
| 269 | 75 | 0.047 |
| 270 | 75 | 0.19 |
| 271 | 75 | 0.019 |
| 272 | 75 | 0.09 |
| 273 | 75 | 0.081 |
| 274 | 74 | 0.099 |
| 275 | 74 | 0.1 |
| 276 | 74 | 0.065 |
| 277 | 74 | 0.074 |
| 278 | 74 | 0.086 |
| 279 | 74 | 0.14 |
| 280 | 73 | 0.31 |
| 281 | 73 | 0.046 |
| 282 | 73 | 0.11 |
| 283 | 72 | 0.15 |
| 284 | 72 | 0.063 |
| 285 | 71 | |
| 286 | 71 | 0.054 |
| 287 | 71 | 0.15 |
| 288 | 70 | 0.16 |
| 289 | 70 | 0.078 |
| 290 | 70 | |
| 291 | 102 | |
| 292 | 102 | 0.0013 |
| 293 | 102 | 0.0046 |
| 294 | 101 | 0.0083 |
| 295 | 101 | 0.0073 |
| 296 | 100 | 0.0003 |
| 297 | 100 | 0.004 |
| 298 | 100 | 0.004 |
| 299 | 100 | 0.001 |
| 300 | 99 | 0.0014 |
| 301 | 99 | 0.0027 |
| 302 | 99 | 0.0016 |
| 303 | 99 | 0.019 |
| 304 | 99 | 0.015 |
| 305 | 98 | 0.012 |
| 306 | 98 | 0.0099 |
| 307 | 98 | 0.0062 |
| 308 | 98 | 0.0074 |
| 309 | 98 | 0.0056 |
| 310 | 98 | 0.016 |
| 311 | 98 | 0.011 |
| 312 | 97 | 0.053 |
| 313 | 97 | 0.035 |
| 314 | 97 | 0.0042 |
| 315 | 97 | 0.16 |
| 316 | 96 | |
| 317 | 95 | 0.029 |
| 318 | 95 | 0.023 |
| 319 | 95 | 0.015 |
| 320 | 95 | 0.028 |
| 321 | 95 | 0.022 |
| 322 | 95 | 0.031 |
| 323 | 95 | 0.015 |
| 324 | 95 | 0.022 |
| 325 | 94 | 0.034 |
| 326 | 94 | 0.011 |
| 327 | 94 | 0.063 |
| 328 | 94 | 0.016 |
| 329 | 94 | 0.035 |
| 330 | 94 | 0.039 |
| 331 | 93 | 0.011 |
| 332 | 93 | 0.02 |
| 333 | 92 | 0.017 |
| 334 | 92 | 0.062 |
| 335 | 92 | 0.033 |
| 336 | 92 | 0.039 |
| 337 | 92 | |
| 338 | 91 | 0.028 |
| 339 | 91 | 0.025 |
| 340 | 91 | 0.055 |
| 341 | 91 | 0.013 |
| 342 | 90 | 0.028 |
| 343 | 90 | |
| 344 | 90 | 0.013 |
| 345 | 90 | 0.013 |
| 346 | 90 | 0.065 |
| 347 | 90 | 0.026 |
| 348 | 89 | 0.03 |
| 349 | 89 | 0.05 |
| 350 | 89 | 0.037 |
| 351 | 89 | 0.058 |
| 352 | 87 | |
| 353 | 87 | 0.096 |
| 354 | 86 | 0.053 |
| 355 | 86 | 0.12 |
| 356 | 86 | 0.12 |
| 357 | 86 | 0.06 |
| 358 | 86 | 0.011 |
| 359 | 86 | |
| 360 | 86 | 0.035 |
| 361 | 85 | 0.042 |
| 362 | 85 | 0.06 |
| 363 | 85 | 0.038 |
| 364 | 85 | 0.035 |
| 365 | 85 | 0.074 |
| 366 | 85 | 0.056 |
| 367 | 85 | 0.11 |
| 368 | 84 | 0.034 |
| 369 | 84 | 0.068 |
| 370 | 84 | 0.081 |
| 371 | 84 | 0.13 |
| 372 | 84 | 0.033 |
| 373 | 84 | 0.061 |
| 374 | 84 | |
| 375 | 84 | |
| 376 | 84 | 0.04 |
| 378 | 83 | 0.055 |
| 379 | 83 | |
| 380 | 83 | 0.095 |
| 381 | 83 | 0.099 |
| 382 | 83 | |
| 383 | 83 | 0.086 |
| 384 | 82 | 0.038 |
| 385 | 82 | 0.068 |
| 386 | 82 | 0.1 |
| 387 | 81 | 0.07 |
| 388 | 81 | 0.036 |
| 389 | 81 | 0.058 |
| 390 | 81 | |
| 391 | 81 | 0.026 |
| 392 | 80 | 0.18 |
| 393 | 80 | 0.044 |
| 394 | 79 | 0.048 |
| 395 | 81 | 0.046 |
| 396 | 97 | 0.012 |
| 397 | 97 | 0.0072 |
| 398 | 101 | 0.0074 |
| 399 | 80 | 0.11 |
| 400 | 94 | 0.023 |
| 401 | 97 | 0.011 |
| 402 | 96 | 0.0079 |
| 403 | 81 | 0.074 |
| 404 | 97 | 0.019 |
| 405 | 88 | 0.025 |

TABLE 20-continued

µ affinity of the acylated amines

| Comp. | µ-Opioid receptor, % inhibition [1 µM] | µ-Opioid receptor, $K_i$ [µM] |
|---|---|---|
| 406 | 81 | 0.04 |
| 407 | 87 | 0.048 |
| 408 | 82 | 0.012 |
| 409 | 84 | 0.028 |
| 410 | 88 | 0.0058 |
| 411 | 99 | 0.011 |
| 412 | 93 | 0.032 |
| 413 | 81 | 0.031 |
| 414 | 99 | 0.0046 |
| 415 | 99 | 0.0051 |
| 416 | 86 | 0.019 |
| 417 | 91 | 0.031 |
| 418 | 92 | 0.043 |
| 419 | 86 | 0.032 |
| 420 | 94 | 0.016 |
| 421 | 80 | 0.091 |
| 422 | 83 | 0.035 |
| 423 | 83 | 0.015 |
| 424 | 99 | 0.0027 |
| 425 | 94 | 0.006 |
| 426 | 99 | 0.0058 |
| 427 | 84 | 0.04 |
| 428 | 97 | 0.0054 |
| 429 | 88 | 0.055 |
| 430 | 101 | 0.0044 |
| 431 | 93 | 0.026 |
| 432 | 95 | 0.018 |
| 433 | 89 | 0.0038 |
| 434 | 85 | 0.024 |
| 435 | 99 | 0.014 |
| 436 | 91 | 0.029 |
| 437 | 80 | 0.1 |
| 438 | 87 | 0.1 |
| 439 | 85 | 0.052 |
| 440 | 95 | 0.015 |
| 441 | 83 | 0.2 |
| 442 | 86 | 0.11 |
| 443 | 96 | 0.04 |
| 444 | 101 | 0.011 |
| 445 | 86 | 0.069 |
| 446 | 99 | 0.0064 |
| 447 | 83 | 0.13 |
| 448 | 95 | 0.033 |
| 449 | 88 | 0.036 |
| 450 | 89 | 0.081 |
| 451 | 92 | 0.024 |
| 452 | 99 | 0.012 |
| 453 | 83 | 0.043 |
| 454 | 87 | 0.051 |
| 455 | 81 | 0.069 |
| 456 | 96 | 0.023 |
| 457 | 91 | 0.04 |
| 458 | 93 | 0.049 |
| 459 | 90 | 0.031 |
| 460 | 97 | 0.0095 |
| 461 | 100 | 0.017 |
| 462 | 91 | 0.055 |
| 463 | 104 | 0.0086 |
| 464 | 92 | 0.075 |
| 465 | 99 | 0.0031 |
| 466 | 86 | 0.041 |
| 467 | 82 | 0.062 |
| 468 | 83 | 0.16 |
| 469 | 87 | 0.057 |
| 470 | 91 | 0.071 |
| 471 | 82 | 0.087 |
| 472 | 85 | |
| 473 | 91 | 0.018 |
| 474 | 100 | 0.0027 |
| 475 | 97 | 0.0069 |
| 476 | 87 | 0.084 |
| 477 | 96 | 0.013 |
| 478 | 95 | 0.027 |

TABLE 21

Examples 491-501

| No. | Serotonin reuptake, % inhibition [10 µM] | NA reuptake, % inhibition [10 µM] |
|---|---|---|
| 492 | 3 | 54 |
| 493 | 38 | 27 |
| 494 | 40 | 81 |
| 495 | 7 | 16 |
| 496 | 18 | 26 |
| 497 | | 101 |
| 498 | | 99 |
| 499 | | 103 |
| 500 | | 101 |
| 501 | | 106 |

In vivo Studies of Analgesia: Tail-flick Test in the Mouse

The mice were each placed individually into a test cage and the base of the tail was exposed to the focused heat ray of an electric lamp (tail-flick type 50/08/1.bc, Labtec, Dr. Hess). The intensity of the lamp was adjusted so that the time from switching on of the lamp to the sudden twitching away of the tail (latency of pain) in untreated mice was from 3 to 5 seconds. Before administration of the solutions comprising the compound according to the invention, or of the particular comparison solutions, the mice were pre-tested twice in the course of five minutes and the mean of these measurements was calculated as the pre-test mean.

The solutions of the compound of the general formula I according to the invention and the comparison solutions were then administered intravenously.

Pain measurement was carried out in each case 10, 20, 40 and 60 minutes following the intravenous administration. The analgesic activity was determined as the increase in the latency of pain (% of the maximum possible antinociceptive effect) according to the following formula:

$$[(T_1-T_0)/(T_2-T_0)] \times 100$$

where time $T_0$ is the latency before administration, time $T_1$ is the latency after administration of the active ingredient combination and time $T_2$ is the maximum exposure time (12 seconds).

The in-depth study of analgesic activity was carried out in the tail-flick test in the mouse, as described above.

The compounds according to the invention which were tested exhibited analgesic activity. The results of chosen tests are summarised in the table below.

| Compound No. | Dose mg/kg (i.v.) | Activity % MPE | $ED_{50}$ i.v. (4.64-21.5) |
|---|---|---|---|
| 78 | | | 8.94 mg/kg |
| 79 | 10 | 76 | |
| 80 | 10 | 59 | |
| 86 | 21.5 | 100 | |
| 87 | 10 | 39 | |
| 88 | 21.5 | 90 | |
| 91 | 21.5 | 90 | |
| 95 | 1 | 100 | |
| 98 | 10 | 100 | |
| 102 | 10 | 82 | |
| 146 | 10 | 21 | |
| 148 | 10 | 40 | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted cyclohexylmethyl compound corresponding to formula I

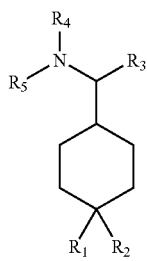

wherein
R$^1$ represents C$_{1-8}$-alkyl, in each case branched or unbranched, saturated or unsaturated, unsubstituted or mono- or poly-substituted; aryl or heteroaryl, which is unsubstituted or mono- or poly-substituted; C$_{3-10}$-cycloalkyl, which is saturated or unsaturated, unsubstituted or mono- or poly-substituted; an aryl or heteroaryl group linked via a C$_{1-4}$-alkyl chain and in each case unsubstituted or mono- or poly-substituted; (CH$_2$)$_m$CHN—OH, (CH$_2$)$_n$NR$^6$R$^7$ or (CH$_2$)$_n$OR$^8$, wherein n represents 0, 1, 2 or 3 and m represents 0, 1 or 2; or C(O)OR$^9$ linked via a C$_{1-3}$-alkyl group, which can be saturated or unsaturated; CONR$^{10}$R$^{11}$;
R$^2$ represents H or OH;
or R$^1$ and R$^2$ together represent

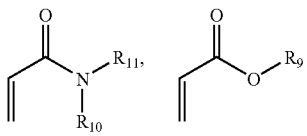

or =N—OH;
R$^3$ represents aryl or heteroaryl, which is unsubstituted or mono- or poly-substituted; or an aryl radical which is linked via a C$_{1-3}$-alkyl group and is unsubstituted or mono- or poly-substituted;
R$^4$ and R$^5$ independently of one another represent H; C$_{1-3}$-alkyl, which is unsubstituted, wherein R$^4$ and R$^5$ are not simultaneously H;
or the R$^4$ and R$^5$ together represent CH$_2$CH$_2$OCH$_2$CH$_2$ or (CH$_2$)$_{3-6}$;
R$^6$ represents H; C$_{1-8}$-alkyl, which is saturated or unsaturated, branched or unbranched, unsubstituted or mono- or poly-substituted; aryl, heteroaryl or C$_{3-10}$-cycloalkyl, in each case unsubstituted or mono- or poly-substituted; or an aryl or heteroaryl group linked via a C$_{1-4}$-alkyl chain and in each case unsubstituted or mono- or poly-substituted;
R$^7$ represents H; C$_{1-8}$-alkyl, which is saturated or unsaturated, branched or unbranched, unsubstituted or mono- or poly-substituted; aryl, heteroaryl or C$_{3-10}$-cycloalkyl, in each case unsubstituted or mono- or poly-substituted; or an aryl or heteroaryl group linked via a C$_{1-4}$-alkyl chain and in each case unsubstituted or mono- or poly-substituted; C(O)NR$^{10}$R$^{11}$, C(S)NR$^{10}$R$^{11}$, SO$_2$R$^{12}$ or C(O)R$^{13}$;
R$^8$ represents H; C$_{1-8}$-alkyl, in each case branched or unbranched, saturated or unsaturated, unsubstituted or mono- or poly-substituted; C$_{3-10}$-cycloalkyl, which is saturated or unsaturated, unsubstituted or mono- or poly-substituted; an aryl or heteroaryl group linked via a C$_{1-4}$-alkyl group and unsubstituted or mono- or poly-substituted;
R$^9$ represents H; C$_{1-8}$-alkyl, which is saturated or unsaturated, branched or unbranched, unsubstituted or mono- or poly-substituted;
R$^{10}$ and R$^{11}$ independently of one another represent H; C$_{3-10}$-cycloalkyl, which is saturated or unsaturated, unsubstituted or mono- or poly-substituted; aryl or heteroaryl, in each case unsubstituted or mono- or poly-substituted; or an aryl or heteroaryl radical linked via a C$_{1-4}$-alkyl chain and in each case unsubstituted or mono- or poly-substituted;
R$^{12}$ represents aryl or heteroaryl, in each case unsubstituted or mono- or poly-substituted; C$_{1-8}$-alkyl, in each case saturated or unsaturated, branched or unbranched, unsubstituted or mono- or poly-substituted; C$_{3-10}$-cycloalkyl, saturated or unsaturated, unsubstituted or mono- or poly-substituted; or an aryl or heteroaryl radical linked via a C$_{1-3}$-alkyl chain and in each case unsubstituted or mono- or poly-substituted;
R$^{13}$ represents C$_{1-8}$-alkyl, which is saturated or unsaturated, branched or unbranched, unsubstituted or mono- or poly-substituted; C$_{3-10}$-cycloalkyl, aryl or heteroaryl, in each case unsubstituted or mono- or poly-substituted; or an aryl or heteroaryl radical linked via a C$_{1-4}$-alkyl chain and in each case unsubstituted or mono- or poly-substituted, wherein the alkyl chain can be branched or unbranched, unsubstituted or mono- or poly-substituted;
or a salt thereof with a physiologically tolerated acid.

2. The compound of claim 1, wherein said compound is present in the form of a pure enantiomer or pure diastereoisomer.

3. The compound of claim 1, wherein said compound is present in the form of a mixture of stereoisomers.

4. A substituted cyclohexylmethyl compound according to claim 1, wherein R$^1$ represents C$_{1-8}$-alkyl, in each case branched or unbranched, saturated or unsaturated, unsubstituted or mono- or poly-substituted; aryl or heteroaryl, unsubstituted or mono- or poly-substituted; C$_{3-10}$-cycloalkyl, saturated or unsaturated, unsubstituted or mono- or poly-substituted; or an aryl or heteroaryl radical linked via a C$_{1-4}$-alkyl chain and in each case unsubstituted or mono- or poly-substituted; and R$^2$ denotes OH.

5. A substituted cyclohexylmethyl compound according to claim 1, wherein R$^1$ represents (CH$_2$)$_m$CHN—OH, (CH$_2$)$_n$NR$^6$R$^7$ or (CH$_2$)$_n$OR$^8$, wherein n represents 0, 1, 2 or 3 and m represents 0, 1 or 2; or C(O)OR$^9$ linked via a C$_{1-3}$-alkyl group, which can be saturated or unsaturated, or CONR$^{10}$R$^{11}$; and R$^2$ denotes H.

6. A substituted cyclohexylmethyl compound according to claim 1, wherein R$^1$ denotes C$_{1-8}$-alkyl, in each case branched or unbranched, saturated or unsaturated, unsubstituted or mono- or poly-substituted by methyl, =O, phenyl or CO$_2$CH$_3$; phenyl, naphthyl, benzyl, phenethyl, 2-pyridyl or 2-thienyl, unsubstituted or mono- or poly-substituted by F, CH$_3$, Cl, tert-butyl, methoxy or CF$_3$; cyclohexyl or cyclopentyl.

7. A substituted cyclohexylmethyl compound according to claim 1, wherein R$^1$ represents 2,4-difluorophenyl, 4-fluoro- 3-methylphenyl, phenyl, 3-methoxy-benzyl, 4-chlorophenyl, benzyl, 2-methylphenyl, 4-tert-butylphenyl, cyclopentyl, 4-fluorophenyl, phenethyl, 2-thienyl, 2,4-dichlorophenyl, 3-methoxyphenyl, 4-methylphenyl, 4-methoxyphenyl, 3,5-difluorophenyl, isopropyl, butyl, ethyl, hexyl, sec-butyl, 2,4,6-trimethylphenyl, pentyl, propyl, 3-fluorophenyl, 3,5-dichloro-phenyl, 4-fluorobenzyl, 4-chloro-3-trifluoromethylphenyl, cyclohexyl, isobutyl or 2,5-dimethoxyphenyl.

8. A substituted cyclohexylmethyl compound according to claim 1, wherein $R^3$ represents phenyl or thienyl, in each case unsubstituted or mono- or poly-substituted by F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl; a phenyl radical bonded via a $C_{1-3}$-alkyl chain, in each case unsubstituted or mono- or poly-substituted by F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl.

9. A substituted cyclohexylmethyl compound according to claim 8, wherein $R^3$ represents phenyl, unsubstituted or monosubstituted by Cl or F; phenethyl or thienyl.

10. A substituted cyclohexylmethyl compound according to claim 1, wherein $R^4$ and $R^5$ represent H or $CH_3$, wherein $R^4$ and $R^5$ are not simultaneously H.

11. A substituted cyclohexylmethyl compound according to claim 1, wherein $R^4$ and $R^5$ together represents $(CH_2)_{3-6}$.

12. A substituted cyclohexylmethyl compound according to claim 1, wherein $R^6$ represents H; $C_{1-8}$-alkyl, saturated or unsaturated, branched or unbranched, unsubstituted or mono- or poly-substituted by F, Cl, —CN, SH, $SCH_3$, $OCH_3$, OH, =O, $CO_2C_2H_5$ or $CO_2CH_3$; aryl, unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl; or an aryl or heteroaryl radical linked via a $C_{1-4}$-alkyl chain and in each case unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl, wherein the alkyl chain can be branched or unbranched, unsubstituted or mono- or poly-substituted by $CO_2C_2H_5$ or $CO_2CH_3$.

13. A substituted cyclohexylmethyl compound according to claim 12, wherein $R^6$ represents 2-indolylethyl, phenethyl, 3-phenylpropyl, benzyl, phenyl, 4-phenylbutyl, 1-(1H-indol-3-yl)propan-2-yl, 4 2-(3-indolyl)propionic acid methyl ester, in each case unsubstituted or monosubstituted by F or $OCH_3$.

14. A substituted cyclohexylmethyl compound according to claim 12, wherein $R^6$ is H.

15. A substituted cyclohexylmethyl compound according to claim 1, wherein $R^7$ represents $C(O)R^{13}$.

16. A substituted cyclohexylmethyl compound according to claim 1, wherein $R^8$ represents H; a phenyl radical linked via a $C_{1-4}$-alkyl group and unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl.

17. A substituted cyclohexylmethyl compound according to claim 16, wherein $R^8$ represents benzyl, unsubstituted or mono- or poly-substituted by F.

18. A substituted cyclohexylmethyl compound according to claim 1, wherein $R^9$ represents $C_{1-8}$-alkyl, which is branched or unbranched.

19. A substituted cyclohexylmethyl compound according to claim 1, wherein $R^{10}$ and $R^{11}$ independently of one another represent H; phenyl, naphthyl, or a phenyl or indolyl radical linked via a $C_{1-4}$-alkyl chain, in each case unsubstituted or substituted by F, Cl, Br, CN, $NH_2$, $NO_2$, SH, $SCH_3$, OH, $OCH_3$, $CF_3$, methyl, ethyl, propyl, butyl or tert-butyl.

20. A cyclohexylmethyl compound according to claim 19, wherein $R^{10}$ and $R^{11}$ independently of one another represent H; naphthyl, phenyl or benzyl, in each case unsubstituted or mono- or poly-substituted by $CF_3$, F, $NO_2$ or Br; or cyclohexyl, wherein $R^{10}$ and $R^{11}$ are not simultaneously H.

21. A cyclohexylmethyl compound according to claim 1, wherein $R^{12}$ represents naphthyl, phenyl or benzyl, in each case unsubstituted or mono- or poly-substituted by F, Cl, Br, CN, $NH_2$, $NO_2$, SH, $SCH_3$, OH, $OCH_3$, $CF_3$, methyl, ethyl, propyl, butyl or tert-butyl.

22. A substituted cyclohexylmethyl compound according to claim 1, wherein $R^{13}$ represents H; $C_{1-8}$-alkyl, saturated or unsaturated, branched or unbranched, unsubstituted or mono- or poly-substituted by F, Cl, —CN, NH—$C_{1-6}$-alkyl, $C_{1-6}$-alkyl, $N(C_{1-6}$-alkyl$)_2$, SH, S—$C_{1-6}$-alkyl, S-benzyl, O—$C_{1-6}$-alkyl, OH, =O, O-benzyl, C(=O)$C_{1-6}$-alkyl, $CO_2H$, $CO_2$—$C_{1-6}$-alkyl, phenyl or benzyl; $C_{3-10}$-cycloalkyl, unsubstituted or mono- or poly-substituted by F, Cl, —CN, NH—$C_{1-6}$-alkyl, $C_{1-6}$-alkyl, $N(C_{1-6}$-alkyl$)_2$, SH, S—$C_{1-6}$-alkyl, $C_{1-6}$-alkyl, S-benzyl, O—$C_{1-6}$-alkyl, OH, =O, O-benzyl, C(=O)$C_{1-6}$-alkyl, $CO_2H$, $CO_2$—$C_{1-6}$-alkyl, phenyl or benzyl; aryl or heteroaryl, in each case unsubstituted or mono- or poly-substituted by F, Cl, Br, CN, $NH_2$, NH—$C_{1-6}$-alkyl, $N(C_{1-6}$-alkyl$)_2$, $NO_2$, SH, pyridyl, S—$C_{1-6}$-alkyl, S-phenyl, OH, $(CH_2)_{0-3}$O—$C_{1-6}$-alkyl, $C_{1-3}$-alkyl-$C_{3-6}$-cycloalkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl, dihydrobenzofuran, $SO_2$-phenyl or $SO_2C_{1-6}$-alkyl; or an aryl or heteroaryl radical linked via a $C_{1-4}$-alkyl chain and in each case unsubstituted or mono- or poly-substituted by F, Cl, Br, CN, $NH_2$, NH—$C_{1-6}$-alkyl, $N(C_{1-6}$-alkyl$)_2$, $NO_2$, SH, pyridyl, S—$C_{1-6}$-alkyl, S-phenyl, OH, O—$C_{1-6}$-alkyl, O—$C_{1-6}$-alkyl-OH, O-phenyl, phenyl, benzyl, C(=O)$C_{1-6}$-alkyl, $CO_2H$, $CO_2$—$C_{1-6}$-alkyl, $CF_3$, $C_{1-6}$-alkyl, $SO_2$-phenyl or $SO_2C_{1-6}$-alkyl, wherein the alkyl chain can be branched or unbranched, unsubstituted or mono- or poly-substituted by F, Cl, —CN, SH, S—$C_{1-6}$-alkyl, S-benzyl, O—$C_{1-6}$-alkyl, OH, O—$C_{1-6}$-alkyl-OH, O-benzyl, $CO_2$—$C_{1-6}$-alkyl, phenyl or benzyl.

23. A substituted cyclohexylmethyl compound according to claim 22, wherein $R^{13}$ represents methyl, ethyl, phenyl, benzyl, 3-pentyl, n-propyl, benzothienyl, 1-(4-chlorophenyl)-cyclopentyl, 4-propylphenyl, 3-cyanophenyl, 3-chlorophenyl, 5-chloro-4-methoxy-thiophen-3-yl, 3-fluoro-5-trifluoromethylphenyl, 4-fluoro-5-trifluoromethylphenyl, 2-thienyl, 3,5-dichlorophenyl, 2,4,5-trifluorophenyl, 3-bromophenyl, 4-methylphenyl, 3-methoxyphenyl, 2,2-dimethylpropyl, 2-tert-butyl-5-methyl-pyrazol-3-yl, 2,4-dimethoxyphenyl, 3-trifluoromethylphenyl, 3,5-difluorophenyl, 2-fluoro-5-trifluoromethylphenyl, 4-chlorobenzyl, 2-methoxyphenyl, 2-methylsulfanyl-3-pyridyl, 3,4,5-trimethoxyphenyl, 2-ethylsulfanyl-3-pyridyl, 2-methyl-5-phenyl-furan-3-yl, 1-phenoxyethyl, tert-butylphenyl, 2-(4-chlorophenylsulfanyl)-3-pyridyl, 2-p-tolyloxy-3-pyridyl, 3-chloro-4-(sulfonyl-2-propyl)-thiophen-2-yl, 5-methylisoxazol-3-yl, 5-bromo-3-pyridyl, naphthyl, 2-methyl-5-(4-chloro-phenyl)-furan-3-yl, 4-(4-chloro-phenyl-sulfonyl)-3-methyl-thiophen-2-yl, 1-phenylpropyl, adamantyl, 2-phenyl-thiazol-4-yl, 4-methyl-2-phenyl-thiazol-5-yl, 2-(2,3-dihydrobenzofuran-5-yl)-thiazol-4-yl, 3-methylphenyl, 3-chloro-4-methylsulfonyl-thiophen-2-yl, benzyloxymethyl, methylthienyl, 4-bromo-2-ethyl-5-methyl-pyrazol-3-yl, 2,5-dimethylfuryl, 5-pyridin-2-yl-thiophene, 3-chloro-4-fluorophenyl, cyclohexyl, 3-nitrophenyl, 2,5-difluorophenyl, 2,6-difluorophenyl, 2-trifluoromethyl-5-fluoro-phenyl, 4-chlorophenoxy-methyl, 2-bromophenyl, cyclopentyl, benzothiadiazolyl, diphenylmethyl, 2-methylphenyl, 3-methoxybenzyl, 2,4,6-trichlorophenyl, 2-butyl, 2-chlorophenyl, 3,5-dinitrophenyl, 4-cyanophenyl, 2,4-dichloro-5-fluorophenyl, 2-chloro-3-pyridyl, 4-nitrophenyl, 2,3,4,5,6-pentafluorophenyl or 3-(2,6-dichloro-phenyl)-5-methyl-isoxazol-4-yl, 5-chloro-4-methylthiophen-3-yl, 4-fluorophenyl, 4-chlorophenyl, 2-fluorophenyl, 3-methylphenyl, 3-bromophenyl, 2,6-dichlorophenyl, 3,4-dichlorophenyl, 4-cyanophenyl, 2,4-difluorophenyl, 2,4-dichlorophenyl, 2,4-dichloro-5-fluorophenyl, 2-chloropyridin-3-yl, 3,5-dimethoxyphenyl, 2,6-dimethoxyphenyl, 2,3,6-trifluorophenyl, 2-(4-chlorophenoxy)-3-pyridyl, 3,4-difluorophenyl, 2-(2,3-dihydro-benzofuran-5-yl)-4-methyl-thiazol-5-yl, 3-methyl-oxadiazolyl, 3-phenyl-oxadiazolyl, 3-cyclopropylmethyl-oxadiazolyl, 3-methoxymethyl-oxadiazolyl or 2,4-dimethoxyphenyl.

24. A substituted cyclohexylmethyl compound according to claim 1, wherein said compound is selected from the group consisting of:

(16) 4-(dimethylamino-phenyl-methyl)-cyclohexanone oxime
(17) 4-(dimethylamino-phenyl-methyl)-cyclohexylamine
(18) 4-[dimethylamino-(4-fluorophenyl)-methyl]-cyclohexanone oxime
(19) 4-[dimethylamino-(4-fluorophenyl)-methyl]-cyclohexylamine
(20) 4-[dimethylamino-(3-fluorophenyl)-methyl]-cyclohexanone oxime
(21) 4-[dimethylamino-(3-fluorophenyl)-methyl]-cyclohexylamine
(22) 4-[(4-chlorophenyl)-dimethylamino-methyl]-cyclohexanone oxime
(23) 4-[(4-chlorophenyl)-dimethylamino-methyl]-cyclohexylamine
(24) 4-(dimethylamino-thiophen-2-yl-methyl)-cyclohexanone oxime
(25) 4-(dimethylamino-thiophen-2-yl-methyl)-cyclohexylamine
(26) 4-(1-dimethylamino-3-phenyl-propyl)-cyclohexanone oxime
(27) 4-(1-dimethylamino-3-phenyl-propyl)-cyclohexylamine
(29) 4-(dimethylamino-phenyl-methyl)-cyclohexane-carbaldehyde oxime
(30) [(4-aminomethyl-cyclohexyl)-phenyl-methyl]-dimethylamine
(32) 4-[dimethylamino-(4-fluorophenyl)-methyl]-cyclohexanecarbaldehyde oxime
(33) [(4-aminomethyl-cyclohexyl)-(4-fluorophenyl)-methyl]-dimethylamine
(35) 4-[dimethylamino-(3-fluorophenyl)-methyl]-cyclohexanecarbaldehyde oxime
(36) [(4-aminomethyl-cyclohexyl)-(3-fluorophenyl)-methyl]-dimethylamine
(38) 4-[(4-chlorophenyl)-dimethylamino-methyl]-cyclohexanecarbaldehyde oxime
(39) [(4-aminomethyl-cyclohexyl)-(4-chlorophenyl)-methyl]-dimethylamine
(41) 4-(dimethylamino-thiophen-2-yl-methyl)-cyclohexanecarbaldehyde oxime
(42) [(4-aminomethyl-cyclohexyl)-thiophen-2-yl-methyl]-dimethylamine
(44) 4-(1-dimethylamino-3-phenyl-propyl)-cyclohexanecarbaldehyde oxime
(45) [1-(4-aminomethyl-cyclohexyl)-3-phenyl-propyl]-dimethylamine
(47) [4-(dimethylamino-phenyl-methyl)-cyclohexyl]-acetaldehyde oxime
(48) 2-[4-dimethylamino-phenyl-methyl)-cyclohexyl]-ethylamine
(50) {4-[dimethylamino-(4-fluorophenyl)-methyl]-cyclohexyl}-acetaldehyde oxime
(51) 2-{4-[dimethylamino-(4-fluorophenyl)-methyl]-cyclohexyl}-ethylamine
(53) {4-[dimethylamino-(3-fluorophenyl)-methyl]-cyclohexyl}-acetaldehyde oxime
(54) 2-{4-[dimethylamino-(3-fluorophenyl)-methyl]-cyclohexyl}-ethylamine
(56) {4-[dimethylamino-(4-chlorophenyl)-methyl]-cyclohexyl}-acetaldehyde oxime
(66) 2-{4-[dimethylamino-(4-chlorophenyl)-methyl]-cyclohexyl}-ethylamine
(68) 2-(4-((dimethylamino)(thiophen-2-yl)methyl)cyclohexyl)acetaldehyde oxime
(69) 2-[4-(dimethylamino-thiophen-2-yl-methyl)-cyclohexyl]-ethylamine
(71) [4-(1-dimethylamino-3-phenyl-propyl)-cyclohexyl]-acetaldehyde oxime
(72) {1-[4-(2-amino-ethyl)-cyclohexyl]-3-phenyl-propyl}-dimethylamine
(111) 4-[dimethylamino-phenyl-methyl]-cyclohexanol
(112) 4-[dimethylamino-(4-fluorophenyl)-methyl]-cyclohexanol
(113) 4-[dimethylamino-(3-fluorophenyl)-methyl]-cyclohexanol
(114) 4-[(4-chlorophenyl)-dimethylamino-methyl]-cyclohexanol
(115) 4-(dimethylamino-thiophen-2-yl-methyl)-cyclohexanol
(116) 4-(1-dimethylamino-3-phenyl-propyl)-cyclohexanol
(117) [4-(dimethylamino-phenyl-methyl)-cyclohexyl]-methanol
(118) {4-[dimethylamino-(4-fluorophenyl)-methyl]-cyclohexyl}-methanol
(119) {4-[dimethylamino-(3-fluorophenyl)-methyl]-cyclohexyl}-methanol
(120) {4-[(4-chlorophenyl)-dimethylamino-methyl]-cyclohexyl}-methanol
(121) [4-(dimethylamino-thiophen-2-yl-methyl)-cyclohexyl]-methanol
(122) [4-(1-dimethylamino-3-phenyl-propyl)-cyclohexyl]-methanol
(123) [4-(dimethylamino-phenyl-methyl)-cyclohexylidene]-acetic acid ethyl ester
(124) [4-(dimethylamino-phenyl-methyl)-cyclohexyl]-acetic acid ethyl ester
(125) 2-[4-(dimethylamino-phenyl-methyl)-cyclohexyl]-ethanol
(126) {4-[dimethylamino-(4-fluorophenyl)-methyl]-cyclohexylidene}-acetic acid ethyl ester
(127) {4-[dimethylamino-(4-fluorophenyl)-methyl]-cyclohexyl}-acetic acid ethyl ester
(128) 2-{4-[dimethylamino-(4-fluorophenyl)-methyl]-cyclohexyl}-ethanol
(129) {4-[dimethylamino-(3-fluorophenyl)-methyl]-cyclohexylidene}-acetic acid ethyl ester
(130) {4-[dimethylamino-(3-fluorophenyl)-methyl]-cyclohexyl}-acetic acid ethyl ester
(131) 2-{4-[dimethylamino-(3-fluorophenyl)-methyl]-cyclohexyl}-ethanol
(132) 3-[4-(dimethylamino-phenyl-methyl)-cyclohexyl]-acrylic acid ethyl ester
(133) 3-[4-(dimethylamino-phenyl-methyl)-cyclohexyl]-propionic acid ethyl ester
(134) 3-[4-(dimethylamino-phenyl-methyl)-cyclohexyl]-propan-1-ol (135) 3-{4-[dimethylamino-(4-fluorophenyl)-methyl]-cyclohexyl}-acrylic acid ethyl ester
(136) 3-{4-[dimethylamino-(4-fluorophenyl)-methyl]-cyclohexyl}-propionic acid ethyl ester
(137) 3-{4-[dimethylamino-(4-fluorophenyl)-methyl]-cyclohexyl}-propan-1-ol
(138) 3-{4-[dimethylamino-(3-fluorophenyl)-methyl]-cyclohexyl}-acrylic acid ethyl ester
(139) 3-{4-[dimethylamino-(3-fluorophenyl)-methyl]-cyclohexyl}-propionic acid ethyl ester
(140) 3-{4-[dimethylamino-(3-fluorophenyl)-methyl]-cyclohexyl}-propan-1-ol
(141) 3-[4-(1-dimethylamino-3-phenyl-propyl)-cyclohexyl]-acrylic acid ethyl ester
(142) 3-[4-(1-dimethylamino-3-phenyl-propyl)-cyclohexyl]-propionic acid ethyl ester
(143) 3-[4-(1-dimethylamino-3-phenyl-propyl)-cyclohexyl]-propan-1-ol
(73) 1-(4-((dimethylamino)(phenyl)methyl)cyclohexyl)-3-(naphthalen-1-yl)urea
(74) 1-(2,4-difluorophenyl)-3-(4-((dimethylamino)(phenyl)methyl)cyclohexyl)urea hydrochloride
(75) 1-(4-((dimethylamino)(phenyl)methyl)cyclohexyl)-3-(3-(trifluoromethyl)-phenyl)urea hydrochloride
(76) 1-(4-((dimethylamino)(phenyl)methyl)cyclohexyl)-3-(2-nitrophenyl)urea hydrochloride
(77) 1-(3-bromophenyl)-3-(4-((dimethylamino)(phenyl)methyl)cyclohexyl)urea hydrochloride
(78) 1-(4-((dimethylamino)(phenyl)methyl)cyclohexyl)-3-phenylurea hydrochloride
(79) 1-benzyl-3-(4-((dimethylamino)(phenyl)methyl)cyclohexyl)urea
(80) 1-cyclohexyl-3-(4-((dimethylamino)(phenyl)methyl)cyclohexyl)urea
(81) 1-(4-bromophenyl)-3-(4-((dimethylamino)(phenyl)methyl)cyclohexyl)urea
(82) 1-(4-((dimethylamino)(phenyl)methyl)cyclohexyl)-3-(4-methoxyphenyl)urea
(83) N-(2-(1H-indol-3-yl)ethyl)-4-((dimethylamino)(phenyl)methyl)-cyclohexanamine hydrochloride
(84) 4-((dimethylamino)(phenyl)methyl)-N-phenethylcyclohexanamine hydrochloride
(85) 4-((dimethylamino)(phenyl)methyl)-N-(3-phenylpropyl)cyclohexanamine dihydrochloride
(86) N-benzyl-4-((dimethylamino)(phenyl)methyl)cyclohexanamine hydrochloride
(87) 4-((dimethylamino)(phenyl)methyl)-N-(4-phenylbutyl)cyclohexanamine hydrochloride
(88) N-(1-(1H-indol-3-yl)propan-2-yl)-4-((dimethylamino)(phenyl)methyl)-cyclohexanamine hydrochloride
(89) N-(4-((dimethylamino)(phenyl)methyl)cyclohexyl)-4-methoxybenzenamine hydrochloride
(90) 4-((dimethylamino)(phenyl)methyl)-N-(4-methoxybenzyl)cyclohexanamine dihydrochloride
(91) 4-((dimethylamino)(phenyl)methyl)-N-(4-fluorobenzyl)cyclohexanamine hydrochloride
(92) N-(4-((dimethylamino)(phenyl)methyl)cyclohexyl)benzenamine hydrochloride
(93) N-(4-((dimethylamino)(phenyl)methyl)cyclohexyl)-2-ethylbutanamide hydrochloride
(94) N-(4-((dimethylamino)(phenyl)methyl)cyclohexyl)benzamide hydrochloride
(95) N-(4-((dimethylamino)(phenyl)methyl)cyclohexyl)-N-(3-phenylpropyl)acetamide hydrochloride
(96) N-(4-((dimethylamino)(phenyl)methyl)cyclohexyl)-N-phenylacetamide hydrochloride
(97) N-(4-((dimethylamino)(phenyl)methyl)cyclohexyl)-N-(4-phenylbutyl)propionamide hydrochloride
(98) N-(4-((dimethylamino)(phenyl)methyl)cyclohexyl)-N-(4-phenylbutyl)-acetamide hydrochloride
(99) N-(4-((dimethylamino)(phenyl)methyl)cyclohexyl)-N-(4-methoxyphenyl)-acetamide hydrochloride
(100) N-benzyl-N-(4-((dimethylamino)(phenyl)methyl)cyclohexyl)acetamide hydrochloride
(101) N-benzyl-N-(4-((dimethylamino)(phenyl)methyl)cyclohexyl)-2-ethylbutanamide hydrochloride
(102) N-benzyl-N-(4-((dimethylamino)(phenyl)methyl)cyclohexyl)butyramide hydrochloride
(103) N-benzyl-N-(4-((dimethylamino)(phenyl)methyl)cyclohexyl)-4-fluoro-benzamide hydrochloride
(104) N-benzyl-N-(4-((dimethylamino)(phenyl)methyl)cyclohexyl)benzamide hydrochloride
(105) N-(4-((dimethylamino)(phenyl)methyl)cyclohexyl)-2-ethyl-N-phenylbutanamide hydrochloride
(106) 4-chloro-N-(4-((dimethylamino)(phenyl)methyl)cyclohexyl)benzene-sulfonamide hydrochloride
(107) N-(4-((dimethylamino)(phenyl)methyl)cyclohexyl)-4-methoxybenzene-sulfonamide hydrochloride
(108) 4-tert-butyl-N-(4-((dimethylamino)(phenyl)methyl)cyclohexyl)benzene-sulfonamide hydrochloride
(109) N-(4-((dimethylamino)(phenyl)methyl)cyclohexyl)-2-nitrobenzene-sulfonamide hydrochloride
(110) N-(4-((dimethylamino)(phenyl)methyl)cyclohexyl)benzenesulfonamide hydrochloride
(144) 4-(benzyloxy)cyclohexyl)-N,N-dimethyl(phenyl)methanamine hydrochloride
(145) 4-(4-fluorobenzyloxy)cyclohexyl)-N,N-dimethyl(phenyl)methanamine hydrochloride
(146) trans-N,N-dimethyl(4-phenethylcyclohexyl)(phenyl)methanamine hydrochloride
(147) 1-benzyl-4-((dimethylamino)(phenyl)methyl)cyclohexanol hydrochloride
(148) 4-((dimethylamino)(phenyl)methyl)-1-(4-fluorobenzyl)cyclohexanol hydrochloride
(149) 1-(2,5-dimethoxyphenyl)-4-((dimethylamino)(phenyl)methyl)cyclohexanol
(150) 4-((dimethylamino)(phenyl)methyl)-1-(4-fluoro-3-methylphenyl)cyclohexanol
(151) 4-(dimethylamino-phenyl-methyl)-1-(4-fluoro-3-methyl-phenyl)-cyclohexanol
(152) 1-benzyl-4-[dimethylamino-(3-fluoro-phenyl)-methyl]-cyclohexanol
(153) 4-[dimethylamino-(3-fluoro-phenyl)-methyl]-1-phenethyl-cyclohexanol
(154) 4-[dimethylamino-(3-fluoro-phenyl)-methyl]-1-pentyl-cyclohexanol
(155) 1-(3,5-dichloro-phenyl)-4-[dimethylamino-(3-fluoro-phenyl)-methyl]-cyclohexanol
(156) 4-[dimethylamino-(3-fluoro-phenyl)-methyl]-1-(3-methoxy-benzyl)-cyclohexanol
(157) 1-(4-chloro-3-trifluoromethyl-phenyl)-4-[dimethylamino-(3-fluoro-phenyl)-methyl]-cyclohexanol
(158) 4-[(4-chloro-phenyl)-dimethylamino-methyl]-1-phenyl-cyclohexanol
(159) 1-benzyl-4-[(4-chloro-phenyl)-dimethylamino-methyl]-cyclohexanol
(160) 4-[(4-chloro-phenyl)-dimethylamino-methyl]-1-(4-fluoro-3-methyl-phenyl)-cyclohexanol
(161) 4-[(4-chloro-phenyl)-dimethylamino-methyl]-1-o-tolyl-cyclohexanol
(162) 4-[(4-chloro-phenyl)-dimethylamino-methyl]-1-(4-fluoro-phenyl)-cyclohexanol (163) 4-[(4-chloro-phenyl)-dimethylamino-methyl]-1-phenethyl-cyclohexanol
(164) 4-[(4-chloro-phenyl)-dimethylamino-methyl]-1-(3-methoxy-phenyl)-cyclohexanol
(165) 4-[(4-chloro-phenyl)-dimethylamino-methyl]-1-p-tolyl-cyclohexanol
(166) 4-[(4-chloro-phenyl)-dimethylamino-methyl]-1-(3,5-difluoro-phenyl)-cyclohexanol
(167) 1-butyl-4-[(4-chloro-phenyl)-dimethylamino-methyl]-cyclohexanol
(168) 4-[(4-chloro-phenyl)-dimethylamino-methyl]-1-hexyl-cyclohexanol
(169) 4-[(4-chloro-phenyl)-dimethylamino-methyl]-1-pentyl-cyclohexanol (more polar diastereoisomer)
(170) 4-[(4-chloro-phenyl)-dimethylamino-methyl]-1-pentyl-cyclohexanol (less polar diastereoisomer)
(171) 4-[(4-chloro-phenyl)-dimethylamino-methyl]-1-(3-fluoro-phenyl)-cyclohexanol
(172) 4-[(4-chloro-phenyl)-dimethylamino-methyl]-1-(4-fluoro-benzyl)-cyclohexanol
(173) 4-[(4-chloro-phenyl)-dimethylamino-methyl]-1-(3-methoxy-benzyl)-cyclohexanol
(174) methyl 2-(4-((dimethylamino)(phenyl)methyl)cyclohexylamino)-3-(1H-indol-3-yl)propanoate (more polar diastereoisomer)
(175) methyl 2-(4-((dimethylamino)(phenyl)methyl)cyclohexylamino)-3-(1H-indol-3-yl)propanoate (less polar diastereoisomer)
(176) N-(4-((dimethylamino)(phenyl)methyl)cyclohexyl)-N-(4-methoxybenzyl)-acetamide
(177) N-(1-(1H-indol-3-yl)propan-2-yl)-N-(4-(dimethylamino)(phenyl)methyl)-cyclohexyl)acetamide (more polar diastereoisomer)
178) N-(1-(1H-indol-3-yl)propan-2-yl)-N-(4-((dimethylamino)(phenyl)methyl)-cyclohexyl)acetamide (less polar diastereoisomer)
(179) N-(4-((dimethylamino)(phenyl)methyl)cyclohexyl)-N-(4-fluorobenzyl)acetamide
(180) N-(4-((dimethylamino)(phenyl)methyl)cyclohexyl)-N-phenylbutyramide
(181) N-(2-(1H-indol-3-yl)ethyl)-N-(4-((dimethylamino)(phenyl)methyl)-cyclohexyl)butyramide
(182) N-(2-(1H-indol-3-yl)ethyl)-N-(4-((dimethylamino)(phenyl)methyl)-cyclohexyl)-acetamide
(183) benzo[b]thiophene-3-carboxylic acid [4-(dimethylamino-phenyl-methyl)-cyclohexyl]-amide
(184) 1-(4-chloro-phenyl)-cyclopentanecarboxylic acid [4-(dimethylamino-phenyl-methyl)-cyclohexyl]-amide
(185) N-[4-(dimethylamino-thiophen-2-yl-methyl)-cyclohexyl]-4-propyl-benzamide
(186) 3-cyano-N-[4-(dimethylamino-thiophen-2-yl-methyl)-cyclohexyl]-benzamide
(187) 3-chloro-N-[4-(dimethylamino-phenyl-methyl)-cyclohexyl]-benzamide
(188) 5-chloro-4-methoxy-thiophene-3-carboxylic acid [4-(dimethylamino-phenyl-methyl)-cyclohexyl]-amide
(189) 3,4-dichloro-N-[4-(dimethylamino-phenyl-methyl)-cyclohexyl]-benzamide
(190) N-[4-(dimethylamino-phenyl-methyl)-cyclohexyl]-3-fluoro-5-trifluoromethyl-benzamide
(191) 5-chloro-4-methoxy-thiophene-3-carboxylic acid {4-[dimethylamino-(3-fluoro-phenyl)-methyl]-cyclohexyl}-amide
(192) N-[4-(dimethylamino-thiophen-2-yl-methyl)-cyclohexyl]-4-fluoro-3-trifluoromethyl-benzamide
(193) thiophene-2-carboxylic acid [4-(dimethylamino-thiophen-2-yl-methyl)-cyclohexyl]-amide
(194) 3,5-dichloro-N-[4-(dimethylamino-thiophen-2-yl-methyl)-cyclohexyl]-benzamide
(195) 5-chloro-4-methoxy-thiophene-3-carboxylic acid [4-(dimethylamino-thiophen-2-yl-methyl)-cyclohexyl]-amide
(196) N-[4-(dimethylamino-phenyl-methyl)-cyclohexyl]-2,4,5-trifluoro-benzamide
(197) 3-bromo-N-[4-(dimethylamino-phenyl-methyl)-cyclohexyl]-benzamide
(198) N-[4-(dimethylamino-thiophen-2-yl-methyl)-cyclohexyl]-4-methyl-benzamide
(199) N-[4-(dimethylamino-thiophen-2-yl-methyl)-cyclohexyl]-3-methoxy-benzamide
(200) N-[4-(dimethylamino-thiophen-2-yl-methyl)-cyclohexyl]-3,3-dimethyl-butyramide
(201) 2-tert-butyl-5-methyl-2H-pyrazole-3-carboxylic acid [4-(dimethylamino-thiophen-2-yl-methyl)-cyclohexyl]-amide
(202) N-[4-(dimethylamino-thiophen-2-yl-methyl)-cyclohexyl]-2,4-dimethoxy-benzamide
(203) N-[4-(dimethylamino-phenyl-methyl)-cyclohexyl]-3-trifluoromethyl-benzamide
(204) N-{4-[dimethylamino-(3-fluoro-phenyl)-methyl]-cyclohexyl}-3,5-difluoro-benzamide
(205) N-[4-(dimethylamino-phenyl-methyl)-cyclohexyl]-2-fluoro-5-trifluoromethyl-benzamide
(206) 2-(4-chloro-phenyl)-N-[4-(dimethylamino-phenyl-methyl)-cyclohexyl]-acetamide
(207) N-[4-(dimethylamino-thiophen-2-yl-methyl)-cyclohexyl]-2-methoxy-benzamide
(208) N-[4-(dimethylamino-thiophen-2-yl-methyl)-cyclohexyl]-2-methylsulfanyl-nicotinamide
(209) 3,4-dichloro-N-{4-[dimethylamino-(3-fluoro-phenyl)-methyl]-cyclohexyl}-benzamide
(210) N-[4-(1-dimethylamino-3-phenyl-propyl)-cyclohexyl]-4-fluoro-3-trifluoromethyl-benzamide (more polar diastereoisomer)
(211) 5-chloro-4-methoxy-thiophene-3-carboxylic acid {4-[dimethylamino-(4-fluoro-phenyl)-methyl]-cyclohexyl}-amide
(212) N-[4-(dimethylamino-thiophen-2-yl-methyl)-cyclohexyl]-3,4,5-trimethoxy-benzamide
(213) N-[4-(dimethylamino-thiophen-2-yl-methyl)-cyclohexyl]-2-ethylsulfanyl-nicotinamide
(214) 2-methyl-5-phenyl-furan-3-carboxylic acid [4-(dimethylamino-phenyl-methyl)-cyclohexyl]-amide
(215) N-{4-[dimethylamino-(3-fluoro-phenyl)-methyl]-cyclohexyl}-2-phenoxy-propionamide (less polar diastereoisomer)
(216) N-[4-(dimethylamino-phenyl-methyl)-cyclohexyl]-2,4-dimethoxy-benzamide
(217) 4-tert-butyl-N-[4-(dimethylamino-phenyl-methyl)-cyclohexyl]-benzamide
(218) 2-(4-chloro-phenylsulfanyl)-N-[4-(dimethylamino-thiophen-2-yl-methyl)-cyclohexyl]-nicotinamide
(219) 2-(4-chloro-phenyl)-N-[4-(dimethylamino-thiophen-2-yl-methyl)-cyclohexyl]-acetamide
(220) N-[4-(dimethylamino-thiophen-2-yl-methyl)-cyclohexyl]-2-p-tolyloxy-nicotinamide
(221) 3-chloro-4-(propan-2-sulfonyl)-thiophene-2-carboxylic acid [4-(dimethylamino-thiophen-2-yl-methyl)-cyclohexyl]-amide
(222) N-{4-[dimethylamino-(3-fluoro-phenyl)-methyl]-cyclohexyl}-2-phenoxy-propionamide (more polar diastereoisomer)

(223) 2-tert-butyl-5-methyl-2H-pyrazole-3-carboxylic acid [4-(dimethylamino-phenyl-methyl)-cyclohexyl]-amide
(224) 5-Methyl-isoxazole-3-carboxylic acid [4-(dimethylamino-thiophen-2-yl-methyl)-cyclohexyl]-amide
(225) 5-bromo-N-[4-(dimethylamino-thiophen-2-yl-methyl)-cyclohexyl]-nicotinamide
(226) naphthyl-1-carboxylic acid [4-(dimethylamino-phenyl-methyl)-cyclohexyl]-amide
(227) N-[4-(1-dimethylamino-3-phenyl-propyl)-cyclohexyl]-4-fluoro-3-trifluoromethyl-benzamide (less polar diastereoisomer)
(228) N-[4-(dimethylamino-phenyl-methyl)-cyclohexyl]-3,3-dimethyl-butyramide (more polar diastereoisomer)
(229) 5-(4-chloro-phenyl)-2-methyl-furan-3-carboxylic acid [4-(dimethylamino-thiophen-2-yl-methyl)-cyclohexyl]-amide
(230) N-[4-(dimethylamino-phenyl-methyl)-cyclohexyl]-2-phenoxy-propionamide
(231) benzo[b]thiophene-2-carboxylic acid {4-[dimethylamino-(3-fluoro-phenyl)-methyl]-cyclohexyl}-amide
(232) 5-(4-chloro-phenyl)-2-methyl-furan-3-carboxylic acid [4-(dimethylamino-phenyl-methyl)-cyclohexyl]-amide
(233) 4-(4-chloro-benzenesulfonyl)-3-methyl-thiophene-2-carboxylic acid [4-(dimethylamino-phenyl-methyl)-cyclohexyl]-amide
(234) N-[4-(dimethylamino-phenyl-methyl)-cyclohexyl]-2-phenyl-butyramide (less polar diastereoisomer)
(235) 5-bromo-N-[4-(dimethylamino-phenyl-methyl)-cyclohexyl]-nicotinamide
(236) adamantane-1-carboxylic acid [4-(dimethylamino-phenyl-methyl)-cyclohexyl]-amide
(237) 2-phenyl-thiazole-4-carboxylic acid [4-(dimethylamino-phenyl-methyl)-cyclohexyl]-amide
(238) 4-methyl-2-phenyl-thiazole-5-carboxylic acid [4-(dimethylamino-phenyl-methyl)-cyclohexyl]-amide
(239) 2-(2,3-dihydro-benzofuran-5-yl)-thiazole-4-carboxylic acid [4-(dimethylamino-thiophen-2-yl-methyl)-cyclohexyl]-amide
(240) N-{4-[dimethylamino-(3-fluoro-phenyl)-methyl]-cyclohexyl}-2-phenyl-acetamide
(241) 3-chloro-N-[4-(1-dimethylamino-3-phenyl-propyl)-cyclohexyl]-benzamide
(242) N-[4-(dimethylamino-phenyl-methyl)-cyclohexyl]-4-methyl-benzamide
(243) 3,5-dichloro-N-{4-[dimethylamino-(3-fluoro-phenyl)-methyl]-cyclohexyl}-benzamide
(244) N-[4-(dimethylamino-phenyl-methyl)-cyclohexyl]-2,3,6-trifluoro-benzamide
(245) thiophene-2-carboxylic acid [4-(dimethylamino-phenyl-methyl)-cyclohexyl]-amide (less polar diastereoisomer)
(246) N-[4-(dimethylamino-phenyl-methyl)-cyclohexyl]-3,3-dimethyl-butyramide (less polar diastereoisomer)
(247) 2-tert-butyl-5-methyl-2H-pyrazole-3-carboxylic acid [4-(dimethylamino-phenyl-methyl)-cyclohexyl]-amide
(248) N-[4-(1-dimethylamino-3-phenyl-propyl)-cyclohexyl]-3-methyl-benzamide
(249) thiophene-2-carboxylic acid [4-(dimethylamino-phenyl-methyl)-cyclohexyl]-amide (more polar diastereoisomer)
(250) N-[4-(dimethylamino-phenyl-methyl)-cyclohexyl]-2-phenyl-butyramide (more polar diastereoisomer)
(251) N-{4-[dimethylamino-(3-fluoro-phenyl)-methyl]-cyclohexyl}-3,3-dimethyl-butyramide
(252) 3-chloro-4-methanesulfonyl-thiophene-2-carboxylic acid [4-(dimethylamino-phenyl-methyl)-cyclohexyl]-amide
(253) 4-(4-chloro-benzenesulfonyl)-3-methyl-thiophene-2-carboxylic acid [4-(dimethylamino-phenyl-methyl)-cyclohexyl]-amide
(254) 2-benzyloxy-N-[4-(dimethylamino-phenyl-methyl)-cyclohexyl]-acetamide
(255) N-[4-(dimethylamino-phenyl-methyl)-cyclohexyl]-2-thiophen-2-yl-acetamide
(256) 4-methyl-2-phenyl-thiazole-5-carboxylic acid {4-[dimethylamino-(3-fluoro-phenyl)-methyl]-cyclohexyl}-amide
(257) 2-(4-chloro-phenoxy)-N-[4-(dimethylamino-thiophen-2-yl-methyl)-cyclohexyl]-nicotinamide
(258) N-[4-(1-dimethylamino-3-phenyl-propyl)-cyclohexyl]-4-fluoro-benzamide
(259) 5-bromo-N-[4-(dimethylamino-phenyl-methyl)-cyclohexyl]-nicotinamide
(260) 4-bromo-2-ethyl-5-methyl-2H-pyrazole-3-carboxylic acid [4-(dimethylamino-thiophen-2-yl-methyl)-cyclohexyl]-amide
(261) 3-cyano-N-[4-(dimethylamino-phenyl-methyl)-cyclohexyl]-benzamide
(262) N-{4-[dimethylamino-(4-fluoro-phenyl)-methyl]-cyclohexyl}-4-fluoro-benzamide
(263) 3-bromo-N-{4-[dimethylamino-(4-fluoro-phenyl)-methyl]-cyclohexyl}-benzamide
(264) 2-phenyl-thiazole-4-carboxylic acid {4-[dimethylamino-(3-fluoro-phenyl)-methyl]-cyclohexyl}-amide
(265) 2,5-dimethyl-furan-3-carboxylic acid {4-[dimethylamino-(3-fluoro-phenyl)-methyl]-cyclohexyl}-amide
(266) 2-methyl-5-phenyl-furan-3-carboxylic acid {4-[dimethylamino-(3-fluoro-phenyl)-methyl]-cyclohexyl}-amide
(267) 5-pyridin-2-yl-thiophene-2-carboxylic acid {4-[dimethylamino-(3-fluoro-phenyl)-methyl]-cyclohexyl}-amide
(268) 4-bromo-2-ethyl-5-methyl-2H-pyrazole-3-carboxylic acid [4-(dimethylamino-phenyl-methyl)-cyclohexyl]-amide
(269) 3-chloro-N-{4-[dimethylamino-(3-fluoro-phenyl)-methyl]-cyclohexyl}-4-fluoro-benzamide
(270) 3,4-dichloro-N-{4-[dimethylamino-(4-fluoro-phenyl)-methyl]-cyclohexyl}-benzamide
(271) N-{4-[dimethylamino-(4-fluoro-phenyl)-methyl]-cyclohexyl}-2,4,5-trifluoro-benzamide
(272) cyclohexanecarboxylic acid [4-(dimethylamino-phenyl-methyl)-cyclohexyl]-amide
(273) N-{4-[dimethylamino-(3-fluoro-phenyl)-methyl]-cyclohexyl}-2-phenyl-butyramide
(274) 2-(4-chloro-phenyl)-N-{4-[dimethylamino-(3-fluoro-phenyl)-methyl]-cyclohexyl}-acetamide
(275) N-[4-(dimethylamino-phenyl-methyl)-cyclohexyl]-3-nitro-benzamide
(276) N-[4-(1-dimethylamino-3-phenyl-propyl)-cyclohexyl]-2,5-difluoro-benzamide
(277) 3-bromo-N-[4-(1-dimethylamino-3-phenyl-propyl)-cyclohexyl]-benzamide
(278) N-{4-[dimethylamino-(3-fluoro-phenyl)-methyl]-cyclohexyl}-2,6-difluoro-benzamide
(279) 2,5-dimethyl-furan-3-carboxylic acid [4-(dimethylamino-phenyl-methyl)-cyclohexyl]-amide
(280) 3-chloro-N-{4-[dimethylamino-(4-fluoro-phenyl)-methyl]-cyclohexyl}-4-fluoro-benzamide
(281) N-[4-(dimethylamino-phenyl-methyl)-cyclohexyl]-5-fluoro-2-trifluoromethyl-benzamide (282) 5-methyl-isoxazole-3-carboxylic acid [4-(dimethylamino-phenyl-methyl)-cyclohexyl]-amide
(283) 2-(2,3-dihydro-benzofuran-5-yl)-4-methyl-thiazole-5-carboxylic acid [4-(dimethylamino-thiophen-2-yl-methyl)-cyclohexyl]-amide
(284) 2-(4-chloro-phenoxy)-N-[4-(dimethylamino-phenyl-methyl)-cyclohexyl]-acetamide
(285) 5-(4-chloro-phenyl)-2-methyl-furan-3-carboxylic acid {4-[dimethylamino-(3-fluoro-phenyl)-methyl]-cyclohexyl}-amide
(286) 2-bromo-N-[4-(dimethylamino-phenyl-methyl)-cyclohexyl]-benzamide
(287) N-[4-(dimethylamino-phenyl-methyl)-cyclohexyl]-2,6-dimethoxy-benzamide
(288) cyclopentanecarboxylic acid [4-(dimethylamino-phenyl-methyl)-cyclohexyl]-amide
(289) 2-(2,3-dihydro-benzofuran-5-yl)-thiazole-4-carboxylic acid [4-(dimethylamino-phenyl-methyl)-cyclohexyl]-amide
(290) benzo[1,2,5]thiadiazole-5-carboxylic acid {4-[dimethylamino-(3-fluoro-phenyl)-methyl]-cyclohexyl}-amide
(291) N-[4-(dimethylamino-thiophen-2-yl-methyl)-cyclohexylmethyl]-2-thiophen-2-yl-acetamide
(292) benzo[b]thiophene-3-carboxylic acid [4-(dimethylamino-phenyl-methyl)-cyclohexylmethyl]-amide
(293) 5-chloro-4-methoxy-thiophene-3-carboxylic acid [4-(dimethylamino-phenyl-methyl)-cyclohexylmethyl]-amide
(294) N-[4-(dimethylamino-phenyl-methyl)-cyclohexylmethyl]-3,4-difluoro-benzamide (less polar diastereoisomer)
(295) N-{4-[dimethylamino-(3-fluoro-phenyl)-methyl]-cyclohexylmethyl}-3,3-dimethyl-butyramide
(296) 2-bromo-N-[4-(dimethylamino-thiophen-2-yl-methyl)-cyclohexylmethyl]-benzamide
(297) N-[4-(dimethylamino-thiophen-2-yl-methyl)-cyclohexylmethyl]-2,2-diphenyl-acetamide
(298) N-[4-(dimethylamino-phenyl-methyl)-cyclohexylmethyl]-3,3-dimethyl-butyramide
(299) N-[4-(dimethylamino-phenyl-methyl)-cyclohexylmethyl]-2-methylsulfanyl-nicotinamide
(300) N-[4-(dimethylamino-thiophen-2-yl-methyl)-cyclohexylmethyl]-2,6-dimethoxy-benzamide
(301) N-[4-(dimethylamino-thiophen-2-yl-methyl)-cyclohexylmethyl]-3,3-dimethyl-butyramide
(302) benzo[b]thiophene-3-carboxylic acid [4-(dimethylamino-thiophen-2-yl-methyl)-cyclohexylmethyl]-amide
(303) 5-chloro-4-methoxy-thiophene-3-carboxylic acid {4-[dimethylamino-(3-fluoro-phenyl)-methyl]-cyclohexylmethyl}-amide
(304) N-[4-(dimethylamino-thiophen-2-yl-methyl)-cyclohexylmethyl]-2-phenoxy-propionamide
(305) N-[4-(dimethylamino-thiophen-2-yl-methyl)-cyclohexylmethyl]-2-methoxy-benzamide
(306) N-[4-(dimethylamino-phenyl-methyl)-cyclohexylmethyl]-2-phenyl-acetamide
(307) 3-bromo-N-[4-(dimethylamino-thiophen-2-yl-methyl)-cyclohexylmethyl]-benzamide
(308) N-[4-(dimethylamino-thiophen-2-yl-methyl)-cyclohexylmethyl]-3-fluoro-5-trifluoromethyl-benzamide
(309) N-{4-[(4-chloro-phenyl)-dimethylamino-methyl]-cyclohexylmethyl}-3,3-dimethyl-butyramide
(310) N-[4-(dimethylamino-phenyl-methyl)-cyclohexylmethyl]-2-ethylsulfanyl-nicotinamide
(311) 2-(4-chloro-phenyl)-N-[4-(dimethylamino-thiophen-2-yl-methyl)-cyclohexyl-methyl]-acetamide
(312) N-{4-[(4-chloro-phenyl)-dimethylamino-methyl]-cyclohexylmethyl}-2,2-diphenyl-acetamide
(313) N-[4-(dimethylamino-thiophen-2-yl-methyl)-cyclohexylmethyl]-2,6-difluoro-benzamide
(314) benzo[b]thiophene-3-carboxylic acid {4-[dimethylamino-(3-fluoro-phenyl)-methyl]-cyclohexylmethyl}-amide
(315) N-{4-[(4-chloro-phenyl)-dimethylamino-methyl]-cyclohexylmethyl}-2-methyl-sulfanyl-nicotinamide
(316) N-{4-[(4-chloro-phenyl)-dimethylamino-methyl]-cyclohexylmethyl}-2-thiophen-2-yl-acetamide
(317) N-[4-(dimethylamino-phenyl-methyl)-cyclohexylmethyl]-2-methyl-benzamide (less polar diastereoisomer)
(318) 1-(4-chloro-phenyl)-cyclopentane-carboxylic acid [4-(dimethylamino-phenyl-methyl)-cyclohexylmethyl]-amide
(319) N-{4-[dimethylamino-(3-fluoro-phenyl)-methyl]-cyclohexylmethyl}-2-phenyl-acetamide (more polar diastereoisomer)
(320) N-{4-[(4-chloro-phenyl)-dimethylamino-methyl]-cyclohexylmethyl}-2-(3-methoxy-phenyl)-acetamide
(321) N-[4-(dimethylamino-phenyl-methyl)-cyclohexylmethyl]-2-phenyl-butyramide
(322) N-{4-[dimethylamino-(4-fluoro-phenyl)-methyl]-cyclohexylmethyl}-3,3-dimethyl-butyramide
(323) N-[4-(dimethylamino-phenyl-methyl)-cyclohexylmethyl]-2-phenoxy-propionamide
(324) 2-(4-chloro-phenyl)-N-[4-(dimethylamino-phenyl-methyl)-cyclohexylmethyl]-acetamide
(325) N-[4-(dimethylamino-phenyl-methyl)-cyclohexylmethyl]-2-methyl-benzamide (more polar diastereoisomer)
(326) N-[4-(dimethylamino-phenyl-methyl)-cyclohexylmethyl]-3-trifluoromethyl-benzamide (less polar diastereoisomer)
(327) 1-(4-chloro-phenyl)-cyclopentane-carboxylic acid {4-[dimethylamino-(3-fluoro-phenyl)-methyl]-cyclohexylmethyl}-amide
(328) thiophene-2-carboxylic acid [4-(dimethylamino-phenyl-methyl)-cyclohexyl-methyl]-amide
(329) 3,5-dichloro-N-[4-(dimethylamino-phenyl-methyl)-cyclohexylmethyl]-benzamide
(330) 2-methyl-5-phenyl-furan-3-carboxylic acid {4-[(4-chloro-phenyl)-dimethylamino-methyl]-cyclohexylmethyl}-amide
(331) 3-chloro-N-[4-(dimethylamino-phenyl-methyl)-cyclohexylmethyl]-benzamide
(332) N-{4-[dimethylamino-(3-fluoro-phenyl)-methyl]-cyclohexylmethyl}-2-phenoxy-propionamide (more polar diastereoisomer)
(333) N-[4-(dimethylamino-phenyl-methyl)-cyclohexylmethyl]-3-trifluoromethyl-benzamide (more polar diastereoisomer)
(334) thiophene-2-carboxylic acid {4-[dimethylamino-(3-fluoro-phenyl)-methyl]-cyclohexylmethyl}-amide (more polar diastereoisomer)
(335) 2-phenyl-thiazole-4-carboxylic acid [4-(dimethylamino-phenyl-methyl)-cyclohexylmethyl]-amide
(336) benzo[b]thiophene-3-carboxylic acid {4-[(4-chloro-phenyl)-dimethylamino-methyl]-cyclohexylmethyl}-amide (less polar diastereoisomer)
(337) N-{4-[dimethylamino-(3-fluoro-phenyl)-methyl]-cyclohexylmethyl}-2-p-tolyloxy-nicotinamide (338) 2,4,6-trichloro-N-[4-(dimethylamino-phenyl-methyl)-cyclohexylmethyl]-benzamide
(339) 1-(4-chloro-phenyl)-cyclopentane-carboxylic acid [4-(dimethylamino-phenyl-methyl)-cyclohexylmethyl]-amide
(340) thiophene-2-carboxylic acid {4-[dimethylamino-(3-fluoro-phenyl)-methyl]-cyclohexylmethyl}-amide (less polar diastereoisomer)
(341) N-{4-[dimethylamino-(3-fluoro-phenyl)-methyl]-cyclohexylmethyl}-2-phenoxy-propionamide (less polar diastereoisomer)
(342) N-{4-[dimethylamino-(3-fluoro-phenyl)-methyl]-cyclohexylmethyl}-2-methyl-butyramide (more polar diastereoisomer)
(343) N-{4-[dimethylamino-(3-fluoro-phenyl)-methyl]-cyclohexylmethyl}-2-thiophen-2-yl-acetamide
(344) benzo[b]thiophene-3-carboxylic acid {4-[dimethylamino-(4-fluoro-phenyl)-methyl]-cyclohexylmethyl}-amide
(345) 2-methyl-5-phenyl-furan-3-carboxylic acid [4-(dimethylamino-phenyl-methyl)-cyclohexylmethyl]-amide
(346) N-{4-[dimethylamino-(3-fluoro-phenyl)-methyl]-cyclohexylmethyl}-2-phenoxy-propionamide
(347) 3-cyano-N-[4-(dimethylamino-thiophen-2-yl-methyl)-cyclohexylmethyl]-benzamide
(348) N-{4-[dimethylamino-(3-fluoro-phenyl)-methyl]-cyclohexylmethyl}-2-phenyl-acetamide (less polar diastereoisomer)
(349) N-[4-(dimethylamino-phenyl-methyl)-cyclohexylmethyl]-2-(3-methoxy-phenyl)-acetamide
(350) N-{4-[dimethylamino-(3-fluoro-phenyl)-methyl]-cyclohexylmethyl}-4-fluoro-3-trifluoromethyl-benzamide
(351) N-{4-[(4-chloro-phenyl)-dimethylamino-methyl]-cyclohexylmethyl}-2-ethyl-sulfanyl-nicotinamide
(352) N-[4-(dimethylamino-thiophen-2-yl-methyl)-cyclohexylmethyl]-2-p-tolyloxy-nicotinamide (more polar diastereoisomer)
(353) 2-methyl-5-phenyl-furan-3-carboxylic acid {4-[dimethylamino-(3-fluoro-phenyl)-methyl]-cyclohexylmethyl}-amide
(354) 2-chloro-N-{4-[(4-chloro-phenyl)-dimethylamino-methyl]-cyclohexylmethyl}-benzamide
(355) 2-chloro-N-[4-(dimethylamino-phenyl-methyl)-cyclohexylmethyl]-nicotinamide
(356) N-[4-(dimethylamino-thiophen-2-yl-methyl)-cyclohexylmethyl]-4-propyl-benzamide
(357) N-[4-(dimethylamino-phenyl-methyl)-cyclohexylmethyl]-3,4-difluoro-benzamide (more polar diastereoisomer)
(358) 3-bromo-N-[4-(dimethylamino-phenyl-methyl)-cyclohexylmethyl]-benzamide
(359) N-{4-[dimethylamino-(4-fluoro-phenyl)-methyl]-cyclohexylmethyl}-2-thiophen-2-yl-acetamide
(360) 2-(4-chloro-phenoxy)-N-[4-(dimethylamino-phenyl-methyl)-cyclohexylmethyl]-nicotinamide (less polar diastereoisomer)
(361) 2,4-dichloro-N-[4-(dimethylamino-phenyl-methyl)-cyclohexylmethyl]-benzamide
(362) N-[4-(dimethylamino-phenyl-methyl)-cyclohexylmethyl]-3-methyl-benzamide
(363) 2-bromo-N-{4-[dimethylamino-(3-fluoro-phenyl)-methyl]-cyclohexylmethyl}-benzamide
(364) N-{4-[dimethylamino-(3-fluoro-phenyl)-methyl]-cyclohexylmethyl}-3-trifluoro-methyl-benzamide
(365) 2-phenyl-thiazole-4-carboxylic acid {4-[dimethylamino-(3-fluoro-phenyl)-methyl]-cyclohexylmethyl}-amide
(366) 2-tert-butyl-5-methyl-2H-pyrazole-3-carboxylic acid [4-(dimethylamino-thiophen-2-yl-methyl)-cyclohexylmethyl]-amide
(367) 3-chloro-4-(propane-2-sulfonyl)-thiophene-2-carboxylic acid [4-(dimethylamino-thiophen-2-yl-methyl)-cyclohexylmethyl]-amide
(368) N-{4-[dimethylamino-(3-fluoro-phenyl)-methyl]-cyclohexylmethyl}-2-methoxy-benzamide
(369) N-{4-[(4-chloro-phenyl)-dimethylamino-methyl]-cyclohexylmethyl}-3-trifluoromethyl-benzamide
(370) 1-(4-chloro-phenyl)-cyclopentane-carboxylic acid {4-[dimethylamino-(4-fluoro-phenyl)-methyl]-cyclohexylmethyl}-amide
(371) 3,5-dichloro-N-{4-[dimethylamino-(3-fluoro-phenyl)-methyl]-cyclohexylmethyl}-benzamide
(372) benzo[b]thiophene-3-carboxylic acid {4-[(4-chloro-phenyl)-dimethylamino-methyl]-cyclohexylmethyl}-amide (more polar diastereoisomer)
(373) 2-methyl-5-phenyl-furan-3-carboxylic acid {4-[dimethylamino-(3-fluoro-phenyl)-methyl]-cyclohexylmethyl}-amide
(374) 2-(4-chloro-phenylsulfanyl)-N-[4-(dimethylamino-phenyl-methyl)-cyclohexyl-methyl]-nicotinamide
(375) 4-bromo-2-ethyl-5-methyl-2H-pyrazole-3-carboxylic acid [4-(dimethylamino-thiophen-2-yl-methyl)-cyclohexylmethyl]-amide
(376) 5-chloro-4-methoxy-thiophene-3-carboxylic acid {4-[dimethylamino-(4-fluoro-phenyl)-methyl]-cyclohexylmethyl}-amide
(378) N-{4-[dimethylamino-(3-fluoro-phenyl)-methyl]-cyclohexylmethyl}-2-methyl-butyramide (less polar diastereoisomer)
(379) 5-methyl-isoxazole-3-carboxylic acid [4-(dimethylamino-phenyl-methyl)-cyclohexylmethyl]-amide
(380) benzo[b]thiophene-3-carboxylic acid [4-(1-dimethylamino-3-phenyl-propyl)-cyclohexylmethyl]-amide
(381) N-{4-[dimethylamino-(4-fluoro-phenyl)-methyl]-cyclohexylmethyl}-2-methyl-sulfanyl-nicotinamide
(382) N-{4-[(4-chloro-phenyl)-dimethylamino-methyl]-cyclohexylmethyl}-2-p-tolyloxy-nicotinamide
(383) 2-(4-chloro-phenoxy)-N-[4-(dimethylamino-phenyl-methyl)-cyclohexylmethyl]-nicotinamide (more polar diastereoisomer)
(384) N-{4-[dimethylamino-(3-fluoro-phenyl)-methyl]-cyclohexylmethyl}-2-methyl-benzamide
(385) 5-methyl-isoxazole-3-carboxylic acid {4-[(4-chloro-phenyl)-dimethylamino-methyl]-cyclohexylmethyl}-amide
(386) 5-bromo-N-[4-(dimethylamino-phenyl-methyl)-cyclohexylmethyl]-nicotinamide
(387) N-[4-(dimethylamino-phenyl-methyl)-cyclohexylmethyl]-2-methyl-butyramide
(388) N-{4-[dimethylamino-(3-fluoro-phenyl)-methyl]-cyclohexylmethyl}-2-ethylsulfanyl-nicotinamide
(389) N-[4-(dimethylamino-thiophen-2-yl-methyl)-cyclohexyl methyl]-2-p-tolyloxy-nicotinamide (less polar diastereoisomer)
(390) 4-bromo-2-ethyl-5-methyl-2H-pyrazole-3-carboxylic acid [4-(dimethylamino-phenyl-methyl)-cyclohexylmethyl]-amide
(391) N-{4-[(4-chloro-phenyl)-dimethylamino-methyl]-cyclohexylmethyl}-2-phenoxy-propionamide (392) N-[4-(dimethylamino-phenyl-methyl)-cyclohexylmethyl]-3,5-dinitro-benzamide
(393) N-{4-[(4-chloro-phenyl)-dimethylamino-methyl]-cyclohexylmethyl}-3-methoxy-benzamide
(394) 2-bromo-N-{4-[(4-chloro-phenyl)-dimethylamino-methyl]-cyclohexylmethyl}-benzamide
(395) 2-bromo-N-(2-{4-[(4-chloro-phenyl)-dimethylamino-methyl]-cyclohexyl}-ethyl)-benzamide
(396) 2-bromo-N-(2-{4-[dimethylamino-(3-fluoro-phenyl)-methyl]-cyclohexyl}-ethyl)-benzamide
(397) 3-chloro-N-{2-[4-(dimethylamino-phenyl-methyl)-cyclohexyl]-ethyl}-benzamide (more polar diastereoisomer)
(398) 3-chloro-N-{2-[4-(dimethylamino-phenyl-methyl)-cyclohexyl]-ethyl}-benzamide (less polar diastereoisomer)
(399) 3-chloro-N-(2-{4-[(4-chloro-phenyl)-dimethylamino-methyl]-cyclohexyl}-ethyl)-benzamide
(400) 3-chloro-N-(2-{4-[dimethylamino-(3-fluoro-phenyl)-methyl]-cyclohexyl}-ethyl)-benzamide (less polar diastereoisomer)
(401) 3-chloro-N-(2-{4-[dimethylamino-(3-fluoro-phenyl)-methyl]-cyclohexyl}-ethyl)-benzamide (more polar diastereoisomer)
(402) 2-chloro-N-{2-[4-(dimethylamino-phenyl-methyl)-cyclohexyl]-ethyl}-benzamide
(403) 2-chloro-N-(2-{4-[(4-chloro-phenyl)-dimethylamino-methyl]-cyclohexyl}-ethyl)-benzamide
(404) 2-chloro-N-(2-{4-[dimethylamino-(3-fluoro-phenyl)-methyl]-cyclohexyl}-ethyl)-benzamide
(405) 4-chloro-N-{2-[4-(dimethylamino-phenyl-methyl)-cyclohexyl]-ethyl}-benzamide
(406) 4-chloro-N-(2-{4-[dimethylamino-(3-fluoro-phenyl)-methyl]-cyclohexyl}-ethyl)-benzamide
(407) N-{2-[4-(dimethylamino-phenyl-methyl)-cyclohexyl]-ethyl}-4-fluoro-benzamide
(408) N-(2-{4-[(4-chloro-phenyl)-dimethylamino-methyl]-cyclohexyl}-ethyl)-4-fluoro-benzamide
(409) N-(2-{4-[dimethylamino-(3-fluoro-phenyl)-methyl]-cyclohexyl}-ethyl)-4-fluoro-benzamide
(410) N-{2-[4-(dimethylamino-phenyl-methyl)-cyclohexyl]-ethyl}-2-fluoro-benzamide
(411) N-(2-{4-[dimethylamino-(3-fluoro-phenyl)-methyl]-cyclohexyl}-ethyl)-2-fluoro-benzamide
(412) N-(2-{4-[dimethylamino-(3-fluoro-phenyl)-methyl]-cyclohexyl}-ethyl)-3-methyl-benzamide
(413) 2,6-dichloro-N-{2-[4-(dimethylamino-phenyl-methyl)-cyclohexyl]-ethyl}-benzamide
(414) N-{2-[4-(dimethylamino-phenyl-methyl)-cyclohexyl]-ethyl}-2-methoxy-benzamide
(415) N-(2-{4-[dimethylamino-(3-fluoro-phenyl)-methyl]-cyclohexyl}-ethyl)-2-methoxy-benzamide
(416) 3,4-dichloro-N-{2-[4-(dimethylamino-phenyl-methyl)-cyclohexyl]-ethyl}-benzamide
(417) N-{2-[4-(dimethylamino-phenyl-methyl)-cyclohexyl]-ethyl}-2-methyl-benzamide (more polar diastereoisomer)
(418) N-{2-[4-(dimethylamino-phenyl-methyl)-cyclohexyl]-ethyl}-2-methyl-benzamide (less polar diastereoisomer)
(419) N-(2-{4-[(4-chloro-phenyl)-dimethylamino-methyl]-cyclohexyl}-ethyl)-2-methyl-benzamide
(420) N-(2-{4-[dimethylamino-(3-fluoro-phenyl)-methyl]-cyclohexyl}-ethyl)-2-methyl-benzamide
(421) 4-cyano-N-{2-[4-(dimethylamino-phenyl-methyl)-cyclohexyl]-ethyl}-benzamide
(422) 3-chloro-N-(2-{4-[dimethylamino-(4-fluoro-phenyl)-methyl]-cyclohexyl}-ethyl)-benzamide (more polar diastereoisomer)
(423) 3-chloro-N-(2-{4-[dimethylamino-(4-fluoro-phenyl)-methyl]-cyclohexyl}-ethyl)-benzamide (less polar diastereoisomer)
(424) 3-chloro-N-{2-[4-(dimethylamino-thiophen-2-yl-methyl)-cyclohexyl]-ethyl}-benzamide
(425) 2-chloro-N-{2-[4-(dimethylamino-thiophen-2-yl-methyl)-cyclohexyl]-ethyl}-benzamide
(426) N-{2-[4-(dimethylamino-thiophen-2-yl-methyl)-cyclohexyl]-ethyl}-4-fluoro-benzamide
(427) N-(2-{4-[dimethylamino-(4-fluoro-phenyl)-methyl]-cyclohexyl}-ethyl)-2-fluoro-benzamide
(428) N-{2-[4-(dimethylamino-thiophen-2-yl-methyl)-cyclohexyl]-ethyl}-2-fluoro-benzamide
(429) N-(2-{4-[dimethylamino-(4-fluoro-phenyl)-methyl]-cyclohexyl}-ethyl)-3-methyl-benzamide
(430) N-{2-[4-(dimethylamino-thiophen-2-yl-methyl)-cyclohexyl]-ethyl}-3-methyl-benzamide
(431) 2,6-dichloro-N-{2-[4-(dimethylamino-thiophen-2-yl-methyl)-cyclohexyl]-ethyl}-benzamide
(432) N-(2-{4-[dimethylamino-(4-fluoro-phenyl)-methyl]-cyclohexyl}-ethyl)-2-methoxy-benzamide
(433) N-{2-[4-(dimethylamino-phenyl-methyl)-cyclohexyl]-ethyl}-3,5-difluoro-benzamide
(434) N-(2-{4-[(4-chloro-phenyl)-dimethylamino-methyl]-cyclohexyl}-ethyl)-3,5-difluoro-benzamide
(435) N-(2-{4-[dimethylamino-(3-fluoro-phenyl)-methyl]-cyclohexyl}-ethyl)-3,5-difluoro-benzamide
(436) N-(2-{4-[(4-chloro-phenyl)-dimethylamino-methyl]-cyclohexyl}-ethyl)-2,4-difluoro-benzamide
(437) 2,4-dichloro-N-(2-{4-[(4-chloro-phenyl)-dimethylamino-methyl]-cyclohexyl}-ethyl)-5-fluoro-benzamide
(438) 2,4-dichloro-N-(2-{4-[dimethylamino-(3-fluoro-phenyl)-methyl]-cyclohexyl}-ethyl)-5-fluoro-benzamide (more polar diastereoisomer)
(439) 2,4-dichloro-N-(2-{4-[dimethylamino-(3-fluoro-phenyl)-methyl]-cyclohexyl}-ethyl)-5-fluoro-benzamide (less polar diastereoisomer)
(440) 2,4-dichloro-N-{2-[4-(dimethylamino-thiophen-2-yl-methyl)-cyclohexyl]-ethyl}-5-fluoro-benzamide
(441) 2-chloro-N-(2-{4-[(4-chloro-phenyl)-dimethylamino-methyl]-cyclohexyl}-ethyl)-nicotinamide
(442) naphthalene-2-carboxylic acid (2-{4-[dimethylamino-(4-fluoro-phenyl)-methyl]-cyclohexyl}-ethyl)-amide
(443) N-{2-[4-(dimethylamino-thiophen-2-yl-methyl)-cyclohexyl]-ethyl}-4-propyl-benzamide
(444) N-{2-[4-(dimethylamino-phenyl-methyl)-cyclohexyl]-ethyl}-3,4-difluoro-benzamide
(445) N-(2-{4-[(4-chloro-phenyl)-dimethylamino-methyl]-cyclohexyl}-ethyl)-3,4-difluoro-benzamide
(446) N-{2-[4-(dimethylamino-thiophen-2-yl-methyl)-cyclohexyl]-ethyl}-3,4-difluoro-benzamide
(447) N-(2-{4-[dimethylamino-(4-fluoro-phenyl)-methyl]-cyclohexyl}-ethyl)-3-methoxy-benzamide
(448) N-{2-[4-(dimethylamino-phenyl-methyl)-cyclohexyl]-ethyl}-2,2-diphenyl-acetamide
(449) 1-(4-chloro-phenyl)-cyclopentane-carboxylic acid {2-[4-(dimethylamino-phenyl-methyl)-cyclohexyl]-ethyl}-amide
(450) 2-benzyloxy-N-{2-[4-(dimethylamino-phenyl-methyl)-cyclohexyl]-ethyl}-acetamide
(451) N-{2-[4-(dimethylamino-phenyl-methyl)-cyclohexyl]-ethyl}-2-phenyl-acetamide (452) thiophene-2-carboxylic acid {2-[4-(dimethylamino-phenyl-methyl)-cyclohexyl]-ethyl}-amide
(453) N-(2-{4-[dimethylamino-(3-fluoro-phenyl)-methyl]-cyclohexyl}-ethyl)-2-(3-methoxy-phenyl)-acetamide
(454) N-{2-[4-(dimethylamino-thiophen-2-yl-methyl)-cyclohexyl]-ethyl}-2-(3-methoxy-phenyl)-acetamide
(455) N-(2-{4-[(4-chloro-phenyl)-dimethylamino-methyl]-cyclohexyl}-ethyl)-2-phenyl-butyramide
(456) N-{2-[4-(dimethylamino-thiophen-2-yl-methyl)-cyclohexyl]-ethyl}-2-phenyl-butyramide
(457) benzo[b]thiophene-2-carboxylic acid {2-[4-(dimethylamino-phenyl-methyl)-cyclohexyl]-ethyl}-amide
(458) N-{2-[4-(dimethylamino-phenyl-methyl)-cyclohexyl]-ethyl}-4-nitro-benzamide
(459) 3-bromo-N-(2-{4-[dimethylamino-(4-fluoro-phenyl)-methyl]-cyclohexyl}-ethyl)-benzamide
(460) N-{2-[4-(dimethylamino-phenyl-methyl)-cyclohexyl]-ethyl}-2,3,4,5,6-pentafluoro-benzamide
(461) N-{2-[4-(dimethylamino-phenyl-methyl)-cyclohexyl]-ethyl}-2,6-difluoro-benzamide
(462) N-(2-{4-[dimethylamino-(3-fluoro-phenyl)-methyl]-cyclohexyl}-ethyl)-2,6-difluoro-benzamide
(463) 2-phenyl-thiazole-4-carboxylic acid {2-[4-(dimethylamino-phenyl-methyl)-cyclohexyl]-ethyl}-amide
(464) 2-phenyl-thiazole-4-carboxylic acid (2-{4-[dimethylamino-(4-fluoro-phenyl)-methyl]-cyclohexyl}-ethyl)-amide
(465) benzo[b]thiophene-3-carboxylic acid {2-[4-(dimethylamino-thiophen-2-yl-methyl)-cyclohexyl]-ethyl}-amide
(466) N-{2-[4-(dimethylamino-phenyl-methyl)-cyclohexyl]-ethyl}-2-methylsulfanyl-nicotinamide
(467) 2-methyl-5-phenyl-furan-3-carboxylic acid {2-[4-(dimethylamino-phenyl-methyl)-cyclohexyl]-ethyl}-amide
(468) 2-(2,3-dihydro-benzofuran-5-yl)-thiazole-4-carboxylic acid {2-[4-(dimethylamino-phenyl-methyl)-cyclohexyl]-ethyl}-amide
(469) 3-(2,6-dichloro-phenyl)-5-methyl-isoxazole-4-carboxylic acid {2-[4-(dimethylamino-thiophen-2-yl-methyl)-cyclohexyl]-ethyl}-amide
(470) 2-(4-chloro-phenylsulfanyl)-N-{2-[4-(dimethylamino-phenyl-methyl)-cyclohexyl]-ethyl}-nicotinamide (more polar diastereoisomer)
(471) 2-(4-chloro-phenylsulfanyl)-N-{2-[4-(dimethylamino-phenyl-methyl)-cyclohexyl]-ethyl}-nicotinamide (less polar diastereoisomer)
(472) benzo[1,2,3]thiadiazole-5-carboxylic acid {2-[4-(dimethylamino-phenyl-methyl)-cyclohexyl]-ethyl}-amide
(473) 5-bromo-N-{2-[4-(dimethylamino-phenyl-methyl)-cyclohexyl]-ethyl}-nicotinamide
(474) 5-chloro-4-methoxy-thiophene-3-carboxylic acid {2-[4-(dimethylamino-phenyl-methyl)-cyclohexyl]-ethyl}-amide
(475) 5-chloro-4-methoxy-thiophene-3-carboxylic acid (2-{4-[dimethylamino-(4-fluoro-phenyl)-methyl]-cyclohexyl}-ethyl)-amide
(476) 5-chloro-4-methoxy-thiophene-3-carboxylic acid {2-[4-(1-dimethylamino-3-phenyl-propyl)-cyclohexyl]-ethyl}-amide
(477) 3-cyano-N-{2-[4-(dimethylamino-phenyl-methyl)-cyclohexyl]-ethyl}-benzamide
(478) N-{2-[4-(dimethylamino-phenyl-methyl)-cyclohexyl]-ethyl}-2,4-dimethoxy-benzamide
(479) 2-chloro-N-((4-((dimethylamino)(phenyl)methyl)cyclohexyl)methyl)-benzamide
(480) N-((4-((dimethylamino)(phenyl)methyl)cyclohexyl)methyl)-4-fluoro-benzamide
(481) N-(2-(4-((dimethylamino)(phenyl)methyl)cyclohexyl)ethyl)-4-fluoro-benzamide
(482) N-((4-((dimethylamino)(phenyl)methyl)cyclohexyl)methyl)-2-fluoro-benzamide
(483) N-((4-((dimethylamino)(phenyl)methyl)cyclohexyl)methyl)-3-methyl-benzamide
(484) N-((4-((dimethylamino)(phenyl)methyl)cyclohexyl)methyl)-2-methoxy-benzamide
(485) N-(2-(4-((dimethylamino)(phenyl)methyl)cyclohexyl)ethyl)-3,5-dimethoxy-benzamide
(486) N-((4-((dimethylamino)(3-fluorophenyl)methyl)cyclohexyl)methyl)-2,6-dimethoxybenzamide
(487) N-((4-((dimethylamino)(phenyl)methyl)cyclohexyl)methyl)-2,4-difluoro-benzamide
(488) N-((4-((dimethylamino)(thiophen-2-yl)methyl)cyclohexyl)methyl)-3-methoxy-benzamide
(489) N-((4-((dimethylamino)(thiophen-2-yl)methyl)cyclohexyl)methyl)-3,4,5-trimethoxybenzamide
(490) 4-((dimethylamino)(phenyl)methyl)-1-(4-fluoro-3-methylphenyl)cyclohexanol
(491) N-cyclohexyl-2-(4-(2-phenyl-1-(pyrrolidin-1-yl)ethyl)cyclohexyl)acetamide
(492) N-(3-methoxyphenyl)-2-(4-(2-phenyl-1-(pyrrolidin-1-yl)ethyl)cyclohexyl)-acetamide
(493) N-(4-methoxyphenyl)-2-(4-(piperidin-1-yl(p-tolyl)methyl)cyclohexylidene)-acetamide
(494) N-phenethyl-2-(4-(piperidin-1-yl(p-tolyl)methyl)cyclohexylidene)acetamide
(495) 2-(4-(2-phenyl-1-(pyrrolidin-1-yl)ethyl)cyclohexylidene)-N-(pyridin-2-ylmethyl)acetamide
(496) N-benzyl-N-methyl-2-(4-(piperidin-1-yl(p-tolyl)methyl)cyclohexylidene)-acetamide
(497) 3-thiophen-2-yl-[1,2,4]oxadiazole-5-carboxylic acid [4-(dimethylamino-phenyl-methyl)-cyclohexyl]-amide
(498) 3-methyl-[1,2,4]oxadiazole-5-carboxylic acid {2-[4-(dimethylamino-phenyl-methyl)-cyclohexyl]-ethyl}-amide
(499) 3-phenyl-[1,2,4]oxadiazole-5-carboxylic acid {4-[dimethylamino-(3-fluoro-phenyl)-methyl]-cyclohexyl}-amide
(500) 3-cyclopropylmethyl-[1,2,4]oxadiazole-5-carboxylic acid {4-[dimethylamino-(3-fluoro-phenyl)-methyl]-cyclohexyl}-amide and
(501) 3-methoxymethyl-[1,2,4]oxadiazole-5-carboxylic acid {2-[4-(1-dimethylamino-3-phenyl-propyl)-cyclohexyl]-ethyl}-amide.

25. A process for preparing a cyclohexylmethyl compound corresponding to formula I

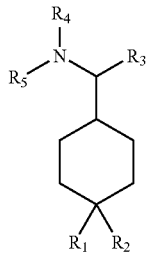

I wherein $R^1$ represents $(CH_2)_nC(O)H$, where n represents 0, 1, 2 or 3;

$R^2$ represents H or OH;

$R^3$ represents aryl or heteroaryl, which is unsubstituted or mono- or poly-substituted; or an aryl radical which is linked via a $C_{1-3}$-alkyl group and is unsubstituted or mono- or poly-substituted;

$R^4$ and $R^5$ independently of one another represent H; $C_{1-3}$-alkyl, which is unsubstituted, wherein $R^4$ and $R^5$ are not simultaneously H;

or the $R^4$ and $R^5$ together represent $CH_2CH_2OCH_2CH_2$ or $(CH_2)_{3-6}$;

or a salt thereof with a physiologically tolerated acid comprising the steps of reacting ketones corresponding to formula G

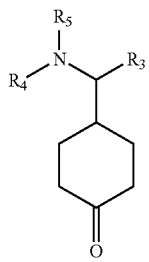

G with (methoxymethyl)triphenylphosphonium chloride and a strong base, at a temperature of from −20° C. to +30° C. to give the corresponding aldehydes H,

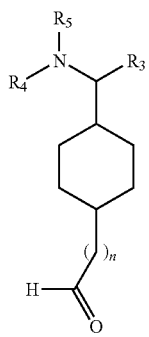

H wherein the reaction step is optionally repeated for the synthesis of aldehydes wherein n>0.

26. The process of claim 25 wherein said base is potassium tert-butylate.

27. A process for preparing a cyclohexylmethyl compound corresponding to formula I

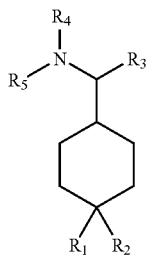

I wherein $R^1$ represents $(CH_2)_mCHN{-}OH$, $={N}{-}OH$, $(CH_2)_nNH_2$, wherein n represents 0, 1, 2 or 3 and m represents 0, 1 or 2;

$R^2$ represents H or OH;

$R^3$ represents aryl or heteroaryl, which is unsubstituted or mono- or poly-substituted; or an aryl radical which is linked via a $C_{1-3}$-alkyl group and is unsubstituted or mono- or poly-substituted;

$R^4$ and $R^5$ independently of one another represent H; $C_{1-3}$-alkyl, which is unsubstituted, wherein $R^4$ and $R^5$ are not simultaneously H;

or $R^4$ and $R^5$ together represent $CH_2CH_2OCH_2CH_2$ or $(CH_2)_{3-6}$;

or a salt thereof with a physiologically tolerated acid comprising the steps of converting the ketone G or the aldehydes H

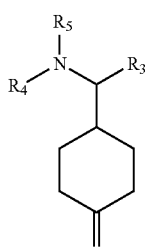

G

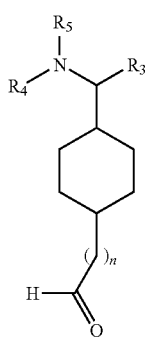

H into oximes corresponding to formula K by reacting with hydroxylamine hydrochloride in an organic solvent with addition of a base and reacting with a reducing agent to form amines corresponding to formula L.

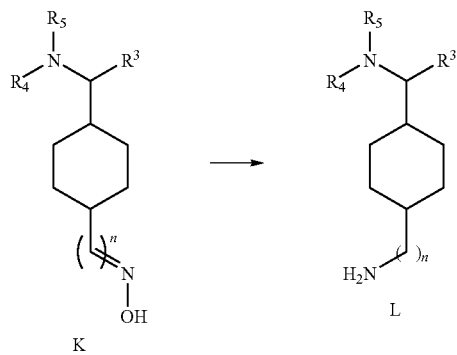

28. The process of claim 27, wherein the organic solvent is ethanol.

29. The process of claim 27, wherein the base is a basic ion exchanger Amberlyst.

30. The process of claim 27, wherein the reducing agent is LiAlH$_4$.

31. A process for preparing a cyclohexylmethyl compound corresponding to formula I

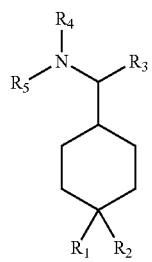

I wherein
wherein R$^1$ represents (CH$_2$)$_n$NHC(O)R$^{13}$ or (CH$_2$)$_n$NHSO$_2$R$^{12}$, wherein n represents 0, 1, 2 or 3;
R$^2$ represents H or OH;
R$^3$ represents aryl or heteroaryl, which is unsubstituted or mono- or poly-substituted; or an aryl radical which is linked via a C$_{1-3}$-alkyl group and is unsubstituted or mono- or poly-substituted;
R$^4$ and R$^5$ independently of one another represent H; C$_{1-3}$-alkyl, which is unsubstituted, wherein R$^4$ and R$^5$ are not simultaneously H;
or R$^4$ and R$^5$ together represent CH$_2$CH$_2$OCH$_2$CH$_2$ or (CH$_2$)$_{3-6}$;
R$^{12}$ represents aryl or heteroaryl, in each case unsubstituted or mono- or poly-substituted; C$_{1-8}$-alkyl, in each case saturated or unsaturated, branched or unbranched, unsubstituted or mono- or poly-substituted; C$_{3-10}$-cycloalkyl, saturated or unsaturated, unsubstituted or mono- or poly-substituted; or an aryl or heteroaryl radical linked via a C$_{1-3}$-alkyl chain and in each case unsubstituted or mono- or poly-substituted;
R$^{13}$ represents C$_{1-8}$-alkyl, which is saturated or unsaturated, branched or unbranched, unsubstituted or mono- or poly-substituted; C$_{3-10}$-cycloalkyl, aryl or heteroaryl, in each case unsubstituted or mono- or poly-substituted; or an aryl or heteroaryl radical linked via a C$_{1-4}$-alkyl chain and in each case unsubstituted or mono- or poly-substituted, wherein the alkyl chain can be branched or unbranched, unsubstituted or mono- or poly-substituted;
or a salt thereof with a physiologically tolerated acid
comprising linking amines corresponding to formula L

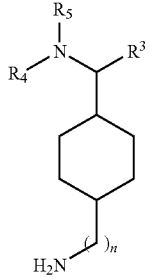

L with carboxylic acids or sulfonic acids with the addition of coupling reagents or by activating an acid component.

32. The process of claim 31 wherein said step of activating an acid component involves preparing the acid chloride.

33. A process for preparing a cyclohexylmethyl compound corresponding to formula I

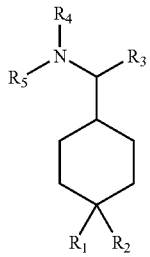

I wherein
wherein R$^1$ represents (CH$_2$)$_n$NHC(O)NR$^{10}$R$^{11}$ or (CH$_2$)$_n$NHC(S)NR$^{10}$R$^1$, wherein n represents 0, 1, 2 or 3;
R$^2$ represents H or OH;
R$^3$ represents aryl or heteroaryl, which is unsubstituted or mono- or poly-substituted; or an aryl radical which is linked via a C$_{1-3}$-alkyl group and is unsubstituted or mono- or poly-substituted;
R$^4$ and R$^5$ independently of one another represent H; C$_{1-3}$-alkyl, which is unsubstituted, wherein R$^4$ and R$^5$ are not simultaneously H;
or R$^4$ and R$^5$ together represent CH$_2$CH$_2$OCH$_2$CH$_2$ or (CH$_2$)$_{3-6}$;
R$^{10}$ and R$^{11}$ independently of one another represent H; C$_{3-10}$-cycloalkyl, which is saturated or unsaturated, unsubstituted or mono- or poly-substituted; aryl or heteroaryl, in each case unsubstituted or mono- or poly-substituted; or an aryl or heteroaryl radical linked via a C$_{1-4}$-alkyl chain and in each case unsubstituted or mono- or poly-substituted;

comprising reacting amines of the general formula L

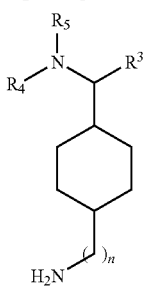

suitable isocyanates corresponding to the formula $R^{10}$—N=C=O or isothiocyanates corresponding to the formula $R^{10}$—N=C=S, optionally in the presence of at least one base, to give a compound of the general formula I
wherein $R^1$ denotes $(CH_2)_n NHC(O)NR^{10}R^{11}$ or $(CH_2)_n NHC(S)NR^{10}R^{11}$ where $R^{11}$ denotes H, and
converting this compound, optionally in the presence of at least one base, into a compound corresponding to formula I wherein $R^1$ denotes $(CH_2)_n NHC(O)NR^{10}R^{11}$ or $(CH_2)_n NHC(S)NR^{10}R^{11}$, wherein $R^{11}$ does not denote H, with a compound corresponding to the formula LG-$R^{11}$ wherein LG represents a leaving group and R11 is not hydrogen.

34. A process for preparing a cyclohexylmethyl compound corresponding to formula I

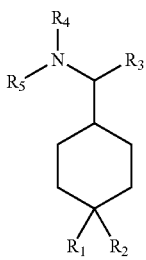

wherein
wherein $R^1$ represents $C(O)OR^9$ linked via a $C_{1-3}$-alkyl group, which is saturated or unsaturated;
or $R^1$ and $R^2$ together represent

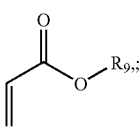

$R^2$ represents H or OH;
$R^3$ represents aryl or heteroaryl, which is unsubstituted or mono- or poly-substituted; or an aryl radical which is linked via a $C_{1-3}$-alkyl group and is unsubstituted or mono- or poly-substituted;
$R^4$ and $R^5$ independently of one another represent H; $C_{1-3}$-alkyl, which is unsubstituted, wherein $R^4$ and $R^5$ are not simultaneously H;
or $R^4$ and $R^5$ together represent $CH_2CH_2OCH_2CH_2$ or $(CH_2)_{3-6}$;
$R^9$ represents H; $C_{1-8}$-alkyl, which is saturated or unsaturated, branched or unbranched, unsubstituted or mono- or poly-substituted;

comprising reacting a phosphonoacetic acid ester, with a strong base, preferably potassium tert-butylate, sodium hydride or butyllithium, then with a ketone of the general formula G or with an aldehyde H

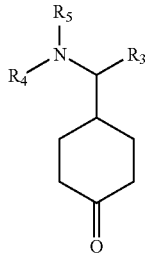

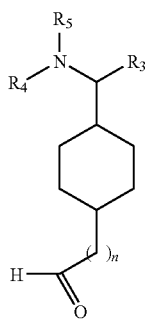

and optionally hydrolyzing the esters with a suitable aqueous, basic solution, at room temperature or slightly elevated temperature to give the corresponding carboxylic acids, or reducing the double bond is reduced, then continuing the ester hydrolysis and optionally reducing the esters to the corresponding alcohols with a reducing agent.

35. The process of claim 34, wherein said phosphonoacetic acid ester is phosphonoacetic acid trimethyl ester or phosphonoacetic acid triethyl ester, or said base is potassium tert-butylate, sodium hydride or butyllithium, or said basic solution is potassium hydroxide or lithium hydroxide solution, or said reducing agent is $LiAlH_4$ or said step of reducing the double bond is performed by heterogeneous catalytic hydrogenation on palladium or platinum catalysts or by homogeneously catalysed hydrogenation with rhodium catalysts, and said reducing, in each case, is performed at temperatures of from room temperature to 60° C. and under hydrogen pressures of from 1 bar to 6 bar.

36. A process for preparing a cyclohexylmethyl compound corresponding to formula I

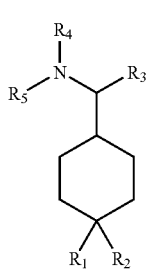

wherein $R^1$ represents $(CH_2)_n C(O)NR^{10}R^{11}$;
$R^2$ represents H or OH;
$R^3$ represents aryl or heteroaryl, which is unsubstituted or mono- or poly-substituted; or an aryl radical which is linked via a $C_{1-3}$-alkyl group and is unsubstituted or mono- or poly-substituted;

$R^4$ and $R^5$ independently of one another represent H; $C_{1-3}$-alkyl, which is unsubstituted, wherein $R^4$ and $R^5$ are not simultaneously H;

or $R^4$ and $R^5$ together represent $CH_2CH_2OCH_2CH_2$ or $(CH_2)_{3-6}$;

$R^{10}$ and $R^{11}$ independently of one another represent H; $C_{3-10}$-cycloalkyl, which is saturated or unsaturated, unsubstituted or mono- or poly-substituted; aryl or heteroaryl, in each case unsubstituted or mono- or poly-substituted; or an aryl or heteroaryl radical linked via a $C_{1-4}$-alkyl chain and in each case unsubstituted or mono- or poly-substituted;

comprising the step of reacting carboxylic acids according to claim 27 with a primary or secondary amine in the presence of water-removing agents or after conversion into an acid chloride or an active ester.

37. A process for preparing a cyclohexylmethyl compound corresponding to formula I

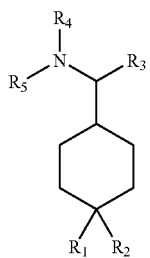

I wherein $R^1$ represents $(CH_2)_nOR^8$;

$R^2$ represents H or OH;

$R^3$ represents aryl or heteroaryl, which is unsubstituted or mono- or poly-substituted; or an aryl radical which is linked via a $C_{1-3}$-alkyl group and is unsubstituted or mono- or poly-substituted;

$R^4$ and $R^5$ independently of one another represent H; $C_{1-3}$-alkyl, which is unsubstituted, wherein $R^4$ and $R^5$ are not simultaneously H;

or $R^4$ and $R^5$ together represent $CH_2CH_2OCH_2CH_2$ or $(CH_2)_{3-6}$;

$R^8$ represents H; $C_{1-8}$-alkyl, in each case branched or unbranched, saturated or unsaturated, unsubstituted or mono- or poly-substituted; $C_{3-10}$-cycloalkyl, which is saturated or unsaturated, unsubstituted or mono- or poly-substituted; an aryl or heteroaryl group linked via a $C_{1-4}$-alkyl group and unsubstituted or mono- or poly-substituted;

comprising the step of converting the ketone G or the aldehydes H

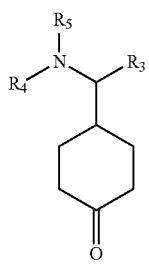

G

-continued

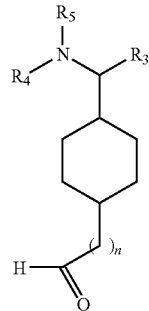

H into compounds in which $R^1$ represents $(CH_2)_nOH$ by reaction with a reducing agent, or reducing the esters of claim 27 to the corresponding alcohols with a reducing agent, and these alcohols are reacted with addition of a base, with a compound corresponding to the formula $R^8Hal$, to give compounds wherein $R^1$ represents $(CH_2)_nOR^8$, wherein $R^8$ is not H.

38. The process of claim 37, wherein in said ketone or aldehyde reaction the reducing agent is sodium borohydride or in said reaction beginning with the esters of claim 27, the reducing agent is $LiAlH_4$; or said base is NaH; wherein said halogen is Cl.

39. A process for preparing a cyclohexylmethyl compound corresponding to formula I

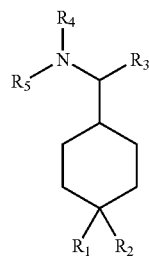

I wherein $R^1$ represents $(CH_2)_nNHR^6$;

$R^2$ represents H or OH;

$R^3$ represents aryl or heteroaryl, which is unsubstituted or mono- or poly-substituted; or an aryl radical which is linked via a $C_{1-3}$-alkyl group and is unsubstituted or mono- or poly-substituted;

$R^4$ and $R^5$ independently of one another represent H; $C_{1-3}$-alkyl, which is unsubstituted, wherein $R^4$ and $R^5$ are not simultaneously H;

or $R^4$ and $R^5$ together represent $CH_2CH_2OCH_2CH_2$ or $(CH_2)_{3-6}$;

$R^6$ represents H; $C_{1-8}$-alkyl, which is saturated or unsaturated, branched or unbranched, unsubstituted or mono- or poly-substituted; aryl, heteroaryl or $C_{3-10}$-cycloalkyl, in each case unsubstituted or mono- or poly-substituted; or an aryl or heteroaryl group linked via a $C_{1-4}$-alkyl chain and in each case unsubstituted or mono- or poly-substituted;

comprising dissolving the ketone G or the aldehydes H

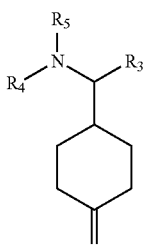

G

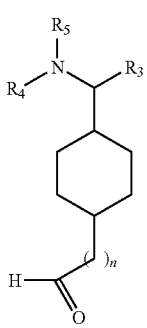

H in a polar aprotic solvent, and reacting with the corresponding amine of the general formula $NH_2R^6$ with addition of a suitable reducing agent.

40. The process of claim 39, wherein said solvent is tetrahydrofuran or said reducing agent is sodium borohydride.

41. A process for preparing a cyclohexylmethyl compound corresponding to formula I

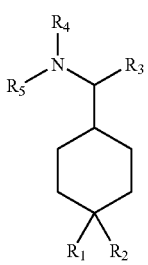

I wherein $R^1$ represents $C_{1-8}$-alkyl, in each case branched or unbranched, saturated or unsaturated, unsubstituted or mono- or poly-substituted; aryl or heteroaryl, unsubstituted or mono- or poly-substituted; $C_{3-10}$-cycloalkyl, saturated or unsaturated, unsubstituted or mono- or poly-substituted; an aryl or heteroaryl radical linked via a $C_{1-4}$-alkyl chain and in each case unsubstituted or mono- or poly-substituted;

$R^2$ represents OH;

$R^3$ represents aryl or heteroaryl, which is unsubstituted or mono- or poly-substituted; or an aryl radical which is linked via a $C_{1-3}$-alkyl group and is unsubstituted or mono- or poly-substituted;

$R^4$ and $R^5$ independently of one another represent H; $C_{1-3}$-alkyl, which is unsubstituted, wherein $R^4$ and $R^5$ are not simultaneously H;

or $R^4$ and $R^5$ together represent $CH_2CH_2OCH_2CH_2$ or $(CH_2)_{3-6}$;

comprising reacting ketones corresponding to formula G

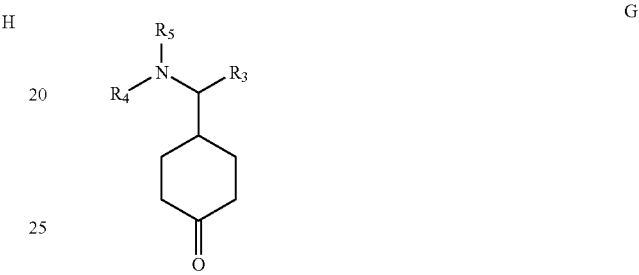

G 10 with organometallic compounds corresponding to formula $R^{1a}$MgHal, wherein Hal=Cl or Br, or $R^{1a}$Li, with cooling at from −30 to +10° C., in an organic solvent, for example diethyl ether or tetrahydrofuran, or adding isopropylmagnesium chloride solution\at a temperature of from −30° C. to 0° to an aryl iodide in an organic solvent, for example tetrahydrofuran, and after a stirring for at least 10 minutes, reacting the solution with a ketone of the formula G to give a compound of the general formula I wherein R2 represents OH and $R_1$ represents aryl.

42. A pharmaceutical formulation comprising at least one substituted cyclohexylmethyl compound according to claim 1 and a pharmaceutically acceptable auxiliary substances.

43. A method of alleviating pain in a mammal, said method comprising administering to said mammal an effective pain alleviating amount of a compound according to claim 1.

44. The method of claim 43, wherein said pain is acute, neuropathic or chronic pain.

45. A method for treating a condition selected from the group consisting of depression, urinary incontinence, diarrhoea, pruritus, alcohol and drug abuse, medicament dependency and lack of drive or for anxiolysis, said method comprising administering to a patient in need thereof a pharmaceutically effective amount of a compound according to claim 1.

* * * * *